US007029897B2

(12) United States Patent
Yue et al.

(10) Patent No.: US 7,029,897 B2
(45) Date of Patent: Apr. 18, 2006

(54) HUMAN PROTEIN PHOSPHATASE 2C

(75) Inventors: Henry Yue, Sunnyvale, CA (US); Li Ding, Creve Coeur, MO (US); Preeti G. Lal, Santa Clara, CA (US); Jennifer A. Griffin, Fremont, CA (US); Rajagopal Gururajan, San Jose, CA (US); Mariah R. Baughn, Los Angeles, CA (US); Craig H. Ison, San Jose, CA (US); Jayalaxmi Ramkumar, Fremont, CA (US); Catherine M. Tribouley, San Francisco, CA (US); Anita Swarnakar, San Francisco, CA (US); Neil Burford, Durham, CT (US); Olga Bandman, Mountain View, CA (US); Michael Thornton, Oakland, CA (US); Farrah A. Khan, Canton, MI (US); Narinder K. Chawla, Union City, CA (US); Danniel B. Nguyen, San Jose, CA (US); Vicki S. Elliott, San Jose, CA (US); Yuming Xu, Mountain View, CA (US); Yan Lu, Mountain View, CA (US); April J. A. Hafalia, Daly City, CA (US); Monique G. Yao, Mountain View, CA (US); Ameena R. Gandhi, San Francisco, CA (US); Chandra S. Arvizu, San Diego, CA (US); Ian J. Forsythe, Edmonton (CA)

(73) Assignee: Incyte Corporation, Wilmington, DE (US)

( * ) Notice: Subject to any disclaimer, the term of this patent is extended or adjusted under 35 U.S.C. 154(b) by 8 days.

(21) Appl. No.: 10/433,794

(22) PCT Filed: Dec. 4, 2001

(86) PCT No.: PCT/US01/47431

§ 371 (c)(1),
(2), (4) Date: Jun. 4, 2003

(87) PCT Pub. No.: WO02/46384

PCT Pub. Date: Jun. 13, 2002

(65) Prior Publication Data

US 2004/0077044 A1 Apr. 22, 2004

Related U.S. Application Data

(60) Provisional application No. 60/266,017, filed on Feb. 2, 2001, provisional application No. 60/264,644, filed on Jan. 26, 2001, provisional application No. 60/260,912, filed on Jan. 10, 2001, provisional application No. 60/257,416, filed on Dec. 22, 2000, provisional application No. 60/256,172, filed on Dec. 15, 2000, provisional application No. 60/255,756, filed on Dec. 14, 2000, provisional application No. 60/251,814, filed on Dec. 7, 2000, provisional application No. 60/254,034, filed on Dec. 6, 2000.

(51) Int. Cl.
C12N 9/16 (2006.01)
C12N 15/00 (2006.01)
C12N 1/20 (2006.01)
C07K 1/00 (2006.01)
C07H 21/04 (2006.01)

(52) U.S. Cl. ............... 435/196; 435/252.3; 435/320.1; 435/6; 536/23.2; 530/350

(58) Field of Classification Search ............... 435/196, 435/69.1, 6, 252.3, 320.1, 325; 536/23.1, 536/23.2; 530/350
See application file for complete search history.

(56) References Cited

U.S. PATENT DOCUMENTS

2002/0090703 A1* 7/2002 Plowman et al. ........... 435/196
2003/0152949 A1* 8/2003 Bandman et al. ............... 435/6

* cited by examiner

Primary Examiner—Maryam Monshipouri
(74) Attorney, Agent, or Firm—Foley & Lardner LLP

(57) ABSTRACT

The invention provides human kinases and phosphatases (KAP) and polnucleotides which identify and encode KAP. The invention also provides expresson vectors, host cells, antibodies, agonists, and antagonists. The invention also provides methods for diagnosing, treating, or preventing disorders associated with aberrant expression of KAP.

22 Claims, No Drawings

HUMAN PROTEIN PHOSPHATASE 2C

This application is a national stage under 35 U.S.C. § 371 of international application PCT/US01/47431, filed on Dec. 4, 2001 and published in English as WO 02/46384 on Jun. 13, 2002; which claims the benefit of provisional applications U.S. Ser. Nos. 60/254,034, filed on Dec. 6, 2000; 60/251,814, filed on Dec. 7, 2000; 60/255,756, filed on Dec. 14, 2000; 60/256,172, filed on Dec. 15, 2000; 60/257,416, filed on Dec. 22, 2000; 60/260,912, filed on Jan. 10, 2001; 60/264,644, filed on Jan. 26, 2001; and 60/266,017, filed on Feb. 2, 2001.

TECHNICAL FIELD

This invention relates to nucleic acid and amino acid sequences of kinases and phosphatases and to the use of these sequences in the diagnosis, treatment, and prevention of cardiovascular diseases, immune system disorders, neurological disorders, disorders affecting growth and development, lipid disorders, cell proliferative disorders, and cancers, and in the assessment of the effects of exogenous compounds on the expression of nucleic acid and amino acid sequences of kinases and phosphatases.

BACKGROUND OF THE INVENTION

Reversible protein phosphorylation is the ubiquitous strategy used to control many of the intracellular events in eukaryotic cells. It is estimated that more than ten percent of proteins active in a typical mammalian cell are phosphorylated. Kinases catalyze the transfer of high-energy phosphate groups from adenosine triphosphate (ATP) to target proteins on the hydroxyamino acid residues serine, threonine, or tyrosine. Phosphatases, in contrast, remove these phosphate groups. Extracellular signals including hormones, neurotransmitters, and growth and differentiation factors can activate kinases, which can occur as cell surface receptors or as the activator of the final effector protein, as well as other locations along the signal transduction pathway. Cascades of kinases occur, as well as kinases sensitive to second messenger molecules. This system allows for the amplification of weak signals (low abundance growth factor molecules, for example), as well as the synthesis of many weak signals into an all-or-nothing response. Phosphatases, then, are essential in determining the extent of phosphorylation in the cell and, together with kinases, regulate key cellular processes such as metabolic enzyme activity, proliferation, cell growth and differentiation, cell adhesion, and cell cycle progression.

Kinases

Kinases comprise the largest known enzyme superfamily and vary widely in their target molecules. Kinases catalyze the transfer of high energy phosphate groups from a phosphate donor to a phosphate acceptor. Nucleotides usually serve as the phosphate donor in these reactions, with most kinases utilizing adenosine triphosphate (ATP). The phosphate acceptor can be any of a variety of molecules, including nucleosides, nucleotides, lipids, carbohydrates, and proteins. Proteins are phosphorylated on hydroxyamino acids. Addition of a phosphate group alters the local charge on the acceptor molecule, causing internal conformational changes and potentially influencing intermolecular contacts. Reversible protein phosphorylation is the primary method for regulating protein activity in eukaryotic cells. In general, proteins are activated by phosphorylation in response to extracellular signals such as hormones, neurotransmitters, and growth and differentiation factors. The activated proteins initiate the cell's intracellular response by way of intracellular signaling pathways and second messenger molecules such as cyclic nucleotides, calcium-calmodulin, inositol, and various mitogens, that regulate protein phosphorylation.

Kinases are involved in all aspects of a cell's function, from basic metabolic processes, such as glycolysis, to cell-cycle regulation, differentiation, and communication with the extracellular environment through signal transduction cascades. Inappropriate phosphorylation of proteins in cells has been linked to changes in cell cycle progression and cell differentiation. Changes in the cell cycle have been linked to induction of apoptosis or cancer. Changes in cell differentiation have been linked to diseases and disorders of the reproductive system, immune system, and skeletal muscle.

There are two classes of protein kinases. One class, protein tyrosine kinases (PTKs), phosphorylates tyrosine residues, and the other class, protein serine/threonine kinases (STKs), phosphorylates serine and threonine residues. Some PTKs and STKs possess structural characteristics of both families and have dual specificity for both tyrosine and serine/threonine residues. Almost all kinases contain a conserved 250–300 amino acid catalytic domain containing specific residues and sequence motifs characteristic of the kinase family. The protein kinase catalytic domain can be further divided into 11 subdomains. N-terminal subdomains I–IV fold into a two-lobed structure which binds and orients the ATP donor molecule, and subdomain V spans the two lobes. C-terminal subdomains VI–XI bind the protein substrate and transfer the gamma phosphate from ATP to the hydroxyl group of a tyrosine, serine, or threonine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. PTKs and STKs also contain distinct sequence motifs in subdomains VI and VIII which may confer hydroxyamino acid specificity.

In addition, kinases may also be classified by additional amino acid sequences, generally between 5 and 100 residues, which either flank or occur within the kinase domain. These additional amino acid sequences regulate kinase activity and determine substrate specificity. (Reviewed in Hardie, G. and S. Hanks (1995) *The Protein Kinase Facts Book*, Vol I, pp. 17–20 Academic Press, San Diego Calif.). In particular, two protein kinase signature sequences have been identified in the kinase domain, the first containing an active site lysine residue involved in ATP binding, and the second containing an aspartate residue important for catalytic activity. If a protein analyzed includes the two protein kinase signatures, the probability of that protein being a protein kinase is close to 100% (PROSITE: PDOC00100, November 1995).

Protein Tyrosine Kinases

Protein tyrosine kinases (PTKs) may be classified as either transmembrane, receptor PTKs or nontransmembrane, nonreceptor PTK proteins. Transmembrane tyrosine kinases function as receptors for most growth factors. Growth factors bind to the receptor tyrosine kinase (RTK), which causes the receptor to phosphorylate itself (autophosphorylation) and specific intracellular second messenger proteins.

Growth factors (GF) that associate with receptor PTKs include epidermal GF, platelet-derived GP, fibroblast GF, hepatocyte GF, insulin and insulin-like GFs, nerve GF, vascular endothelial GF, and macrophage colony stimulating factor.

Nontransmembrane, nonreceptor PTKs lack transmembrane regions and, instead, form signaling complexes with the cytosolic domains of plasma membrane receptors. Receptors that function through non-receptor PTKs include those for cytokines and hormones (growth hormone and prolactin), and antigen-specific receptors on T and B lymphocytes.

Many PTKs were first identified as oncogene products in cancer cells in which PTK activation was no longer subject to normal cellular controls. In fact, about one third of the known oncogenes encode PTKS. Furthermore, cellular transformation (oncogenesis) is often accompanied by increased tyrosine phosphorylation activity (Charbonneau, H. and N. K. Tonks (1992) Annu. Rev. Cell Biol. 8:463–493). Regulation of PTK activity may therefore be an important strategy in controlling some types of cancer.

Protein Serine/Threonine Kinases

Protein serine/threonine kinases (STKs) are nontransmembrane proteins. A subclass of STKs are known as ERKs (extracellular signal regulated kinases) or MAPs (mitogen-activated protein kinases) and are activated after cell stimulation by a variety of hormones and growth factors. Cell stimulation induces a signaling cascade leading to phosphorylation of MEK (MAP/ERK kinase) which, in turn, activates ERK via serine and threonine phosphorylation. A varied number of proteins represent the downstream effectors for the active ERK and implicate it in the control of cell proliferation and differentiation, as well as regulation of the cytoskeleton. Activation of ERK is normally transient, and cells possess dual specificity phosphatases that are responsible for its down-regulation. Also, numerous studies have shown that elevated ERK activity is associated with some cancers. Other STKs include the second messenger dependent protein kinases such as the cyclic-AMP dependent protein kinases (PKA), calcium-calmodulin (CaM) dependent protein kinases, and the mitogen-activated protein kinases (MAP); the cyclin-dependent protein kinases; checkpoint and cell cycle kinases; Numb-associated kinase (Nak); human Fused (hFu); proliferation-related kinases; 5'-AMP-activated protein kinases; and kinases involved in apoptosis.

One member of the ERK family of MAP kinases, ERK 7, is a novel 61-kDa protein that has motif similarities to ERK1 and ERK2, but is not activated by extracellular stimuli as are ERK1 and ERK2 nor by the common activators, c-Jun N-terminal kinase (JNK) and p38 kinase. ERK7 regulates its nuclear localization and inhibition of growth through its C-terminal tail, not through the kinase domain as is typical with other MAP kinases (Abe, M. K. (1999) Mol. Cell. Biol. 19:1301–1312).

The second messenger dependent protein kinases primarily mediate the effects of second messengers such as cyclic AMP (cAMP), cyclic GMP, inositol triphosphate, phosphatidylinositol, 3,4,5-triphosphate, cyclic ADP ribose, arachidonic acid, diacylglycerol and calcium-calmodulin. The PKAs are involved in mediating hormone-induced cellular responses and are activated by cAMP produced within the cell in response to hormone stimulation. cAMP is an intracellular mediator of hormone action in all animal cells that have been studied. Hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cAMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine,* McGraw-Hill, New York N.Y., pp. 416–431, 1887).

The casein kinase I (CKI) gene family is another subfamily of serine/threonine protein kinases. This continuously expanding group of kinases have been implicated in the regulation of numerous cytoplasmic and nuclear processes, including cell metabolism and DNA replication, and repair. CKI enzymes are present in the membranes, nucleus, cytoplasm and cytoskeleton of eukaryotic cells, and on the mitotic spindles of mammalian cells (Fish, K. J. et al. (1995) J. Biol. Chem. 270:14875–14883).

The CKI family members all have a short amino-terminal domain of 9–76 amino acids, a highly conserved kinase domain of 284 amino acids, and a variable carboxyl-terminal domain that ranges from 24 to over 200 amino acids in length (Cegielska, A. et al. (1998) J. Biol. Chem. 273: 1357–1364). The CKI family is comprised of highly related proteins, as seen by the identification of isoforms of casein kinase I from a variety of sources. There are at least five mammalian isoforms, $\alpha$, $\beta$, $\gamma$, $\delta$, and $\epsilon$. Fish et al. identified CKI-epsilon from a human placenta cDNA library. It is a basic protein of 416 amino acids and is closest to CKI-delta. Through recombinant expression, it was determined to phosphorylate known CKI substrates and was inhibited by the CKI-specific inhibitor CKI-7. The human gene for CKI-epsilon was able to rescue yeast with a slow-growth phenotype caused by deletion of the yeast CKI locus, HRR250 (Fish et al., supra).

The mammalian circadian mutation tau was found to be a semidominant autosomal allele of CKI-epsilon that markedly shortens period length of circadian rhythms in Syrian hamsters. The tau locus is encoded by casein kinase I-epsilon, which is also a homolog of the *Drosophila circadian* gene double-time. Studies of both the wildtype and tau mutant CKI-epsilon enzyme indicated that the mutant enzyme has a noticeable reduction in the maximum velocity and autophosphorylation state. Further, in vitro, CKI-epsilon is able to interact with mammalian PERIOD proteins, while the mutant enzyme is deficient in its ability to phosphorylate PERIOD. Lowrey et al. have proposed that CKI-epsilon plays a major role in delaying the negative feedback signal within the transcription-translation-based autoregulatory loop that composes the core of the circadian mechanism. Therefore the CKI-epsilon enzyme is an ideal target for pharmaceutical compounds influencing circadian rhythms, jet-lag and sleep, in addition to other physiologic and metabolic processes under circadian regulation (Lowrey, P. L. et al. (2000) Science 288:483–491).

Calcium-Calmodulin Dependent Protein Kinases

Calcium-calmodulin dependent (CaM) kinases are involved in regulation of smooth muscle contraction, glycogen breakdown (phosphorylase kinase), and neurotransmission (CaM kinase I and CaM kinase II). CaM dependent protein kinases are activated by calmodulin, an intracellular calcium receptor, in response to the concentration of free calcium in the cell. Many CaM kinases are also activated by phosphorylation. Some CaM kinases are also activated by autophosphorylation or by other regulatory kinases. CaM kinase I phosphorylates a variety of substrates including the neurotransmitter-related proteins synapsin I and II, the gene transcription regulator, CREB, and the cystic fibrosis conductance regulator protein, CFTR (Haribabu, B. et al. (1995) EMBO J. 14:3679–3686). CaM kinase II also phosphorylates synapsin at different sites and controls the synthesis of catecholamines in the brain through phosphorylation and activation of tyrosine hydroxylase. CaM kinase II controls the synthesis of catecholamines and seratonin, through phosphorylation/activation of tyrosine hydroxylase and tryptophan hydroxylase, respectively (Fujisawa, H. (1990) BioEssays 12:27–29). The mRNA encoding a calmodulin-binding protein kinase-like protein was found to be enriched in mammalian forebrain. This protein is associated with vesicles in both axons and dendrites and accumulates largely postnatally. The amino acid sequence of this protein is similar to CaM-dependent STKs, and the protein binds calmodulin in the presence of calcium (Godbout, M. et al. (1994) J. Neurosci. 14:1–13).

Homeodomain-interacting protein kinases (HIPKs) are serine/threonine kinases and novel members of the DYRK kinase subfamily (Hofmann, T. G. et al. (2000) Biochimie 82:1123–1127). HIPKs contain a conserved protein kinase domain separated from a domain that interacts with homeoproteins. HIPKs are nuclear kinases, and HIPK2 is highly expressed in neuronal tissue (Kim, Y. H. et al. (1998) J. Biol. Chem. 273:25875–25879; Wang, Y. et al. (2001) Biochim. Biophys. Acta 1518:168–172). HIPKs act as corepressors for homeodomian transcription factors. This corepressor activity is seen in posttranslational modifications such as ubiquitination and phosphorylation, each of which are important in the regulation of cellular protein function (Kim, Y. H. et al. (1999) Proc. Natl. Acad. Sci. USA 96:12350–12355).

The human h-warts protein, a homolog of *Drosophila* warts tumor suppressor gene, maps to chromosome 6q24-25.1. It has a serine/threonine kinase domain and is localized to centrosomes in interphase cells. It is involved in mitosis and functions as a component of the mitotic apparatus (Nishiyama, Y. et al. (1999) FEBS Lett. 459:159–165).

Calcium-Calmodulin Dependent Protein Kinases

Calcium-calmodulin dependent (CaM) kinases are involved in regulation of smooth muscle contraction, glycogen breakdown (phosphorylase kinase), and neurotransmission (CaM kinase I and CaM kinase II). CaM dependent protein kinases are activated by calmodulin, an intracellular calcium receptor, in response to the concentration of free calcium in the cell. Many CaM kinases are also activated by phosphorylation. Some CaM kinases are also activated by autophosphorylation or by other regulatory kinases. CaM kinase I phosphorylates a variety of substrates including the neurotransmitter-related proteins synapsin I and II, the gene transcription regulator, CREB, and the cystic fibrosis conductance regulator protein, CFTR (Haribabu, B. et al. (1995) EMBO J. 14:3679–3686). CaM kinase II also phosphorylates synapsin at different sites and controls the synthesis of catecholamines in the brain through phosphorylation and activation of tyrosine hydroxylase. CaM kinase II controls the synthesis of catecholamines and seratonin, through phosphorylation/activation of tyrosine hydroxylase and tryptophan hydroxylase, respectively (Fujisawa, H. (1990) BioEssays 12:27–29). The mRNA encoding a calmodulin-binding protein kinase-like protein was found to be enriched in mammalian forebrain. This protein is associated with vesicles in both axons and dendrites and accumulates largely postnatally. The amino acid sequence of this protein is similar to CaM-dependent STKs, and the protein binds calmodulin in the presence of calcium (Godbout, M. et al. (1994) J. Neurosci. 14:1–13).

Mitogen-Activated Protein Kinases

The mitogen-activated protein kinases (MAP), which mediate signal transduction from the cell surface to the nucleus via phosphorylation cascades, are another STK family that regulates intracellular signaling pathways. Several subgroups have been identified, and each manifests different substrate specificities and responds to distinct extracellular stimuli (Egan, S. E. and R. A. Weinberg (1993) Nature 365:781–783). There are three kinase modules comprising the MAP kinase cascade: MAPK (MAP), MAPK kinase (MAP2K, MAPKK, or MKK), and MKK kinase (MAP3K, MAPKKK, OR MEKK) (Wang, X. S. et al (1998) Biochem. Biophys. Res. Commun. 253:33–37). The extracellular-regulated kinase (ERK) pathway is activated by growth factors and mitogens, for example, epidermal growth factor (EGF), ultraviolet light, hyperosmolar medium, heat shock, or endotoxic lipopolysaccharide (LPS). The closely related though distinct parallel pathways, the c-Jun N-terminal kinase (JNK), or stress-activated kinase (SAPK) pathway, and the p38 kinase pathway are activated by stress stimuli and proinflammatory cytokines such as tumor necrosis factor (TNF) and interleukin-1 (IL-1). Altered MAP kinase expression is implicated in a variety of disease conditions including cancer, inflammation, immune disorders, and disorders affecting growth and development. MAP kinase signaling pathways are present in mammalian cells as well as in yeast.

The family of p21-activated protein kinases (PAKs) appear to be present in all organisms that have Cdc42-like GTPases. In mammalian cells, PAKs have been implicated in the activation of mitogen-activated protein kinase cascades. PAK functions also include the dissolution of cytoskeletal stress fibers and reorganization of focal complexes (Manser, E. et al. (1997) Mol. Cell Biol. 17(3):1129–1143).

Cyclin-Dependent Protein Kinases

The cyclin-dependent protein kinases (CDKs) are STKs that control the progression of cells through the cell cycle. The entry and exit of a cell from mitosis are regulated by the synthesis and destruction of a family of activating proteins called cyclins. Cyclins are small regulatory proteins that bind to and activate CDKs, which then phosphorylate and activate selected proteins involved in the mitotic process. CDKs are unique in that they require multiple inputs to become activated. In addition to cyclin binding, CDK activation requires the phosphorylation of a specific threonine residue and the dephosphorylation of a specific tyrosine residue on the CDK.

Another family of STKs associated with the cell cycle are the NIMA (never in mitosis)-related kinases (Neks). Both CDKs and Neks are involved in duplication, maturation, and separation of the microtubule organizing center, the centrosome, in animal cells (Fry, A. M. et al. (1998) EMBO J. 17:470–481).

Checkpoint and Cell Cycle Kinases

In the process of cell division, the order and timing of cell cycle transitions are under control of cell cycle checkpoints, which ensure that critical events such as DNA replication and chromosome segregation are carried out with precision. If DNA is damaged, e.g. by radiation, a checkpoint pathway is activated that arrests the cell cycle to provide time for repair. If the damage is extensive, apoptosis is induced. In the absence of such checkpoints, the damaged DNA is inherited by aberrant cells which may cause proliferative disorders such as cancer. Protein kinases play an important role in this process. For example, a specific kinase, checkpoint kinase 1 (Chk1), has been identified in yeast and mammals, and is activated by DNA damage in yeast. Activation of Chk1 leads to the arrest of the cell at the G2/M transition (Sanchez, Y. et al. (1997) Science 277:1497–1501). Specifically, Chk1 phosphorylates the cell division cycle phosphatase CDC25, inhibiting its normal function which is to dephosphorylate and activate the cyclin-dependent kinase Cdc2. Cdc2 activation controls the entry of cells into mitosis (Peng, C.-Y. et al. (1997) Science 277:1501–1505). Thus, activation of Chk1 prevents the damaged cell from entering mitosis. A deficiency in a checkpoint kinase, such as Chk1, may also contribute to cancer by failure to arrest cells with damaged DNA at other checkpoints such as G2/M.

Proliferation-Related Kinases

Proliferation-related kinase is a serum/cytokine inducible STK that is involved in regulation of the cell cycle and cell proliferation in human megakarocytic cells (Li, B. et al. (1996) J. Biol. Chem 271:19402–19408). Proliferation-related kinase is related to the polo (derived from *Drosophila* polo gene) family of STKs implicated in cell division. Proliferation-related kinase is downregulated in lung tumor tissue and may be a proto-oncogene whose deregulated expression in normal tissue leads to oncogenic transformation.

5'-AMP-Activated Protein Kinase

A ligand-activated STK protein kinase is 5'-AMP-activated protein kinase (AMPK) (Gao, G. et al. (1996) J. Biol Chem. 271:8675–8681). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The RET (rearranged during transfection) proto-oncogene encodes a tyrosine kinase receptor involved in both multiple endocrine neoplasia type 2, an inherited cancer syndrome, and Hirschsprung disease, a developmental defect of enteric neurons. RET and its functional ligand, glial cell line-derived neurotrophic factor, play key roles in the development of the human enteric nervous system (Pachnis, V. et al. (1998) Am. J. Physiol. 275:G183-G186).

Kinases in Apoptosis

Apoptosis is a highly regulated signaling pathway leading to cell death that plays a crucial role in tissue development and homeostasis. Deregulation of this process is associated with the pathogenesis of a number of diseases including autoimmune diseases, neurodegenerative disorders, and cancer. Various STXs play key roles in this process. ZIP kinase is an STK containing a C-terminal leucine zipper domain in addition to its N-terminal protein kinase domain. This C-terminal domain appears to mediate homodimerization and activation of the kinase as well as interactions with transcription factors such as activating transcription factor, ATF4, a member of the cyclic-AMP responsive element binding protein (ATF/CREB) family of transcriptional factors (Sanjo, H. et al. (1998) J. Biol. Chem. 273:29066–29071). DRAK1 and DRAK2 are STKs that share homology with the death-associated protein kinases (DAP kinases), known to function in interferon-γ induced apoptosis (Sanjo et al., supra). Like ZIP kinase, DAP kinases contain a C-terminal protein-protein interaction domain, in the form of ankyrin repeats, in addition to the N-terminal kinase domain. ZIP, DAP, and DRAK kinases induce morphological changes associated with apoptosis when transfected into NIH3T3 cells (Sanjo et al., supra). However, deletion of either the N-terminal kinase catalytic domain or the C-terminal domain of these proteins abolishes apoptosis activity, indicating that in addition to the kinase activity, activity in the C-terminal domain is also necessary for apoptosis, possibly as an interacting domain with a regulator or a specific substrate.

RICK is another STK recently identified as mediating a specific apoptotic pathway involving the death receptor, CD95 (Inohara, N. et al. (1998) J. Biol. Chem 273:12296–12300). CD95 is a member of the tumor necrosis factor receptor superfamily and plays a critical role in the regulation and homeostasis of the immune system (Nagata, S. (1997) Cell 88:355–365). The CD95 receptor signaling pathway involves recruitment of various intracellular molecules to a receptor complex following ligand binding. This process includes recruitment of the cysteine protease caspase-8 which, in turn, activates a caspase cascade leading to cell death. RICK is composed of an N-terminal kinase catalytic domain and a C-terminal "caspase-recruitment" domain that interacts with caspase-like domains, indicating that RICK plays a role in the recruitment of caspase-8. This interpretation is supported by the fact that the expression of RICK in human 293T cells promotes activation of caspase-8 and potentiates the induction of apoptosis by various proteins involved in the CD95 apoptosis pathway (Inohara et al., supra).

Mitochondrial Protein Kinases

A novel class of eukaryotic kinases, related by sequence to prokaryotic histidine protein kinases, are the mitochondrial protein kinases (MPKs) which seem to have no sequence similarity with other eukaryotic protein kinases. These protein kinases are located exclusively in the mitochondrial matrix space and may have evolved from genes originally present in respiration-dependent bacteria which were endocytosed by primitive eukaryotic cells. MPKs are responsible for phosphorylation and inactivation of the branched-chain alpha-ketoacid dehydrogenase and pyruvate dehydrogenase complexes (Harris, R. A. et al. (1995) Adv. Enzyme Regul. 34:147–162). Five MPKs have been identified. Four members correspond to pyruvate dehydrogenase kinase isozymes, regulating the activity of the pyruvate dehydrogenase complex, which is an important regulatory enzyme at the interface between glycolysis and the citric acid cycle. The fifth member corresponds to a branched-chain alpha-ketoacid dehydrogenase kinase, important in the regulation of the pathway for the disposal of branched-chain amino acids. (Harris, R. A. et al. (1997) Adv. Enzyme Regul. 37:271–293). Both starvation and the diabetic state are known to result in a great increase in the activity of the pyruvate dehydrogenase kinase in the liver, heart and muscle of the rat. This increase contributes in both disease states to the phosphorylation and inactivation of the pyruvate dehydrogenase complex and conservation of pyruvate and lactate for gluconeogenesis (Harris (1995) supra).

Kinases with Non-Protein Substrates

Lipid and Inositol Kinases

Lipid kinases phosphorylate hydroxyl residues on lipid head groups. A family of kinases involved in phosphorylation of phosphatidylinositol (PI) has been described, each member phosphorylating a specific carbon on the inositol ring (Leevers, S. J. et al. (1999) Curr. Opin. Cell. Biol. 11:219–225). The phosphorylation of phosphatidylinositol is involved in activation of the protein kinase C signaling pathway. The inositol phospholipids (phosphoinositides) intracellular signaling pathway begins with binding of a signaling molecule to a G-protein linked receptor in the plasma membrane. This leads to the phosphorylation of phosphatidylinositol (PI) residues on the inner side of the plasma membrane by inositol kinases, thus converting PI residues to the biphosphate state ($PIP_2$). $PIP_2$ is then cleaved into inositol triphosphate ($IP_3$) and diacylglycerol. These two products act as mediators for separate signaling pathways. Cellular responses that are mediated by these pathways are glycogen breakdown in the liver in response to vasopressin, smooth muscle contraction in response to acetylcholine, and thrombin-induced platelet aggregation.

PI 3-kinase (PI3K), which phosphorylates the D3 position of PI and its derivatives, has a central role in growth factor signal cascades involved in cell growth, differentiation, and metabolism PI3K is a heterodimer consisting of an adapter subunit and a catalytic subunit. The adapter subunit acts as a scaffolding protein, interacting with specific tyrosine-phosphorylated proteins, lipid moieties, and other cytosolic factors. When the adapter subunit binds tyrosine phosphorylated targets, such as the insulin responsive substrate (IRS)-1, the catalytic subunit is activated and converts PI (4,5) bisphosphate ($PIP_2$) to PI (3,4,5) $P_3$ ($PIP_3$). $PIP_3$ then activates a number of other proteins, including PKA, protein kinase B (PKB), protein kinase C (PKC), glycogen synthase kinase (GSK)-3, and p70 ribosomal s6 kinase. PI3K also interacts directly with the cytoskeletal organizing proteins, Rac, rho, and cdc42 (Shepherd, P. R. et al. (1998) Biochem. J. 333:471–490). Animal models for diabetes, such as obese and fat mice, have altered PI3K adapter subunit levels. Specific mutations in the adapter subunit have also been found in an insulin-resistant Danish population, suggesting a role for PI3K in type-2 diabetes (Shepard, supra).

An example of lipid kinase phosphorylation activity is the phosphorylation of D-erythro-sphingosine to the sphingolipid metabolite, sphingosine-1-phosphate (SPP). SPP has emerged as a novel lipid second-messenger with both extracellular and intracellular actions (Kohama, T. et al. (1998) J. Biol. Chem 273:23722–23728). Extracellularly, SPP is a ligand for the G-protein coupled receptor EDG-1 (endothelial-derived, G-protein coupled receptor). Intracellularly, SPP regulates cell growth, survival, motility, and cytoskeletal changes. SPP levels are regulated by sphingosine kinases that specifically phosphorylate D-erythro-sphingosine to SPP. The importance of sphingosine kinase in cell signaling is indicated by the fact that various stimuli, including platelet-derived growth factor (PDGF), nerve growth factor, and activation of protein kinase C, increase cellular levels of SPP by activation of sphingosine kinase, and the fact that competitive inhibitors of the enzyme selectively inhibit cell proliferation induced by PDGF (Kohama et al., supra).

PKC is also activated by diacylglycerol (DAG). Phorbol esters (PE) are analogs of DAG and tumor promoters that cause a variety of physiological changes when administered to cells and tissues. PE and DAG bind to the N-terminal region of PKC. This region contains one or more copies of a cysteine-rich domain about 50 amino-acid residues long and essential for DAG/PE-binding. Diacylglycerol kinase (DGK), the enzyme that converts DAG into phosphatidate, contains two copies of the DAG/PE-binding domain in its N-terminal section (Azzi, A. et al. (1992) Eur. J. Biochem. 208:547–557).

An example of lipid kinase phosphorylation activity is the phosphorylation of D-erythro-sphingosine to the sphingolipid metabolite, sphingosine-1-phosphate (SPP). SPP has emerged as a novel lipid second-messenger with both extracellular and intracellular actions (Kohama, T. et al. (1998) J. Biol. Chem 273:23722–23728). Extracellularly, SPP is a ligand for the G-protein coupled receptor EDG-1 (endothelial-derived, G-protein coupled receptor). Intracellularly, SPP regulates cell growth, survival, motility, and cytoskeletal changes. SPP levels are regulated by sphingosine kinases that specifically phosphorylate D-erythro-sphingosine to SPP. The importance of sphingosine kinase in cell signaling is indicated by the fact that various stimuli, including platelet-derived growth factor (PDGF), nerve growth factor, and activation of protein kinase C, increase cellular levels of SPP by activation of sphingosine kinase, and the fact that competitive inhibitors of the enzyme selectively inhibit cell proliferation induced by PDGF (Kohama et al. supra).

Purine Nucleotide Kinases

The purine nucleotide kinases, adenylate kinase (ATP: AMP phosphotransferase, or AdK) and guanylate kinase (ATP:GMP phosphotransferase, or GuK) play a key role in nucleotide metabolism and are crucial to the synthesis and regulation of cellular levels of ATP and GTP, respectively. These two molecules are precursors in DNA and RNA synthesis in growing cells and provide the primary source of biochemical energy in cells (ATP), and signal transduction pathways (GTP). Inhibition of various steps in the synthesis of these two molecules has been the basis of many antiproliferative drugs for cancer and antiviral therapy (Pillwein, K. et al. (1990) Cancer Res. 50:1576–1579).

AdK is found in almost all cell types and is especially abundant in cells having high rates of ATP synthesis and utilization such as skeletal muscle. In these cells AdK is physically associated with mitochondria and myofibrils, the subcellular structures that are involved in energy production and utilization, respectively. Recent studies have demonstrated a major function for AdK in transferring high energy phosphoryls from metabolic processes generating ATP to cellular components consuming ATP (Zeleznikar, R. J. et al. (1995) J. Biol. Chem. 270:7311–7319). Thus AdK may have a pivotal role in maintaining energy production in cells, particularly those having a high rate of growth or metabolism such as cancer cells, and may provide a target for suppression of its activity in order to treat certain cancers. Alternatively, reduced AdK activity may be a source of various metabolic, muscle-energy disorders that can result in cardiac or respiratory failure and may be treatable by increasing AdK activity.

GuK, in addition to providing a key step in the synthesis of GTP for RNA and DNA synthesis, also fulfills an essential function in signal transduction pathways of cells through the regulation of GDP and GTP. Specifically, GTP binding to membrane associated G proteins mediates the activation of cell receptors, subsequent intracellular activation of adenyl cyclase, and production of the second messenger, cyclic AMP. GDP binding to G proteins inhibits these processes. GDP and GTP levels also control the activity of certain oncogenic proteins such as p21$^{ras}$ known to be involved in control of cell proliferation and oncogenesis (Bos, J. L. (1989) Cancer Res. 49:4682–4689). High ratios of GTP:GDP caused by suppression of GuK cause activation of p21$^{ras}$ and promote oncogenesis. Increasing GuK activity to increase levels of GDP and reduce the GTP:GDP ratio may provide a therapeutic strategy to reverse oncogenesis.

GuK is an important enzyme in the phosphorylation and activation of certain antiviral drugs useful in the treatment of herpes virus infections. These drugs include the guanine homologs acyclovir and buciclovir (Miller, W. H. and R. L. Miller (1980) J. Biol. Chem. 255:7204–7207; Stenberg, K. et al. (1986) J. Biol. Chem. 261:2134–2139). Increasing GuK activity in infected cells may provide a therapeutic strategy for augmenting the effectiveness of these drugs and possibly for reducing the necessary dosages of the drugs.

Pyrimidine Kinases

The pyrimidine kinases are deoxycytidine kinase and thymidine kinase 1 and 2. Deoxycytidine kinase is located in the nucleus, and thymidine kinase 1 and 2 are found in the cytosol (Johansson, M. et al. (1997) Proc. Natl. Acad. Sci. USA 94:11941–11945). Phosphorylation of deoxyribonucleosides by pyrimidine kinases provides an alternative pathway for de novo synthesis of DNA precursors. The role of pyrimidine kinases, like purine kinases, in phosphorylation is critical to the activation of several chemotherapeutically important nucleoside analogues (Armer E. S. and S. Eriksson (1995) Pharmacol. Ther. 67:155–186).

Phosphatases

Protein phosphatases are generally characterized as either serine/threonine- or tyrosine-specific based on their preferred phospho-amino acid substrate. However, some phosphatases (DSPs, for dual specificity phosphatases) can act on phosphorylated tyrosine, serine, or threonine residues. The protein serine/threonine phosphatases (PSPs) are important regulators of many cAMP-mediated hormone responses in cells. Protein tyrosine phosphatases (PTPs) play a significant role in cell cycle and cell signaling processes. Another family of phosphatases is the acid phosphatase or histidine acid phosphatase (HAP) family whose members hydrolyze phosphate esters at acidic pH conditions.

PSPs are found in the cytosol, nucleus, and mitochondria and in association with cytoskeletal and membranous structures in most tissues, especially the brain. Some PSPs require divalent cations, such as Ca$^{2+}$ or Mn$^{2+}$, for activity. PSPs play important roles in glycogen metabolism, muscle contraction, protein synthesis, T cell function, neuronal activity, oocyte maturation, and hepatic metabolism (reviewed in Cohen, P. (1989) Annu. Rev. Biochem. 58:453–508). PSPs can be separated into two classes. The PPP class includes PP1, PP2A, PP2B/calcineurin, PP4, PP5, PP6, and PP7. Members of this class are composed of a homologous catalytic subunit bearing a very highly conserved signature sequence, coupled with one or more regulatory subunits (PROSITE PDOC00115). Further interactions with scaffold and anchoring molecules determine the intracellular localization of PSPs and substrate specificity. The PPM class consists of several closely related isoforms of PP2C and is evolutionarily unrelated to the PPP class.

PP1 dephosphorylates many of the proteins phosphorylated by cyclic AMP-dependent protein kinase (PKA) and is an important regulator of many cAMP-mediated hormone responses in cells. A number of isoforms have been identified, with the alpha and beta forms being produced by alternative splicing of the same gene. Both ubiquitous and tissue-specific targeting proteins for PP1 have been identified. In the brain, inhibition of PP1 activity by the dopamine and adenosine 3',5'-monophosphate-regulated phosphoprotein of 32 kDa (DARPP-32) is necessary for normal dopamine response in neostriatal neurons (reviewed in Price, N. E. and M. C. Mumby (1999) Curr. Opin. Neurobiol. 9:336–342). PP1, along with PP2A, has been shown to limit motility in microvascular endothelial cells, suggesting a role for PSPs in the inhibition of angiogenesis (Gabel, S. et al. (1999) Otolaryngol. Head Neck Surg. 121:463–468).

PP2A is the main serine/threonine phosphatase. The core PP2A enzyme consists of a single 36 kDa catalytic subunit (C) associated with a 65 kDa scaffold subunit (A), whose role is to recruit additional regulatory subunits (B). Three gene families encoding B subunits are known (PR55, PR61, and PR72), each of which contain multiple isoforms, and additional families may exist (Millward, T. A et al. (1999) Trends Biosci. 24:186–191). These "B-type" subunits are cell type- and tissue-specific and determine the substrate specificity, enzymatic activity, and subcellular localization of the holoenzyme. The PR55 family is highly conserved and bears a conserved motif (PROSITE PDOC00785). PR55 increases PP2A activity toward mitogen-activated protein kinase (MAPK) and MAPK kinase (MEK). PP2A dephosphorylates the MAPK active site, inhibiting the cell's entry into mitosis. Several proteins can compete with PR55 for PP2A core enzyme binding, including the CKII kinase catalytic subunit, polyomavirus middle and small T antigens, and SV40 small t antigen. Viruses may use this mechanism to commandeer PP2A and stimulate progression of the cell through the cell cycle (Pallas, D. C. et al. (1992) J. Virol. 66:886–893). Altered MAP kinase expression is also implicated in a variety of disease conditions including cancer, inflammation, immune disorders, and disorders affecting growth and development. PP2A, in fact, can dephosphorylate and modulate the activities of more than 30 protein kinases in vitro, and other evidence suggests that the same is true in vivo for such kinases as PKB, PKC, the calmodulin-dependent kinases, ERK family MAP kinases, cyclin-dependent kinases, and the IκK kinases (reviewed in Millward et al., supra. PP2A is itself a substrate for CKI and CKII kinases, and can be stimulated by polycationic macromolecules. A PP2A-like phosphatase is necessary to maintain the G1 phase destruction of mammalian cyclins A and B (Bastians, H. et al. (1999) Mol. Biol. Cell 10:3927–3941). PP2A is a major activity in the brain and is implicated in regulating neurofilament stability and normal neural function, particularly the phosphorylation of the microtubule-associated protein tau. Hyperphosphorylation of tau has been proposed to lead to the neuronal degeneration seen in Alzheimer's disease (reviewed in Price and Mumby, supra).

PP2B, or calcineurin, is a Ca$^{2+}$-activated dimeric phosphatase and is particularly abundant in the brain. It consists of catalytic and regulatory subunits, and is activated by the binding of the calcium/calmodulin complex. Calcineurin is the target of the immunosuppressant drugs cyclosporine and FK506. Along with other cellular factors, these drugs interact with calcineurin and inhibit phosphatase activity. In T cells, this blocks the calcium dependent activation of the NF-AT family of transcription factors, leading to immunosuppression. This family is widely distributed, and it is likely that calcineurin regulates gene expression in other tissues as well. In neurons, calcineurin modulates functions which range from the inhibition of neurotransmitter release to desensitization of postsynaptic NMDA-receptor coupled calcium channels to long term memory (reviewed in Price and Mumby, supra).

Other members of the PPP class have recently been identified (Cohen, P. T. (1997) Trends Biochem. Sci. 22:245–251). One of them, PP5, contains regulatory domains with tetratricopeptide repeats. It can be activated by polyunsaturated fatty acids and anionic phospholipids in vitro and appears to be involved in a number of signaling pathways, including those controlled by atrial natriuretic peptide or steroid hormones (reviewed in Andreeva, A. V. and M. A. Kutuzov (1999) Cell Signal. 11:555–562).

PP2C is a ~42kDa monomer with broad substrate specificity and is dependent on divalent cations (mainly $Mn^{2+}$ or $Mg^{2+}$) for its activity. PP2C proteins share a conserved N-terminal region with an invariant DGH motif, which contains an aspartate residue involved in cation binding (PROSITE PDOC00792). Targeting proteins and mechanisms regulating PP2C activity have not been identified. PP2C has been shown to inhibit the stress-responsive p38 and Jun kinase (JNK) pathways (Takekawa, M. et al. (1998) EMBO J. 17:4744–4752).

In contrast to PSPs, tyrosine-specific phosphatases (PTPs) are generally monomeric proteins of very diverse size (from 20 kDa to greater than 100 kDa) and structure that function primarily in the transduction of signals across the plasma membrane. PTPs are categorized as either soluble phosphatases or transmembrane receptor proteins that contain a phosphatase domain. All PTPs share a conserved catalytic domain of about 300 amino acids which contains the active site. The active site consensus sequence includes a cysteine residue which executes a nucleophilic attack on the phosphate moiety during catalysis (Neel, B. G. and N. K. Tonks (1997) Curr. Opin. Cell Biol. 9:193–204). Receptor PTPs are made up of an N-terminal extracellular domain of variable length, a transmembrane region, and a cytoplasmic region that generally contains two copies of the catalytic domain. Although only the first copy seems to have enzymatic activity, the second copy apparently affects the substrate specificity of the first. The extracellular domains of some receptor PTPs contain fibronectin-like repeats, immunoglobulin-like domains, MAM domains (an extracellular motif likely to have an adhesive function), or carbonic anhydrase-like domains (PROSITE PDOC 00323). This wide variety of structural motifs accounts for the diversity in size and specificity of PTPs.

PTPs play important roles in biological processes such as cell adhesion, lymphocyte activation, and cell proliferation. PTPs μ and κ are involved in cell-cell contacts, perhaps regulating cadherin/catenin function. A number of PTPs affect cell spreading, focal adhesions, and cell motility, most of them via the integrin/tyrosine kinase signaling pathway (reviewed in Neel and Tonks, supra). CD45 phosphatases regulate signal transduction and lymphocyte activation (Ledbetter, J. A. et al. (1988) Proc. Natl. Acad. Sci. USA 85:8628–8632). Soluble PTPs containing Src-homology-2 domains have been identified (SHPs), suggesting that these molecules might interact with receptor tyrosine kinases. SHP-1 regulates cytokine receptor signaling by controlling the Janus family PTKs in hematopoietic cells, as well as signaling by the T-cell receptor and c-Kit (reviewed in Neel and Tonks, supra). M-phase inducer phosphatase plays a key role in the induction of mitosis by dephosphorylating and activating the PTK CDC2, leading to cell division (Sadhu, K. et al. (1990) Proc. Natl. Acad. Sci. USA 87:5139–5143). In addition, the genes encoding at least eight PTPs have been mapped to chromosomal regions that are translocated or rearranged in various neoplastic conditions, including lymphoma, small cell lung carcinoma, leukemia, adenocarcinoma, and neuroblastoma (reviewed in Charbonneau, IL and N. K. Tonks (1992) Annu. Rev. Cell Biol. 8:463–493). The PTP enzyme active site comprises the consensus sequence of the MTM1 gene family. The MTM1 gene is responsible for X-linked recessive myotubular myopathy, a congenital muscle disorder that has been linked to Xq28 (Kioschis, P. et al., (1998) Genomics 54:256–266). Many PTKs are encoded by oncogenes, and it is well known that oncogenesis is often accompanied by increased tyrosine phosphorylation activity. It is therefore possible that PTPs may serve to prevent or reverse cell transformation and the growth of various cancers by controlling the levels of tyrosine phosphorylation in cells. This is supported by studies showing that overexpression of PTP can suppress transformation in cells and that specific inhibition of PIP can enhance cell transformation (Charbonneau and Tonks, supra).

Dual specificity phosphatases (DSPs) are structurally more similar to the PTPs than the PSPs. DSPs bear an extended PTP active site motif with an additional 7 amino acid residues. DSPs are primarily associated with cell proliferation and include the cell cycle regulators cdc25A, B, and C. The phosphatases DUSP1 and DUSP2 inactivate the MAPK family members ERK (extracellular signal-regulated kinase), JNK (c-Jun N-terminal kinase), and p38 on both tyrosine and threonine residues (PROSITE PDOC 00323, supra). In the activated state, these kinases have been implicated in neuronal differentiation, proliferation, oncogenic transformation, platelet aggregation, and apoptosis. Thus, DSPs are necessary for proper regulation of these processes (Muda, M. et al. (1996) J. Biol. Chem 271: 27205–27208). The tumor suppressor PTEN is a DSP that also shows lipid phosphatase activity. It seems to negatively regulate interactions with the extracellular matrix and maintains sensitivity to apoptosis. PTEN has been implicated in the prevention of angiogenesis (Giri, D. and M. Ittmann (1999) Hum. Pathol. 30:419–424) and abnormalities in its expression are associated with numerous cancers (reviewed in Tamura, M. et al. (1999) J. Natl. Cancer Inst. 91:1820–1828).

Histidine acid phosphatase (HAP; EXPASY EC 3.1.3.2), also known as acid phosphatase, hydrolyzes a wide spectrum of substrates including alkyl, aryl, and acyl orthophosphate monoesters and phosphorylated proteins at low pH. HAPs share two regions of conserved sequences, each centered around a histidine residue which is involved in catalytic activity. Members of the HAP family include lysosomal acid phosphatase (LAP) and prostatic acid phosphatase (PAP), both sensitive to inhibition by L-tartrate (PROSITE PDOC00538).

LAP, an orthophosphoric monoester of the endosomal/lysosomal compartment is a housekeeping gene whose enzymatic activity has been detected in all tissues examined (Geier, C. et al. (1989) Eur. J. Biochem. 183:611–616). LAP-deficient mice have progressive skeletal disorder and an increased disposition toward generalized seizures (Saftig, P. et al. (1997) J. Biol. Chem. 272:18628–18635). LAP-deficient patients were found to have the following clinical features: intermittent vomiting, hypotonia, lethargy, opisthotonos, terminal bleeding, seizures, and death in early infancy (Online Mendelian Inheritance in Man (OMIM) *200950).

PAP, a prostate epithelium-specific differentiation antigen produced by the prostate gland, has been used to diagnose and stage prostate cancer. In prostate carcinomas, the enzymatic activity of PAP was shown to be decreased compared with normal or benign prostate hypertrophy cells (Foti, A. G. et al. (1977) Cancer Res. 37: 4120–4124). Two forms of PAP have been identified, secreted and intracellular. Mature secreted PAP is detected in the seminal fluid and is active as a glycosylated homodimer with a molecular weight of approximately 100-kilodalton. Intracellular PAP is found to exhibit endogenous phosphotyrosyl protein phosphatase activity and is involved in regulating prostate cell growth (Meng, T. C. and Lin, M. F. (1998) J. Biol. Chem. 34: 22096–22104).

Synaptojanin, a polyphosphoinositide phosphatase, dephosphorylates phosphoinositides at positions 3, 4 and 5 of the inositol ring. Synaptojanin is a major presynaptic protein found at clathrin-coated endocytic intermediates in nerve terminals, and binds the clathrin coat-associated protein, EPS15. This binding is mediated by the C-terminal region of synaptojanin-170, which has 3 Asp-Pro-Phe amino acid repeats. Further, this 3 residue repeat bad been found to be the binding site for the EH domains of EPS15 (Haffner, C. et al. (1997) FEBS Lett. 419:175–180). Additionally, synaptojanin may potentially regulate interactions of endocytic proteins with the plasma membrane, and be involved in synaptic vesicle recycling (Brodin, L. et al. (2000) Curr. Opin. Neurobiol. 10:312–320). Studies in mice with a targeted disruption in the synaptojanin 1 gene (Synj1) were shown to support coat formation of endocytic vesicles more effectively than was seen in wild-type mice, suggesting that Synj1 can act as a negative regulator of membrane-coat protein interactions. These findings provide genetic evidence for a crucial role of phosphoinositide metabolism in synaptic vesicle recycling (Cremona, O. et al. (1999) Cell 99:179–188).

The discovery of new kinases and phosphatases, and the polynucleotides encoding them, satisfies a need in the art by providing new compositions which are useful in the diagnosis, prevention, and treatment of cardiovascular diseases, immune system disorders, neurological disorders, disorders affecting growth and development, lipid disorders, cell proliferative disorders, and cancers, and in the assessment of the effects of exogenous compounds on the expression of nucleic acid and amino acid sequences of kinases and phosphatases.

SUMMARY OF THE INVENTION

The invention features purified polypeptides, kinases and phosphatases, referred to collectively as "KAP" and individually as "KAP-1," "KAP-2," "KAP-3," "KAP-4," "KAP-5," "KAP-6," "KAP-7," "KAP-8," "KAP-9," "KAP-10," "KAP-11," "KAP-12," "KAP-13," "KAP-14," "KAP-15," "KAP-16," "KAP-17," "KAP-18," "KAP-19," and "KAP-20." In one aspect, the invention provides an isolated polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20. In one alternative, the invention provides an isolated polypeptide comprising the amino acid sequence of SEQ ID NO:1–20.

The invention further provides an isolated polynucleotide encoding a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20. In one alternative, the polynucleotide encodes a polypeptide selected from the group consisting of SEQ ID NO:1–20. In another alternative, the polynucleotide is selected from the group consisting of SEQ ID NO:21–40.

Additionally, the invention provides a recombinant polynucleotide comprising a promoter sequence operably linked to a polynucleotide encoding a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20. In one alternative, the invention provides a cell transformed with the recombinant polynucleotide. In another alternative, the invention provides a transgenic organism comprising the recombinant polynucleotide.

The invention also provides a method for producing a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20.

The invention further provides an isolated polynucleotide selected from the group consisting of a) a polynucleotide comprising a polynucleotide sequence selected from the group consisting of SEQ ID NO:21–40, b) a polynucleotide comprising a naturally occurring polynucleotide sequence at least 90% identical to a polynucleotide sequence selected from the group consisting of SEQ ID NO:21–40, c) a polynucleotide complementary to the polynucleotide of a), d) a polynucleotide complementary to the polynucleotide of b), and e) an RNA equivalent of a)–d). In one alternative, the polynucleotide comprises at least 60 contiguous nucleotides.

Additionally, the invention provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:21–40, b) a polynucleotide comprising a naturally occurring polynucleotide sequence at least 90% identical to a polynucleotide sequence selected from the group consisting of SEQ ID NO:21–40, c) a polynucleotide complementary to the polynucleotide of a), d) a polynucleotide complementary to the polynucleotide of b), and e) an RNA equivalent of a)–d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:21–40, b) a polynucleotide comprising a naturally occurring polynucleotide sequence at least 90% identical to a polynucleotide sequence selected from the group consisting of SEQ ID NO:21–40, c) a polynucleotide complementary to the polynucleotide of a), d) a polynucleotide complementary to the polynucleotide of b), and e) an RNA equivalent of a)–d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20, and a pharmaceutically acceptable excipient. In one embodiment, the composition comprises an amino acid sequence selected from the group consisting of SEQ ID NO:1–20. The invention additionally provides a method of treating a disease or condition associated with decreased expression of functional KAP, comprising administering to a patient in need of such treatment the composition.

The invention also provides a method for screening a compound for effectiveness as an agonist of a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional KAP, comprising administering to a patient in need of such treatment the composition.

Additionally, the invention provides a method for screening a compound for effectiveness as an antagonist of a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional KAP, comprising administering to a patient in need of such treatment the composition.

The invention further provides a method of screening for a compound that specifically binds to a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide selected from the group consisting of a) a polypeptide comprising an amino acid sequence selected from the group consisting of SEQ ID NO:1–20, b) a polypeptide comprising a naturally occurring amino acid sequence at least 90% identical to an amino acid sequence selected from the group consisting of SEQ ID NO:1–20, c) a biologically active fragment of a polypeptide having an amino acid sequence selected from the group consisting of SEQ ID NO:1–20, and d) an immunogenic fragment of a polypeptide having an amino acid sequence selected from the group consisting of SEQ ID NO:1–20. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a polynucleotide sequence selected from the group consisting of SEQ ID NO:21–40, the method comprising a) exposing a sample comprising the target polynucleotide to a compound, b) detecting altered expression of the target polynucleotide, and c) comparing the expression of the target polynucleotide in the presence of varying amounts of the compound and in the absence of the compound.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide selected from the group consisting of i) a polynucleotide comprising a polynucleotide sequence selected from the group consisting of SEQ ID NO:21–40, ii) a polynucleotide comprising a naturally occurring polynucleotide sequence at least 90% identical to a polynucleotide sequence selected from the group consisting of SEQ ID NO:21–40, iii) a polynucleotide having a sequence complementary to i), iv) a polynucleotide complementary to the polynucleotide of ii), and v) an RNA equivalent of i)–iv). Hybridization occurs under conditions whereby a specific hybridization complex is formed between said probe and a target polynucleotide in the biological sample, said target polynucleotide selected from the group consisting of i) a polynucleotide comprising a polynucleotide sequence selected from the group consisting of SEQ ID NO:21–40, ii) a polynucleotide comprising a naturally occurring polynucleotide sequence at least 90% identical to a polynucleotide sequence selected from the group consisting of SEQ ID NO:21–40, iii) a polynucleotide complementary to the polynucleotide of i), iv) a polynucleotide complementary to the polynucleotide of ii), and v) an RNA equivalent of i)–iv). Alternatively, the target polynucleotide comprises a fragment of a polynucleotide sequence selected from the group consisting of i)–v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 summarizes the nomenclature for the full length polynucleotide and polypeptide sequences of the present invention.

Table 2 shows the GenBank identification number and annotation of the nearest GenBank homolog for polypeptides of the invention. The probability scores for the matches between each polypeptide and its homolog(s) are also shown.

Table 3 shows structural features of polypeptide sequences of the invention, including predicted motifs and domains, along with the methods, algorithms, and searchable databases used for analysis of the polypeptides.

Table 4 lists the cDNA and/or genomic DNA fragments which were used to assemble polynucleotide sequences of the invention, along with selected fragments of the polynucleotide sequences.

Table 5 shows the representative cDNA library for polynucleotides of the invention.

Table 6 provides an appendix which describes the tissues and vectors used for construction of the cDNA libraries shown in Table 5.

Table 7 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"KAP" refers to the amino acid sequences of substantially purified KAP obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of KAP. Agonists may include proteins, nucleic acids, carbohydrates, small molecules, or any other compound or composition which modulates the activity of KAP either by directly interacting with KAP or by acting on components of the biological pathway in which KAP participates.

An "allelic variant" is an alternative form of the gene encoding KAP. Allelic variants may result from at least one mutation in the nucleic acid sequence and may result in altered mRNAs or in polypeptides whose structure or function may or may not be altered. A gene may have none, one, or many allelic variants of its naturally occurring form.

Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding KAP include those sequences with deletions, insertions, or substitutions of different nucleotides, resulting in a polypeptide the same as KAP or a polypeptide with at least one functional characteristic of KAP. Included within this definition are polymorphisms which may or may not be readily detectable using a particular oligonucleotide probe of the polynucleotide encoding KAP, and improper or unexpected hybridization to allelic variants, with a locus other than the normal chromosomal locus for the polynucleotide sequence encoding KAP. The encoded protein may also be "altered," and may contain deletions, insertions, or substitutions of amino acid residues which produce a silent change and result in a functionally equivalent KAP. Deliberate amino acid substitutions may be made on the basis of similarity in polarity, charge, solubility, hydrophobicity, hydrophilicity, and/or the amphipathic nature of the residues, as long as the biological or immunological activity of KAP is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of KAP. Antagonists may include proteins such as antibodies, nucleic acids, carbohydrates, small molecules, or any other compound or composition which modulates the activity of KAP either by directly interacting with KAP or by acting on components of the biological pathway in which KAP participates.

The term "antibody" refers to intact immunoglobulin molecules as well as to fragments thereof, such as Fab, F(ab')$_2$, and Fv fragments, which are capable of binding an epitopic determinant. Antibodies that bind KAP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), described in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker. (See, e.g., Brody, E. N. and L. Gold (2000) J. Biotechnol. 74:5–13.)

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl Acad. Sci. USA 96:3606–3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

The term "antisense" refers to any composition capable of base-pairing with the "sense" (coding) strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic KAP, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding KAP or fragments of KAP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (GCG, Madison Wis.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function-of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

"Differential expression" refers to increased or upregulated; or decreased, downregulated, or absent gene or protein expression, determined by comparing at least two different samples. Such comparisons may be carried out between, for example, a treated and an untreated sample, or a diseased and a normal sample.

"Exon shuffling" refers to the recombination of different coding regions (exons). Since an exon may represent a structural or functional domain of the encoded protein, new proteins may be assembled through the novel reassortment of stable substructures, thus allowing acceleration of the evolution of new protein functions.

A "fragment" is a unique portion of KAP or the polynucleotide encoding KAP which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ D NO:21–40 comprises a region of unique polynucleotide sequence that specifically identifies SEQ ID NO:21–40, for example, as distinct from any other sequence in the genome from which the fragment was obtained. A fragment of SEQ ID NO:21–40 is useful, for example, in hybridization and amplification technologies and in analogous methods that distinguish SEQ ID NO:21–40 from related polynucleotide sequences. The precise length of a fragment of SEQ ID NO:21–40 and the region of SEQ ID NO:21–40 to which the fragment corresponds are routinely determinable by one of ordinary skill in the art based on the intended purpose for the fragment.

A fragment of SEQ ID NO:1–20 is encoded by a fragment of SEQ ID NO:21–40. A fragment of SEQ ID NO:1–20 comprises a region of unique amino acid sequence that specifically identifies SEQ ID NO:1–20. For example, a fragment of SEQ ID NO:1–20 is useful as an immunogenic peptide for the development of antibodies that specifically recognize SEQ ID NO:1–20. The precise length of a fragment of SEQ ID NO:1–20 and the region of SEQ ID NO:1–20 to which the fragment corresponds are routinely determinable by one of ordinary skill in the art based on the intended purpose for the fragment.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151–153 and in Higgins, D. G. et al. (1992) CABIOS 8:189–191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequences.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403–410), which is available from several sources, including the NCBL, Bethesda, Md., and on the Internet at the NCBI website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap x drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap x drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al. (1989) *Molecular Cloning: A Laboratory Manual*, $2^{nd}$ ed., vol. 1–3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100–200 µg/ml. Organic solvent, such as formamide at a concentration of about 35–50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of KAP which is capable of eliciting an immune response when introduced into a living organism, for example, a mammal. The term "immunogenic fragment" also includes any polypeptide or oligopeptide fragment of KAP which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of KAP. For example, modulation may cause an increase or a decrease in protein activity, binding characteristics, or any other biological, functional, or immunological properties of KAP.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an KAP may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of KAP.

"Probe" refers to nucleic acid sequences encoding KAP, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook, J. et al. (1989) *Molecular Cloning: A Laboratory Manual*, 2$^{nd}$ ed., vol. 1–3, Cold Spring Harbor Press, Plainview N.Y.; Ausubel, F. M. et al. (1987) *Current Protocols in Molecular Biology*, Greene Publ. Assoc. & Wiley-Intersciences, New York N.Y.; Innis, M. et al. (1990) *PCR Protocols. A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing KAP, nucleic acids encoding KAP, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" or "expression profile" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length. A variant may be described as, for example, an "allelic" (as defined above), "splice," "species," or "polymorphic" variant A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides will generally have significant amino acid identity relative to each other. A polymoiphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides.

THE INVENTION

The invention is based on the discovery of new human kinases and phosphatases (KAP), the polynucleotides encoding KAP, and the use of these compositions for the diagnosis, treatment, or prevention of cardiovascular diseases, immune system disorders, neurological disorders, disorders affecting growth and development, lipid disorders, cell proliferative disorders, and cancers.

Table 1 summarzes the nomenclature for the full length polynucleotide and polypeptide sequences of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown.

Table 2 shows sequences with homology to the polypeptides of the invention as identified by BLAST analysis against the GenBank protein (genpept) database. Columns 1 and 2 show the polypeptide sequence identification number (Polypeptide SEQ ID NO:) and the corresponding Incyte polypeptide sequence number (Incyte Polypeptide ID) for polypeptides of the invention. Column 3 shows the GenBank identification number (GenBank ID NO:) of the nearest GenBank homolog. Column 4 shows the probability scores for the matches between each polypeptide and its homolog(s). Column 5 shows the annotation of the GenBank homolog(s) along with relevant citations where applicable, all of which are expressly incorporated by reference herein.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Genetics Computer Group, Madison Wis.). Column 6 shows amino acid residues comprising signature sequences, domains, and motifs. Column 7 shows analytical methods for protein structure/function analysis and in some cases, searchable databases to which the analytical methods were applied.

Together, Tables 2 and 3 summarize the properties of polypeptides of the invention, and these properties establish that the claimed polypeptides are kinases and phosphatases. For example, SEQ ID NO:1 is 79% identical to rat protein tyrosine phosphatase TD14 (GenBank ID g3598974) as determined by the Basic Local Alignment Search Tool (BLAST). (See Table 2.) The BLAST probability score is 0.0, which indicates the probability of obtaining the observed polypeptide sequence alignment by chance. SEQ ID NO:1 also contains protein-tyrosine phosphatase domain as determined by searching for statistically significant matches in the hidden Markov model (HMM)based PFAM database of conserved protein family domains. (See Table 3.) Data from BLIMPS, PROFILESCAN and MOTIFS analyses provide further corroborative evidence that SEQ ID NO:1 is a protein-tyrosine phosphatase.

In an alternative example, SEQ ID NO:3 is 34% identical to *Fagus sylvatica* protein phosphatase 2C (PP2C, GenBank ID g7768151) as determined by the Basic Local Alignment Search Tool (BLAST). (See Table 2.) The BLAST probability score is 6.4e-17, which indicates the probability of obtaining the observed polypeptide sequence alignment by chance. SEQ ID NO:3 also shares 45% identity with a putative *Caenorhabditis elegans* PP2C (GenBank ID g2804429), based on BLAST analysis, with a probability score of 2.4e-71. SEQ ID NO:3 contains protein phosphatase 2C domains as determined by searching for statistically significant matches in the hidden Markov model (HMM)-based PFAM database of conserved protein family domains. (See Table 3.) Data from BUMPS analysis provide further corroborative evidence that SEQ ID NO:3 is a protein phosphatase 2C.

In an alternative example, SEQ ID NO:5 is 25% identical to human protein kinase PAK5 (GenBank ID g7649810) as determined by the Basic Local Alignment Search Tool (BLAST). (See Table 2.) The BLAST probability score is 7.2e-14, which indicates the probability of obtaining the observed polypeptide sequence alignment by chance. SEQ ID NO:5 also contains a eukaryotic protein kinase domain as determined by searching for statistically significant matches in the hidden Markov model (MM)-based PFAM database of conserved protein family domains. (See Table 3.) Data from TMAP analysis as well as BLIMPS and BLAST analyses of the PRODOM and DOMO databases provide further corroborative evidence that SEQ ID NO:5 is a membrane-bound kinase.

In an alternative example, SEQ ID NO:6 is 1511 amino acid residues in length and is 97% identical over 1494 residues to human MEK kinase I (GenBank ID g2815888) as determined by the Basic Local Alignment Search Tool (BLAST). (See Table 2.) The BLAST probability score is 0.0, which indicates the probability of obtaining the observed polypeptide sequence alignment by chance. SEQ ID NO:6 also contains a eukaryotic protein kinase domain as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:6 is protein kinase. In an alternative example, SEQ ID NO:9 is 87% identical to murine protein kinase (GenBank ID g406058) as determined by the Basic Local Alignment Search Tool (BLAST). (See Table 2.) The BLAST probability score is 0.0, which indicates the probability of obtaining the observed polypeptide sequence alignment by chance. SEQ ID NO:9 also contains an eukaryotic protein kinase domain and a PDZ domain as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:9 is a protein kinase.

In an alternative example, SEQ ID NO:16 is 61% identical to human mitogen-activated kinase kinase kinase 5 (GenBank ID g1679668) as determined by the Basic Local Alignment Search Tool (BLAST). (See Table 2.) The BLAST probability score is 0.0, which indicates the probability of obtaining the observed polypeptide sequence alignment by chance. SEQ ID NO:16 also contains a eukaryotic protein kinase domain as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:16 is a mitogen activated protein kinase kinase kinase.

In an alternative example, SEQ ID NO:18 is 83% identical from residues 4 to 372 to mouse protein kinase (GenBank ID g406058) as determined by the Basic Local Alignment Search Tool (BLAST). (See Table 2.) The BLAST probability score is 0.0, which indicates the probability of obtaining the observed polypeptide sequence alignment by chance. SEQ ID NO:18 also contains a eukaryotic protein kinase domain and a PDZ domain as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:18 is a serine/threonine protein kinase.

In an alternative example, SEQ ID NO:19 is 95% identical, from residue M1 to residue V988, to *Rattus norvegius* mytonic dystrophy kinase-related Cdc42-binding kinase (GenBank ID g2736151) as determined by the Basic Local Alignment Search Tool (BLAST). (See Table 2.) The BLAST probability score is 0.0, which indicates the probability of obtaining the observed polypeptide sequence alignment by chance. SEQ ID NO:19 also contains a protein kinase C terminal domain and a eukaryotic protein kinase domain as determined by searching for statistically significant matches in the hidden Markov model (HMM)-based PFAM database of conserved protein family domains. (See Table 3.) Data from BLIMPS, MOTIFS, and additional BLAST analyses provide further corroborative evidence that SEQ ID NO:19 is a protein kinase.

SEQ ID NO:2, SEQ ID NO:4, SEQ ID NO:7, SEQ ID NO:8, SEQ ID NO:10–15, SEQ ID NO:17, and SEQ ID NO:20 were analyzed and annotated in a similar manner. The algorithms and parameters for the analysis of SEQ ID NO:1–20 are described in Table 7.

As shown in Table 4, the full length polynucleotide sequences of the present invention were assembled using cDNA sequences or coding (exon) sequences derived from genomic DNA, or any combination of these two types of sequences. Column 1 lists the polynucleotide sequence identification number (Polynucleotide SEQ ID NO:), the corresponding Incyte polynucleotide consensus sequence number (Incyte ID) for each polynucleotide of the invention, and the length of each polynucleotide sequence in basepairs. Column 2 shows the nucleotide start (5') and stop (3') positions of the cDNA and/or genomic sequences used to assemble the full length polynucleotide sequences of the invention, and of fragments of the polynucleotide sequences which are useful, for example, in hybridization or amplification technologies that identify SEQ ID NO:21–40 or that distinguish between SEQ ID NO:21–40 and related polynucleotide sequences.

The polynucleotide fragments described in Column 2 of Table 4 may refer specifically, for example, to Incyte cDNAs derived from tissue-specific cDNA libraries or from pooled cDNA libraries. Alternatively, the polynucleotide fragments described in column 2 may refer to GenBank cDNAs or ESTs which contributed to the assembly of the full length polynucleotide sequences. In addition, the polynucleotide fragments described in column 2 may identify sequences derived from the ENSEMBL (The Sanger Centre, Cambridge, UK) database (i.e., those sequences including the designation "ENST"). Alternatively, the polynucleotide fragments described in column 2 may be derived from the NCBI RefSeq Nucleotide Sequence Records Database (i.e., those sequences including the designation "NM" or "NT") or the NCBI RefSeq Protein Sequence Records (i.e., those sequences including the designation "NP"). Alternatively, the polynucleotide fragments described in column 2 may refer to assemblages of both cDNA and Genscan-predicted exons brought together by an "exon stitching" algorithm. For example, a polynucleotide sequence identified as FL_XXXXXX_N$_1$_N$_2$_YYYYY_N$_3$_N$_4$ represents a "stitched" sequence in which XXXXXX is the identification number of the cluster of sequences to which the algorithm was applied, and YYYYY is the number of the prediction generated by the algorithm, and N$_{1,2,3}$ . . . , if present, represent specific exons that may have been manually edited during analysis (See Example V). Alternatively, the polynucleotide fragments in column 2 may refer to assemblages of exons brought together by an "exon-stretching" algorithm. For example, a polynucleotide sequence identified as FLXXXXXX_gAAAAA_gBBBBB_1_N is a "stretched" sequence, with XXXXXX being the Incyte project identification number, gAAAAA being the GenBank identification number of the human genomic sequence to which the "exon-stretching" algorithm was applied, gBBBBB being the GenBank identification number or NCBI RefSeq identification number of the nearest GenBank protein homolog, and N referring to specific exons (See Example V). In instances where a RefSeq sequence was used as a protein homolog for the "exon-stretching" algorithm, a RefSeq identifier (denoted by "NM," "NP," or "NT") may be used in place of the GenBank identifier (i.e., gBBBBB).

Alternatively, a prefix identifies component sequences that were hand-edited, predicted from genomic DNA sequences, or derived from a combination of sequence analysis methods. The following Table lists examples of component sequence prefixes and corresponding sequence analysis methods associated with the prefixes (see Example IV and Example V).

| Prefix | Type of analysis and/or examples of programs |
|---|---|
| GNN, GFG, ENST | Exon prediction from genomic sequences using, for example, GENSCAN (Stanford University, CA, U.S.A.) or FGENES (Computer Genomics Group, The Sanger Centre, Cambridge, UK). |
| GBI | Hand-edited analysis of genomic sequences. |
| FL | Stitched or stretched genomic sequences (see Example V). |
| INCY | Full length transcript and exon prediction from mapping of EST sequences to the genome. Genomic location and EST composition data are combined to predict the exons and resulting transcript. |

In some cases, Incyte cDNA coverage redundant with the sequence coverage shown in Table 4 was obtained to confirm the final consensus polynucleotide sequence, but the relevant Incyte cDNA identification numbers are not shown.

Table 5 shows the representative cDNA libraries for those full length polynucleotide sequences which were assembled using Incyte cDNA sequences. The representative cDNA library is the Incyte cDNA library which is most frequently represented by the Incyte cDNA sequences which were used to assemble and confirm the above polynucleotide sequences. The tissues and vectors which were used to construct the cDNA libraries shown in Table 5 are described in Table 6.

The invention also encompasses KAP variants. A preferred KAP variant is one which has at least about 80%, or alternatively at least about 90%, or even at least about 95% amino acid sequence identity to the KAP amino acid sequence, and which contains at least one functional or structural characteristic of KAP.

The invention also encompasses polynucleotides which encode KAP. In a particular embodiment, the invention encompasses a polynucleotide sequence comprising a sequence selected from the group consisting of SEQ ID NO:21–40, which encodes KAP. The polynucleotide sequences of SEQ ID NO:21–40, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding KAP. In particular, such a variant polynucleotide sequence will have at least about 70%, or alternatively at least about 85%, or even at least about 95% polynucleotide sequence identity to the polynucleotide sequence encoding KAP. A particular aspect of the invention encompasses a variant of a polynucleotide sequence comprising a sequence selected from the group consisting of SEQ ID NO:21–40 which has at least about 70%, or alternatively at least about 85%, or even at least about 95% polynucleotide sequence identity to a nucleic acid sequence selected from the group consisting of SEQ ID NO:21–40. Any one of the polynucleotide variants described above can encode an amino acid sequence which contains at least one functional or structural characteristic of KAP.

In addition, or in the alternative, a polynucleotide variant of the invention is a splice variant of a polynucleotide sequence encoding KAP. A splice variant may have portions which have significant sequence identity to the polynucleotide sequence encoding KAP, but will generally have a greater or lesser number of polynucleotides due to additions or deletions of blocks of sequence arising from alternate splicing of exons during mRNA processing. A splice variant may have less than about 70%, or alternatively less than about 60%, or alternatively less than about 50% polynucleotide sequence identity to the polynucleotide sequence encoding KAP over its entire length; however, portions of the splice variant will have at least about 70%, or alternatively at least about 85%, or alternatively at least about 95%, or alternatively 100% polynucleotide sequence identity to portions of the polynucleotide sequence encoding KAP. Any one of the splice variants described above can encode an amino acid sequence which contains at least one functional or structural characteristic of KAP.

It will be appreciated by those skilled in the art that as a result of the degeneracy of the genetic code, a multitude of polynucleotide sequences encoding KAP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring KAP, and all such variations are to be considered as being specifically disclosed.

Although nucleotide sequences which encode KAP and its variants are generally capable of hybridizing to the nucleotide sequence of the naturally occurring KAP under appropriately selected conditions of stringency, it may be advantageous to produce nucleotide sequences encoding KAP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding KAP and its derivatives without altering the encoded amino acid sequences include the production of RNA transcripts having more desirable properties, such as a greater half-life, than transcripts produced from the naturally occurring sequence.

The invention also encompasses production of DNA sequences which encode KAP and KAP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding KAP or any fragment thereof.

Also encompassed by the invention are polynucleotide sequences that are capable of hybridizing to the claimed polynucleotide sequences, and, in particular, to those shown in SEQ ID NO:21–40 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding KAP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode KAP may be cloned in recombinant DNA molecules that direct expression of KAP, or fragments or functional equivalents thereof, in appropriate host cells. Due to the inherent degeneracy of the genetic code, other DNA sequences which encode substantially the same or a functionally equivalent amino acid sequence may be produced and used to express KAP.

The nucleotide sequences of the present invention can be engineered using methods generally known in the art in order to alter KAP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULAR-BREEDING (Maxygen Inc., Santa Clara Calif.; described in U.S. Pat. No. 5,837,458; Chang, C. -C. et al. (1999) Nat. Biotechnol. 17:793–797; Christians, F. C. et al. (1999) Nat Biotechnol. 17:259–264; and Crameri, A. et al. (1996) Nat. Biotechnol. 14:315–319) to alter or improve the biological properties of KAP, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding KAP may be synthesized, in whole or in part, using chemical methods well known in the art. (See, e.g., Caruthers, M. H. et al. (1980) Nucleic Acids Symp. Ser. 7:215–223; and Horn, T. et al. (1980) Nucleic Acids Symp. Ser. 7:225–232.) Alternatively, KAP itself or a fragment thereof may be synthesized using chemical methods. For example, peptide synthesis can be performed using various solution-phase or solid-phase techniques. (See, e.g., Creighton, T. (1984) Proteins, Structures and Molecular Properties, W H Freeman, New York N.Y., pp. 5560; and Roberge, J. Y. et al. (1995) Science 269:202–204.) Automated synthesis may be achieved using the ABI 431A peptide synthesizer (Applied Biosystems). Additionally, the amino acid sequence of KAP, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182: 392–421.) The composition of the synthetic peptides may be confirmed by amino acid analysis or by sequencing. (See, e.g., Creighton, supra, pp. 28–53.)

In order to express a biologically active KAP, the nucleotide sequences encoding KAP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding KAP. Such elements may vary in their strength and specificity. Specific initiation signals may also be used to achieve more efficient translation of sequences encoding KAP. Such signals include the ATG initiation codon and adjacent sequences, e.g. the Kozak sequence. In cases where sequences encoding KAP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding KAP and appropriate transcriptional and translational control elements. These methods include in vitro recombinant DNA techniques, synthetic techniques, and in vivo genetic recombination. (See, e.g., Sambrook, J. et al. (1989) Molecular Cloning. A Laboratory Manual, Cold Spring Harbor Press, Plainview N.Y., ch. 4, 8, and 16–17; Ausubel, F. M. et al. (1995) Current Protocols in Molecular Biolog, John Wiley & Sons, New York N.Y., ch. 9, 13, and 16.)

A variety of expression vector/host systems may be utilized to contain and express sequences encoding KAP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503–5509; Engelhard, E. K. et al. (1994) Proc. Natl. Acad. Sci. USA 91:3224–3227; Sandig, V. et al. (1996) Hum Gene Ther. 7:1937–1945; Takamatsu, N. (1987) EMBO J. 6:307–311; The McGraw Hill Yearbook of Science and Technology (1992) McGraw Hill, New York N.Y., pp. 191–196; Logan, J. and T. Shenk (1984) Proc. Natl. Acad. Sci. USA 81:3655–3659; and Harrington, J. J. et al. (1997) Nat Genet. 15:345–355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350–356; Yu, M. et al. (1993) Proc. Natl. Acad. Sci. USA 90(13):6340–6344; Buller, R. M. et al. (1985) Nature 317(6040):813–815; McGregor, D. P. et al. (1994) Mol. Immunol. 31(3):219–226; and Verma, I. M. and N. Somia (1997) Nature 389:239–242.) The invention is not limited by the host cell employed.

In bacterial systems, a number of cloning and expression vectors may be selected depending upon the use intended for polynucleotide sequences encoding KAP. For example, routine cloning, subcloning, and propagation of polynucleotide sequences encoding KAP can be achieved using a multifunctional *E. coli* vector such as PBLUESCRIPT (Stratagene, La Jolla Calif.) or PSPORT1 plasmid (Life Technologies). Ligation of sequences encoding KAP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of KAP are needed, e.g. for the production of antibodies, vectors which direct high level expression of KAP may be used. For example, vectors containing the strong, inducible SP6 or T7 bacteriophage promoter may be used.

Yeast expression systems may be used for production of KAP. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Bitter, G. A. et al. (1987) Methods Enzymol. 153:516–544; and Scorer, C. A. et al. (1994) Bio/Technology 12:181–184.)

Plant systems may also be used for expression of KAP. Transcription of sequences encoding KAP may be driven by viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding KAP may be ligated into an adenovirus transcription/translation complex consisting of the late promoter and tripartite leader sequence. Insertion in a non-essential E1 or E3 region of the viral genome may be used to obtain infective virus which expresses KAP in host cells. (See, e.g., Logan, J. and T. Shenk (1984) Proc. Natl. Acad. Sci. USA 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of KAP in cell lines is preferred. For example, sequences encoding KAP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ and apr⁻ cells, respectively. (See, e.g., Wigler, M. et al. (1977) Cell 11:223–232; Lowy, I. et al. (1980) Cell. 22:817–823.) Also, antimetabolite, antibiotic, or herbicide resistance can be used as the basis for selection. For example, dhfr confers resistance to methotrexate; neo confers resistance to the aminoglycosides neomycin and G-418; and als and pat confer resistance to chlorsulfuron and phosphinotricin acetyltransferase, respectively. (See, e.g., Wigler, M. et al. (1980) Proc. Natl. Acad. Sci. USA 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartan, S. C. and R. C. Mulligan (1988) Proc. Natl. Acad. Sci. USA 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding KAP is inserted within a marker gene sequence, transformed cells containing sequences encoding KAP can be identified by the absence of marker gene function. Alternatively, a marker gene can be placed in tandem with a sequence encoding KAP under the control of a single promoter. Expression of the marker gene in response to induction or selection usually indicates expression of the tandem gene as well.

In general, host cells that contain the nucleic acid sequence encoding KAP and that express KAP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of KAP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on KAP is preferred, but a competitive binding assay may be employed. These and other assays are well known in the art. (See, e.g., Hampton, R. et al. (1990) *Serological Methods, a Laboratory Manual*, APS Press, St. Paul Minn., Sect. IV; Coligan, J. E. et al.

(1997) *Current Protocols in Immunology*, Greene Pub. Associates and Wiley-Interscience, New York N.Y.; and Pound, J. D. (1998) *Immunochemical Protocols,* Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding KAP include oligolabeling, nick translation, end-labeling, or PCR amplification using a labeled nucleotide. Alternatively, the sequences encoding KAP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding KAP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode KAP may be designed to contain signal sequences which direct secretion of KAP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Va.) and may be chosen to ensure the correct modification and processing of the foreign protein.

In another embodiment of the invention, natural, modified, or recombinant nucleic acid sequences encoding KAP may be ligated to a heterologous sequence resulting in translation of a fusion protein in any of the aforementioned host systems. For example, a chimeric KAP protein containing a heterologous moiety that can be recognized by a commercially available antibody may facilitate the screening of peptide libraries for inhibitors of KAP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), $^6$-His, FLAG, c-myc, and hemagglutinin (HA). GST, MBP, Trx, CBP, and 6His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the KAP encoding sequence and the heterologous protein sequence, so that KAP may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled KAP may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

KAP of the present invention or fragments thereof may be used to screen for compounds that specifically bind to KAP. At least one and up to a plurality of test compounds may be screened for specific binding to KAP. Examples of test compounds include antibodies, oligonucleotides, proteins (e.g., receptors), or small molecules.

In one embodiment, the compound thus identified is closely related to the natural ligand of KAP, e.g., a ligand or fragment thereof, a natural substrate, a structural or functional mimetic, or a natural binding partner. (See, e.g., Coligan, J. E. et al. (1991) *Current Protocols in Immunology* 1(2):Chapter 5.) Similarly, the compound can be closely related to the natural receptor to which KAP binds, or to at least a fragment of the receptor, e.g., the ligand binding site. In either case, the compound can be rationally designed using known techniques. In one embodiment, screening for these compounds involves producing appropriate cells which express KAP, either as a secreted protein or on the cell membrane. Preferred cells include cells from mammals, yeast, *Drosophila,* or *E. coli*. Cells expressing KAP or cell membrane fractions which contain KAP are then contacted with a test compound and binding, stimulation, or inhibition of activity of either KAP or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with KAP, either in solution or affixed to a solid support, and detecting the binding of KAP to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

KAP of the present invention or fragments thereof may be used to screen for compounds that modulate the activity of KAP. Such compounds may include agonists, antagonists, or partial or inverse agonists. In one embodiment, an assay is performed under conditions permissive for KAP activity, wherein KAP is combined with at least one test compound, and the activity of KAP in the presence of a test compound is compared with the activity of KAP in the absence of the test compound. A change in the activity of KAP in the presence of the test compound is indicative of a compound that modulates the activity of KAP. Alternatively, a test compound is combined with an in vitro or cell-free system comprising KAP under conditions suitable for KAP activity, and the assay is performed. In either of these assays, a test compound which modulates the activity of KAP may do so indirectly and need not come in direct contact with the test compound. At least one and up to a plurality of test compounds may be screened.

In another embodiment, polynucleotides encoding KAP or their mammalian homologs may be "knocked out" in an animal model system using homologous recombination in embryonic stem (ES) cells. Such techniques are well known in the art and are useful for the generation of animal models of human disease. (See, e.g., U.S. Pat. No. 5,175,383 and U.S. Pat. No. 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288–1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999–2002; Wagner, K. U. et al. (1997) Nucleic Acids Res. 25:4323–4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding KAP may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282: 1145–1147).

Polynucleotides encoding KAP can also be used to create "knockin" humanized animals (pigs) or transgenic animals (mice or rats) to model human disease. With knockin technology, a region of a polynucleotide encoding KAP is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress KAP, e.g., by secreting KAP in its milk, may also serve as a convenient source of that protein (Janne, J. et al. (1998) Biotechnol. Annu. Rev. 4:55–74).

Therapeutics

Chemical and structural similarity, e.g., in the context of sequences and motifs, exists between regions of KAP and kinases and phosphatases. In addition, examples of tissues expressing KAP can be found in Table 6. Therefore, KAP appears to play a role in cardiovascular diseases, immune system disorders, neurological disorders, disorders affecting growth and development, lipid disorders, cell proliferative disorders, and cancers. In the treatment of disorders associated with increased KAP expression or activity, it is desirable to decrease the expression or activity of KAP. In the treatment of disorders associated with decreased KAP expression or activity, it is desirable to increase the expression or activity of KAP.

Therefore, in one embodiment, KAP or a fragment or derivative thereof may be administered to a subject to treat or prevent a disorder associated with decreased expression or activity of KAP. Examples of such disorders include, but are not limited to, a cardiovascular disorder such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft: surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation; an immune disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathycandidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and hehninthic infections, and trauma; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a growth and developmental disorder such as actinic keratosis, arteriosclerosis, atherosclerosis, bursitis, cirrhosis, hepatitis, mixed connective tissue disease (MCID), myelofibrosis, paroxysmal nocturnal hemoglobinuria, polycythemia vera, psoriasis, primary thrombocythemia, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; a lipid disorder such as fatty liver, cholestasis, primary biliary cirrhosis, carnitine deficiency, carnitine palnitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoff's disease, hyperlipidemia, hyperlipemia, lipid myopathies, and obesity; and a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, uterus, leukemias such as multiple myeloma, and lymphomas such as Hodgkin's disease.

In another embodiment, a vector capable of expressing KAP or a fragment or derivative thereof may be administered to a subject to treat or prevent a disorder associated with decreased expression or activity of KAP including, but not limited to, those described above.

In a further embodiment, a composition comprising a substantially purified KAP in conjunction with a suitable pharmaceutical carrier may be administered to a subject to treat or prevent a disorder associated with decreased expression or activity of KAP including, but not limited to, those provided above.

In still another embodiment, an agonist which modulates the activity of KAP may be administered to a subject to treat or prevent a disorder associated with decreased expression or activity of KAP including, but not limited to, those listed above.

In a further embodiment, an antagonist of KAP may be administered to a subject to treat or prevent a disorder associated with increased expression or activity of KAP. Examples of such disorders include, but are not limited to, those cardiovascular diseases, immune system disorders, neurological disorders, disorders affecting growth and development, lipid disorders, cell proliferative disorders, and cancers described above. In one aspect, an antibody which specifically binds KAP may be used directly as an antagonist or indirectly as a targeting or delivery mechanism for bringing a pharmaceutical agent to cells or tissues which express KAP.

In an additional embodiment, a vector expressing the complement of the polynucleotide encoding KAP may be administered to a subject to treat or prevent a disorder associated with increased expression or activity of KAP including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of KAP may be produced using methods which are generally known in the art. In particular, purified KAP may be used to produce antibodies or to screen libraries of pharmaceutical agents to identify those which specifically bind KAP. Antibodies to KAP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with KAP or with any fragment or oligopeptide thereof which has immunogenic properties.

Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLK, and dinitrophenol. Among adjuvants used in humans, BCG (*bacilli Calmette-Guerin*) and *Corynebacterium parvum* are especially preferable.

It is preferred that the oligopeptides, peptides, or fragments used to induce antibodies to KAP have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of KAP amino acids may be fused with those of another protein, such as KLH, and antibodies to the chimeric molecule may be produced.

Monoclonal antibodies to KAP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256: 495–497; Kozbor, D. et al. (1985) J. Immunol. Methods 81:31–42; Cote, R. J. et al. (1983) Proc. Natl. Acad. Sci. USA 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce KAP-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833–3837; Winter, G. et al. (1991) Nature 349:293–299.)

Antibody fragments which contain specific binding sites for KAP may also be generated. For example, such fragments include, but are not limited to, $F(ab')_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between KAP and its specific antibody. A two-site, monoclonal-based immunoassay utilizing monoclonal antibodies reactive to two non-interfering KAP epitopes is generally used, but a competitive binding assay may also be employed (Pound, supra).

Various methods such as Scatchard analysis in conjunction with radioimmunoassay techniques may be used to assess the affinity of antibodies for KAP. Affinity is expressed as an association constant, $K_a$, which is defined as the molar concentration of KAP-antibody complex divided by the molar concentrations of free antigen and free antibody under equilibrium conditions. The $K_a$ determined for a preparation of polyclonal antibodies, which are heterogeneous in their affinities for multiple KAP epitopes, represents the average affinity, or avidity, of the antibodies for KAP. The $K_a$ determined for a preparation of monoclonal antibodies, which are monospecific for a particular KAP epitope, represents a true measure of affinity. High-affinity antibody preparations with $K_a$ ranging from about $10^9$ to $10^{12}$ L/mole are preferred for use in immunoassays in which the KAP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of KAP, preferably in active form, from the antibody (Catty, D. (1988) *Antibodies, Volume I: A Practical Approach,* IRL Press, Washington DC; Liddell, J. E. and A. Cryer (1991) *A Practical Guide to Monoclonal Antibodies,* John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is generally employed in procedures requiring precipitation of KAP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding KAP, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding KAP. Such technology is well known in the art, and antisense oligonucleotides or larger fragments can be designed from various locations along the coding or control regions of sequences encoding KAP. (See, e.g., Agrawal, S., ed. (1996) *Antisense Therapeutics,* Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al. (1998) J. Allergy Clin. Immunol. 102(3):469–475; and Scanlon, K. J. et al. (1995) 9(13): 1288–1296.) Antisense sequences can also be introduced intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmacol. Ther. 63(3):323–347.) Other gene delivery mechanisms include liposome-derived systems, artificial viral envelopes, and other systems known in the art. (See, e.g., Rossi, J. J. (1995) Br. Med. Bull. 51(1):217–225; Boado, R. J. et al. (1998) J.

Pharm. Sci. 87(11):1308–1315; and Morris, M. C. et al. (1997) Nucleic Acids Res. 25(14):2730–2736.)

In another embodiment of the invention, polynucleotides encoding KAP may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669–672), severe combined immunodeficiency syndrome associated with an inherited adenosine deaminase (ADA) deficiency (Blaese, R. M. et al. (1995) Science 270:475–480; Bordignon, C. et al. (1995) Science 270:470–475), cystic fibrosis (Zabner, J. et al. (1993) Cell 75:207–216; Crystal, R. G. et al. (1995) Hum. Gene Therapy 6:643–666; Crystal, R. G. et al. (1995) Hum. Gene Therapy 6:667–703), thalassamias, familial hypercholesterolemia, and hemophilia resulting from Factor VIII or Factor IX deficiencies (Crystal, R. G. (1995) Science 270:404–410; Verma, I. M. and N. Somia (1997) Nature 389:239–242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335:395–396; Poeschla, E. et al. (1996) Proc. Natl. Acad. Sci. USA 93:11395–11399), hepatitis B or C virus (HBV, HCV); fungal parasites, such as *Candida albicans* and *Paracoccidioides brasiliensis;* and protozoan parasites such as *Plasmodium falciparum* and *Trypanosoma cruzi*). In the case where a genetic deficiency in KAP expression or regulation causes disease, the expression of KAP from an appropriate population of transduced cells may alleviate the clinical manifestations caused by the genetic deficiency.

In a further embodiment of the invention, diseases or disorders caused by deficiencies in KAP are treated by constructing mammalian expression vectors encoding KAP and introducing these vectors by mechanical means into KAP-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem 62:191–217; Ivics, Z. (1997) Cell 91:501–510; Boulay, J-L. and IL Récipon (1998) Curr. Opin. Biotechnol. 9:445–450).

Expression vectors that may be effective for the expression of KAP include, but are not limited to, the PCDNA 3.1, EPITAG, PRCCMV2, PREP, PVAX, PCR2-TOPOTA vectors (Invitrogen, Carlsbad Calif.), PCMV-SCRIPT, PCMV-TAG, PEGSHIPERV (Stratagene, La Jolla Calif.), and PTET-OFF, PTET-ON, PTRE2, PTRE2-LUC, PTK-HYG (Clontech, Palo Alto Calif.). KAP may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. USA 89:5547–5551; Gossen, M. et al. (1995) Science 268:1766–1769; Rossi, F. M. V. and H. M. Blau (1998) Curr. Opin. Biotechnol. 9:451–456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and H. M. Blau, supra)), or (iii) a tissue-specific promoter or the native promoter of the endogenous gene encoding KAP from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456–467), or by electroporation (Neumann, E. et al. (1982) EMBO J. 1:841–845). The introduction of DNA to primary cells requires modification of these standardized mammalian transfection protocols.

In another embodiment of the invention, diseases or disorders caused by genetic defects with respect to KAP expression are treated by constructing a retrovirus vector consisting of (i) the polynucleotide encoding KAP under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. USA 92:6733–6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647–1650; Bender, M. A. et al. (1987) J. Virol. 61:1639–1646; Adam, M. A. and A. D. Miller (1988) J. Virol. 62:3802–3806; Dull, T. et al. (1998) J. Virol. 72:8463–8471; Zufferey R. et al. (1998) J. Virol. 72:9873–9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4$^+$ T-cells), and the return of transduced cells to a patient are procedures well known to persons skilled in the art of gene therapy and have been well documented (Ranga, U. et al. (1997) J. Virol. 71:7020–7029; Bauer, G. et al. (1997) Blood 89:2259–2267; Bonyhadi, M. L. (1997) J. Virol. 71:4707–4716; Ranga, U. et al. (1998) Proc. Natl. Acad. Sci. USA 95:1201–1206; Su, L. (1997) Blood 89:2283–2290).

In the alternative, an adenovirus-based gene therapy delivery system is used to deliver polynucleotides encoding KAP to cells which have one or more genetic abnormalities with respect to the expression of KAP. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263–268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511–544 and Verma, I. M. and N. Somia (1997) Nature 18:389:239–242, both incorporated by reference herein.

In another alternative, a herpes-based, gene therapy delivery system is used to deliver polynucleotides encoding KAP to target cells which have one or more genetic abnormalities with respect to the expression of KAP. The use of herpes simplex virus (HSV)-based vectors may be especially valuable for introducing KAP to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385–395). The construction of a HSV-1 virus vector has also been disclosed in detail in U.S. Pat. No. 5,804,413 to DeLuca ("Herpes simplex virus strans for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999) J. Virol. 73:519–532 and Xu, H. et al. (1994) Dev. Biol. 163:152–161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding KAP to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464–469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for KAP into the alphavirus genome in place of the capsid-coding region results in the production of a large number of KAP-coding RNAs and the synthesis of high levels of KAP in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74–83). The wide host range of alphaviruses will allow the introduction of KAP into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding KAP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding KAP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding KAP. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased KAP expression or activity, a compound which specifically inhibits expression of the polynucleotide encoding KAP may be therapeutically useful, and in the treatment of disorders associated with decreased KAP expression or activity, a compound which specifically promotes expression of the polynucleotide encoding KAP may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding KAP is exposed to at least one test compound thus obtained. The sample may comprise, for example, an intact or permeabilized cell, or an in vitro cell-free or reconstituted biochemical system. Alterations in the expression of a polynucleotide encoding KAP are assayed by any method commonly known in the art. Typically, the expression of a specific nucleotide is detected by hybridization with a probe having a nucleotide sequence complementary to the sequence of the polynucleotide encoding KAP. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268: 8–13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nat. Biotechnol. 15:462–466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of KAP, antibodies to KAP, and mimetics, agonists, antagonists, or inhibitors of KAP.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising KAP or fragments thereof. For example, liposome preparations containing a cell-impermeable macromolecule may promote cell fusion and intracellular delivery of the macromolecule. Alternatively, KAP or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569–1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example KAP or fragments thereof, antibodies of KAP, and agonists, antagonists or inhibitors of KAP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment.

Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind KAP may be used for the diagnosis of disorders characterized by expression of KAP, or in assays to monitor patients being treated with KAP or agonists, antagonists, or inhibitors of KAP. Antibodies useful for diagnostic purposes may be prepared in the same manner as described above for therapeutics. Diagnostic assays for KAP include methods which utilize the antibody and a label to detect KAP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring KAP, including ELISAs, RIAs, and FACS, are known in the art and provide a basis for diagnosing altered or abnormal levels of KAP expression. Normal or standard values for KAP expression are established by combining body fluids or cell extracts taken from normal mammalian subjects, for example, human subjects, with antibodies to KAP under conditions suitable for complex formation. The amount of standard complex formation may be quantitated by various methods, such as photometric means. Quantities of KAP expressed in subject, control, and disease samples from biopsied tissues are compared with the standard values. Deviation between standard and subject values establishes the parameters for diagnosing disease.

In another embodiment of the invention, the polynucleotides encoding KAP may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of KAP may be correlated with disease. The diagnostic assay may be used to determine absence, presence, and excess expression of KAP, and to monitor regulation of KAP levels during therapeutic intervention.

In one aspect, hybridization with PCR probes which are capable of detecting polynucleotide sequences, including genomic sequences, encoding KAP or closely related molecules may be used to identify nucleic acid sequences which encode KAP. The specificity of the probe, whether it is made from a highly specific region, e.g., the 5'regulatory region, or from a less specific region, e.g., a conserved motif, and the stringency of the hybridization or amplification will determine whether the probe identifies only naturally occurring sequences encoding KAP, allelic variants, or related sequences.

Probes may also be used for the detection of related sequences, and may have at least 50% sequence identity to any of the KAP encoding sequences. The hybridization probes of the subject invention may be DNA or RNA and may be derived from the sequence of SEQ ID NO:21–40 or from genomic sequences including promoters, enhancers, and introns of the KAP gene.

Means for producing specific hybridization probes for DNAs encoding KAP include the cloning of polynucleotide sequences encoding KAP or KAP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^3$P or $^{35}$S, or by enzymatic labels, such as alkaline phosphatase coupled to the probe via avidin/biotin coupling systems, and the like.

Polynucleotide sequences encoding KAP may be used for the diagnosis of disorders associated with expression of KAP. Examples of such disorders include, but are not limited to, a cardiovascular disorder such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation; an immune disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes meritus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a growth and developmental disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; a lipid disorder such as fatty liver, cholestasis, primary. bilary cirrhosis, carnitine deficiency, carnitine palmitoyltransferase deficiency, myoadenylate deaminase deficiency, hypertriglyceridemia, lipid storage disorders such as Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoff's disease, hyperlipidemia, hyperlipemia, lipid myopathies, and obesity; and a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, uterus, leukemias such as multiple myeloma, and lymphomas such as Hodgkin's disease. The polynucleotide sequences encoding KAP may be used in Southern or northern analysis, dot blot, or other membrane-based technologies; in PCR technologies; in dipstick, pin, and multiformat ELISA-like assays; and in microarrays utilizing fluids or tissues from patients to detect altered KAP expression. Such qualitative or quantitative methods are well known in the art.

In a particular aspect, the nucleotide sequences encoding KAP may be useful in assays that detect the presence of associated disorders, particularly those mentioned above. The nucleotide sequences encoding KAP may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of nucleotide sequences encoding KAP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of KAP, a normal or standard profile for expression is established. This may be accomplished by combining body fluids or cell extracts taken from normal subjects, either animal or human, with a sequence, or a fragment thereof, encoding KAP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding KAP may involve the use of PCR. These oligomers may be chemically synthesized, generated enzymatically, or produced in vitro. Oligomers will preferably contain a fragment of a polynucleotide encoding KAP, or a fragment of a polynucleotide complementary to the polynucleotide encoding KAP, and will be employed under optimized conditions for identification of a specific gene or condition. Oligomers may also be employed under less stringent conditions for detection or quantification of closely related DNA or RNA sequences.

In a particular aspect, oligonucleotide primers derived from the polynucleotide sequences encoding KAP may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding KAP are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (isSNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of KAP include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, KAP, fragments of KAP, or antibodies specific for KAP may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time. (See Seilhamer et al., "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153–159; Steiner, S. and N. L. Anderson (2000) Toxicol. Lett. 112–113:467471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00–02 from the National Institute of Environmental Health Sciences ("NIEHS"), released Feb. 29, 2000, available at the NIEHS website.) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of the present invention. In some cases, further sequence data may be obtained for definitive protein identification.

A proteomic profile may also be generated using antibodies specific for KAP to quantify the levels of KAP expression. In one embodiment, the antibodies are used as elements on a microarray, and protein expression levels are quantified by exposing the microarray to the sample and detecting the levels of protein bound to each array element (Lueking, A. et al. (1999) Axial. Biochem. 270:103–111; Mendoze, L. G. et al. (1999) Biotechniques 27:778–788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533–537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150–2155; and Heller, M. J. et al. (1997) U.S. Pat. No. 5,605,662.) Various types of microarrays are well known and thoroughly described in *DNA Microarrays: A Practical Approach*, M. Schena, ed. (1999) Oxford University Press, London, hereby expressly incorporated by reference.

In another embodiment of the invention, nucleic acid sequences encoding KAP may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, for example, Lander, E. S. and D. Botstein (1986) Proc. Natl. Acad. Sci. USA 83:7353–7357.)

Fluorescent in situ hybridization (FISH) may be correlated with other physical and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) World Wide Web site. Correlation between the location of the gene encoding KAP on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the instant invention may also be used to detect differences in the chromosomal location due to translocation, inversion, etc., among normal, carrier, or affected individuals.

In another embodiment of the invention, KAP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between KAP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with KAP, or fragments thereof, and washed. Bound KAP is then detected by methods well known in the art. Purified KAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding KAP specifically compete with a test compound for binding KAP. In this manner, antibodies can be used to detect the presence of any peptide which shares one or more antigenic determinants with KAP.

In additional embodiments, the nucleotide sequences which encode KAP may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications and publications, mentioned above and below, including U.S. Ser. No. 60/254,034, U.S. Ser. No. 60/255,756, U.S. Ser. No. 60/251,814, U.S. Ser. No. 60/256,172, U.S. Ser. No. 60/257,416, U.S. Ser. No. 60/260,912, U.S. Ser. No. 60/264,344, and U.S. Ser. No.60/266,017, are expressly incorporated by reference herein.

EXAMPLES

I. Construction of cDNA Libraries

Incyte cDNAs were derived from cDNA libraries described in the LIFESEQ GOLD database (Incyte Genomics, Palo Alto Calif.). Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+ RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (Invitrogen, Carlsbad Calif.), PBK-CMV plasmid (Stratagene), PCR2-TOPOTA plasmid (Invitrogen), PCMV-ICIS plasmid (Stratagene), pIGEN (Incyte Genomics, Palo Alto Calif.), pRARE (Incyte Genomics), or pINCY (Incyte Genomics), or derivatives thereof. Recombinant plasmids were transformed into competent E. coli cells including XL1-Blue, XL1-BlueMRF, or SOLR from Stratagene or DH5α, DH10B, or ElectroMAX DH10B from Life Technologies.

II. Isolation f cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene OR) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Applied Biosystems) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM; PROTEOME databases with sequences from *Homo sapiens, Rattus norvegicus, Mus musculus, Caenorhabditis elegans, Saccharomyces cerevisiae, Schizosaccharomyces pombe,* and *Candida albicans* (Incyte Genomics, Palo Alto Calif.); and hidden Markov model (HMM)-based protein family databases such as PFAM. (HMM is a probabilistic approach which analyzes consensus primary structures of gene families. See, for example, Eddy, S. R. (1996) Curr. Opin. Struct. Biol. 6:361–365.) The queries were performed using programs based on BLAST, FASTA, BLIMPS, and HMMER. The Incyte cDNA sequences were assembled to produce full length polynucleotide sequences. Alternatively, GenBank cDNAs, GenBank ESTs, stitched sequences, stretched sequences, or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and PASTA. The full length polynucleotide sequences were translated to derive the corresponding full length polypeptide sequences. Alternatively, a polypeptide of the invention may begin at any of the methionine residues of the full length translated polypeptide. Full length polypeptide sequences were subsequently analyzed by querying against databases such as the GenBank protein databases (genpept), SwissProt, the PROTEOME databases, BLOCKS, PRINTS, DOMO, PRODOM, Prosite, and hidden Markov model (HMM)-based protein family databases such as PFAM. Full length polynucleotide sequences are also analyzed using MACDNASIS PRO software (Hitachi Software Engineering, South San Francisco Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes the tools, programs, and algorithms used for the analysis and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences were also used to identify polynucleotide sequence fragments from SEQ ID NO:21–40. Fragments from about 20 to about 4000 nucleotides which are useful in hybridization and amplification technologies are described in Table 4, column 2.

IV. Identification and Editing of Coding Sequences from Genomic DNA

Putative kinases and phosphatases were initially identified by running the Genscan gene identification program against public genomic sequence databases (e.g., gbpri and gbhtg). Genscan is a general-purpose gene identification program which analyzes genomic DNA sequences from a variety of organisms (See Burge, C. and S. Karlin (1997) J. Mol. Biol. 268:78–94, and Burge, C. and S. Karlin (1998) Curr. Opin. Struct. Biol. 8:346–354). The program concatenates predicted exons to form an assembled cDNA sequence extending from a methionine to a stop codon. The output of Genscan is a PASTA database of polynucleotide and polypeptide sequences. The maximum range of sequence for Genscan to analyze at once was set to 30 kb. To determine which of these Genscan predicted cDNA sequences encode kinases and phosphatases, the encoded polypeptides were analyzed by querying against PFAM models for kinases and phosphatases. Potential kinases and phosphatases were also identified by homology to Incyte cDNA sequences that had been annotated as kinases and phosphatases. These selected Genscan-predicted sequences were then compared by BLAST analysis to the genpept and gbpri public databases. Where necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence. Full length polynucleotide sequences were obtained by assembling Genscan-predicted coding sequences with Incyte cDNA sequences and/or public cDNA sequences using the assembly process described in Example III. Alternatively, full length polynucleotide sequences were derived entirely from edited or unedited Genscan-predicted coding sequences.

V. Assembly of Genomic Sequence Data with cDNA Sequence Data "Stitched" Sequences Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then all three intervals were considered to be equivalent. This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan were corrected by comparison to the top BLAST hit from genpept. Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example III were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gene.

VI. Chromosomal Mapping of KAP Encoding Polynucleotides

The sequences which were used to assemble SEQ ID NO:21–40 were compared with sequences from the Incyte LIFESEQ database and public domain databases using BLAST and other implementations of the Smith-Waterman algorithm. Sequences from these databases that matched SEQ ID NO:21–40 were assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Genethon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, of human chromosomes. The map position of an interval, in centiMorgans, is measured relative to the terminus of the chromosome's p-arm (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Genethon which provide boundaries for radiation hybrid markers whose sequences were included in each of the clusters. Human genome maps and other resources available to the public, such as the NCBI "GeneMap'99" World Wide Web site, can be employed to determine if previously identified disease genes map within or in proximity to the intervals indicated above.

In this manner, SEQ ID NO:33 was mapped to chromosome 12 within the interval from 97.10 to 113.30 centiMorgans. SEQ ID NO:35 was mapped to chromosome 3 within the interval from 16.50 to 30.40 centiMorgans. SEQ ID NO:29 was mapped to chromosome 13 within the interval from 11.60 to 22.80 centiMorgans, to chromosome 15 within the interval from 72.30 to 77.30 centiMorgans, and to chromosome 20 within the interval from 57.70 to 64.10 centiMorgans. More than one map location is reported for SEQ ID NO:29, indicating that sequences having different map locations were assembled into a single cluster. This situation occurs, for example, when sequences having strong similarity, but not complete identity, are assembled into a single cluster.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel (1995) supra, ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{\text{BLAST Score} \times \text{Percent Identity}}{5 \times \text{minimum}\{\text{length (Seq. 1), length (Seq. 2)}\}}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 tires the length of the shorter of the two sequences). The BLAST score is calculated by assigning a score of +5 for every base that matches in a high-scoring segment pair (HSP), and −4 for every mismatch. Two sequences may share more than one HSP (separated by gaps). If there is more than one HSP, then the pair with the highest BLAST score is used to calculate the product score. The product score represents a balance between fractional overlap and quality in a BLAST alignment For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotide sequences encoding KAP are analyzed with respect to the tissue sources from which they were derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified/mixed; or urinary tract. The number of libraries in each category is counted and divided by the total number of libraries across all categories. Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding KAP. cDNA sequences and cDNA library/tissue information are found in the LIFESEQ GOLD database (Incyte Genomics, Palo Alto Calif.).

VIII. Extension of KAP Encoding Polynucleotides

Full length polynucleotide sequences were also produced by extension of an appropriate fragment of the full length molecule using oligonucleotide primers designed from this fragment. One primer was synthesized to initiate 5' extension of the known fragment, and the other primer was synthesized to initiate 3'extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1×TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, and individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimnethysulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Applied Biosystems).

In like manner, full length polynucleotide sequences are verified using the above procedure or are used to obtain 5'regulatory sequences using the above procedure along with oligonucleotides designed for such extension, and an appropriate genomic library.

IX. Labeling and Use of Individual Hybridization Probes

Hybridization probes derived from SEQ ID NO:21–40 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [$\gamma$-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing 10$^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under conditions of up to, for example, 0.1× saline sodium citrate and 0.5% sodium dodecyl sulfate. Hybridization patterns are visualized using autoradiography or an alternative imaging means and compared.

X. Microarrays

The linkage or synthesis of array elements upon a microarray can be achieved utilizing photolithography, piezoelectric printing (ink-jet printing, See, e.g., Baldeschweiler, supra.), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena, M. et al. (1995) Science 270:467–470; Shalon, D. et al. (1996) Genome Res. 6:639–645; Marshall, A. and J. Hodgson (1998) Nat. Biotechnol. 16:27–31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorbtion and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly (A)$^+$ RNA sample is reverse transcribed using MMLV reverse-transcriptase, 0.05 pg/µl oligo-(dT) primer (21mer), 1× first strand buffer, 0.03 units/µl RNase inhibitor, 500 µM dATP, 500 µM dGTP, 500 µM dTTP, 40 µM dCTP, 40 µM dCTP-Cy3 (BDS) or dCTP-Cy5 (Amersham Pharmacia Biotech). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 µl 5×SSC/ 0.2% SDS.

Microarry Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1–2 ng to a final quantity greater than 5 µg. Amplified array elements are then purified using SEPHACRYL-400 (Amersham Pharmacia Biotech).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 µl of the array element DNA, at an average concentration of 100 ng/µl, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 µl of sample mixture consisting of 0.2 µg each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm² coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte).

XI. Complementary Polynucleotides

Sequences complementary to the KAP-encoding sequences, or any parts thereof, are used to detect, decrease, or inhibit expression of naturally occurring KAP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of KAP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the KAP-encoding transcript.

XII. Expression of KAP

Expression and purification of KAP is achieved using bacterial or virus-based expression systems. For expression of KAP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express KAP upon induction with isopropyl beta-D-thiogalactopyranoside (IPTG). Expression of KAP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding KAP by either homologous recombination or bacterial-mediated transposition involving transfer plasmid intermediates. Viral infectivity is maintained and the strong polyhedrin promoter drives high levels of cDNA transcription. Recombinant baculovirus is used to infect Spodoptera frugiperda (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum Gene Ther. 7:1937–1945.)

In most expression systems, KAP is synthesized as a fusion protein with, e.g., glutathione Stransferase (GST) or a peptide epitope tag, such as FLAG or 6-His, permitting rapid, single-step, affinity-based purification of recombinant fusion protein from crude cell lysates. GST, a 26-kilodalton enzyme from Schistosoma japonicum, enables the purification of fusion proteins on immobilized glutathione under conditions that maintain protein activity and antigenicity (Amersham Pharmacia Biotech). Following purification, the GST moiety can be proteolytically cleaved from KAP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch. 10 and 16). Purified KAP obtained by these methods can be used directly in the assays shown in Examples XVI, XVII, XVIII, XIX, XX, and XXI where applicable.

XIII. Functional Assays

KAP function is assessed by expressing the sequences encoding KAP at physiologically elevated levels in mammalian cell culture systems. cDNA is subcloned into a mammalian expression vector containing a strong promoter that drives high levels of cDNA expression. Vectors of choice include PCMV SPORT (Life Technologies) and PCR3.1 (Invitrogen, Carlsbad Calif.), both of which contain the cytomegalovirus promoter. 5–10 µg of recombinant vector are transiently transfected into a human cell line, for example, an endothelial or hematopoietic cell line, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (CM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of KAP on gene expression can be assessed using highly purified populations of cells transfected with sequences encoding KAP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding KAP and other genes of interest can be analyzed by northern analysis or microarray techniques.

XIV. Production of KAP Specific Antibodies

KAP substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the KAP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides of about 15 residues in length are synthesized using an ABI 431A peptide synthesizer (Applied Biosystems) using FMOC chemistry and coupled to KLH (Sigma-Aldrich, St. Louis Mo.) by reaction with N-malemidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant Resulting antisera are tested for antipeptide and anti-KAP activity by, for example, binding the peptide or KAP to a substrate, blocking with 1% BSA, reacting with rabbit antisera, washing, and reacting with radio-iodinated goat anti-rabbit IgG.

XV. Purification of Naturally Occurring KAP Using Specific Antibodies

Naturally occurring or recombinant KAP is substantially purified by immunoaffinity chromatography using antibodies specific for KAP. An immunoaffinity column is constructed by covalently coupling anti-KAP antibody to an activated chromatographic resin, such as CNBr-activated SEPHAROSE (Amersham Pharmacia Biotech). After the coupling, the resin is blocked and washed according to the manufacturer's instructions.

Media containing KAP are passed over the immunoaffinity column, and the column is washed under conditions that allow the preferential absorbance of KAP (e.g., high ionic strength buffers in the presence of detergent). The column is eluted under conditions that disrupt antibody/KAP binding (e.g., a buffer of pH 2 to pH 3, or a high concentration of a chaotrope; such as urea or thiocyanate ion), and KAP is collected.

XVI. Identification of Molecules which Interact with KAP

KAP, or biologically active fragments thereof, are labeled with $^{125}$I Bolton-Hunter reagent. (See, e.g., Bolton, A. E. and W. H. Hunter (1973) Biochem. J. 133:529–539.) Candidate molecules previously arrayed in the wells of a multi-well plate are incubated with the labeled KAP, washed, and any wells with labeled KAP complex are assayed. Data obtained using different concentrations of KAP are used to calculate values for the number, affinity, and association of KAP with the candidate molecules.

Alternatively, molecules interacting with KAP are analyzed using the yeast two-hybrid system as described in Fields, S. and O. Song (1989) Nature 340:245–246, or using commercially available kits based on the two-hybrid system, such as the MATCHMAKER system (Clontech).

KAP may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVII. Demonstration of KAP Activity

Generally, protein kinase activity is measured by quantifying the phosphorylation of a protein substrate by KAP in the presence of [γ-$^{32}$P]ATP. KAP is incubated with the protein substrate, $^{32}$P-ATP, and an appropriate kinase buffer. The $^{32}$P incorporated into the substrate is separated from free $^{32}$P-ATP by electrophoresis and the incorporated $^{32}$P is counted using a radioisotope counter. The amount of incorporated $^{32}$P is proportional to the activity of KAP. A determination of the specific amino acid residue phosphorylated is made by phosphoamino acid analysis of the hydrolyzed protein.

In one alternative, protein kinase activity is measured by quantifying the transfer of gamma phosphate from adenosine triphosphate (ATP) to a serine, threonine or tyrosine residue in a protein substrate. The reaction occurs between a protein kinase sample with a biotinylated peptide substrate and gamma $^{32}$P-ATP. Following the reaction, free avidin in solution is added for binding to the biotinylated $^{32}$P-peptide product. The binding sample then undergoes a centrifugal ultrafiltration process with a membrane which will retain the product-avidin complex and allow passage of free gamma $^{32}$P-ATP. The reservoir of the centrifuged unit containing the $^{32}$P-peptide product as retentate is then counted in a scintillation counter. This procedure allows the assay of any type of protein kinase sample, depending on the peptide substrate and kinase reaction buffer selected. This assay is provided in kit form (ASUA, Affinity Ultrafiltration Separation Assay, Transbio Corporation, Baltimore Md., U.S. Pat. No. 5,869, 275). Suggested substrates and their respective enzymes include but are not limited to: Histone H1 (Sigma) and p34$^{cdc2}$kinase, Annexin I, Angiotensin (Sigma) and EGF receptor kinase, Annexin II and src kinase, ERK1 & ERK2 substrates and MEK, and myelin basic protein and ERK (Pearson, J. D. et al. (1991) Methods Enzymol. 200:62–81).

In another alternative, protein kinase activity of KAP is demonstrated in an assay containing KAP, 50 μl of kinase buffer, 1 μg substrate, such as myelin basic protein (MBP) or synthetic peptide substrates, 1 mM DTT, 10 μg ATP, and 0.5 μCi [γ-$^{32}$P]ATP. The reaction is incubated at 30° C. for 30 minutes and stopped by pipetting onto P81 paper. The unincorporated [γ-$^{32}$P]ATP is removed by washing and the incorporated radioactivity is measured using a scintillation counter. Alternatively, the reaction is stopped by heating to 100° C. in the presence of SDS loading buffer and resolved on a 12% SDS polyacrylamide gel followed by autoradiography. The amount of incorporated $^{32}$P is proportional to the activity of KAP.

In yet another alternative, adenylate kinase or guanylate kinase activity of KAP may be measured by the incorporation of $^{32}$P from [γ-$^{32}$P]ATP into ADP or GDP using a gamma radioisotope counter. KAP, in a kinase buffer, is incubated together with the appropriate nucleotide monophosphate substrate (AMP or GMP) and $^{32}$P-labeled ATP as the phosphate donor. The reaction is incubated at 37° C. and terminated by addition of trichloroacetic acid. The acid extract is neutralized and subjected to gel electrophoresis to separate the mono, di-, and triphosphonucleotide fractions. The diphosphonucleotide fraction is excised and counted. The radioactivity recovered is proportional to the activity of KAP.

In yet another alternative, other assays for KAP include scintillation proximity assays (SPA), scintillation plate technology and filter binding assays. Useful substrates include recombinant proteins tagged with glutathione transferase, or synthetic peptide substrates tagged with biotin. Inhibitors of KAP activity, such as small organic molecules, proteins or peptides, may be identified by such assays.

In another alternative, phosphatase activity of KAP is measured by the hydrolysis of para-nitrophenyl phosphate (PNPP). KAP is incubated together with PNPP in HEPES buffer pH 7.5, in the presence of 0.1% β-mercaptoethanol at 37° C. for 60 min. The reaction is stopped by the addition of 6 ml of 10 N NaOH (Diamond, R. H. et al. (1994) Mol. Cell. Biol. 14:3752–62). Alternatively, acid phosphatase activity of KAP is demonstrated by incubating KAP-containing extract with 100 μl of 10 mM PNPP in 0.1 M sodium citrate, pH 4.5, and 50 μl of 40 mM NaCl at 37° C. for 20 min. The reaction is stopped by the addition of 0.5 ml of 0.4 M glycine/NaOH, pH 10.4 (Saftig, P. et al. (1997) J. Biol. Chem 272:18628–18635). The increase in light absorbance at 410 nm resulting from the hydrolysis of PNPP is measured using a spectrophotometer. The increase in light absorbance is proportional to the activity of KAP in the assay.

In the alternative, KAP activity is determined by measuring the amount of phosphate removed from a phosphorylated protein substrate. Reactions are performed with 2 or 4 nM KAP in a final volume of 30 μl containing 60 mM Tris, pH 7.6, 1 mM EDTA, 1 mM EGTA, 0.1% β-mercaptoethanol and 10 μM substrate, $^{32}$P-labeled on serine/threonine or tyrosine, as appropriate. Reactions are initiated with substrate and incubated at 30° C. for 10–15 min. Reactions are quenched with 450 μl of 4% (w/v) activated charcoal in 0.6

M HCl, 90 mM $Na_4P_2O_7$, and 2 mM $NaH_2PO_4$, then centrifuged at 12,000×g for 5 min. Acid-soluble $^{32}Pi$ is quantified by liquid scintillation counting (Sinclair, C. et al. (1999) J. Biol. Chem. 274:23666–23672).

XVIII. Kinase Binding Assay

Binding of KAP to a FLAG-CD44 cyt fusion protein can be determined by incubating KAP with anti-KAP-conjugated immunoaffinity beads followed by incubating portions of the beads (having 10–20 ng of protein) with 0.5 ml of a binding buffer (20 mM Tris-HCL (pH 7.4), 150 mM NaCl, 0.1% bovine serum albumin, and 0.05% Triton X-100) in the presence of $^{125}I$-labeled FLAG-CD44cyt fusion protein (5,000 cpm/ng protein ) at 4° C. for 5 hours. Following binding, beads were washed thoroughly in the binding buffer and the bead-bound radioactivity measured in a scintillation counter (Bourguignon, L. Y. W. et al. (2001) J. Biol. Chem 276:7327–7336). The amount of incorporated $^{32}P$ is proportional to the amount of bound KAP.

XIX. Identification of KAP Inhibitors

Compounds to be tested are arrayed in the wells of a 384-well plate in varying concentrations along with an appropriate buffer and substrate, as described in the assays in Example XVII. KAP activity is measured for each well and the ability of each compound to inhibit KAP activity can be determined, as well as the dose-response kinetics. This assay could also be used to identify molecules which enhance KAP activity.

XX. Identification of KAP Substrates

A KAP "substrate-trapping" assay takes advantage of the increased substrate affinity that may be conferred by certain mutations in the PTP signature sequence of protein tyrosine phosphatases. KAP bearing these mutations form a stable complex with their substrate; this complex may be isolated biochemically. Site-directed mutagenesis of invariant residues in the PTP signature sequence in a clone encoding the catalytic domain of KAP is performed using a method standard in the art or a commercial kit, such as the MUTA-GENE kit from BIO-RAD. For expression of KAP mutants in *Escherichia coli,* DNA fragments containing the mutation are exchanged with the corresponding wild-type sequence in an expression vector bearing the sequence encoding KAP or a glutathione S-transferase (GST)-KAP fusion protein. KAP mutants are expressed in *E. coli* and purified by chromatography.

The expression vector is transfected into COS1 or 293 cells via calcium phosphate-mediated transfection with 20 μg of CsCl-purified DNA per 10-cm dish of cells or 8 μg per 6cm dish. Forty-eight hours after transfection, cells are stimulated with 100 ng/ml epidermal growth factor to increase tyrosine phosphorylation in cells, as the tyrosine kinase EGFR is abundant in COS cells. Cells are lysed in 50 mM TrisHCl, pH 7.5/5 mM EDTA/150 mM NaCl/1% Triton X-100/5 mM iodoacetic acid/10 mM sodium phosphate/10 mM NaF/5 μg/ml leupeptin/5 μg/ml aprotinin/1 mM benza midine (1 ml per 10-cm dish, 0.5 ml per 6-cm dish). KAP is immunoprecipitated from lysates with an appropriate antibody. GST-KAP fusion proteins are precipitated with glutathione-Sepharose, 4 μg of mAb or 10 μl of beads respectively per mg of cell lysate. Complexes can be visualized by PAGE or further purified to identify substrate molecules (Flint, A. J. et al. (1997) Proc. Natl. Acad. Sci. USA 94:1680–1685).

XXI. Enhancement/Inhibition of Protein Kinase Activity

Agonists or antagonists of KAP activation or inhibition may be tested using assays described in section XVII. Agonists cause an increase in KAP activity and antagonists cause a decrease in KAP activity.

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Incyte Project ID | Polypeptide SEQ ID NO: | Incyte Polypeptide ID | Polynucleotide SEQ ID NO: | Incyte Polynucleotide ID |
|---|---|---|---|---|
| 4615110 | 1 | 4615110CD1 | 21 | 4615110CB1 |
| 4622229 | 2 | 4622229CD1 | 22 | 4622229CB1 |
| 72358203 | 3 | 72358203CD1 | 23 | 72358203CB1 |
| 4885040 | 4 | 4885040CD1 | 24 | 4885040CB1 |
| 7484507 | 5 | 7484507CD1 | 25 | 7484507CB1 |
| 7198931 | 6 | 7198931CD1 | 26 | 7198931CB1 |
| 7482905 | 7 | 7482905CD1 | 27 | 7482905CB1 |
| 7483019 | 8 | 7483019CD1 | 28 | 7483019CB1 |
| 5455490 | 9 | 5455490CD1 | 29 | 5455490CB1 |
| 5547067 | 10 | 5547067CD1 | 30 | 5547067CB1 |
| 71675660 | 11 | 71675660CD1 | 31 | 71675660CB1 |
| 71678683 | 12 | 71678683CD1 | 32 | 71678683CB1 |
| 7474567 | 13 | 7474567CD1 | 33 | 7474567CB1 |
| 3838946 | 14 | 3838946CD1 | 34 | 3838946CB1 |
| 72001176 | 15 | 72001176CD1 | 35 | 72001176CB1 |
| 55064363 | 16 | 55064363CD1 | 36 | 55064363CB1 |
| 7482044 | 17 | 7482044CD1 | 37 | 7482044CB1 |
| 7476595 | 18 | 7476595CD1 | 38 | 7476595CB1 |
| 71824382 | 19 | 71824382CD1 | 39 | 71824382CB1 |
| 3566882 | 20 | 3566882CD1 | 40 | 3566882CB1 |

TABLE 2

| Polypeptide SEQ ID NO: | Incyte Polypeptide ID | GenBank ID NO: or PROTEOME ID NO: | Probability Score | Annotation |
|---|---|---|---|---|
| 1 | 4615110CD1 | g3598974 | 0 | [*Rattus norvegicus*] protein tyrosine phosphatase TD14. Cao, L. et al. (1998) J. Biol. Chem. 273: 21077–21083 |
| 2 | 4622229CD1 | g4079673 | 0 | myotubularin related 1 [*Homo sapiens*]. Kioschis, P. et al. (1998) Genomics 54: 256–266 |
| 3 | 72358203CD1 | g7768151 | 6.40E−17 | Protein phosphatase 2C (PP2C) [*Fagus sylvatica*]. |
| 4 | 4885040CD1 | g6468206 | 1.20E−119 | [*Mus musculus*] thiamin pyrophosphokinase. Nosaka, K. et al. (1999) J. Biol. Chem. 274: 34129–34133 |
| 5 | 7484507CD1 | g7649810 | 7.20E−14 | [*Homo sapiens*] protein kinase PAK5 |
| 6 | 7198931CD1 | g2815888 | 0 | [*Homo sapiens*] MEK kinase 1. Xia, Y. et al. (1998) Genes Dev. 12: 3369–3381 |
| 7 | 7482905CD1 | g256855 | 2.10E−161 | [Mus sp.] serine/threonine-and tyrosine-specific protein kinase, Nek1 = NIMA cell cycle regulator homolog. Letwin, K., et al. (1992) EMBO J. 11: 3521–3531 |
| 8 | 7483019CD1 | g6552404 | 8.40E−197 | [*Rattus norvegicus*] DLG6 alpha. Inagaki, H. et al. (1999) Biochem. Biophys. Res. Commun. 265: 462–468 |
| 9 | 5455490CD1 | g406058 | 0 | protein kinase [*Mus musculus*]. (Walden, P. D. and Cowan, N. J. (1993) Mol. Cell. Biol. 13: 7625–7635) |
| 10 | 5547067CD1 | g1033033 | 5.90E−41 | ribosomal S6 kinase [*Homo sapiens*]. (Zhao, Y. et al. (1995) Mol. Cell. Biol. 15: 4353–4363) |
| 11 | 71675660CD1 | g2738898 | 9.40E−175 | protein kinase [*Mus musculus*]. (Kueng, P. et al. (1997) J. Cell Biol. 139: 1851–1859) |
| 12 | 71678683CD1 | g2738898 | 4.00E−174 | protein kinase [*Mus musculus*]. (Kueng, P. et al. (1997) J. Cell Biol. 139: 1851–1859) |
| 13 | 7474567CD1 | p6723964 | 2.50E−72 | putative serine/threonine protein kinase [*Schizosaccharomyces pombe*] |
| 14 | 3838946CD1 | g4982155 | 2.80E−53 | glycerate kinase, putative [*Thermotoga maritima*]. (Nelson, K. E. et al. (1999) Nature 399: 323–329) |
| 15 | 72001176CD1 | g11177010 | 5.70E−232 | casein kinase 1 gamma 1L [*Homo sapiens*] |
| 16 | 55064363CD1 | g1679668 | 0 | Mitogen-activated kinase kinase kinase 5 [*Homo sapiens*] (Wang, X. S. et al. (1996) J. Biol. Chem. 271: 31607–31611) |
| 17 | 7482044CD1 | g11527775 | 0 | Mitogen-activated protein kinase kinase kinase [*Homo sapiens*] |
| 18 | 7476595CD1 | g406058 | 0 | [*Mus musculus*] protein kinase. Walden, P. D. and Cowan, N. J. (1993) A Novel 205-kDa Testis-specific Serine/Threonine Protein Kinase Associated with Microtubules of the Spermatid Manchette. Mol. Cell. Biol. 13, 7625–7635 |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 4615110CD1 | 1636 | S86 S101 S136 S193 S275 S311 S429 S455 S487 S546 S645 S869 S1056 S1122 S1218 S1231 S1238 S1247 S1290 S1322 S1342 S1475 S1506 S1533 S1575 S1593 S1625 T95 T293 T352 T434 T450 T486 T511 T882 T1068 T1144 T1269 T1305 T1328 T1354 Y272 Y320 Y1165 Y1229 | N652 N1245 N1634 | Protein-tyrosine phosphatase: Y1217-R1451 | HMMER_PFAM |
| | | | | | Tyrosine specific protein phosphatases proteins BL00383: K1220-V1234, D1241-V1249, D1272-V1282, H1349-P1361, V1390-G1400, R1429-F1444 | BLIMPS_BLOCKS |
| | | | | | Tyrosine specific protein phosphatases signature and profiles: L1367-M1428 | PROFILESCAN |
| | | | | | Protein tyrosine phosphatase signature PR00700: D1242-V1249, I1259-E1279, R1345-D1362, P1387-L1405, P1419-H1434, M1435-C1445 | BLIMPS_PRINTS |
| | | | | | PROTEIN TYROSINE PHOSPHATASE TD14 EC 3.1.3.48 HYDROLASE PD180360: F967-L1219 | BLAST_PRODOM |
| | | | | | PROTEIN TYROSINE PHOSPHATASE TD14 EC 3.1.3.48 HYDROLASE PD184907: K713-G952 | BLAST_PRODOM |
| | | | | | PROTEIN TYROSINE PHOSPHATASE TD14 EC 3.1.3.48 HYDROLASE PD169419: A1567-T1636 | BLAST_PRODOM |
| | | | | | PROTEIN-TYROSINE-PHOSPHATASE DM00089|P17706|4-277: K1220-V1450 | BLAST_DOMO |
| | | | | | PROTEIN-TYROSINE-PHOSPHATASE DM00089|P26045|632-904: K1220-Q1455 | BLAST_DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | PROTEIN-TYROSINE-PHOSPHATASE DM00089\|P29074\|641–914: K1220-Q1455 | BLAST_DOMO |
| | | | | | PROTEIN-TYROSINE-PHOSPHATASE DM00089\|P43378\|285–577: K1220-Q1455 | BLAST_DOMO |
| | | | | | Tyrosine specific protein phosphatases active site: V1390-F1402 | MOTIFS |
| 2 | 4622229CD1 | 673 | S53 S113 S163 S172 S225 S253 S261 S278 S342 S354 S391 S402 S410 S437 S525 S575 S600 S654 S656 T136 T334 T358 T470 T476 T536 Y331 Y400 Y563 | N78 N251 N359 | Transmembrane domains: W517-S543; N-terminus is cytosolic | TMAP |
| | | | | | Tyrosine specific protein phosphatases proteins BL00383: W570-D578, Q511-R521, V444-A454 | BLIMPS_ BLOCKS |
| | | | | | Tyrosine specific protein phosphatases signature and profiles: L424-K480 | PROFILESCAN |
| | | | | | HYDROLASE PROTEIN MYOTUBULARIN DISEASE MUTATION F53A2.8 PROTEIN TYROSINE PHOSPHATASE C19A8.03 CPA2NNF1 PD014611: C178-Y372, D504-H591 | BLAST_ PRODOM |
| | | | | | MYOTUBULARIN DISEASE MUTATION HYDROLASE PD144999: H601-T671 | BLAST_ PRODOM |
| | | | | | Tyrosine specific protein phosphatases active site: V444-L456 | MOTIFS |
| 3 | 72358203CD1 | 459 | S50, T257, T278, S306, T364, S430, S438 | | Protein phosphatase 2C: Q326-K415, L187-L265 | HMMER-PFAM |
| | | | | | Protein phosphatase 2C: BL01032: Y120-G129, L187-G204, G214-S223, N232-E271, R328-D341, D376-D388 | BLIMPS_ BLOCKS |
| | | | | | PROTEIN PHOSPHATASE 2C MAGNESIUM HYDROLASE MANGANESE MULTIGENE FAMILY PP2C ISOFORM: PD001101: G322-L403, Y120-D289 | BLAST_ PRODOM |
| | | | | | PROTEIN PHOSPHATASE 2C: DM00377\|P49596\|1–295: A191-I262, R328-S456, Y120-E149 | BLAST-DOMO |
| 4 | 4885040CD1 | 243 | S74 S92 T6 T56 T176 | N203 | Ribokinase signature PR00990 V121-F132 | BLIMPS_ PRINTS |
| | | | | | THIAMIN PYROPHOSPHOKINASE PUTATIVE TPK KINASE, PD106295: H170-M239; PD036502: L21-Q144 | BLAST_ PRODOM |
| 5 | 7484507CD1 | 632 | S6 S20 S114 S212 S231 S244 S251 S283 S300 S318 S504 S575 S587 S601 S607 T12 T183 T258 T269 T287 T338 T418 | N208 | Eukaryotic protein kinase domain: V55-L173, W201-L297 | HMMER_PFAM |
| | | | | | Transmembrane domains: E421-N448 M472-G487, N terminus cytosolic | TMAP |
| | | | | | Tyrosine kinase catalytic domain PROO109, Y147-L165, F197-L207, S215-E237 | BLIMPS_ PRINTS |
| | | | | | PHOSPHORYLASE KINASE ALP PD01841: L422-L458, A464-I505, G567-L603, E23-E72, L142-E193 | BLIMPS_ PRODOM |
| | | | | | PROTEIN KINASE DOMAIN DM00004; P51955\|10–261: V30-M233; S43968\|28–311: Q33-K289, R271-I288 A55480\|28–320: Q33-K289, R271-L297; P49186\|28–320: Q33-K289, R271-L297 | BLAST_DOMO |
| 6 | 7198931CD1 | 1511 | S35 S118 S232 S258 S275 S281 S300 S394 S397 S398 S429 S434 S507 S514 S531 S588 S669 S782 S816 S823 S900 S923 S928 S1025 S1038 S1087 S1088 S1129 S1130 S1281 T20 | N346 N540 N744 N806 N1068 N1085 N1099 N1128 N1278 N1347 | Eukaryotic protein kinase domain: W1242-F1507 | HMMER_PFAM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | T169 T261 T304 T379 T457 T657 T705 T911 T946 T996 T1020 T1069 T1113 T1147 T1165 T1279 Y1166 | | | |
| | | | | | Transmembrane domains: S348-L368, A1392-L1420; N-terminus is cytosolic | TMAP |
| | | | | | Protein kinases signatures and profile: V1344-G1398 | PROFILESCAN |
| | | | | | Tyrosine kinase catalytic domain signature PR00109: L1476-S1498, Y1358-I1376, G1410-L1420, C1429-E1451 | BLIMPS__ PRINTS |
| | | | | | MAPK/ERK KINASE 1 EC 2.7.1. MEK MEKK TRANSFERASE SERINE/THREONINE PROTEIN ATP BINDING PHOSPHORYLATION PD144583: M1-E601 | BLAST__ PRODOM |
| | | | | | MAPK/ERK KINASE 1 EC 2.7.1. MEK MEKK TRANSFERASE SERINE/THREONINE PROTEIN ATP BINDING PHOSPHORYLATION PD146039: Q624-Q1247 | BLAST__ PRODOM |
| | | | | | PROTEIN KINASE DOMAIN DM00004\|P53349\|405–658: K1244-S1498 | BLAST__DOMO |
| | | | | | PROTEIN KINASE DOMAIN DM00004\|A48084\|98–348: K1244-R1495 | BLAST__DOMO |
| | | | | | PROTEIN KINASE DOMAIN DM00004\|Q01389\|1176–1430: L1243-P1496 | BLAST__DOMO |
| | | | | | PROTEIN KINASE DOMAIN DM00004\|Q10407\|826–1084: L1243-L1488 | BLAST__DOMO |
| | | | | | Protein kinases ATP-binding region signature: I1248-K1271 | MOTIFS |
| | | | | | Serine/Threonine protein kinases active-site signature: I1364-I1376 | MOTIFS |
| 7 | 7482905CD1 | 830 | S54 S179 S260 S279 S280 S327 S352 S370 S378 S440 S457 S525 S545 S580 S624 S664 S698 S708 S741 S747 T267 T354 T358 T403 T481 T490 T512 T634 T640 T674 | N159 N303 N401 N540 N715 | signal_cleavage: M1-S54 | SPSCAN |
| | | | | | SERINE/THREONINE PROTEIN KINASE NEK1 EC 2.7.1. NIMA RELATED PROTEIN 1 TRANSFERASE ATP BINDING MITOSIS NUCLEAR PHOSPHORYLATION CELL CYCLE DIVISION TYROSINE PROTEIN PD144030: M1-L394 | BLAST__ PRODOM |
| 8 | 7483019CD1 | 455 | S142 S200 S208 S242 S308 S374 S421 S450 T16 T280 T283 Y307 Y317 Y359 | N419 | Guanylate kinase: T281-Y385 | HMMER__PFAM |
| | | | | | PDZ domain: I3-V83 | HMMER__PFAM |
| | | | | | Guanylate kinase protein BL00856: | BLIMPS__ BLOCKS |
| | | | | | SH3 domain signature PR00452: A115-Q130, D132-I141, C147-R159 | BLIMPS__ PRINTS |
| | | | | | PROTEIN DOMAIN SH3 KINASE GUANYLATE TRANSFERASE ATP BINDING REPEAT GMP MEMBRANE PD001338: T280-Q373 | BLAST__ PRODOM |
| | | | | | PROTEIN MAGUK P55 SUBFAMILY MEMBER MPP3 DISCS LARGE HOMOLOG SH3 PD090357: P169-T280 | BLAST__ PRODOM |
| | | | | | PROTEIN MAGUK P55 SUBFAMILY MEMBER DISCS LARGE HOMOLOG SH3 DOMAIN PD152180: V94-Q161 | BLAST__ PRODOM |
| | | | | | GUANYLATE KINASE DM00755\|A57653\|370–570: P241-P444 | BLAST__DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | GUANYLATE KINASE DM00755\|P54936\|769–955: R246-K372, M388-P444 | BLAST_DOMO |
| | | | | | GUANYLATE KINASE DM00755\|I38757\|709–898: R246-P444 | BLAST_DOMO |
| | | | | | GUANYLATE KINASE DM00755\|P31007\|765–954: R246-P444 | BLAST_DOMO |
| | | | | | Guanylate kinase signature: T280-V297 | MOTIFS |
| 9 | 5455490CD1 | 1720 | S75 S82 S86 S115 S119 S140 S152 S175 S203 S402 S425 S430 S455 S697 S728 S733 S739 S747 S768 S776 S782 S796 S831 S836 S853 S1006 S1022 S1117 S1127 S1136 S1147 S1151 S1152 S1178 S1194 S1254 S1259 S1340 S1347 S1351 S1369 S1381 S1413 S1425 S1426 S1463 S1572 S1579 S1582 S1593 S1620 S1639 S1693 T188 T428 T436 T487 T503 T651 T681 T708 T737 T793 T838 T847 T871 T936 T958 T962 T1039 T1111 T1158 T1166 T1346 T1402 T1597 T1687 | N1115 N1174 N1215 | Signal Peptide: M1-S68 | SPSCAN |
| | | | | | Signal Peptide: M31-S56 | HMMER |
| | | | | | PDZ domain (or DHR, or GLGF): P1026-L1113 | HMMER_PFAM |
| | | | | | Eukaryotic protein kinase domain: F434-F707 | HMMER_PFAM |
| | | | | | Transmembrane domains: V328-E350, D629-F647; N terminus is cytosolic. | TMAP |
| | | | | | Protein kinases signatures and profile: F501-I581 | PROFILESCAN |
| | | | | | Tyrosine kinase catalytic domain sig. PR00109: M511-K524, Y547-I565, V628-D650 | BLIMPS_ PRINTS |
| | | | | | MICROTUBULE ASSOCIATED TESTIS SPECIFIC SERINE/THREONINE KINASE PD142315: H1235-T1720; PD182663: E785-H1061; PD135564: C83-Y242; PD041650: K243-D433 | BLAST_ PRODOM |
| | | | | | PROTEIN KINASE DOMAIN: DM00004\|A54602\|455–712: T436-G694; DM08046\|P05986\|1–397: S430-K580; DM00004\|S42867\|75–498: I437-T588; DM00004\|S42864\|41–325: E435-K580, H594-T695 | BLAST_DOMO |
| | | | | | Serine/Threonine protein kinases active-site signature: I553-I565 | MOTIFS |
| 10 | 5547067CD1 | 449 | S17 S45 S89 S107 S208 S244 S358 S425 T86 T167 T187 T337 T356 | | Eukaryotic protein kinase domain: L146-F398 | HMMER_PFAM |
| | | | | | Transmembrane domains: S244-R267, D324-P341; N terminus is cytosolic. | TMAP |
| | | | | | Protein kinases signatures and profile: F248-A297 | PROFILESCAN |
| | | | | | Tyrosine kinase catalytic domain signature, PR00109: Y258-L276, G304-L314, A323-E345 | BLIMPS_ PRINTS |
| | | | | | PROTEIN KINASE DOMAIN: DM00004\|A53300\|64–305: L146-L386; DM08046\|P06244\|1–396: Q144-F435; DM00004\|A57459\|61–302: L146-L386; DM00004\|S56639\|153–391: I148-L386 | BLAST_DOMO |
| | | | | | Serine/Threonine protein kinases active-site signature: I264-L276 | MOTIFS |
| 11 | 71675660CD1 | 358 | S31 S158 S258 S284 S349 T48 T340 Y293 | N240 | Eukaryotic protein kinase domain: Y12-L272 | HMMER_PFAM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Transmembrane domain: V196-M224; N terminus is non-cytosolic. | TMAP |
| | | | | | Protein kinases signatures and profile: D111-S165 | PROFILESCAN |
| | | | | | Tyrosine kinase catalytic domain signature: PR00109: M90-K103, Y126-L144, L241-I263 | BLIMPS_PRINTS |
| | | | | | TESTIS SPECIFIC SERINE/ THREONINE KINASE 2 PROTEIN KINASE; PD029090: L272-T358 | BLAST_PRODOM |
| | | | | | PROTEIN KINASE DOMAIN: DM00004|P27448|58–297: L18-L253; DM00004|JC1446|20–261: V14-I263; DM00004|S24578|18–262: V14-I263; DM00004|I48609|55–294: L18-R260 | BLAST_DOMO |
| | | | | | Serine/Threonine protein kinases active-site signature: I132-L144 | MOTIFS |
| | | | | | Protein kinases ATP-binding region signature: L18-K41 | MOTIFS |
| 12 | 71678683CD1 | 358 | S31 S158 S258 S284 S349 T48 T340 Y293 | N240 | Eukaryotic protein kinase domain: Y12-L272 | HMMER_PFAM |
| | | | | | Transmembrane domain: V196-M224; N terminus is non-cytosolic. | TMAP |
| | | | | | Protein kinases signatures and profile: D111-S165 | PROFILESCAN |
| | | | | | Tyrosine kinase catalytic domain signature, PR00109: M90-K103, Y126-L144, G177-L187, Y197-S219, L241-I263 | BLIMPS_PRINTS |
| | | | | | TESTIS SPECIFIC SERINE/THREONINE KINASE 2 PROTEIN KINASE, PD029090: L272-T358 | BLAST_PRODOM |
| | | | | | PROTEIN KINASE DOMAIN: DM00004|P27448|58–297: L18-L253; DM00004|JC1446|20–261: V14-I263; DM00004|S24578|18–262: V14-I263; DM00004|I48609|55–294: L18-R260 | BLAST_DOMO |
| | | | | | Serine/Threonine protein kinases active-site signature: I132-L144 | MOTIFS |
| | | | | | Protein kinases ATP-binding region signature: L18-K41 | MOTIFS |
| 13 | 7474567CD1 | 929 | S56 S85 S171 S207 S483 S660 S677 T53 T57 T245 T313 T401 T440 T555 T608 T658 T679 T712 T722 T737 T760 T765 | N51 N187 N630 N726 N768 N916 | Eukaryotic protein kinase domain: L159-F327, F32-H106 | HMMER_PFAM |
| | | | | | Tyrosine kinase catalytic domain signature, PR00109: L168-L186, S247-V269, I296-A318 | BLIMPS_PRINTS |
| 14 | 3838946CD1 | 523 | S283 S289 S367 S417 T166 T191 T208 T214 Y328 | N487 | Transmembrane domain: E163-L183, N-terminus is non-cytosolic | TMAP |
| | | | | | HYDROXYPYRUVATE REDUCTASE PLASMID OXIDOREDUCTASE NADP PROTEIN GLYCERATE KINASE, PD014236: K131-T357, T357-L520 | BLAST_PRODOM |
| 15 | 72001176CD1 | 459 | S96 S124 S150 S229 S373 T14 T137 T199 T214 T258 T269 T273 T355 T411 T454 | N370 N388 | Eukaryotic protein kinase domain: F44-E276 | HMMER_PFAM |
| | | | | | Transmembrane domain: D133-I161 N-terminus is cytosolic. | TMAP |
| | | | | | Protein kinases signatures and profile: T140-E198 | PROFILESCAN |
| | | | | | CASEIN KINASE I, GAMMA 1 ISOFORM EC 2.7.1. GAMMA TRANSFERASE SERINE/THREONINE ATP BINDING MULTIGENE FAMILY PHOSPHORYLATION; PD049080: M1-N43, PD015080: F315-W379 | BLAST_PRODOM |
| | | | | | PROTEIN KINASE DOMAIN: DM00004|A56711|46–303: V46-Y304; DM00004|C56711|45–301: V46-Y304; DM00004|B56711|48–303: V46-Y304; DM00004|D56406|31–276: V46-V293 | BLAST_DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Protein kinases ATP-binding region signature: I50-K73 | MOTIFS |
| | | | | | Serine/Threonine protein kinases active-site signature: L160-I172 | MOTIFS |
| 16 | 55064363CD1 | 1360 | S23 S56 S212 S253 S338 S382 S432 S486 S550 S609 S625 S632 S655 S677 S762 S843 S934 S991 S1025 S1031 S1040 S1041 S1056 S1084 T48 T205 T218 T428 T466 T545 T685 T796 T842 T887 T893 T945 T983 T1234 T1287 T1314 T1323 Y810 Y1313 | N381 N620 | Eukaryotic protein kinase domain: V704-L955 | HMMER-PFAM |
| | | | | | Transmembrane domains: S445-T466, S1129-V1146; N-terminus is cytosolic | TMAP |
| | | | | | Protein kinases signature: T796-G848 | ProfileScan |
| | | | | | Protein kinases ATP-binding region signature: L705-K728 | MOTIFS |
| | | | | | Serine/Threonine protein kinases active-site signature: I816-V828 | MOTIFS |
| | | | | | Tyrosine kinase catalytic domain signature PR00109: M773-R786, Y810-V828, G858-I868, A879-L901, L924-T946 | BLIMPS-PRINTS |
| | | | | | Kinase, apoptosis, ASK1, MEK signal-regulating, mitogen-activated, MEKK5, MAP/ERK, MAPKKK5 PD018410: V75-N620 | BLAST_PRODOM |
| | | | | | Kinase, apoptosis, ASK1, MEK signal-regulating, mitogen-activated, MEKK5, MAP/ERK, MAPKKK5 PD014104: P982-G1205 | BLAST_PRODOM |
| | | | | | Kinase, apoptosis, ASK1, MEK signal-regulating, mitogen-activated, MEKK5, MAP/ERK, MAPKKK5 PD024456: E1215-R1348 | BLAST_PRODOM |
| | | | | | Kinase, apoptosis, ASK1, MEK signal-regulating, mitogen-activated, MEKK5, MAP/ERK, MAPKKK5 PD012471: F621-D697 | BLAST_PRODOM |
| | | | | | Protein kinase domains: DM00004|A48084|98–348: V704-R943; DM00004|Q01389|1176–1430: V704-T945; DM00004|Q10407|826–1084: V704-T945; DM00004|P41892|11–249: L705-T946 | BLAST-DOMO |
| 17 | 7482044CD1 | 1345 | S31 S35 S191 S250 S323 S338 S517 S600 S625 S1131 S1160 S1165 T67 T136 T154 T174 T203 T218 T268 T333 T396 T459 T492 T1161 T1201 T1231 T1251 T1273 T1294 Y428 | | Eukaryotic protein kinase domain: L181-F439 | HMMER-PFAM |
| | | | | | Transmembrane domain: A868-A890; N-terminus is cytosolic | TMAP |
| | | | | | Protein kinases signature: L284-F339 | ProfileScan |
| | | | | | Serine/Threonine protein kinases active-site signature: I305-I317 | MOTIFS |
| | | | | | Leucine zipper pattern: L826-L847 | MOTIFS |
| | | | | | Protein kinase domains: DM00004|A48084|98–348: V704-R943; DM00004|Q01389|1176–1430: V704-T945; DM00004|Q10407|826–1084: V704-T945; DM00004|P41892|11–249: L705-T946; DM00004|P51957|8–251: L187-R427, DM00004|P41892|11–249: L187-V395, DM00004|Q05609|553–797: E186-C419 | BLAST-DOMO |
| 18 | 7476595CD1 | 2038 | S18 S28 S324 S329 S335 S365 S407 S448 S536 S562 S647 S657 S666 S669 S674 S680 S707 S721 S728 | N16 N645 N703 N740 N1266 N1282 N1473 | PDZ domain (Also known as DHR or GLGF): Q555-F643 | HMMER_PFAM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | S731 S780 S785 S871 S878 S882 S895 S903 S930 S938 S974 S1000 S1007 S1027 S1073 S1109 S1182 S1199 S1231 S1262 S1270 S1278 S1305 S1340 S1389 S1398 S1514 S1517 S1574 S1583 S1590 S1606 S1629 S1650 S1660 S1745 S1863 S1879 S1899 S1913 S1938 S1960 S2028 T32 T83 T99 T247 T333 T343 T349 T435 T465 T511 T569 T641 T695 T886 T1059 T1079 T1177 T1184 T1321 T1327 T1395 T1407 T1420 T1436 T1554 T1692 T1753 T1769 T1780 T1790 T1844 T1931 T1971 T2006 Y1794 | | | |
| | | | | | Eukaryotic protein kinase domain: F30-F303 | HMMER_PFAM |
| | | | | | TMAP: D225-F243; N-terminus is cytosolic | TMAP |
| | | | | | Protein kinases signatures and profile protein: F97-V177 | PROFILESCAN |
| | | | | | Tyrosine kinase catalytic domain signature PR00109: M107-K120, Y143-V161, V224-D246, P269-T291 | BLIMPS_PRINTS |
| | | | | | MICROTUBULE ASSOCIATED TESTIS SPECIFIC SERINE/THREONINE PROTEIN KINASE 205 KD TESTISSPECIFIC SERINE/THREONINE PROTEIN KINASE MAST205 KINASE, PD142315: H760-A1021, P1578-P1716, P1498-P1609, PD069998: T639-D734, PD182663: E499-N591 | BLAST_PRODOM |
| | | | | | PROTEIN KINASE SERINE/THREONINE KIN4 MICROTUBULE ASSOCIATED TESTIS SPECIFIC TESTISSPECIFIC MAST205, PD040805: L306-N374 | BLAST_PRODOM |
| | | | | | PROTEIN KINASE DOMAIN; DM00004\|A54602\|455-712: T32-G290; DM00004\|S42867\|75-498: I33-K176, H190-F331; DM08046\|P05986\|1-397: S28-K176, V203-D351; DM08046\|P06244\|1-396: D29-K176, V203-F354 | BLAST_DOMO |
| | | | | | ATP/GTP-binding site motif A (P-loop): A1450-T1457 | MOTIFS |
| | | | | | Serine/Threonine protein kinases active-site signature: I149-V161 | MOTIFS |
| 19 | 71824382CD1 | 1770 | S167 S286 S344 S364 S369 S411 S459 S475 S507 S555 S616 S705 S750 S752 S781 S813 S877 S884 S917 S926 S940 S977 S997 S1013 S1193 S1322 S1334 S1357 S1457 S1568 S1583 S1658 S1673 S1694 S1702 S1731 S1751 T30 T64 T423 T591 T624 T691 T746 T780 T788 T959 T1011 T1032 | N560 N792 N854 N1680 N1739 N1742 | CNH domain: K1266-K1550 | HMMER_PFAM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | T1050 T1121 T1223 T1293 T1543 T1763 Y358 Y1252 | | | |
| | | | | | Phorbol esters/diacylglycerol binding domain: H1051-C1100 | HMMER_PFAM |
| | | | | | PH domain: T1121-K1239 | HMMER_PFAM |
| | | | | | Eukaryotic protein kinase domain: F77-F343 | HMMER_PFAM |
| | | | | | Protein kinase C terminal domain: S344-D372 | HMMER_PFAM |
| | | | | | Phorbol esters/diacylglycerol binding domain dag_pe_binding_domain: C1064-A1122 | PROFILESCAN |
| | | | | | Tyrosine kinase catalytic domain signature PR00109: M154-S167, S191-M209, C263-E285 | BLIMPS_PRINTS |
| | | | | | Domain found in NIK1-lik PF00780B: I738-T780 PF00780F: T1050-A1096 PF00780G: K1195-H1238 FF00780I: M1485-N1514 | BLIMPS_PFAM |
| | | | | | MYTONIC DYSTROPHY KINASE-RELATED CDC42-BINDING KINASE PHORBOLESTER BINDING KIAA0451 PROTEIN PD143271: R1643-P1770 | BLAST_PRODOM |
| | | | | | MYTONIC DYSTROPHY KINASE-RELATED CDC42-BINDING KINASE PHORBOLESTER BINDING PD075023: E630-N713 | BLAST_PRODOM |
| | | | | | PHORBOLESTER BINDING KINASE DYSTROPHY KINASE-RELATED CDC42-BINDING SIMILAR SERINE/THREONINE PROTEIN GENGHIS KHAN PD150840: W1518-S1642 | BLAST_PRODOM |
| | | | | | PHORBOLESTER BINDING DYSTROPHY KINASE-RELATED CDC42-BINDING KINASE GENGHIS KHAN MYTONIC MYOTONIC PD011252: D833-F967 | BLAST_PRODOM |
| | | | | | PROTEIN KINASE DOMAIN DM00004; |Q09013|83–336: I79-Q331; |S42867|75–498: I79-L226, V238-Y404, P1653-D1728; |I38133|90–369: E78-L226, V238-G330; |P53894|353–658: L80-G221, D205-Q331 | BLAST_DOMO |
| | | | | | Leucine zipper pattern L772-L793 L779-L800 L786-L807 | MOTIFS |
| | | | | | C-type lectin domain signature C1067-C1088 | MOTIFS |
| | | | | | Phorbol esters/diacylglycerol binding domain H1051-C1100 | MOTIFS |
| | | | | | Protein kinases ATP-binding region signature I83-K106 | MOTIFS |
| | | | | | Serine/Threonine protein kinases active-site signature Y197-M209 | MOTIFS |
| 20 | 3566882CD1 | 720 | S91 S117 S146 S148 S264 S268 S299 S690 S697 T17 T166 T398 Y314 | | Ank repeat: E448-R480, D382-R414, V580-Q612, E415-A447, N481-Q513, S349-E381, Q547-A579, S613-K645, V646-G678 | HMMER_PFAM |
| | | | | | Eukaryotic protein kinase domain: S156-P231 | HMMER_PFAM |
| | | | | | Transmembrane domain: S146-Y171 | TMAP |
| | | | | | Tyrosine kinase catalytic domain signature PR00109: M94-S107, L152-L174, E211-F233 | BLIMPS_PRINTS |

TABLE 4

| Polynucleotide SEQ ID NO:/ Incyte ID/ Sequence Length | Sequence Fragments |
|---|---|
| 21/4615110CB1/ 5200 | 1–224, 1–277, 4–272, 14–161, 14–225, 42–679, 43–503, 43–609, 43–708, 43–714, 43–872, 48–688, 124–438, 178–4215, 199–420, 200–720, 240–549, 352–679, 355–637, 355–756, 371–754, 374–992, 446–992, 459–1093, 506–1102, 545–827, 564–824, 763–1296, 825–1296, 869–1286, 869–1296, 870–1296, 958–1636, 1046–1625, 1049–1527, 1063–1697, 1098–1689, 1103–1299, 1103–1774, 1133–1736, 1250–1743, 1250–1768, 1250–1840, 1312–1857, 1376–1857, 1416–1857, 1426–1857, 1429–1857, 1496–2036, 1508–1998, 1515–2107, 1554–2211, 1635–2249, 1713–2241, 1716–2315, 1728–2380, 1775–2322, 1796–2438, 1809–2049, 2006–5055, 2020–2679, 2029–2385, 2056–2732, 2069–2702, 2107–2752, 2186–2443, 2196–2638, 2231–2580, |

TABLE 4-continued

| Polynucleotide SEQ ID NO:/ Incyte ID/ Sequence Length | Sequence Fragments |
|---|---|
| | 2232–2698, 2271–2775, 2287–2580, 2302–2741, 2335–2806, 2407–2857, 2409–2669, 2432–2980, 2796–2997, 2799–2997, 2810–3016, 2824–2994, 2950–3400, 3029–3604, 3029–3684, 3064–3648, 3100–3372, 3139–3684, 3186–3766, 3194–3457, 3212–3473, 3219–3456, 3228–3737, 3234–3704, 3236–3485, 3236–3719, 3245–3503, 3273–3839, 3273–3887, 3295–3689, 3317–3583, 3317–3604, 3317–3939, 3341–3634, 3351–3979, 3357–3615, 3375–3621, 3396–3971, 3428–4081, 3454–4092, 3475–4060, <br> 3479–4086, 3488–4156, 3491–3759, 3511–3828, 3511–3977, 3540–3825, 3540–3985, 3540–4047, 3548–3834, 3550–4216, 3580–3916, 3590–3928, 3599–4202, 3611–4211, 3627–4351, 3629–4099, 3629–4339, 3630–3907, 3630–4382, 3634–4382, 3641–4215, 3645–3920, 3649–3932, 3649–3933, 3650–3889, 3651–3904, 3654–4181, 3654–4215, 3660–4212, 3662–4080, 3664–4226, 3667–4162, 3667–4210, 3672–4212, 3675–4215, 3683–4211, 3693–4230, 3704–4211, 3706–4173, 3712–4215, 3728–4215, 3729–4215, 3730–4214, 3735–4214, 3737–4112, 3748–4213, 3752–4575, 3755–4025, 3766–4216, 3770–4382, 3771–4382, 3774–4215, <br> 3776–4192, 3781–4216, 3782–4215, 3784–4215, 3786–4023, 3786–4216, 3791–4211, 3795–4211, 3796–4215, 3796–4216, 3805–4090, 3805–4164, 3807–4164, 3808–4215, 3809–4197, 3810–4144, 3817–4215, 3821–4112, 3821–4152, 3833–4162, 3835–4084, 3843–4103, 3850–4145, 3852–4205, 3852–4215, 3854–4442, 3858–4165, 3863–4121, 3876–4442, 3884–4139, 3885–4382, 3888–4216, 3905–4380, 3941–4382, 3947–4215, 4013–4562, 4081–4243, 4171–4645, 4178–4610, 4194–4692, 4194–4697, 4194–4698, 4194–4699, 4194–4749, 4194–4780, 4194–4904, 4194–4933, 4207–4496, 4208–4470, 4208–4486, 4208–4492, 4208–4493, 4208–4496, 4208–4525, 4208–4644, 4208–4680, 4208–4683, 4208–4687, 4208–4691, 4208–4694, 4208–4702, 4208–4707, 4210–4526, 4211–4680, 4215–4496, 4216–4496, 4217–4480, 4222–4496, 4241–4382, 4241–4496, 4243–4629, 4252–4612, 4257–4522, 4257–4534, 4257–4541, 4257–4542, 4257–4545, 4257–4562, 4291–4707, 4292–4575, 4298–4605, 4298–4771, 4304–4549, 4304–4659, 4304–4837, 4310–4709, 4310–4711, 4323–4580, 4342–5179, 4363–4639, 4363–5016, 4364–4642, 4364–4916, 4383–4647, 4399–4664, 4410–4663, 4410–4670, 4422–4681, 4429–4677, 4439–4715, 4442–5010, <br> 4452–4699, 4453–5005, 4454–5025, 4484–5200, 4495–4669, 4495–4686, 4495–4691, 4495–4696, 4495–4697, 4496–4762, 4500–5187, 4502–5200, 4510–4749, 4511–4768, 4517–5200, 4521–5200, 4530–5185, 4537–5200, 4551–5183, 4575–4860, 4588–4844, 4591–4866, 4598–5157, 4605–5200, 4619–5197, 4626–5200, 4637–4904, 4647–5200, 4666–5190, 4679–5191, 4682–5200, 4701–5200, 4703–4958, 4707–4961, 4716–4959, 4716–4999, 4719–4946, 4725–4965, 4732–4999, 4736–5021, 4738–4989, 4753–5200, 4757–5013, 4758–5200, 4780–5200, 4794–5200, 4797–5200, 4799–5192, 4806–5135, 4808–5108, 4815–4988, 4819–5088, 4842–5200, 4844–5200, 4848–5200, 4853–5200, 4854–5200, 4858–5200, 4859–5200, 4893–5200, 4904–5200, 4909–5200, 4928–5200, 4945–5200, 4946–5200, 4950–5200, 4956–5200, 4971–5200, 4972–5200, 4973–5200, 4976–5200, 4979–5200, 4980–5178, 4980–5199, 4980–5200, 4984–5200, 4985–5200, 4986–5200, 4989–5200, 4994–5200, 4996–5200, 4998–5200, 5007–5200, 5008–5200, 5010–5200, 5011–5200, 5017–5200, 5028–5200, 5033–5200, 5034–5200, 5046–5200, 5053–5200, 5055–5200, 5093–5200, 5154–5200 |
| 22/4622229CB1/ 4330 | 1–300, 1–484, 24–275, 101–700, 299–820, 301–964, 315–925, 414–1033, 419–994, 516–1036, 612–884, 764–1443, 792–1443, 978–1595, 992–1545, 999–1687, 1037–1301, 1192–1430, 1216–1495, 1222–1799, 1279–1779, 1357–1615, 1428–1746, 1429–1793, 1464–1655, 1464–1684, 1495–1880, 1529–2045, 1575–2005, 1629–2219, 1678–1992, 1714–2170, 1744–2317, 1819–1946, 1912–2384, 1933–2610, 1940–2459, 1960–2540, 1968–2426, 2009–2522, 2055–2660, 2100–2591, 2116–2640, 2131–2638, 2138–2479, 2149–2475, 2152–2750, 2153–2822, 2157–2700, 2191–2517, 2285–2439, 2301–2559, 2306–2520, 2307–2542, 2378–2872, 2411–2699, 2443–2997, 2533–3044, 2546–2787, 2546–3136, 2689–2945, 2709–2985, 2733–3001, 2734–2972, 2734–3009, 2843–3050, 2918–3155, 2918–3182, 2918–3201, 2918–3214, 2918–3218, 2930–3512, 2937–3238, 2997–3246, 3003–3135, 3004–3532, 3019–3269, 3046–3295, 3058–3348, 3107–3358, 3114–3383, 3148–3416, 3236–3489, 3251–3489, 3251–3682, 3251–3802, 3275–3534, 3276–3517, 3282–3554, 3282–3557, 3294–3562, 3319–3572, 3340–3600, 3376–3644, 3387–3675, 3424–3662, 3450–3715, 3505–3728, 3524–3759, 3542–3825, 3552–4117, 3580–4260, 3590–4105, 3605–3731, 3607–3859, 3625–4321, 3634–4156, 3645–3871, 3645–4133, 3672–4313, 3677–4295, 3678–3918, 3684–3945, 3684–4124, 3694–4321, 3709–4317, 3715–4290, 3718–4311, 3733–4151, 3755–3919, 3786–4041, 3786–4044, 3786–4064, 3786–4255, 3786–4313, 3787–4076, 3791–4317, 3811–4329, 3814–4214, 3838–4082, 3839–4051, 3848–4100, 3848–4329, 3852–4315, 3853–4330, 3861–4328, 3877–4133, 3877–4134, 3877–4141, 3877–4330, 3879–4230, 3883–4329, 3885–4300, 3885–4329, 3886–4132, 3887–4329, 3888–4330, 3889–4328, 3890–4271, 3890–4329, 3898–4316, 3899–4330, 3901–4329, 3903–4321, 3903–4328, 3906–4329, 3907–4330, 3909–4330, 3910–4329, 3913–4330, 3914–4324, 3916–4247, 3916–4300, 3916–4328, 3916–4330, 3923–4329, 3923–4330, 3936–4051, 3936–4327, 3936–4330, 3940–4328, 3944–4329, 3965–4328, 3967–4203, 3990–4329, 3998–4329, 3999–4329, 4001–4329, 4010–4230, 4013–4330, 4026–4230, 4027–4230, 4027–4330, 4028–4328, 4030–4230, 4031–4230, 4031–4330, 4052–4229, 4052–4230, 4053–4328, 4053–4330, 4056–4329, 4061–4327, 4062–4329, 4066–4218, 4067–4329, 4068–4279, 4069–4330, 4082–4197, 4099–4328, 4099–4329, 4100–4330, 4109–4249, 4113–4329, 4156–4328 |
| 23/72358203CB1/ 2851 | 1–557, 1–886, 238–885, 550–724, 718–1202, 726–885, 726–886, 736–1198, 774–885, 774–1041, 774–1145, 774–1200, 905–1196, 927–1169, 928–1431, 931–1516, 942–1251, 942–1347, 949–1235, 980–1452, 997–1452, 1002–1259, 1021–1312, 1038–1324, 1042–1522, 1049–1452, 1073–1452, 1085–1259, 1114–1319, 1114–1659, 1142–1259, 1157–1259, 1158–1259, 1174–1259, 1190–1463, 1190–1647, 1210–1295, 1238–1531, 1250–1496, 1259–1428, 1259–1457, 1259–1483, 1259–1538, 1261–1538, 1275–1573, 1290–1896, 1292–1587, 1372–1853, 1437–1689, 1440–1699, 1445–2001, 1446–1717, 1456–1483, 1456–1576, 1456–1603, 1461–1483, 1470–1719, 1470–2068, 1472–1673, 1472–2034, 1478–1711, 1512–1797, 1530–1661, 1533–1736, 1544–1786, 1575–1603, 1609–1898, 1669–2000, 1712–1983, 1732–1877, 1774–1894, 1793–1981, 1793–2297, 1838–2104, 1840–2189, 1843–2639, 1852–2120, 1869–2773, 1888–2221, 1890–2496, 1892–2624, 1904–2510, 1909–2108, 1909–2133, 1911–2454, 1929–2096, 1929–2544, 1941–2198, 1941–2624, 1942–2226, 1943–2214, 1945–2632, 1961–2628, 1966–2208, 1971–2227, 1975–2058, 1984–2068, 1987–2319, 1997–2287, 1997–2291, 1999–2469, 2002–2577, 2004–2799, 2032–2673, 2053–2544, 2063–2239, 2075–2109, 2110–2605, 2111–2639, 2117–2687, 2131–2751, 2132–2808, 2140–2481, <br> 2144–2741, 2146–2695, 2156–2359, 2176–2469, 2184–2816, 2188–2687, 2201–2453, 2202–2815, 2205–2683, 2208–2682, 2209–2764, 2211–2834, 2215–2575, 2215–2771, 2227–2784, 2228–2795, 2228–2844, 2229–2626, 2231–2551, 2232–2632, 2245–2499, 2250–2814, 2272–2725, 2272–2757, 2275–2829, 2282–2532, 2282–2580, 2282–2738, 2282–2815, 2282–2839, 2283–2587, 2295–2742, 2305–2562, 2305–2669, 2310–2552, 2315–2704, 2319–2550, 2324–2565, 2331–2824, 2337–2851, 2354–2601, 2355–2533, 2356–2851, 2360–2779, 2368–2824, 2372–2826, 2373–2824, 2374–2822, 2375–2684, 2376–2830, 2378–2626, 2379–2831, 2381–2824, 2386–2824, 2388–2824, 2395–2828, 2399–2771, 2402–2824, 2402–2833, 2406–2828, 2418–2818, 2418–2829, 2427–2702, 2432–2710, 2437–2700, 2452–2824 |
| 24/4885040CB1/ 2361 | 1–426, 20–113, 361–537, 410–605, 410–773, 410–832, 410–894, 410–915, 410–919, 410–983, 410–988, 410–1030, 420–1060, 430–819, 458–848, 488–1093, 682–1293, 728–1328, 735–1165, 753–1063, 985–1072, 986–1601, 1132–1757, 1191–1641, |

TABLE 4-continued

| Polynucleotide SEQ ID NO:/ Incyte ID/ Sequence Length | Sequence Fragments |
|---|---|
| | 1201–1845, 1202–1733, 1241–1721, 1313–1857, 1378–1619, 1378–1874, 1384–1943, 1432–1895, 1522–1797, 1610–1902, 1722–2311, 1745–2323, 1792–2222, 1794–2184, 1797–2036, 1810–2061, 1812–2139, 1816–2361, 1833–2352, 1871–2361, 1903–2361 |
| 25/7484507CB1/ 2285 | 1–262, 10–408, 16–408, 76–325, 93–408, 109–285, 109–290, 109–293, 109–323, 109–537, 109–541, 109–548, 109–582, 109–590, 110–281, 110–285, 110–290, 112–281, 112–285, 112–544, 119–590, 414–777, 414–2004, 499–590, 526–590, 776–1001, 776–1060, 906–1060, 913–1060, 953–1060, 967–1060, 1408–1964, 1409–2045, 1410–1946, 1413–1949, 1450–1500, 1463–2003, 1489–2121, 1504–2003, 1511–1616, 1512–2037, 1526–2216, 1530–2059, 1575–2117, 1593–2260, 1596–2255, 1632–2261, 1685–2142, 1685–2145, 1708–2257, 1730–2238, 1730–2263, 1790–2261, 1818–2263, 1830–2263, 1835–2223, 1835–2283, 1835–2284, 1835–2285, 1837–2256, 1839–2285, 1845–2285 |
| 26/7198931CB1/ 4858 | 1–189, 59–4745, 429–469, 484–949, 499–637, 500–896, 502–884, 502–896, 633–743, 808–994, 808–1187, 810–1183, 888–1187, 1108–1468, 1108–1779, 1108–1813, 1108–1834, 1108–1853, 1108–1878, 1108–1888, 1110–1468, 1111–1834, 1141–1834, 1145–1834, 1166–1834, 1353–2083, 1362–2083, 1372–2083, 1387–2092, 1391–1927, 1392–2083, 1399–2083, 1403–2044, 1407–2044, 1422–1893, 1425–2042, 1444–2092, 1504–2044, 1628–2092, 1852–2044, 1894–2439, 2099–2690, 2121–2632, 2267–2715, 2382–3037, 2382–3046, 2382–3127, 2652–2880, 3173–3755, 3270–3734, 3327–3623, 3349–4153, 3392–4150, 3534–4063, 3534–4255, 3592–3774, 3592–4210, 3805–4436, 3828–4523, 3896–4167, 3898–4377, 3898–4564, 3920–4557, 3933–4577, 3945–4194, 3959–4214, 3979–4273, 3991–4591, 4036–4172, 4112–4254, 4113–4311, 4113–4500, 4114–4254, 4192–4450, 4215–4858, 4257–4326 |
| 27/7482905CB1/ 2903 | 1–607, 266–444, 363–941, 406–1048, 438–711, 459–1020, 497–607, 502–851, 536–607, 570–711, 710–918, 710–922, 710–931, 774–941, 867–1100, 869–1525, 870–1150, 879–1447, 962–1227, 969–1100, 974–1583, 1100–1699, 1300–1767, 1304–1767, 1333–1616, 1394–1684, 1394–2033, 1434–1944, 1434–2021, 1466–1642, 1591–1879, 1725–1996, 1746–2126, 1847–2508, 1935–2183, 2073–2183, 2091–2459, 2091–2643, 2091–2648, 2186–2666, 2350–2616, 2350–2903, 2365–2856, 2367–2663, 2435–2677, 2435–2808 |
| 28/7483019CB1/ 1812 | 1–235, 20–323, 22–235, 154–235, 154–321, 194–991, 196–823, 196–883, 196–900, 196–901, 196–903, 196–906, 196–913, 196–914, 196–919, 196–938, 196–940, 196–945, 196–966, 196–967, 196–973, 196–983, 196–996, 196–1014, 201–948, 236–321, 236–323, 322–590, 421–573, 487–1202, 487–1247, 487–1249, 487–1284, 487–1292, 487–1324, 550–1321, 568–1321, 574–1321, 586–1273, 590–655, 591–1321, 597–1321, 600–1321, 603–1321, 607–1321, 611–1321, 612–1321, 622–1321, 625–1321, 628–1321, 634–1321, 662–1321, 674–1321, 680–1282, 692–1321, 728–1282, 728–1285, 728–1287, 729–1287, 730–1287, 745–1285, 794–869, 795–1287, 827–1285, 854–1287, 950–1043, 950–1152, 985–1287, 1044–1287, 1151–1219, 1151–1285, 1151–1287, 1151–1689, 1153–1287, 1153–1482, 1159–1224, 1159–1421, 1159–1539, 1159–1638, 1159–1752, 1187–1287, 1187–1810, 1188–1812, 1238–1285, 1238–1287, 1287–1598, 1287–1635, 1287–1809, 1288–1482 |
| 29/5455490CB1/ 5480 | 1–689, 28–689, 373–686, 373–689, 413–867, 414–694, 414–715, 414–754, 414–843, 439–843, 448–1239, 508–843, 514–689, 529–843, 582–843, 597–843, 598–684, 598–689, 598–888, 598–994, 598–1070, 598–1081, 598–1176, 598–1230, 606–843, 610–867, 610–1172, 610–1237, 626–820, 634–1250, 715–1294, 723–1016, 723–1182, 767–1375, 796–1488, 910–1439, 920–1358, 969–1492, 982–1633, 1039–1581, 1056–1465, 1065–1334, 1065–1666, 1072–1435, 1098–1650, 1122–5330, 1129–1672, 1165–1318, 1204–1637, 1206–1459, 1206–1922, 1211–1485, 1244–1834, 1268–1874, 1274–1565, 1282–1907, 1284–1407, 1307–1749, 1312–1874, 1335–1884, 1340–1470, 1348–1562, 1406–1851, 1421–1625, 1444–1781, 1444–1927, 1557–2181, 1704–1965, 1710–2022, 1710–2260, 1723–2016, 1727–1947, 1785–2306, 1793–2282, 1805–2216, 1805–2244, 1944–2299, 1952–1985, 1953–2130, 1953–2235, 2067–2693, 2088–2746, 2105–2320, 2105–2586, 2105–2627, 2151–2380, 2152–2711, 2174–2711, 2263–2711, 2270–3062, 2284–3062, 2287–3062, 2321–2876, 2349–3062, 2351–2957, 2357–2977, 2383–2960, 2383–3004, 2387–3159, 2389–3038, 2393–3059, 2404–3015, 2426–2804, 2449–2838, 2451–2987, 2453–2936, 2459–2908, 2461–2869, 2462–3139, 2464–3062, 2466–3070, 2483–2926, 2485–3017, 2492–3045, 2494–2712, 2494–2739, 2494–2940, 2504–2757, 2519–3062, 2526–3141, 2555–3179, 2565–3047, 2565–3085, 2565–3092, 2570–2773, 2579–2791, 2580–3023, 2597–3176, 2621–3045, 2626–3176, 2641–3044, 2659–2912, 2660–2945, 2660–2958, 2665–2931, 2666–2931, 2675–3333, 2740–3115, 2743–2824, 2752–3027, 2753–2977, 2754–3031, 2766–3182, 2781–3328, 2798–3012, 2807–2985, 2866–3078, 2883–3205, 2886–3032, 2902–3151, 2915–3092, 2923–3119, 2923–3120, 2924–3102, 2926–3120, 2929–3205, 2930–3125, 2955–3069, 2956–3584, 3002–3120, 3037–3637, 3057–3205, 3073–3719, 3082–3205, 3108–3749, 3108–3783, 3119–3576, 3131–3717, 3141–3671, 3156–3337, 3194–3496, 3217–3372, 3228–3544, 3254–3611, 3261–3507, 3266–3652, 3266–3766, 3266–3801, 3270–3658, 3286–3913, 3292–3498, 3298–3847, 3301–3562, 3329–3962, 3347–3538, 3351–3546, 3353–3596, 3353–3850, 3353–3869, 3356–3626, 3361–3606, 3363–3605, 3364–3921, 3374–3989, 3388–3996, 3393–3990, 3423–3733, 3424–3906, 3426–4005, 3443–3563, 3443–3633, 3443–3717, 3443–3801, 3456–3715, 3457–3846, 3459–3965, 3460–3782, 3460–3882, 3460–3935, 3472–3726, 3481–3801, 3521–4146, 3529–3932, 3532–3965, 3533–3833, 3577–4095, 3657–3801, 3686–4203, 3705–3974, 3722–4164, 3724–4107, 3724–4157, 3732–4019, 3746–4376, 3785–3954, 3800–4054, 3807–4090, 3811–4093, 3814–4088, 3825–4115, 3826–4341, 3827–4467, 3829–3936, 3829–4354, 3844–4075, 3875–4086, 3875–4361, 3891–4548, 3901–3987, 3954–4219, 3967–4299, 3987–4614, 4001–4639, 4004–4281, 4011–4175, 4021–4129, 4021–4296, 4026–4177, 4035–4305, 4035–4547, 4041–4120, 4044–4182, 4044–4330, 4047–4592, 4048–4382, 4048–4387, 4048–4711, 4077–4494, 4088–4256, 4088–4286, 4088–4311, 4088–4323, 4088–4331, 4088–4384, 4088–4450, 4088–4466, 4088–4472, 4088–4473, 4088–4482, 4088–4510, 4088–4530, 4091–4492, 4099–4707, 4109–4419, 4111–4335, 4111–4536, 4112–4767, 4115–4379, 4121–4991, 4125–4720, 4128–4762, 4144–4790, 4151–4594, 4156–4622, 4161–4404, 4161–4576, 4164–4396, 4164–4421, 4170–4428, 4173–4684, 4173–4781, 4178–4743, 4180–4415, 4180–4417, 4183–4531, 4188–4455, 4204–4449, 4211–4826, 4213–4422, 4239–4494, 4240–4570, 4244–4333, 4250–4732, 4250–5021, 4250–5047, 4256–4385, 4264–4526, 4265–4590, 4267–4628, 4269–4587, 4283–4887, 4293–4546, 4297–4446, 4297–4752, 4301–4743, 4303–4605, 4311–4634, 4311–4640, 4311–4649, 4316–4771, 4317–4633, 4325–4715, 4334–4986, 4343–4598, 4343–4900, 4345–4933, 4358–4660, 4359–4743, 4361–4667, 4387–4836, 4395–4845, 4418–4678, 4421–5005, 4423–5012, 4431–4698, 4431–4709, 4431–4865, 4433–4782, 4433–5002, 4436–4816, 4439–4584, 4455–5346, 4458–5128, 4463–4723, 4464–4995, 4469–5095, 4478–4974, 4485–5050, 4489–4766, 4491–4772, 4517–5333, 4525–4868, 4530–4715, 4530–5009, 4530–5214, 4534–4970, 4536–5140, 4541–4995, 4541–5049, 4541–5153, 4547–4796, 4548–4819, 4551–5007, 4551–5013, 4551–5028, 4553–4846, 4574–4878, 4587–4818, 4596–4843, 4616–4924, 4616–5049, 4626–5314, 4630–4830, 4630–5177, 4637–4827, 4641–5151, 4646–4847, 4674–5333, 4703–5359, 4709–5376, 4720–5333, 4727–5374, 4745–5283, 4747–5387, 4754–5376, 4754–5386, 4773–5294, 4786–5333, 4791–5385, 4799–5480, 4806–5376, 4817–5385, 4817–5388, 4822–5378, 4838–5383, 4843–5388, 4857–5372, 4859–5374, 4874–5312, 4876–5349, 4876–5385, 4877–5345, 4888–5373, 4901–5324, 4904–5386, 4909–5379, 4913–5338, 4914–5386, 4918–5385, 4923–5386, 4923–5388, 4932–5386, 4936–5388, 4940–5386, 4962–5362, 4962–5386, 4968–5339, 4968–5376, 4968–5385, 4968–5392, 4970–5385, 4972–5386, 4975–5388, 4980–5476, 4981–5388, 5000–5386, 5004–5300, 5004–5342, 5004–5385, 5005–5293, 5009–5385, 5016–5386, 5032–5386, |

TABLE 4-continued

| Polynucleotide SEQ ID NO:/ Incyte ID/ Sequence Length | Sequence Fragments |
|---|---|
| | 5039–5307, 5046–5360, 5048–5386, 5053–5385, 5061–5385, 5061–5388, 5073–5368, 5077–5339, 5080–5386, 5092–5385, 5098–5366, 5099–5387, 5100–5385, 5104–5385, 5121–5364, 5123–5369, 5123–5387, 5129–5386, 5129–5387, 5136–5338, 5136–5376, 5136–5385, 5136–5386, 5141–5352, 5143–5386, 5145–5388, 5148–5386, 5154–5385, 5154–5386, 5162–5386, 5163–5388, 5194–5386, 5198–5385, 5203–5385, 5207–5382, 5211–5386, 5217–5385, 5240–5388, 5259–5385, 5264–5382, 5264–5387, 5267–5385, 5279–5386, 5286–5381, 5286–5386 |
| 30/5547067CB1/ 1568 | 1–372, 1–382, 1–386, 4–386, 5–382, 5–384, 5–386, 7–386, 11–385, 24–386, 60–386, 66–386, 67–386, 87–386, 116–386, 127–386, 136–386, 158–454, 170–386, 312–632, 387–458, 387–546, 387–547, 387–561, 387–584, 387–585, 387–598, 387–632, 387–674, 387–701, 387–729, 387–757, 387–785, 387–855, 387–859, 387–862, 387–873, 387–882, 387–883, 388–585, 388–883, 391–841, 391–883, 417–632, 436–883, 553–883, 564–1066, 717–785, 722–997, 722–1208, 770–1029, 1052–1568, 1120–1146, 1120–1161, 1120–1163, 1120–1206, 1120–1208, 1121–1208, 1209–1312, 1236–1317, 1320–1561, 1320–1568 |
| 31/71675660CB1/ 2365 | 1–505, 2–540, 20–479, 67–732, 162–239, 198–505, 224–660, 267–529, 305–540, 376–897, 390–977, 431–1088, 448–1007, 528–1183, 540–1091, 565–931, 611–1271, 635–1150, 648–1187, 666–826, 694–1334, 696–1390, 698–868, 727–1316, 794–1494, 813–1423, 850–1066, 860–1482, 875–1530, 884–1146, 895–1239, 955–1649, 978–1215, 980–1470, 1007–1545, 1027–1669, 1036–1526, 1036–1532, 1045–1593, 1062–1638, 1068–1306, 1068–1547, 1068–1630, 1068–1665, 1143–1679, 1155–1681, 1166–1822, 1175–1595, 1177–1797, 1340–2015, 1459–1757, 1526–1827, 1535–1865, 1621–2243, 1628–2243, 1733–2001, 1900–2361, 1903–2351, 1916–2355, 1929–2362, 1934–2102, 1941–2243, 1956–2365, 2004–2364, 2005–2358, 2170–2364 |
| 32/71678683CB1/ 2626 | 1–505, 2–540, 67–732, 198–505, 224–660, 305–540, 376–897, 431–1088, 448–1007, 528–1183, 565–931, 611–1271, 635–1150, 648–1187, 666–826, 694–1334, 696–1390, 698–868, 727–1316, 794–1494, 813–1423, 850–1066, 860–1482, 875–1530, 884–1146, 895–1239, 955–1649, 979–1215, 980–1470, 1007–1545, 1027–1669, 1036–1526, 1036–1532, 1045–1593, 1062–1638, 1068–1306, 1068–1547, 1068–1630, 1143–1679, 1155–1681, 1166–1822, 1175–1595, 1177–1797, 1364–1970, 1397–1892, 1459–1757, 1490–2081, 1623–2284, 1638–2233, 1657–2346, 1709–2276, 1810–2103, 1904–2310, 1927–2350, 1963–2341, 2002–2362, 2039–2446, 2045–2264, 2055–2351, 2086–2362, 2171–2626, 2228–2350 |
| 33/7474567CB1/ 3961 | 1–45, 1–780, 1–784, 1–795, 1–826, 1–847, 8–843, 44–495, 45–464, 153–854, 188–526, 215–870, 282–1131, 286–1131, 288–1131, 296–1131, 303–1131, 319–910, 319–975, 320–1131, 322–1131, 330–1124, 331–822, 350–1127, 561–870, 697–846, 801–1413, 869–1153, 879–1537, 895–1480, 1183–1827, 1217–1845, 1423–1950, 1499–2034, 1722–2344, 1770–2045, 1770–2383, 1801–2083, 1815–2058, 1942–2482, 1975–2115, 2006–2328, 2079–2335, 2079–2361, 2182–2416, 2182–2433, 2182–2651, 2260–2522, 2337–2590, 2420–2698, 2522–2746, 2523–2808, 2590–2994, 2680–2920, 2680–2932, 2684–3237, 2712–2990, 2727–2969, 2755–2995, 2814–3063, 2814–3082, 2869–3146, 2903–3147, 2903–3398, 2934–3172, 2966–3245, 2966–3250, 3060–3375, 3097–3380, 3144–3359, 3144–3438, 3182–3464, 3229–3476, 3229–3531, 3300–3584, 3312–3561, 3319–3954, 3344–3961, 3346–3587, 3359–3613, 3379–3641, 3426–3958, 3449–3639, 3449–3701 |
| 34/3838946CB1/ 2210 | 1–578, 65–574, 86–644, 137–536, 186–811, 219–513, 219–702, 240–465, 240–774, 240–811, 280–1851, 657–809, 689–1227, 711–1211, 768–1040, 777–1069, 807–1145, 812–1066, 818–1295, 847–1068, 915–1567, 915–1571, 945–1295, 1095–1361, 1095–1596, 1230–1708, 1324–1581, 1414–1953, 1446–1727, 1467–1748, 1469–1909, 1470–2130, 1560–1914, 1583–1896, 1585–2036, 1610–2182, 1615–2193, 1637–2206, 1638–1810, 1638–2195, 1644–2181, 1645–2168, 1660–2144, 1721–2210, 1733–2178, 1752–1888, 1764–2210, 1771–2076, 1815–2197, 1833–2103, 1839–2145, 1859–2125, 2001–2161 |
| 35/72001176CB1/ 4869 | 1–479, 53–662, 58–592, 241–462, 257–449, 272–519, 273–522, 288–515, 326–604, 346–597, 353–980, 361–626, 380–647, 397–637, 397–648, 407–652, 407–661, 410–664, 434–664, 498–664, 534–980, 804–1243, 804–1456, 804–1479, 927–1594, 988–1620, 989–1692, 1005–1712, 1023–1620, 1042–1628, 1074–1727, 1103–1712, 1134–1681, 1139–1832, 1187–1841, 1229–1743, 1274–1949, 1279–1978, 1306–1889, 1320–1915, 1358–1830, 1362–2392, 1403–1975, 1462–2010, 1566–2182, 1868–2595, 1961–2788, 2107–2953, 2131–2766, 2198–2343, 2198–2827, 2199–3008, 2244–2906, 2286–2869, 2308–2853, 2315–2983, 2315–3101, 2316–2903, 2325–2915, 2325–2989, 2357–3005, 2399–2903, 2402–2749, 2408–3224, 2410–2930, 2416–3025, 2433–3061, 2438–3059, 2448–3091, 2482–3141, 2498–3216, 2507–3110, 2510–3217, 2514–3181, 2516–3150, 2531–3231, 2538–3209, 2539–3234, 2547–3234, 2551–3042, 2555–3119, 2560–3319, 2561–3236, 2570–3186, 2573–3355, 2582–3167, 2582–3207, 2614–3163, 2617–2958, 2627–3197, 2630–3164, 2662–3068, 2672–3229, 2677–3217, 2682–3203, 2770–2914, 2858–3620, 2966–3770, 3112–3915, 3235–3980, 3241–3922, 3308–3991, 3350–4097, 3522–4032, 3658–3893, 4188–4662, 4193–4869 |
| 36/55064363CB1/ 4480 | 1–642, 92–502, 478–1155, 503–666, 533–1344, 554–1344, 556–1344, 595–1113, 595–1170, 595–1203, 595–1210, 595–1213, 595–1239, 602–1252, 676–1102, 686–853, 687–841, 689–1344, 689–1398, 693–1127, 865–1391, 881–1584, 893–1330, 900–1459, 918–1679, 930–1656, 934–1635, 934–1660, 935–1562, 972–1441, 1001–1690, 1006–1517, 1019–1650, 1039–1344, 1049–1609, 1094–1421, 1100–1698, 1100–1722, 1100–1742, 1100–1837, 1103–1771, 1110–1454, 1135–1647, 1135–1828, 1171–1364, 1190–1667, 1221–1593, 1234–1752, 1248–1682, 1275–1949, 1295–2112, 1302–2112, 1316–2112, 1319–2112, 1329–2112, 1332–2112, 1345–2112, 1359–2112, 1403–2112, 1459–2025, 1459–2137, 1591–2392, 1599–2396, 1603–2388, 1607–2397, 1640–2396, 1641–2392, 1644–2397, 1646–2010, 1647–2108, 1647–2112, 1647–2396, 1665–2396, 1692–2187, 1701–2166, 1701–2289, 1701–2369, 1708–2112, 1708–2397, 1732–1889, 1732–1985, 1732–2112, 1781–2392, 1787–2610, 1790–2146, 1792–2146, 1794–2122, 1794–2228, 1817–2527, 1822–2201, 1839–2396, 1840–2396, 1843–2495, 1844–2504, 1856–2610, 1873–2610, 1964–2497, 1984–2496, 1984–2610, 1987–2610, 2007–2497, 2015–2497, 2021–2532, 2044–2745, 2047–2738, 2065–2737, 2074–2497, 2096–2567, 2096–2589, 2096–2710, 2096–2729, 2096–2736, 2096–2769, 2114–2745, 2150–2793, 2153–2787, 2162–2883, 2175–2787, 2189–2810, 2225–2497, 2240–2883, 2247–2802, 2300–2979, 2315–2979, 2332–2962, 2332–2972, 2332–2975, 2332–2981, 2349–3040, 2363–2890, 2365–2802, 2390–2890, 2430–2890, 2431–2832, 2431–2862, 2431–2865, 2431–2877, 2431–2912, 2431–2917, 2431–2934, 2431–2946, 2431–2954, 2431–2961, 2431–2963, 2431–2964, 2431–2983, 2431–3012, 2431–3019, 2431–3021, 2431–3032, 2431–3036, 2431–3042, 2431–3043, 2431–3077, 2431–3081, 2431–3088, 2431–3092, 2431–3096, 2431–3105, 2431–3106, 2431–3112, 2431–3114, 2431–3135, 2431–3138, 2431–3150, 2431–3166, 2431–3213, 2431–3220, 2431–3247, 2432–3129, 2433–3018, 2433–3077, 2439–3016, 2440–3277, 2443–3272, 2452–3232, 2464–2564, 2467–3211, 2471–3331, 2481–3204, 2528–3084, 2534–3050, 2543–3140, 2545–3409, 2547–3003, 2551–2573, 2577–3158, 2578–3261, 2578–3325, 2603–3141, 2609–3435, 2625–3296, 2638–3102, 2642–3100, 2642–3304, 2644–3201, 2652–3310, 2661–3353, 2668–3243, 2697–3281, 2697–3412, 2700–3249, 2702–3295, 2713–3316, 2731–3243, 2731–3431, 2750–3502, 2757–3318, 2765–3299, 2768–3508, 2769–3435, 2771–3268, 2782–3526, 2784–3347, 2787–3461, 2798–3326, 2811–3703, 2818–3441, 2820–3277, 2832–3592, 2847–3563, 2850–3410, 2860–3442, 2861–3438, 2869–3445, 2882–3578, 2882–3608, 2882–3703, 2885–3558, 2909–3493, 2920–3505, 2922–3698, 2926–3505, 2928–3490, 2951–3452, 2952–3591, 2952–3742, 2954–3623, 2956–3537, 2960–3510, 2964–3516, 2965–3591, 2972–3426, 2972–3532, 2980–3528, 2989–3682, 2990–3583, 2993–3728, 2994–3764, 2995–3755, 2997–3776, 3006–3605, 3007–3587, 3014–3621, 3016–3624, 3031–3532, 3032–3547, 3062–3716, 3075–3396, 3075–3431, 3075–3437, 3075–3442, 3075–3479, 3075–3483, 3075–3587, 3075–3626, 3075–3645, 3082–3637, 3088–3691, 3091–3706, |

TABLE 4-continued

| Polynucleotide SEQ ID NO:/ Incyte ID/ Sequence Length | Sequence Fragments |
|---|---|
| | 3114–3754, 3140–3731, 3169–3692, 3185–3851, 3200–3768, 3219–3947, 3219–4035, 3232–3868, 3255–3926, 3276–4111, 3277–3854, 3280–3926, 3297–3948, 3303–3926, 3323–4150, 3334–4100, 3343–4047, 3373–4075, 3382–4047, 3391–4236, 3401–4234, 3405–4041, 3411–4036, 3412–3983, 3428–4086, 3430–4247, 3445–4047, 3467–4160, 3471–3963, 3476–3989, 3478–4056, 3480–3961, 3493–3965, 3508–4217, 3520–3991, 3534–4200, 3534–4290, 3538–3979, 3540–4209, 3551–4070, 3565–4249, 3580–4090, 3592–4072, 3606–3966, 3611–4118, 3616–4234, 3655–4315, 3672–4200, 3680–4207, 3696–4087, 3720–4228, 3738–4416, 3747–4169, 3756–4199, 3760–4279, 3783–4480, 3802–4277, 3805–4418, 3807–4313, 3834–4419, 3886–4224, 3896–4447, 3900–4480, 3907–4476, 3911–4480 |
| 37/7482044CB1/ 4415 | 1–246, 1–460, 1–559, 1–669, 325–710, 385–719, 388–719, 456–716, 456–732, 456–1068, 516–719, 516–723, 549–719, 549–723, 587–1072, 643–1258, 686–1270, 716–1264, 805–1055, 805–1344, 805–1347, 805–1444, 805–1581, 864–1495, 960–1613, 993–1519, 1268–1816, 1305–2012, 1338–2003, 1438–1929, 1438–1980, 1438–1991, 1589–2102, 1864–2232, 1891–2477, 2015–2237, 2015–2667, 2079–2518, 2237–2516, 2237–2528, 2237–2529, 2237–2554, 2237–2560, 2237–2563, 2237–2564, 2237–2571, 2237–2574, 2237–2575, 2237–2604, 2237–2605, 2237–2624, 2237–2653, 2237–2678, 2237–2688, 2237–2693, 2237–2701, 2237–2717, 2237–2720, 2237–2730, 2237–2745, 2237–2753, 2237–2758, 2237–2770, 2237–2795, 2237–2803, 2237–2818, 2240–2510, 2240–2520, 2241–2688, 2241–2833, 2287–2863, 2290–2809, 2350–2846, 2404–2763, 2489–3189, 2513–3099, 2550–3188, 2589–2818, 2594–3281, 2604–2867, 2604–2886, 2604–2914, 2610–3232, 2612–2883, 2635–2886, 2644–3093, 2662–3238, 2701–3162, 2728–3227, 2772–3374, 2867–3472, 2889–3227, 2892–3628, 2905–3716, 2931–3606, 2937–3675, 2937–3699, 2947–3625, 2968–3645, 2990–3796, 2998–3725, 3010–3612, 3015–3648, 3023–3708, 3030–3516, 3031–3669, 3070–3653, 3083–3684, 3090–3797, 3136–3695, 3141–3768, 3165–3655, 3185–3727, 3187–4006, 3204–3852, 3204–3861, 3204–3877, 3204–3887, 3210–3861, 3212–3890, 3213–3856, 3220–3899, 3222–3695, 3226–3984, 3227–3889, 3256–3794, 3260–3715, 3265–4018, 3269–3986, 3274–3987, 3277–3817, 3277–3877, 3285–3878, 3304–3996, 3306–4011, 3316–3855, 3320–3914, 3334–3898, 3340–3900, 3343–3911, 3346–3727, 3348–4071, 3349–3995, 3367–3896, 3391–3916, 3393–3990, 3400–4086, 3425–3958, 3441–3947, 3479–4168, 3489–3990, 3494–4035, 3497–4105, 3504–4086, 3504–4096, 3515–4172, 3516–4172, 3517–3797, 3537–4145, 3539–4255, 3540–3943, 3540–3984, 3542–4171, 3542–4172, 3549–4348, 3562–4019, 3565–4153, 3583–4352, 3585–4122, 3585–4150, 3648–3995, 3653–4413, 3657–3981, 3667–4383, 3668–4327, 3677–4182, 3678–3995, 3711–4087, 3732–4286, 3738–4414, 3739–4354, 3740–4377, 3746–4398, 3746–4415, 3750–4392, 3776–3842, 3779–4415, 3808–4415, 3856–4415, 3863–4415, 3865–4415, 3895–4415, 3908–4415, 3917–4415, 3925–4415, 3972–4415 |
| 38/7476595CB1/ 6306 | 1–829, 191–944, 191–950, 191–959, 191–964, 191–971, 192–488, 193–488, 223–488, 234–999, 244–488, 319–999, 398–999, 683–1074, 796–961, 796–1063, 961–6306, 962–1186, 1064–1186, 1064–1299, 1187–1299 |
| 39/71824382CB1/ 7151 | 1–525, 1–532, 188–467, 221–432, 266–533, 403–563, 435–718, 501–740, 585–1133, 594–876, 758–1034, 791–1005, 793–1247, 799–1047, 809–1248, 899–1172, 947–1206, 1077–1708, 1097–1737, 1172–1542, 1173–1583, 1260–1448, 1260–1748, 1283–1763, 1289–1744, 1309–1751, 1320–1744, 1341–1742, 1346–1706, 1385–1749, 1428–2103, 1457–1763, 1511–2109, 1530–2109, 1595–2109, 1612–1752, 1655–2102, 1655–2109, 1739–2109, 1924–2368, 1941–2109, 1946–2109, 1974–2526, 1979–2366, 1979–2642, 1980–2534, 2039–2274, 2039–2319, 2039–2536, 2039–2644, 2043–2109, 2148–2316, 2148–2335, 2148–2484, 2148–2542, 2148–2579, 2148–2588, 2148–2649, 2148–2753, 2148–2757, 2151–2757, 2156–2306, 2168–2413, 2202–2278, 2242–2889, 2243–2917, 2253–2609, 2284–2829, 2288–2829, 2326–2589, 2326–2934, 2326–2959, 2326–2975, 2388–3083, 2398–2526, 2445–2757, 2447–2757, 2503–3181, 2576–3079, 2581–2757, 2630–2740, 2634–3079, 2658–3181, 2704–2909, 2977–3181, 3102–3691, 3102–3769, 3104–3769, 3126–3181, 3333–3941, 3415–3943, 3452–3911, 3616–3912, 3616–4100, 3634–4171, 3634–4205, 3693–4292, 3890–4478, 3976–4399, 3976–4654, 4023–4452, 4090–4498, 4156–4417, 4202–4705, 4254–4915, 4254–4945, 4303–4705, 4431–4984, 4513–5252, 4548–5253, 4613–4854, 4822–5203, 4885–5133, 4901–5173, 4901–5554, 4905–5581, 4968–5531, 4980–5438, 5006–5562, 5022–5182, 5028–5697, 5044–5663, 5061–5737, 5063–5562, 5064–5562, 5125–5430, 5154–5300, 5225–5505, 5293–5602, 5332–5781, 5335–5590, 5397–5697, 5409–5913, 5453–5715, 5507–5701, 5518–6120, 5569–6181, 5647–6231, 5667–6078, 5716–5948, 5806–6163, 5906–6157, 5906–6536, 6047–6292, 6147–6420, 6175–6590, 6176–6467, 6238–6447, 6238–7024, 6254–6429, 6269–6560, 6284–6600, 6397–6655, 6397–6973, 6423–7036, 6471–6717, 6497–7118, 6497–7125, 6521–7122, 6629–7087, 6643–6908, 6657–7116, 6820–7062, 6820–7124, 6820–7151, 6829–7077, 6838–7069, 6901–7136 |
| 40/3566882CB1/ 2378 | 1–219, 54–238, 54–571, 517–1197, 517–1241, 695–1241, 757–2216, 1241–1477, 1241–1534, 1241–1706, 1241–1779, 1241–1810, 1241–1812, 1241–1835, 1241–1846, 1241–1864, 1241–1873, 1242–1794, 1347–2004, 1372–1910, 1376–1881, 1488–1808, 1519–2155, 1542–2088, 1573–2221, 1576–2112, 1615–2026, 1618–2182, 1624–2139, 1641–2155, 1645–2316, 1652–2139, 1711–2218, 1717–1968, 1767–2370, 1785–2378, 1826–2367, 1844–2258, 1928–2143, 2032–2202, 2036–2206, 2304–2361 |

TABLE 5

| Polynucleotide SEQ ID NO: | Incyte Project ID: | Representative Library |
|---|---|---|
| 21 | 4615110CB1 | BRAYDIN03 |
| 22 | 4622229CB1 | BRAINON01 |
| 23 | 72358203CB1 | BRAITUT03 |
| 24 | 4885040CB1 | ENDANOT01 |
| 25 | 7484507CB1 | BRAIFEN08 |
| 26 | 7198931CB1 | SYNORAB01 |
| 27 | 7482905CB1 | BMARTXE01 |
| 28 | 7483019CB1 | BMARTXT02 |
| 29 | 5455490CB1 | HNT2AGT01 |
| 30 | 5547067CB1 | BRAIFEE05 |
| 31 | 71675660CB1 | TESTNOT17 |
| 32 | 71678683CB1 | TESTNOT17 |
| 33 | 7474567CB1 | UCMCNOT02 |
| 34 | 3838946CB1 | NOSEDIN01 |
| 35 | 72001176CB1 | THP1NOT03 |
| 36 | 55064363CB1 | BRAIFET02 |
| 37 | 7482044CB1 | BRAUNOR01 |
| 39 | 71824382CB1 | BRABDIR01 |
| 40 | 3566882CB1 | LUNLTUE02 |

TABLE 6

| Library | Vector | Library Description |
|---|---|---|
| BMARTXE01 | pINCY | This 5' biased random primed library was constructed using RNA isolated from treated SH-SY5Y cells derived from a metastatic bone marrow neuroblastoma, removed from a 4-year-old Caucasian female (Schering AG). The medium was MEM/HAM'S F12 with 10% fetal calf serum. After reaching about 80% confluency cells were treated with 6-Hydroxydopamine (6-OHDA) at 100 microM for 8 hours. |
| BMARTXT02 | pINCY | Library was constructed using RNA isolated from treated SH-SY5Y cell line derived from bone marrow neuroblastoma tumor cells removed from a 4-year-old Caucasian female. The cells were cultured in the presence of retinoic acid. |
| BRABDIR01 | pINCY | Library was constructed using RNA isolated from diseased cerebellum tissue removed from the brain of a 57-year-old Caucasian male, who died from a cerebrovascular accident. Patient history included Huntington's disease, emphysema, and tobacco abuse. |
| BRAIFEE05 | PCDNA2.1 | This 5' biased random primed library was constructed using RNA isolated from brain tissue removed from a Caucasian male fetus who was stillborn with a hypoplastic left heart at 23 weeks' gestation. |
| BRAIFEN08 | pINCY | This normalized fetal brain tissue library was constructed from 400 thousand independent clones from a fetal brain tissue library. Starting RNA was made from brain tissue removed from a Caucasian male fetus who was stillborn with a hypoplastic left heart at 23 weeks' gestation. The library was normalized in 2 rounds using conditions adapted from Soares et al., PNAS (1994) 91: 9228 and Bonaldo et al., Genome Research (1996) 6: 791, except that a significantly longer (48 hours/round) reannealing hybridization was used. |
| BRAIFET02 | pINCY | Library was constructed using RNA isolated from brain tissue removed from a Caucasian male fetus, who was stillborn with a hypoplastic left heart at 23 weeks' gestation. |
| BRAINON01 | PSPORT1 | Library was constructed and normalized from 4.88 million independent clones from the BRAINOT03 library. RNA was made from brain tissue removed from a 26-year-old Caucasian male during cranioplasty and excision of a cerebral meningeal lesion. Pathology for the associated tumor tissue indicated a grade 4 oligoastrocytoma in the right fronto-parietal part of the brain. |
| BRAITUT03 | PSPORT1 | Library was constructed using RNA isolated from brain tumor tissue removed from the left frontal lobe of a 17-year-old Caucasian female during excision of a cerebral meningeal lesion. Pathology indicated a grade 4 fibrillary giant and small-cell astrocytoma. Family history included benign hypertension and cerebrovascular disease. |
| BRAUNOR01 | pINCY | This random primed library was constructed using RNA isolated from striatum, globus pallidus and posterior putamen tissue removed from an 81-year-old Caucasian female who died from a hemorrhage and ruptured thoracic aorta due to atherosclerosis. Pathology indicated moderate atherosclerosis involving the internal carotids, bilaterally; microscopic infarcts of the frontal cortex and hippocampus; and scattered diffuse amyloid plaques and neurofibrillary tangles, consistent with age. Grossly, the leptomeninges showed only mild thickening and hyalinization along the superior sagittal sinus. The remainder of the leptomeninges was thin and contained some congested blood vessels. Mild atrophy was found mostly in the frontal poles and lobes, and temporal lobes, bilaterally. Microscopically, there were pairs of Alzheimer type II astrocytes within the deep layers of the neocortex. There was increased satellitosis around neurons in the deep gray matter in the middle frontal cortex. The amygdala contained rare diffuse plaques and neurofibrillary tangles. The posterior hippocampus contained a microscopic area of cystic cavitation with hemosiderin laden macrophages surrounded by reactive gliosis. Patient history included sepsis, cholangitis, post-operative atelectasis, pneumonia CAD, cardiomegaly due to left ventricular hypertrophy, splenomegaly, arteriolonephrosclerosis, nodular colloidal goiter, emphysema, CHF, hypothyroidism, and peripheral vascular disease. |
| BRAYDIN03 | pINCY | This normalized library was constructed from 6.7 million independent clones from a brain tissue library. Starting RNA was made from RNA isolated from diseased hypothalamus tissue removed from a 57-year-old Caucasian male who died from a cerebrovascular accident. Patient history included Huntington's disease and emphysema. The library was normalized in 2 rounds using conditions adapted from Soares et al., PNAS (1994) 91: 9228 and Bonaldo et al., Genome Research (1996) 6: 791, except that a significantly longer (48-hours/round) reannealing hybridization was used. The library was linearized and recircularized to select for insert containing clones. |
| ENDANOT01 | PBLUESCRIPT | Library was constructed using RNA isolated from aortic endothelial cell tissue from an explanted heart removed from a male during a heart transplant. |
| HNT2AGT01 | PBLUESCRIPT | Library was constructed at Stratagene (STR937233), using RNA isolated from the hNT2 cell line derived from a human teratocarcinoma that exhibited properties characteristic of a committed neuronal precursor. Cells were treated with retinoic acid for 5 weeks and with mitotic inhibitors for two weeks and allowed to mature for an additional 4 weeks in conditioned medium. |
| LUNLTUE02 | PCDNA2.1 | This 5' biased random primed library was constructed using RNA isolated from left upper lobe lung tumor tissue removed from a 56-year-old Caucasian male during complete pneumonectomy, pericardectomy and regional lymph node excision. Pathology indicated grade 3 squamous cell carcinoma forming a mass in the left upper lobe centrally. The tumor extended through pleura into adjacent pericardium. Patient history included hemoptysis and tobacco abuse. Family history included benign hypertension, cerebrovascular accident, atherosclerotic coronary artery disease in the mother; prostate cancer in the father; and type II diabetes in the sibling(s). |
| NOSEDIN01 | pINCY | This normalized nasal polyp tissue library was constructed from 1.08 million independent clones from a pooled nasal polyp tissue library. Starting RNA was made from pooled cDNA from two donors. cDNA was generated using mRNA isolated from a nasal polyp removed from a 78-year-old Caucasian male during nasal polypectomy (donor A) and from nasal polyps from another donor (donor B). Pathology (A) indicated a nasal polyp and striking eosinophilia, especially deep in the epithelium. In many instances, eosinophils were undergoing frank necrosis with striking deposition of Charcot-Leyden crystals. Foci of eosinophil infiltration in small islands of cells were seen in certain areas, and those areas closer to the appearance surface were losing definition and evidently undergoing necrosis. Examination of respiratory epithelium showed loss of surface epithelium in many areas, and there was a tendency for cells to aggregate around the epithelium. This nasal polyp showed typical histology for polypoid change associated with allergic disease. Patient history included asthma, allergy tests (which were positive for histamine but negative for common substances), a pulmonary function test (PFT, which showed reduction in the forced expiratory volume (FEV), with increase after use of a bronchodilator), and nasal polyps. Patient |

TABLE 6-continued

| Library | Vector | Library Description |
|---|---|---|
| | | history (A) included asthma. Previous surgery (A) included a nasal polypectomy. The patient was not using glucocorticoids in treatment for asthma. The library was normalized in 1 round using conditions adapted from Soares et al., PNAS (1994) 91: 9228–9232 and Bonaldo et al., Genome Research 6 (1996): 791, except that a significantly longer (48 hours/round) reannealing hybridization was used. |
| SYNORAB01 | PBLUESCRIPT | Library was constructed using RNA isolated from the synovial membrane tissue of a 68-year-old Caucasian female with rheumatoid arthritis. |
| TESTNOT17 | pINCY | Library was constructed from testis tissue removed from a 26-year-old Caucasian male who died from head trauma due to a motor vehicle accident. Serologies were negative. Patient history included a hernia at birth, tobacco use (1 1/2 ppd), marijuana use, and daily alcohol use (beer and hard liquor). |
| THP1NOT03 | pINCY | Library was constructed using RNA isolated from untreated THP-1 cells. THP-1 is a human promonocyte line derived from the peripheral blood of a 1-year-old Caucasian male with acute monocytic leukemia (ref. int. j. Cancer (1980) 26: 171) |
| UCMCNOT02 | pINCY | Library was constructed using RNA isolated from mononuclear cells obtained from the umbilical cord blood of nine individuals. |

TABLE 7

| Program | Description | Reference | Parameter Threshold |
|---|---|---|---|
| ABI FACTURA | A program that removes vector sequences and masks ambiguous bases in nucleic acid sequences. | Applied Biosystems, Foster City, CA. | |
| ABI/PARACEL FDF | A Fast Data Finder useful in comparing and annotating amino acid or nucleic acid sequences. | Applied Biosystems, Foster City, CA; Paracel Inc., Pasadena, CA. | Mismatch < 50% |
| ABI Auto-Assembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403–410; Altschul, S. F. et al. (1997) Nucleic Acids Res. 25: 3389–3402. | ESTs: Probability value = 1.0E–8 or less Full Length sequences: Probability value = 1.0E–10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444–2448; Pearson, W. R. (1990) Methods Enzymol. 183: 63–98; and Smith, T. F. and M. S. Waterman (1981) Adv. Appl. Math. 2: 482–489. | ESTs: fasta E value = 1.06E–6 Assembled ESTs: fasta Identity = 95% or greater and Match length = 200 bases or greater; fastx E value = 1.0E–8 or less Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565–6572; Henikoff, J. G. and S. Henikoff (1996) Methods Enzymol. 266: 88–105; and Attwood, T. K. et al. (1997) J. Chem. Inf. Comput. Sci. 37: 417–424. | Probability value = 1.0E–3 or less |
| HMMER | An algorithm for searching a query sequence against hidden Markov model (HMM)-based databases of protein family consensus sequences, such as PFAM. | Krogh, A. et al. (1994) J. Mol. Biol. 235: 1501–1531; Sonnhammer, E. L. L. et al. (1988) Nucleic Acids Res. 26: 320–322; Durbin, R. et al. (1998) Our World View, in a Nutshell, Cambridge Univ. Press, pp. 1–350. | PFAM hits: Probability value = 1.0E–3 or less Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61–66; Gribskov, M. et al. (1989) Methods Enzymol. 183: 146–159; Bairoch, A. et al. (1997) Nucleic Acids Res. 25: 217–221. | Normalized quality score ≧ GCG-specified "HIGH" value for that particular Prosite motif. Generally, score = 1.4–2.1. |
| Phred | A base-calling algorithm that examines automated sequencer traces with high sensitivity and probability. | Ewing, B. et al. (1998) Genome Res. 8: 175–185; Ewing, B. and P. Green (1998) Genome Res. 8: 186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482–489; Smith, T. F. and M. S. Waterman (1981) J. Mol. Biol. 147: 195–197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8: 195–202. | |
| SPScan | A weight matrix analysis program that scans protein sequences for the presence of secretory signal peptides. | Nielson, H. et al. (1997) Protein Engineering 10: 1–6; Claverie, J. M. and S. Audic (1997) CABIOS 12: 431–439. | Score = 3.5 or greater |
| TMAP | A program that uses weight matrices to delineate transmembrane segments on protein sequences and determine orientation. | Persson, B. and P. Argos (1994) J. Mol. Biol. 237: 182–192; Persson, B. and P. Argos (1996) Protein Sci. 5: 363–371. | |
| TMHMMER | A program that uses a hidden Markov model (HMM) to delineate transmembrane segments on protein sequences and determine orientation. | Sonnhammer, E. L. et al. (1998) Proc. Sixth Intl. Conf. on Intelligent Systems for Mol. Biol., Glasgow et al., eds., The Am. Assoc. | |

TABLE 7-continued

| Program | Description | Reference | Parameter Threshold |
|---|---|---|---|
| Motifs | A program that searches amino acid sequences for patterns that matched those defined in Prosite. | for Artificial Intelligence Press, Menlo Park, CA, pp. 175–182. Bairoch, A. et al. (1997) Nucleic Acids Res. 25: 217–221; Wisconsin Package Program Manual, version 9, page M51–59, Genetics Computer Group, Madison, WI. | |

What is claimed is:

1. An isolated polypeptide selected from the group consisting of:
   a) a polypeptide comprising an amino acid sequence of SEQ ID NO:3, and
   b) a polypeptide comprising an amino acid sequence having at least about 95% sequence identity to an amino acid sequence of SEQ ID NO:3, wherein the polypeptide has protein phosphatase 2C activity.

2. The isolated polypeptide of claim 1 comprising an amino acid sequence of SEQ ID NO:3.

3. An isolated polynucleotide encoding a polypeptide selected from the group consisting of:
   a) a polypeptide comprising an amino acid sequence of SEQ ID NO:3; and
   b) a polypeptide comprising an amino acid sequence having at least about 95% sequence identity to an amino acid sequence of SEQ ID NO:3, wherein the polypeptide has protein phosphatase 2C activity.

4. The isolated polynucleotide of claim 3 encoding a polypeptide comprising an amino acid sequence of SEQ ID NO:3.

5. The isolated polynucleotide of claim 4 comprising a polynucleotide sequence of SEQ ID NO:23.

6. A recombinant polynucleotide comprising a promoter sequence operably linked to the polynucleotide of claim 3.

7. An isolated cell transformed with the recombinant polynucleotide of claim 6.

8. A method of producing the polypeptide of claim 1, the method comprising:
   a) culturing a cell under conditions suitable for expression of the polypeptide, wherein said cell is transformed with a recombinant polynucleotide, and said recombinant polynucleotide comprise a promoter sequence operably linked to a polynucleotide encoding the polypeptide of claim 1, and
   b) recovering the polypeptide so expressed.

9. The method of claim 8, wherein the polypeptide comprises an amino acid sequence of SEQ ID NO:3.

10. An isolated polynucleotide selected from the group consisting of:
    a) a polynucleotide comprising a polynucleotide sequence of SEQ ID NO:23,
    b) a polynucleotide comprising a polynucleotide sequence having at least about 95% sequence identity to a polynucleotide sequence of SEQ ID NO:23, wherein the polynucleotide encodes a polypeptide that has protein phosphatase 2C activity,
    c) a polynucleotide complementary to the polynucleotide of a),
    d) a polynucleotide complementary to the polynucleotide of b), and
    e) an RNA equivalent of a)–d).

11. A composition comprising the polypeptide of claim 1 and a pharmaceutically acceptable excipient.

12. The composition of claim 11, wherein the polypeptide comprises an amino acid sequence of SEQ ID NO:3.

13. The isolated polypeptide of claim 1, comprising an amino acid sequence having at least about 96% sequence identity to an amino acid sequence of SEQ ID NO:3, wherein the polypeptide has protein phosphatase 2C activity.

14. The isolated polypeptide of claim 1, comprising an amino acid sequence having at least about 97% sequence identity to an amino acid sequence of SEQ ID NO:3, wherein the polypeptide has protein phosphatase 2C activity.

15. The isolated polypeptide of claim 1, comprising an amino acid sequence having at least about 98% sequence identity to an amino acid sequence of SEQ ID NO:3, wherein the polypeptide has protein phosphatase 2C activity.

16. The isolated polypeptide of claim 1, comprising an amino acid sequence having at least about 99% sequence identity to an amino acid sequence of SEQ ID NO:3, wherein the polypeptide has protein phosphatase 2C activity.

17. The isolated polypeptide of claim 1, wherein the polypeptide is a human polypeptide.

18. The isolated polynucleotide of claim 10, comprising a polynucleotide sequence having at least about 96% sequence identity to a polynucleotide sequence of SEQ ID NO:23, wherein the polynucleotide encodes a polypeptide that has protein phosphatase 2C activity.

19. The isolated polynucleotide of claim 10, comprising a polynucleotide sequence having at least about 97% sequence identity to a polynucleotide sequence of SEQ ID NO:23, wherein the polynucleotide encodes a polypeptide that has protein phosphatase 2C activity.

20. The isolated polynucleotide of claim 10, comprising a polynucleotide sequence having at least about 98% sequence identity to a polynucleotide sequence of SEQ ID NO:23, wherein thepolynucleotide encodes a polypeptide that has protein phosphatase 2C activity.

21. The isolated polynucleotide of claim 10, comprising a polynucleotide sequence having at least about 99% sequence identity to a polynucleotide sequence of SEQ ID NO:23, wherein the polynucleotide encodes a polypeptide that has protein phosphatase 2C activity.

22. The isolated polynucleotide of claim 10, wherein the polynucleotide is a human polynucleotide.

* * * * *

SEQUENCE LISTING

<160> NUMBER OF SEQ ID NOS: 40

<210> SEQ ID NO 1
<211> LENGTH: 1636
<212> TYPE: PRT
<213> ORGANISM: Homo sapiens
<220> FEATURE:
<221> NAME/KEY: misc_feature
<223> OTHER INFORMATION: Incyte ID No: 4615110CD1

<400> SEQUENCE: 1

```
Met Glu Ala Val Pro Arg Met Pro Met Ile Trp Leu Asp Leu Lys
1               5                  10                  15

Glu Ala Gly Asp Phe His Phe Gln Pro Ala Val Lys Lys Phe Val
                20                  25                  30

Leu Lys Asn Tyr Gly Glu Asn Pro Glu Ala Tyr Asn Glu Glu Leu
                35                  40                  45

Lys Lys Leu Glu Leu Leu Arg Gln Asn Ala Val Arg Val Pro Arg
                50                  55                  60

Asp Phe Glu Gly Cys Ser Val Leu Arg Lys Tyr Leu Gly Gln Leu
                65                  70                  75

His Tyr Leu Gln Ser Arg Val Pro Met Gly Ser Gly Gln Glu Ala
                80                  85                  90

Ala Val Pro Val Thr Trp Thr Glu Ile Phe Ser Gly Lys Ser Val
                95                  100                 105

Ala His Glu Asp Ile Lys Tyr Glu Gln Ala Cys Ile Leu Tyr Asn
                110                 115                 120

Leu Gly Ala Leu His Ser Met Leu Gly Ala Met Asp Lys Arg Val
                125                 130                 135

Ser Glu Glu Gly Met Lys Val Ser Cys Thr His Phe Gln Cys Ala
                140                 145                 150

Ala Gly Ala Phe Ala Tyr Leu Arg Glu His Phe Pro Gln Ala Tyr
                155                 160                 165

Ser Val Asp Met Ser Arg Gln Ile Leu Thr Leu Asn Val Asn Leu
                170                 175                 180

Met Leu Gly Gln Ala Gln Glu Cys Leu Leu Glu Lys Ser Met Leu
                185                 190                 195

Asp Asn Arg Lys Ser Phe Leu Val Ala Arg Ile Ser Ala Gln Val
                200                 205                 210

Val Asp Tyr Tyr Lys Glu Ala Cys Arg Ala Leu Glu Asn Pro Asp
                215                 220                 225

Thr Ala Ser Leu Leu Gly Arg Ile Gln Lys Asp Trp Lys Lys Leu
                230                 235                 240

Val Gln Met Lys Ile Tyr Tyr Phe Ala Ala Val Ala His Leu His
                245                 250                 255
```

-continued

```
Met Gly Lys Gln Ala Glu Glu Gln Gln Lys Phe Gly Glu Arg Val
            260                 265                 270

Ala Tyr Phe Gln Ser Ala Leu Asp Lys Leu Asn Glu Ala Ile Lys
            275                 280                 285

Leu Ala Lys Gly Gln Pro Asp Thr Val Gln Asp Ala Leu Arg Phe
            290                 295                 300

Thr Met Asp Val Ile Gly Gly Lys Tyr Asn Ser Ala Lys Lys Asp
            305                 310                 315

Asn Asp Phe Ile Tyr His Glu Ala Val Pro Ala Leu Asp Thr Leu
            320                 325                 330

Gln Pro Val Lys Gly Ala Pro Leu Val Lys Pro Leu Pro Val Asn
            335                 340                 345

Pro Thr Asp Pro Ala Val Thr Gly Pro Asp Ile Phe Ala Lys Leu
            350                 355                 360

Val Pro Met Ala Ala His Glu Ala Ser Ser Leu Tyr Ser Glu Glu
            365                 370                 375

Lys Ala Lys Leu Leu Arg Glu Met Met Ala Lys Ile Glu Asp Lys
            380                 385                 390

Asn Glu Val Leu Asp Gln Phe Met Asp Ser Met Gln Leu Asp Pro
            395                 400                 405

Glu Thr Val Asp Asn Leu Asp Ala Tyr Ser His Ile Pro Pro Gln
            410                 415                 420

Leu Met Glu Lys Cys Ala Ala Leu Ser Val Arg Pro Asp Thr Val
            425                 430                 435

Arg Asn Leu Val Gln Ser Met Gln Val Leu Ser Gly Val Phe Thr
            440                 445                 450

Asp Val Glu Ala Ser Leu Lys Asp Ile Arg Asp Leu Leu Glu Glu
            455                 460                 465

Asp Glu Leu Leu Glu Gln Lys Phe Gln Glu Ala Val Gly Gln Ala
            470                 475                 480

Gly Ala Ile Ser Ile Thr Ser Lys Ala Glu Leu Ala Glu Val Arg
            485                 490                 495

Arg Glu Trp Ala Lys Tyr Met Glu Val His Glu Lys Ala Ser Phe
            500                 505                 510

Thr Asn Ser Glu Leu His Arg Ala Met Asn Leu His Val Gly Asn
            515                 520                 525

Leu Arg Leu Leu Ser Gly Pro Leu Asp Gln Val Arg Ala Ala Leu
            530                 535                 540

Pro Thr Pro Ala Leu Ser Pro Glu Asp Lys Ala Val Leu Gln Asn
            545                 550                 555

Leu Lys Arg Ile Leu Ala Lys Val Gln Glu Met Arg Asp Gln Arg
            560                 565                 570

Val Ser Leu Glu Gln Gln Leu Arg Glu Leu Ile Gln Lys Asp Asp
            575                 580                 585

Ile Thr Ala Ser Leu Val Thr Thr Asp His Ser Glu Met Lys Lys
            590                 595                 600

Leu Phe Glu Glu Gln Leu Lys Lys Tyr Asp Gln Leu Lys Val Tyr
            605                 610                 615

Leu Glu Gln Asn Leu Ala Ala Gln Asp Arg Val Leu Cys Ala Leu
            620                 625                 630

Thr Glu Ala Asn Val Gln Tyr Ala Ala Val Arg Arg Val Leu Ser
            635                 640                 645
```

-continued

```
Asp Leu Asp Gln Lys Trp Asn Ser Thr Leu Gln Thr Leu Val Ala
             650                 655                 660

Ser Tyr Glu Ala Tyr Glu Asp Leu Met Lys Lys Ser Gln Glu Gly
             665                 670                 675

Arg Asp Phe Tyr Ala Asp Leu Glu Ser Lys Val Ala Ala Leu Leu
             680                 685                 690

Glu Arg Thr Gln Ser Thr Cys Gln Ala Arg Glu Ala Ala Arg Gln
             695                 700                 705

Gln Leu Leu Asp Arg Glu Leu Lys Lys Pro Pro Pro Arg Pro
             710                 715                 720

Thr Ala Pro Lys Pro Leu Leu Pro Arg Glu Glu Ser Glu Ala
             725                 730                 735

Val Glu Ala Gly Asp Pro Pro Glu Glu Leu Arg Ser Leu Pro Pro
             740                 745                 750

Asp Met Val Ala Gly Pro Arg Leu Pro Asp Thr Phe Leu Gly Ser
             755                 760                 765

Ala Thr Pro Leu His Phe Pro Pro Ser Pro Phe Pro Ser Ser Thr
             770                 775                 780

Gly Pro Gly Pro His Tyr Leu Ser Gly Pro Leu Pro Pro Gly Thr
             785                 790                 795

Tyr Ser Gly Pro Thr Gln Leu Ile Gln Pro Arg Ala Pro Gly Pro
             800                 805                 810

His Ala Met Pro Val Ala Pro Gly Pro Ala Leu Tyr Pro Ala Pro
             815                 820                 825

Ala Tyr Thr Pro Glu Leu Gly Leu Val Pro Arg Ser Ser Pro Gln
             830                 835                 840

His Gly Val Val Ser Ser Pro Tyr Val Gly Val Gly Pro Ala Pro
             845                 850                 855

Pro Val Ala Gly Leu Pro Ser Ala Pro Pro Gln Phe Ser Gly
             860                 865                 870

Pro Glu Leu Ala Met Ala Val Arg Pro Ala Thr Thr Thr Val Asp
             875                 880                 885

Ser Ile Gln Ala Pro Ile Pro Ser His Thr Ala Pro Arg Pro Asn
             890                 895                 900

Pro Thr Pro Ala Pro Pro Pro Cys Phe Pro Val Pro Pro Pro
             905                 910                 915

Gln Pro Leu Pro Thr Pro Tyr Thr Tyr Pro Ala Gly Ala Lys Gln
             920                 925                 930

Pro Ile Pro Ala Gln His His Phe Ser Ser Gly Ile Pro Thr Gly
             935                 940                 945

Phe Pro Ala Pro Arg Ile Gly Pro Gln Pro Gln Pro His Pro Gln
             950                 955                 960

Pro His Pro Ser Gln Ala Phe Gly Pro Gln Pro Pro Gln Gln Pro
             965                 970                 975

Leu Pro Leu Gln His Pro His Leu Phe Pro Pro Gln Ala Pro Gly
             980                 985                 990

Leu Leu Pro Pro Gln Ser Pro Tyr Pro Tyr Ala Pro Gln Pro Gly
             995                1000                1005

Val Leu Gly Gln Pro Pro Pro Leu His Thr Gln Leu Tyr Pro
            1010                1015                1020

Gly Pro Ala Gln Asp Pro Leu Pro Ala His Ser Gly Ala Leu Pro
            1025                1030                1035

Phe Pro Ser Pro Gly Pro Pro Gln Pro Pro His Pro Pro Leu Ala
```

-continued

```
                    1040                1045                1050
Tyr Gly Pro Ala Pro Ser Thr Arg Pro Met Gly Pro Gln Ala Ala
                    1055                1060                1065
Pro Leu Thr Ile Arg Gly Pro Ser Ser Ala Gly Gln Ser Thr Pro
                    1070                1075                1080
Ser Pro His Leu Val Pro Ser Pro Ala Pro Ser Pro Gly Pro Gly
                    1085                1090                1095
Pro Val Pro Pro Arg Pro Ala Ala Glu Pro Pro Cys Leu
                    1100                1105                1110
Arg Arg Gly Ala Ala Ala Asp Leu Leu Ser Ser Pro Glu
                    1115                1120                1125
Ser Gln His Gly Gly Thr Gln Ser Pro Gly Gly Gln Pro Leu
                    1130                1135                1140
Leu Gln Pro Thr Lys Val Asp Ala Ala Glu Gly Arg Arg Pro Gln
                    1145                1150                1155
Ala Leu Arg Leu Ile Glu Arg Asp Pro Tyr Glu His Pro Glu Arg
                    1160                1165                1170
Leu Arg Gln Leu Gln Gln Glu Leu Glu Ala Phe Arg Gly Gln Leu
                    1175                1180                1185
Gly Asp Val Gly Ala Leu Asp Thr Val Trp Arg Glu Leu Gln Asp
                    1190                1195                1200
Ala Gln Glu His Asp Ala Arg Gly Arg Ser Ile Ala Ile Ala Arg
                    1205                1210                1215
Cys Tyr Ser Leu Lys Asn Arg His Gln Asp Val Met Pro Tyr Asp
                    1220                1225                1230
Ser Asn Arg Val Val Leu Arg Ser Gly Lys Asp Asp Tyr Ile Asn
                    1235                1240                1245
Ala Ser Cys Val Glu Gly Leu Ser Pro Tyr Cys Pro Pro Leu Val
                    1250                1255                1260
Ala Thr Gln Ala Pro Leu Pro Gly Thr Ala Ala Asp Phe Trp Leu
                    1265                1270                1275
Met Val His Glu Gln Lys Val Ser Val Ile Val Met Leu Val Ser
                    1280                1285                1290
Glu Ala Glu Met Glu Lys Gln Lys Val Ala Arg Tyr Phe Pro Thr
                    1295                1300                1305
Glu Arg Gly Gln Pro Met Val His Gly Ala Leu Ser Leu Ala Leu
                    1310                1315                1320
Ser Ser Val Arg Ser Thr Glu Thr His Val Glu Arg Val Leu Ser
                    1325                1330                1335
Leu Gln Phe Arg Asp Gln Ser Leu Lys Arg Ser Leu Val His Leu
                    1340                1345                1350
His Phe Pro Thr Trp Pro Glu Leu Gly Leu Pro Asp Ser Pro Ser
                    1355                1360                1365
Asn Leu Leu Arg Phe Ile Gln Glu Val His Ala His Tyr Leu His
                    1370                1375                1380
Gln Arg Pro Leu His Thr Pro Ile Ile Val His Cys Ser Ser Gly
                    1385                1390                1395
Val Gly Arg Thr Gly Ala Phe Ala Leu Leu Tyr Ala Ala Val Gln
                    1400                1405                1410
Glu Val Glu Ala Gly Asn Gly Ile Pro Glu Leu Pro Gln Leu Val
                    1415                1420                1425
Arg Arg Met Arg Gln Gln Arg Lys His Met Leu Gln Glu Lys Leu
                    1430                1435                1440
```

-continued

His Leu Arg Phe Cys Tyr Glu Ala Val Val Arg His Val Glu Gln
                1445                1450                1455

Val Leu Gln Arg His Gly Val Pro Pro Cys Lys Pro Leu Ala
            1460                1465                1470

Ser Ala Ser Ile Ser Gln Lys Asn His Leu Pro Gln Asp Ser Gln
                1475                1480                1485

Asp Leu Val Leu Gly Gly Asp Val Pro Ile Ser Ser Ile Gln Ala
                1490                1495                1500

Thr Ile Ala Lys Leu Ser Ile Arg Pro Gly Gly Leu Glu Ser
                1505                1510                1515

Pro Val Ala Ser Leu Pro Gly Pro Ala Glu Pro Pro Gly Leu Pro
                1520                1525                1530

Pro Ala Ser Leu Pro Glu Ser Thr Pro Ile Pro Ser Ser Pro
                1535                1540                1545

Pro Pro Leu Ser Ser Pro Leu Pro Glu Ala Pro Gln Pro Lys Glu
                1550                1555                1560

Glu Pro Pro Val Pro Glu Ala Pro Ser Ser Gly Pro Ser Ser
                1565                1570                1575

Ser Leu Glu Leu Leu Ala Ser Leu Thr Pro Glu Ala Phe Ser Leu
                1580                1585                1590

Asp Ser Ser Leu Arg Gly Lys Gln Arg Met Ser Lys His Asn Phe
                1595                1600                1605

Leu Gln Ala His Asn Gly Gln Gly Leu Arg Ala Thr Arg Pro Ser
                1610                1615                1620

Asp Asp Pro Leu Ser Leu Leu Asp Pro Leu Trp Thr Leu Asn Lys
                1625                1630                1635

Thr

<210> SEQ ID NO 2
<211> LENGTH: 673
<212> TYPE: PRT
<213> ORGANISM: Homo sapiens
<220> FEATURE:
<221> NAME/KEY: misc_feature
<223> OTHER INFORMATION: Incyte ID No: 4622229CD1

<400> SEQUENCE: 2

Met Asp Arg Pro Ala Ala Ala Ala Ala Gly Cys Glu Gly Gly
1               5                   10                  15

Gly Gly Pro Asn Pro Gly Pro Ala Gly Gly Arg Arg Pro Pro Arg
                20                  25                  30

Ala Ala Gly Gly Ala Thr Ala Gly Ser Arg Gln Pro Ser Val Glu
                35                  40                  45

Thr Leu Asp Ser Pro Thr Gly Ser His Val Glu Trp Cys Lys Gln
                50                  55                  60

Leu Ile Ala Ala Thr Ile Ser Ser Gln Ile Ser Gly Ser Val Thr
                65                  70                  75

Ser Glu Asn Val Ser Arg Asp Tyr Lys Val Phe Arg Arg Pro Asp
                80                  85                  90

Leu Arg Ala Leu Arg Asp Gly Asn Lys Leu Ala Gln Met Glu Glu
                95                  100                 105

Ala Pro Leu Phe Pro Gly Glu Ser Ile Lys Ala Ile Val Lys Asp
                110                 115                 120

Val Met Tyr Ile Cys Pro Phe Met Gly Ala Val Ser Gly Thr Leu
                125                 130                 135

-continued

```
Thr Val Thr Asp Phe Lys Leu Tyr Phe Lys Asn Val Glu Arg Asp
            140                 145                 150
Pro His Phe Ile Leu Asp Val Pro Leu Gly Val Ile Ser Arg Val
            155                 160                 165
Glu Lys Ile Gly Ala Gln Ser His Gly Asp Asn Ser Cys Gly Ile
            170                 175                 180
Glu Ile Val Cys Lys Asp Met Arg Asn Leu Arg Leu Ala Tyr Lys
            185                 190                 195
Gln Glu Glu Gln Ser Lys Leu Gly Ile Phe Glu Asn Leu Asn Lys
            200                 205                 210
His Ala Phe Pro Leu Ser Asn Gly Gln Ala Leu Phe Ala Phe Ser
            215                 220                 225
Tyr Lys Glu Lys Phe Pro Ile Asn Gly Trp Lys Val Tyr Asp Pro
            230                 235                 240
Val Ser Glu Tyr Lys Arg Gln Gly Leu Pro Asn Glu Ser Trp Lys
            245                 250                 255
Ile Ser Lys Ile Asn Ser Asn Tyr Glu Phe Cys Asp Thr Tyr Pro
            260                 265                 270
Ala Ile Ile Val Val Pro Thr Ser Val Lys Asp Asp Leu Ser
            275                 280                 285
Lys Val Ala Ala Phe Arg Ala Lys Gly Arg Val Pro Val Leu Ser
            290                 295                 300
Trp Ile His Pro Glu Ser Gln Ala Thr Ile Thr Arg Cys Ser Gln
            305                 310                 315
Pro Leu Val Gly Pro Asn Asp Lys Arg Cys Lys Glu Asp Glu Lys
            320                 325                 330
Tyr Leu Gln Thr Ile Met Asp Ala Asn Ala Gln Ser His Lys Leu
            335                 340                 345
Ile Ile Phe Asp Ala Arg Gln Asn Ser Val Ala Asp Thr Asn Lys
            350                 355                 360
Thr Lys Gly Gly Gly Tyr Glu Ser Glu Ser Ala Tyr Pro Asn Ala
            365                 370                 375
Glu Leu Val Phe Leu Glu Ile His Asn Ile His Val Met Arg Glu
            380                 385                 390
Ser Leu Arg Lys Leu Lys Glu Ile Val Tyr Pro Ser Ile Asp Glu
            395                 400                 405
Ala Arg Trp Leu Ser Asn Val Asp Gly Thr His Trp Leu Glu Tyr
            410                 415                 420
Ile Arg Met Leu Leu Ala Gly Ala Val Arg Ile Ala Asp Lys Ile
            425                 430                 435
Glu Ser Gly Lys Thr Ser Val Val His Cys Ser Asp Gly Trp
            440                 445                 450
Asp Arg Thr Ala Gln Leu Thr Ser Leu Ala Met Leu Met Leu Asp
            455                 460                 465
Ser Tyr Tyr Arg Thr Ile Lys Gly Phe Glu Thr Leu Val Glu Lys
            470                 475                 480
Glu Trp Ile Ser Phe Gly His Arg Phe Ala Leu Arg Val Gly His
            485                 490                 495
Gly Asn Asp Asn His Ala Asp Ala Asp Arg Ser Pro Ile Phe Leu
            500                 505                 510
Gln Phe Val Asp Cys Val Trp Gln Met Thr Arg Gln Phe Pro Ser
            515                 520                 525
```

-continued

```
Ala Phe Glu Phe Asn Glu Leu Phe Leu Ile Thr Ile Leu Asp His
                530                 535                 540

Leu Tyr Ser Cys Leu Phe Gly Thr Phe Leu Cys Asn Cys Glu Gln
                545                 550                 555

Gln Arg Phe Lys Glu Asp Val Tyr Thr Lys Thr Ile Ser Leu Trp
                560                 565                 570

Ser Tyr Ile Asn Ser Gln Leu Asp Glu Phe Ser Asn Pro Phe Phe
                575                 580                 585

Val Asn Tyr Glu Asn His Val Leu Tyr Pro Val Ala Ser Leu Ser
                590                 595                 600

His Leu Glu Leu Trp Val Asn Tyr Tyr Val Arg Trp Asn Pro Arg
                605                 610                 615

Met Arg Pro Gln Met Pro Ile His Gln Asn Leu Lys Glu Leu Leu
                620                 625                 630

Ala Val Arg Ala Glu Leu Gln Lys Arg Val Glu Gly Leu Gln Arg
                635                 640                 645

Glu Val Ala Thr Arg Ala Val Ser Ser Ser Glu Arg Gly Ser
                650                 655                 660

Ser Pro Ser His Ser Ala Thr Ser Val His Thr Ser Val
                665                 670

<210> SEQ ID NO 3
<211> LENGTH: 459
<212> TYPE: PRT
<213> ORGANISM: Homo sapiens
<220> FEATURE:
<221> NAME/KEY: misc_feature
<223> OTHER INFORMATION: Incyte ID No: 72358203CD1

<400> SEQUENCE: 3

Met Ser Ala Gly Trp Phe Arg Arg Phe Leu Pro Gly Glu Pro
1               5                   10                  15

Leu Pro Ala Pro Arg Pro Gly Pro His Ala Ser Pro Val Pro
                20                  25                  30

Tyr Arg Arg Pro Arg Phe Leu Arg Gly Ser Ser Ser Pro Gly
                35                  40                  45

Ala Ala Asp Ala Ser Arg Arg Pro Asp Ser Arg Pro Val Arg Ser
                50                  55                  60

Pro Ala Arg Gly Arg Thr Leu Pro Trp Asn Ala Gly Tyr Ala Glu
65                  70                  75

Ile Ile Asn Ala Glu Lys Ser Glu Phe Asn Glu Asp Gln Ala Ala
                80                  85                  90

Cys Gly Lys Leu Cys Ile Arg Arg Cys Glu Phe Gly Ala Glu Glu
                95                  100                 105

Glu Trp Leu Thr Leu Cys Pro Glu Glu Phe Leu Thr Gly His Tyr
                110                 115                 120

Trp Ala Leu Phe Asp Gly His Gly Gly Pro Ala Ala Ile Leu
                125                 130                 135

Ala Ala Asn Thr Leu His Ser Cys Leu Arg Arg Gln Leu Glu Ala
                140                 145                 150

Val Val Glu Gly Leu Val Ala Thr Gln Pro Pro Met His Leu Asn
                155                 160                 165

Gly Arg Cys Ile Cys Pro Ser Asp Pro Gln Phe Val Glu Lys
                170                 175                 180

Gly Ile Arg Ala Glu Asp Leu Val Ile Gly Ala Leu Glu Ser Ala
                185                 190                 195
```

-continued

```
Phe Gln Glu Cys Asp Glu Val Ile Gly Arg Glu Leu Glu Ala Ser
                200                 205                 210
Gly Gln Met Gly Gly Cys Thr Ala Leu Val Ala Val Ser Leu Gln
            215                 220                 225
Gly Lys Leu Tyr Met Ala Asn Ala Gly Asp Ser Arg Ala Ile Leu
        230                 235                 240
Val Arg Arg Asp Glu Ile Arg Pro Leu Ser Phe Glu Phe Thr Pro
    245                 250                 255
Glu Thr Glu Arg Gln Arg Ile Gln Gln Leu Ala Phe Val Tyr Pro
260                 265                 270
Glu Leu Leu Ala Gly Glu Phe Thr Arg Leu Glu Phe Pro Arg Arg
                275                 280                 285
Leu Lys Gly Asp Asp Leu Gly Gln Lys Val Leu Phe Arg Asp His
            290                 295                 300
His Met Ser Gly Trp Ser Tyr Lys Arg Val Glu Lys Ser Asp Leu
        305                 310                 315
Lys Tyr Pro Leu Ile His Gly Gln Gly Arg Gln Ala Arg Leu Leu
    320                 325                 330
Gly Thr Leu Ala Val Ser Arg Gly Leu Gly Asp His Gln Leu Arg
335                 340                 345
Val Leu Asp Thr Asn Ile Gln Leu Lys Pro Phe Leu Leu Ser Val
                350                 355                 360
Pro Gln Val Thr Val Leu Asp Val Asp Gln Leu Glu Leu Gln Glu
            365                 370                 375
Asp Asp Val Val Val Met Ala Thr Asp Gly Leu Trp Asp Val Leu
        380                 385                 390
Ser Asn Glu Gln Val Ala Trp Leu Val Arg Ser Phe Leu Pro Gly
    395                 400                 405
Asn Gln Glu Asp Pro His Arg Phe Ser Lys Leu Ala Gln Met Leu
410                 415                 420
Ile His Ser Thr Gln Gly Lys Glu Asp Ser Leu Thr Glu Glu Gly
                425                 430                 435
Gln Val Ser Tyr Asp Asp Val Ser Val Phe Val Ile Pro Leu His
            440                 445                 450
Ser Gln Gly Gln Glu Ser Ser Asp His
        455

<210> SEQ ID NO 4
<211> LENGTH: 243
<212> TYPE: PRT
<213> ORGANISM: Homo sapiens
<220> FEATURE:
<221> NAME/KEY: misc_feature
<223> OTHER INFORMATION: Incyte ID No: 4885040CD1

<400> SEQUENCE: 4

Met Glu His Ala Phe Thr Pro Leu Glu Pro Leu Leu Ser Thr Gly
1               5                   10                  15
Asn Leu Lys Tyr Cys Leu Val Ile Leu Asn Gln Pro Leu Asp Asn
                20                  25                  30
Tyr Phe Arg His Leu Trp Asn Lys Ala Leu Leu Arg Ala Cys Ala
            35                  40                  45
Asp Gly Gly Ala Asn Arg Leu Tyr Asp Ile Thr Glu Gly Glu Arg
        50                  55                  60
Glu Ser Phe Leu Pro Glu Phe Ile Asn Gly Asp Phe Asp Ser Ile
```

```
                       65                  70                  75
Arg Pro Glu Val Arg Glu Tyr Tyr Ala Thr Lys Gly Cys Glu Leu
                80                  85                  90

Ile Ser Thr Pro Asp Gln Asp His Thr Asp Phe Thr Lys Cys Leu
                95                 100                 105

Lys Met Leu Gln Lys Lys Ile Glu Lys Asp Leu Lys Val Asp
            110                 115                 120

Val Ile Val Thr Leu Gly Gly Leu Ala Gly Arg Phe Asp Gln Ile
            125                 130                 135

Met Ala Ser Val Asn Thr Leu Phe Gln Ala Thr His Ile Thr Pro
            140                 145                 150

Phe Pro Ile Ile Ile Gln Glu Glu Ser Leu Ile Tyr Leu Leu
            155                 160                 165

Gln Pro Gly Lys His Arg Leu His Val Asp Thr Gly Met Glu Gly
            170                 175                 180

Asp Trp Cys Gly Leu Ile Pro Val Gly Gln Pro Cys Met Gln Val
            185                 190                 195

Thr Thr Thr Gly Leu Lys Trp Asn Leu Thr Asn Asp Val Leu Ala
            200                 205                 210

Phe Gly Thr Leu Val Ser Thr Ser Asn Thr Tyr Asp Gly Ser Gly
            215                 220                 225

Val Val Thr Val Glu Thr Asp His Pro Leu Leu Trp Thr Met Ala
            230                 235                 240

Ile Lys Ser

<210> SEQ ID NO 5
<211> LENGTH: 632
<212> TYPE: PRT
<213> ORGANISM: Homo sapiens
<220> FEATURE:
<221> NAME/KEY: misc_feature
<223> OTHER INFORMATION: Incyte ID No: 7484507CD1

<400> SEQUENCE: 5

Met Leu Gly Pro Gly Ser Asn Arg Arg Pro Thr Gln Gly Glu
1               5                  10                  15

Arg Gly Pro Gly Ser Pro Gly Glu Pro Met Glu Lys Tyr Gln Val
                20                  25                  30

Leu Tyr Gln Leu Asn Pro Gly Ala Leu Gly Val Asn Leu Val Val
                35                  40                  45

Glu Glu Met Glu Thr Lys Val Lys His Val Ile Lys Gln Val Glu
                50                  55                  60

Cys Met Asp Asp His Tyr Ala Ser Gln Ala Leu Glu Glu Leu Met
                65                  70                  75

Pro Leu Leu Lys Leu Arg His Ala His Ile Ser Val Tyr Gln Glu
                80                  85                  90

Leu Phe Ile Thr Trp Asn Gly Glu Ile Ser Ser Leu Tyr Leu Cys
                95                 100                 105

Leu Val Met Glu Phe Asn Glu Leu Ser Phe Gln Glu Val Ile Glu
            110                 115                 120

Asp Lys Arg Lys Ala Lys Lys Ile Ile Asp Ser Glu Trp Met Gln
            125                 130                 135

Asn Val Leu Gly Gln Val Leu Asp Ala Leu Glu Tyr Leu His His
            140                 145                 150

Leu Asp Ile Ile His Arg Asn Leu Lys Pro Ser Asn Ile Ile Leu
```

```
                    155                 160                 165
Ile Ser Ser Asp His Cys Lys Leu Gln Asp Leu Ser Ser Asn Val
                170                 175                 180

Leu Met Thr Asp Lys Ala Lys Trp Asn Ile Arg Ala Glu Glu Asp
                185                 190                 195

Pro Phe Arg Lys Ser Trp Met Ala Pro Glu Ala Leu Asn Phe Ser
                200                 205                 210

Phe Ser Gln Lys Ser Asp Ile Trp Ser Leu Gly Cys Ile Ile Leu
                215                 220                 225

Asp Met Thr Ser Cys Ser Phe Met Asp Gly Thr Glu Ala Met His
                230                 235                 240

Leu Arg Lys Ser Leu Arg Gln Ser Pro Gly Ser Leu Lys Ala Val
                245                 250                 255

Leu Lys Thr Met Glu Glu Lys Gln Ile Pro Asp Val Glu Thr Phe
                260                 265                 270

Arg Asn Leu Leu Pro Leu Met Leu Gln Ile Asp Pro Ser Asp Arg
                275                 280                 285

Ile Thr Ile Lys Asp Val Val His Ile Thr Phe Leu Arg Gly Ser
                290                 295                 300

Phe Lys Ser Ser Cys Val Ser Leu Thr Leu His Arg Gln Met Val
                305                 310                 315

Pro Ala Ser Ile Thr Asp Met Leu Leu Glu Gly Asn Val Ala Ser
                320                 325                 330

Ile Leu Gly Asp Ala Gly Asp Thr Lys Gly Glu Arg Ala Leu Lys
                335                 340                 345

Leu Leu Ser Met Ala Leu Ala Ser Tyr Cys Leu Val Pro Glu Gly
                350                 355                 360

Ser Leu Phe Met Pro Leu Ala Leu Leu His Met His Asp Gln Trp
                365                 370                 375

Leu Ser Cys Asp Gln Asp Arg Val Pro Gly Lys Arg Asp Phe Ala
                380                 385                 390

Ser Leu Gly Lys Leu Gly Lys Leu Leu Gly Pro Ile Pro Lys Gly
                395                 400                 405

Leu Pro Trp Pro Pro Glu Leu Val Glu Val Val Thr Thr Met
                410                 415                 420

Glu Leu His Asp Arg Val Leu Asp Val Gln Leu Cys Ala Cys Ser
                425                 430                 435

Leu Leu Leu His Leu Leu Gly Gln Gly Ile Ile Val Asn Lys Ala
                440                 445                 450

Pro Leu Glu Lys Val Pro Asp Leu Ile Ser Gln Val Leu Ala Thr
                455                 460                 465

Tyr Pro Ala Asp Gly Glu Met Ala Glu Ala Ser Cys Gly Val Phe
                470                 475                 480

Trp Leu Leu Ser Leu Leu Gly Cys Ile Lys Glu Gln Gln Phe Glu
                485                 490                 495

Gln Val Val Ala Leu Leu Leu Gln Ser Ile Arg Leu Cys Gln Asp
                500                 505                 510

Arg Ala Leu Leu Val Asn Asn Ala Tyr Arg Gly Leu Ala Ser Leu
                515                 520                 525

Val Lys Val Ser Glu Leu Ala Ala Phe Lys Val Val Gln Glu
                530                 535                 540

Glu Gly Gly Ser Gly Leu Ser Leu Ile Lys Glu Thr Tyr Gln Leu
                545                 550                 555
```

```
His Arg Asp Asp Pro Glu Val Val Glu Asn Val Gly Met Leu Leu
            560                 565                 570

Val His Leu Ala Ser Tyr Glu Glu Ile Leu Pro Glu Leu Val Ser
            575                 580                 585

Ser Ser Met Lys Ala Leu Leu Gln Glu Ile Lys Glu Arg Phe Thr
            590                 595                 600

Ser Ser Leu Glu Leu Val Ser Cys Ala Glu Lys Val Leu Leu Arg
            605                 610                 615

Leu Glu Ala Ala Thr Ser Pro Ser Pro Leu Gly Gly Glu Ala Ala
            620                 625                 630

Gln Pro

<210> SEQ ID NO 6
<211> LENGTH: 1511
<212> TYPE: PRT
<213> ORGANISM: Homo sapiens
<220> FEATURE:
<221> NAME/KEY: misc_feature
<223> OTHER INFORMATION: Incyte ID No: 7198931CD1

<400> SEQUENCE: 6

Met Ala Ala Ala Gly Asn Arg Ala Ser Ser Ser Gly Phe Pro
1               5                   10                  15

Gly Ala Arg Ala Thr Ser Pro Glu Ala Gly Gly Gly Gly Ala
            20                  25                  30

Leu Lys Ala Ser Ser Ala Arg Ala Ala Ala Gly Leu Leu Arg
            35                  40                  45

Glu Ala Gly Ser Gly Gly Arg Glu Arg Ala Asp Trp Arg Arg Arg
            50                  55                  60

Gln Leu Arg Lys Val Arg Ser Val Glu Leu Asp Gln Leu Pro Glu
            65                  70                  75

Gln Pro Leu Phe Leu Ala Ala Ser Pro Ala Ser Ser Thr Ser
            80                  85                  90

Pro Ser Pro Glu Pro Ala Asp Ala Ala Gly Ser Gly Thr Gly Phe
            95                  100                 105

Gln Pro Val Ala Val Pro Pro His Gly Ala Ala Ser Arg Arg
            110                 115                 120

Gly Ala His Leu Thr Glu Ser Val Ala Pro Asp Ser Gly Ala
            125                 130                 135

Ser Ser Pro Ala Ala Ala Glu Pro Gly Glu Lys Arg Ala Pro Ala
            140                 145                 150

Ala Glu Pro Ser Pro Ala Ala Ala Pro Ala Gly Arg Glu Met Glu
            155                 160                 165

Asn Lys Glu Thr Leu Lys Gly Leu His Lys Met Asp Asp Arg Pro
            170                 175                 180

Glu Glu Arg Met Ile Arg Glu Lys Leu Lys Ala Thr Cys Met Pro
            185                 190                 195

Ala Trp Lys His Glu Trp Leu Glu Arg Arg Asn Arg Arg Gly Pro
            200                 205                 210

Val Val Val Lys Pro Ile Pro Val Lys Gly Asp Gly Ser Glu Met
            215                 220                 225

Asn His Leu Ala Ala Glu Ser Pro Gly Glu Val Gln Ala Ser Ala
            230                 235                 240

Ala Ser Pro Ala Ser Lys Gly Arg Arg Ser Pro Ser Pro Gly Asn
            245                 250                 255
```

-continued

```
Ser Pro Ser Gly Arg Thr Val Lys Ser Glu Ser Pro Gly Val Arg
            260                 265                 270

Arg Lys Arg Val Ser Pro Val Pro Phe Gln Ser Gly Arg Ile Thr
            275                 280                 285

Pro Pro Arg Arg Ala Pro Ser Pro Asp Gly Phe Ser Pro Tyr Ser
            290                 295                 300

Pro Glu Glu Thr Asn Arg Arg Val Asn Lys Val Met Arg Ala Arg
            305                 310                 315

Leu Tyr Leu Leu Gln Gln Ile Gly Pro Asn Ser Phe Leu Ile Gly
            320                 325                 330

Gly Asp Ser Pro Asp Asn Lys Tyr Arg Val Phe Ile Gly Pro Gln
            335                 340                 345

Asn Cys Ser Cys Ala Arg Gly Thr Phe Cys Ile His Leu Leu Phe
            350                 355                 360

Val Met Leu Arg Val Phe Gln Leu Glu Pro Ser Asp Pro Met Leu
            365                 370                 375

Trp Arg Lys Thr Leu Lys Asn Phe Glu Val Glu Ser Leu Phe Gln
            380                 385                 390

Lys Tyr His Ser Arg Arg Ser Arg Ile Lys Ala Pro Ser Arg
            395                 400                 405

Asn Thr Ile Gln Lys Phe Val Ser Arg Met Ser Asn Ser His Thr
            410                 415                 420

Leu Ser Ser Ser Thr Ser Thr Ser Ser Glu Asn Ser Ile
            425                 430                 435

Lys Asp Glu Glu Glu Gln Met Cys Pro Ile Cys Leu Leu Gly Met
            440                 445                 450

Leu Asp Glu Glu Ser Leu Thr Val Cys Glu Asp Gly Cys Arg Asn
            455                 460                 465

Lys Leu His His His Cys Met Ser Ile Trp Ala Glu Glu Cys Arg
            470                 475                 480

Arg Asn Arg Glu Pro Leu Ile Cys Pro Leu Cys Arg Ser Lys Trp
            485                 490                 495

Arg Ser His Asp Phe Tyr Ser His Glu Leu Ser Ser Pro Val Asp
            500                 505                 510

Ser Pro Ser Ser Leu Arg Ala Ala Gln Gln Thr Val Gln Gln
            515                 520                 525

Gln Pro Leu Ala Gly Ser Arg Arg Asn Gln Glu Ser Asn Phe Asn
            530                 535                 540

Leu Thr His Tyr Gly Thr Gln Gln Ile Pro Pro Ala Tyr Lys Asp
            545                 550                 555

Leu Ala Glu Pro Trp Ile Gln Val Phe Gly Met Glu Leu Val Gly
            560                 565                 570

Cys Leu Phe Ser Arg Asn Trp Asn Val Arg Glu Met Ala Leu Arg
            575                 580                 585

Arg Leu Ser His Asp Val Ser Gly Ala Leu Leu Leu Ala Asn Gly
            590                 595                 600

Glu Ser Thr Gly Asn Ser Gly Gly Ser Ser Gly Ser Ser Pro Ser
            605                 610                 615

Gly Gly Ala Thr Ser Gly Ser Ser Gln Thr Ser Ile Ser Gly Asp
            620                 625                 630

Val Val Glu Ala Cys Cys Ser Val Leu Ser Met Val Cys Ala Asp
            635                 640                 645
```

```
Pro Val Tyr Lys Val Tyr Val Ala Ala Leu Lys Thr Leu Arg Ala
            650                 655                 660
Met Leu Val Tyr Thr Pro Cys His Ser Leu Ala Glu Arg Ile Lys
            665                 670                 675
Leu Gln Arg Leu Leu Gln Pro Val Val Asp Thr Ile Leu Val Lys
            680                 685                 690
Cys Ala Asp Ala Asn Ser Arg Thr Ser Gln Leu Ser Ile Ser Thr
            695                 700                 705
Leu Leu Glu Leu Cys Lys Gly Gln Ala Gly Glu Leu Ala Val Gly
            710                 715                 720
Arg Glu Ile Leu Lys Ala Gly Ser Ile Gly Ile Gly Gly Val Asp
            725                 730                 735
Tyr Val Leu Asn Cys Ile Leu Gly Asn Gln Thr Glu Ser Asn Asn
            740                 745                 750
Trp Gln Glu Leu Leu Gly Arg Leu Cys Leu Ile Asp Arg Leu Leu
            755                 760                 765
Leu Glu Phe Pro Ala Glu Phe Tyr Pro His Ile Val Ser Thr Asp
            770                 775                 780
Val Ser Gln Ala Glu Pro Val Glu Ile Arg Tyr Lys Lys Leu Leu
            785                 790                 795
Ser Leu Leu Thr Phe Ala Leu Gln Ser Ile Asn Asn Ser His Ser
            800                 805                 810
Met Val Gly Lys Leu Ser Arg Arg Ile Tyr Leu Ser Ser Ala Arg
            815                 820                 825
Met Val Thr Thr Val Pro His Val Phe Ser Lys Leu Leu Glu Met
            830                 835                 840
Leu Ser Val Ser Ser Thr His Phe Thr Arg Met Arg Arg Arg
            845                 850                 855
Leu Met Ala Ile Thr Asp Glu Val Glu Ile Ala Glu Ala Ile Gln
            860                 865                 870
Leu Gly Val Glu Asp Thr Leu Asp Gly Gln Gln Asp Ser Phe Leu
            875                 880                 885
Gln Ala Ser Val Pro Asn Asn Tyr Leu Glu Thr Thr Glu Asn Ser
            890                 895                 900
Ser Pro Glu Cys Thr Ile His Leu Glu Lys Thr Gly Lys Gly Leu
            905                 910                 915
Cys Ala Thr Lys Leu Ser Ala Ser Ser Glu Asp Ile Ser Glu Arg
            920                 925                 930
Leu Ala Ser Ile Ser Val Gly Pro Ser Ser Thr Thr Thr Thr
            935                 940                 945
Thr Thr Thr Glu Gln Pro Lys Pro Met Val Gln Thr Lys Gly Arg
            950                 955                 960
Pro His Ser Gln Cys Leu Asn Ser Ser Pro Leu Ser His His Ser
            965                 970                 975
Gln Leu Met Phe Pro Ala Leu Ser Thr Pro Ser Ser Ser Thr Pro
            980                 985                 990
Ser Val Pro Ala Gly Thr Ala Thr Asp Val Ser Lys His Arg Leu
            995                 1000                1005
Gln Gly Phe Ile Pro Cys Arg Ile Pro Ser Ala Ser Pro Gln Thr
            1010                1015                1020
Gln Arg Lys Phe Ser Leu Gln Phe His Arg Asn Cys Pro Glu Asn
            1025                1030                1035
Lys Asp Ser Asp Lys Leu Ser Pro Val Phe Thr Gln Ser Arg Pro
```

-continued

```
            1040                1045                1050
Leu Pro Ser Ser Asn Ile His Arg Pro Lys Pro Ser Arg Pro Thr
            1055                1060                1065
Pro Gly Asn Thr Ser Lys Gln Gly Asp Pro Ser Lys Asn Ser Met
            1070                1075                1080
Thr Leu Asp Leu Asn Ser Ser Lys Cys Asp Asp Ser Phe Gly
            1085                1090                1095
Cys Ser Ser Asn Ser Ser Asn Ala Val Ile Pro Ser Asp Glu Thr
            1100                1105                1110
Val Phe Thr Pro Val Glu Glu Lys Cys Arg Leu Asp Val Asn Thr
            1115                1120                1125
Glu Leu Asn Ser Ser Ile Glu Asp Leu Leu Glu Ala Ser Met Pro
            1130                1135                1140
Ser Ser Asp Thr Thr Val Thr Phe Lys Ser Glu Val Ala Val Leu
            1145                1150                1155
Ser Pro Glu Lys Ala Glu Asn Asp Asp Thr Tyr Lys Asp Asp Val
            1160                1165                1170
Asn His Asn Gln Lys Cys Lys Glu Lys Met Glu Ala Glu Glu
            1175                1180                1185
Glu Ala Leu Ala Ile Ala Met Ala Met Ser Ala Ser Gln Asp Ala
            1190                1195                1200
Leu Pro Ile Val Pro Gln Leu Gln Val Glu Asn Gly Glu Asp Ile
            1205                1210                1215
Ile Ile Ile Gln Gln Asp Thr Pro Glu Thr Leu Pro Gly His Thr
            1220                1225                1230
Lys Ala Lys Gln Pro Tyr Arg Glu Asp Thr Glu Trp Leu Lys Gly
            1235                1240                1245
Gln Gln Ile Gly Leu Gly Ala Phe Ser Ser Cys Tyr Gln Ala Gln
            1250                1255                1260
Asp Val Gly Thr Gly Thr Leu Met Ala Val Lys Gln Val Thr Tyr
            1265                1270                1275
Val Arg Asn Thr Ser Ser Glu Gln Glu Glu Val Val Glu Ala Leu
            1280                1285                1290
Arg Glu Glu Ile Arg Met Met Ser His Leu Asn His Pro Asn Ile
            1295                1300                1305
Ile Arg Met Leu Gly Ala Thr Cys Glu Lys Ser Asn Tyr Asn Leu
            1310                1315                1320
Phe Ile Glu Trp Met Ala Gly Gly Ser Val Ala His Leu Leu Ser
            1325                1330                1335
Lys Tyr Gly Ala Phe Lys Glu Ser Val Val Ile Asn Tyr Thr Glu
            1340                1345                1350
Gln Leu Leu Arg Gly Leu Ser Tyr Leu His Glu Asn Gln Ile Ile
            1355                1360                1365
His Arg Asp Val Lys Gly Ala Asn Leu Leu Ile Asp Ser Thr Gly
            1370                1375                1380
Gln Arg Leu Arg Ile Ala Asp Phe Gly Ala Ala Ala Arg Leu Ala
            1385                1390                1395
Ser Lys Gly Thr Gly Ala Gly Glu Phe Gln Gly Gln Leu Leu Gly
            1400                1405                1410
Thr Ile Ala Phe Met Ala Pro Glu Val Leu Arg Gly Gln Gln Tyr
            1415                1420                1425
Gly Arg Ser Cys Asp Val Trp Ser Val Gly Cys Ala Ile Ile Glu
            1430                1435                1440
```

-continued

Met Ala Cys Ala Lys Pro Pro Trp Asn Ala Glu Lys His Ser Asn
                1445                1450                1455

His Leu Ala Leu Ile Phe Lys Ile Ala Ser Ala Thr Thr Ala Pro
                1460                1465                1470

Ser Ile Pro Ser His Leu Ser Pro Gly Leu Arg Asp Val Ala Leu
                1475                1480                1485

Arg Cys Leu Glu Leu Gln Pro Gln Asp Arg Pro Pro Ser Arg Glu
                1490                1495                1500

Leu Leu Lys His Pro Val Phe Arg Thr Thr Trp
                1505                1510

<210> SEQ ID NO 7
<211> LENGTH: 830
<212> TYPE: PRT
<213> ORGANISM: Homo sapiens
<220> FEATURE:
<221> NAME/KEY: misc_feature
<223> OTHER INFORMATION: Incyte ID No: 7482905CD1

<400> SEQUENCE: 7

Met Lys Ala Glu Gln Met Lys Arg Gln Glu Lys Glu Arg Leu Glu
1               5                   10                  15

Arg Ile Asn Arg Ala Arg Glu Gln Gly Trp Arg Asn Val Leu Ser
                20                  25                  30

Ala Gly Gly Ser Gly Glu Val Lys Ala Pro Phe Leu Gly Ser Gly
                35                  40                  45

Gly Thr Ile Ala Pro Ser Ser Phe Ser Arg Gly Gln Tyr Glu
                50                  55                  60

His Tyr His Ala Ile Phe Asp Gln Met Gln Gln Gln Arg Ala Glu
                65                  70                  75

Asp Asn Glu Ala Lys Trp Lys Arg Glu Ile Tyr Gly Arg Gly Leu
                80                  85                  90

Pro Glu Arg Gln Lys Gly Gln Leu Ala Val Glu Arg Ala Lys Gln
                95                  100                 105

Val Glu Glu Phe Leu Gln Arg Lys Arg Glu Ala Met Gln Asn Lys
                110                 115                 120

Ala Arg Ala Glu Gly His Met Val Tyr Leu Ala Arg Leu Arg Gln
                125                 130                 135

Ile Arg Leu Gln Asn Phe Asn Glu Arg Gln Gln Ile Lys Ala Lys
                140                 145                 150

Leu Arg Gly Glu Lys Lys Glu Ala Asn His Ser Glu Gly Gln Glu
                155                 160                 165

Gly Ser Glu Glu Ala Asp Met Arg Arg Lys Lys Ile Glu Ser Leu
                170                 175                 180

Lys Ala His Ala Asn Ala Arg Ala Ala Val Leu Lys Glu Gln Leu
                185                 190                 195

Glu Arg Lys Arg Lys Glu Ala Tyr Glu Arg Glu Lys Lys Val Trp
                200                 205                 210

Glu Glu His Leu Val Ala Lys Gly Val Lys Ser Ser Asp Val Ser
                215                 220                 225

Pro Pro Leu Gly Gln His Glu Thr Gly Gly Ser Pro Ser Lys Gln
                230                 235                 240

Gln Met Arg Ser Val Ile Ser Val Thr Ser Ala Leu Lys Glu Val
                245                 250                 255

Gly Val Asp Ser Ser Leu Thr Asp Thr Arg Glu Thr Ser Glu Glu

-continued

```
                260                 265                 270
Met Gln Lys Thr Asn Asn Ala Ile Ser Ser Lys Arg Glu Ile Leu
                275                 280                 285
Arg Arg Leu Asn Glu Asn Leu Lys Ala Gln Glu Asp Glu Lys Gly
                290                 295                 300
Lys Gln Asn Leu Ser Asp Thr Phe Glu Ile Asn Val His Glu Asp
                305                 310                 315
Ala Lys Glu His Glu Lys Lys Ser Val Ser Ser Asp Arg Lys
                320                 325                 330
Lys Trp Glu Ala Gly Gln Leu Val Ile Pro Leu Asp Glu Leu
                335                 340                 345
Thr Leu Asp Thr Ser Phe Ser Thr Thr Glu Arg His Thr Val Gly
                350                 355                 360
Glu Val Ile Lys Leu Gly Pro Asn Gly Ser Pro Arg Arg Ala Trp
                365                 370                 375
Gly Lys Ser Pro Thr Asp Ser Val Leu Lys Ile Leu Gly Glu Ala
                380                 385                 390
Glu Leu Gln Leu Gln Thr Glu Leu Leu Glu Asn Thr Thr Ile Arg
                395                 400                 405
Ser Glu Ile Ser Pro Glu Gly Glu Lys Tyr Lys Pro Leu Ile Thr
                410                 415                 420
Gly Glu Lys Lys Val Gln Cys Ile Ser His Glu Ile Asn Pro Ser
                425                 430                 435
Ala Ile Val Asp Ser Pro Val Glu Thr Lys Ser Pro Glu Phe Ser
                440                 445                 450
Glu Ala Ser Pro Gln Met Ser Leu Lys Leu Glu Gly Asn Leu Glu
                455                 460                 465
Glu Pro Asp Asp Leu Glu Thr Glu Ile Leu Gln Glu Pro Ser Gly
                470                 475                 480
Thr Asn Lys Asp Glu Ser Leu Pro Cys Thr Ile Thr Asp Val Trp
                485                 490                 495
Ile Ser Glu Glu Lys Glu Thr Lys Glu Thr Gln Ser Ala Asp Arg
                500                 505                 510
Ile Thr Ile Gln Glu Asn Glu Val Ser Glu Asp Gly Val Ser Ser
                515                 520                 525
Thr Val Asp Gln Leu Ser Asp Ile His Ile Glu Pro Gly Thr Asn
                530                 535                 540
Asp Ser Gln His Ser Lys Cys Asp Val Asp Lys Ser Val Gln Pro
                545                 550                 555
Glu Pro Phe Phe His Lys Val Val His Ser Glu His Leu Asn Leu
                560                 565                 570
Val Pro Gln Val Gln Ser Val Gln Cys Ser Pro Glu Glu Ser Phe
                575                 580                 585
Ala Phe Arg Ser His Ser His Leu Pro Pro Lys Asn Lys Asn Lys
                590                 595                 600
Asn Ser Leu Leu Ile Gly Leu Ser Thr Gly Leu Phe Asp Ala Asn
                605                 610                 615
Asn Pro Lys Met Leu Arg Thr Cys Ser Leu Pro Asp Leu Ser Lys
                620                 625                 630
Leu Phe Arg Thr Leu Met Asp Val Pro Thr Val Gly Asp Val Arg
                635                 640                 645
Gln Asp Asn Leu Glu Ile Asp Glu Ile Glu Asp Glu Asn Ile Lys
                650                 655                 660
```

```
Glu Gly Pro Ser Asp Ser Glu Asp Ile Val Phe Glu Glu Thr Asp
                665                 670                 675
Thr Asp Leu Gln Glu Leu Gln Ala Ser Met Glu Gln Leu Leu Arg
                680                 685                 690
Glu Gln Pro Gly Glu Glu Tyr Ser Glu Glu Glu Ser Val Leu
                695                 700                 705
Lys Asn Ser Asp Val Glu Pro Thr Ala Asn Gly Thr Asp Val Ala
                710                 715                 720
Asp Glu Asp Asp Asn Pro Ser Ser Glu Ser Ala Leu Asn Glu
                725                 730                 735
Trp His Ser Asp Asn Ser Asp Gly Glu Ile Ala Ser Glu Cys Glu
                740                 745                 750
Cys Asp Ser Val Phe Asn His Leu Glu Leu Arg Leu His Leu
                755                 760                 765
Glu Gln Glu Met Gly Phe Glu Lys Phe Glu Val Tyr Glu Lys
                770                 775                 780
Ile Lys Ala Ile His Glu Asp Glu Asp Glu Asn Ile Glu Ile Cys
                785                 790                 795
Ser Lys Ile Val Gln Asn Ile Leu Gly Asn Glu His Gln His Leu
                800                 805                 810
Tyr Ala Lys Ile Leu His Leu Val Met Ala Asp Gly Ala Tyr Gln
                815                 820                 825
Glu Asp Asn Asp Glu
                830

<210> SEQ ID NO 8
<211> LENGTH: 455
<212> TYPE: PRT
<213> ORGANISM: Homo sapiens
<220> FEATURE:
<221> NAME/KEY: misc_feature
<223> OTHER INFORMATION: Incyte ID No: 7483019CD1

<400> SEQUENCE: 8

Met Arg Ile Val Cys Leu Val Lys Asn Gln Gln Pro Leu Gly Ala
1               5                   10                  15
Thr Ile Lys Arg His Glu Met Thr Gly Asp Ile Leu Val Ala Arg
                20                  25                  30
Ile Ile His Gly Gly Leu Ala Glu Arg Ser Gly Leu Leu Tyr Ala
                35                  40                  45
Gly Asp Lys Leu Val Glu Val Asn Gly Val Ser Val Glu Gly Leu
                50                  55                  60
Asp Pro Glu Gln Val Ile His Ile Leu Ala Met Ser Arg Gly Thr
                65                  70                  75
Ile Met Phe Lys Val Val Pro Val Ser Asp Pro Pro Val Asn Ser
                80                  85                  90
Gln Gln Met Val Tyr Val Arg Ala Met Thr Glu Tyr Trp Pro Gln
                95                  100                 105
Glu Asp Pro Asp Ile Pro Cys Met Asp Ala Gly Leu Pro Phe Gln
                110                 115                 120
Lys Gly Asp Ile Leu Gln Ile Val Asp Gln Asn Asp Ala Leu Trp
                125                 130                 135
Trp Gln Ala Arg Lys Ile Ser Asp Pro Ala Thr Cys Ala Gly Leu
                140                 145                 150
Val Pro Ser Asn His Leu Leu Lys Arg Lys Gln Arg Glu Phe Trp
```

-continued

```
                                155                 160                 165
Trp Ser Gln Pro Tyr Gln Pro His Thr Cys Leu Lys Ser Thr Leu
                170                 175                 180
Tyr Lys Glu Glu Phe Val Gly Tyr Gly Gln Lys Phe Ile Ala
            185                 190                 195
Gly Phe Arg Arg Ser Met Arg Leu Cys Arg Arg Lys Ser His Leu
        200                 205                 210
Ser Pro Leu His Ala Ser Val Cys Cys Thr Gly Ser Cys Tyr Ser
        215                 220                 225
Ala Val Gly Ala Pro Tyr Glu Glu Val Val Arg Tyr Gln Arg Arg
        230                 235                 240
Pro Ser Asp Lys Tyr Arg Leu Ile Val Leu Met Gly Pro Ser Gly
        245                 250                 255
Val Gly Val Asn Glu Leu Arg Arg Gln Leu Ile Glu Phe Asn Pro
        260                 265                 270
Ser His Phe Gln Ser Ala Val Pro His Thr Thr Arg Thr Lys Lys
        275                 280                 285
Ser Tyr Glu Thr Asn Gly Arg Glu Tyr His Tyr Val Ser Lys Glu
        290                 295                 300
Thr Phe Glu Asn Leu Ile Tyr Ser His Arg Met Leu Glu Tyr Gly
        305                 310                 315
Glu Tyr Lys Gly His Leu Tyr Gly Thr Ser Val Gly Ala Val Gln
        320                 325                 330
Thr Val Leu Val Glu Gly Lys Ile Cys Val Met Asp Leu Glu Pro
        335                 340                 345
Gln Asp Ile Gln Gly Val Arg Thr His Glu Leu Lys Pro Tyr Val
        350                 355                 360
Ile Phe Ile Lys Pro Ser Asn Met Arg Cys Met Lys Gln Ser Arg
        365                 370                 375
Lys Asn Ala Lys Val Ile Thr Asp Tyr Tyr Val Asp Met Lys Phe
        380                 385                 390
Lys Asp Glu Asp Leu Gln Glu Met Glu Asn Leu Ala Gln Arg Met
        395                 400                 405
Glu Thr Gln Phe Gly Gln Phe Phe Asp His Val Ile Val Asn Asp
        410                 415                 420
Ser Leu His Asp Ala Cys Ala Gln Leu Leu Ser Ala Ile Gln Lys
        425                 430                 435
Ala Gln Glu Glu Pro Gln Trp Val Pro Ala Thr Trp Ile Ser Ser
        440                 445                 450
Asp Thr Glu Ser Gln
        455

<210> SEQ ID NO 9
<211> LENGTH: 1720
<212> TYPE: PRT
<213> ORGANISM: Homo sapiens
<220> FEATURE:
<221> NAME/KEY: misc_feature
<223> OTHER INFORMATION: Incyte ID No: 5455490CD1

<400> SEQUENCE: 9

Met Met Lys Arg Arg Arg Glu Arg Leu Gly Ala Pro Cys Leu Arg
1               5                   10                  15
Ile Gln Ile Ser Thr Leu Cys Arg Gly Ala Glu Val Asn Gln His
                20                  25                  30
```

```
Met Phe Ser Pro Thr Ser Ala Pro Ala Leu Phe Leu Thr Lys Val
             35                  40                  45

Pro Phe Ser Ala Asp Cys Ala Leu Ala Thr Ser Pro Leu Ala Ile
             50                  55                  60

Phe Leu Asn Pro Arg Ala His Ser Ser Pro Gly Thr Pro Cys Ser
             65                  70                  75

Ser Arg Pro Leu Pro Trp Ser Cys Arg Thr Ser Asn Arg Lys Ser
             80                  85                  90

Leu Ile Val Thr Ser Ser Thr Ser Pro Thr Leu Pro Arg Pro His
             95                 100                 105

Ser Pro Leu His Gly His Thr Gly Asn Ser Pro Leu Asp Ser Pro
            110                 115                 120

Arg Asn Phe Ser Pro Asn Ala Pro Ala His Phe Ser Phe Val Pro
            125                 130                 135

Ala Arg Ser His Ser His Arg Ala Asp Arg Thr Asp Gly Arg Arg
            140                 145                 150

Trp Ser Leu Ala Ser Leu Pro Ser Ser Gly Tyr Gly Thr Asn Thr
            155                 160                 165

Pro Ser Ser Thr Val Ser Ser Ser Cys Ser Ser Gln Glu Lys Leu
            170                 175                 180

His Gln Leu Pro Phe Gln Pro Thr Ala Asp Glu Leu His Phe Leu
            185                 190                 195

Thr Lys His Phe Ser Thr Glu Ser Val Pro Asp Glu Glu Gly Arg
            200                 205                 210

Gln Ser Pro Ala Met Arg Pro Arg Ser Arg Ser Leu Ser Pro Gly
            215                 220                 225

Arg Ser Pro Val Ser Phe Asp Ser Glu Ile Ile Met Met Asn His
            230                 235                 240

Val Tyr Lys Glu Arg Phe Pro Lys Ala Thr Ala Gln Met Glu Glu
            245                 250                 255

Arg Leu Ala Glu Phe Ile Ser Ser Asn Thr Pro Asp Ser Val Leu
            260                 265                 270

Pro Leu Ala Asp Gly Ala Leu Ser Phe Ile His His Gln Val Ile
            275                 280                 285

Glu Met Ala Arg Asp Cys Leu Asp Lys Ser Arg Ser Gly Leu Ile
            290                 295                 300

Thr Ser Gln Tyr Phe Tyr Glu Leu Gln Glu Asn Leu Glu Lys Leu
            305                 310                 315

Leu Gln Asp Ala His Glu Arg Ser Glu Ser Ser Glu Val Ala Phe
            320                 325                 330

Val Met Gln Leu Val Lys Lys Leu Met Ile Ile Ile Ala Arg Pro
            335                 340                 345

Ala Arg Leu Leu Glu Cys Leu Glu Phe Asp Pro Glu Glu Phe Tyr
            350                 355                 360

His Leu Leu Glu Ala Ala Glu Gly His Ala Lys Glu Gly Gln Gly
            365                 370                 375

Ile Lys Cys Asp Ile Pro Arg Tyr Ile Val Ser Gln Leu Gly Leu
            380                 385                 390

Thr Arg Asp Pro Leu Glu Glu Met Ala Gln Leu Ser Ser Cys Asp
            395                 400                 405

Ser Pro Asp Thr Pro Glu Thr Asp Asp Ser Ile Glu Gly His Gly
            410                 415                 420

Ala Ser Leu Pro Ser Lys Lys Thr Pro Ser Glu Glu Asp Phe Glu
```

-continued

```
                425                 430                 435
Thr Ile Lys Leu Ile Ser Asn Gly Ala Tyr Gly Ala Val Phe Leu
                440                 445                 450
Val Arg His Lys Ser Thr Arg Gln Arg Phe Ala Met Lys Lys Ile
                455                 460                 465
Asn Lys Gln Asn Leu Ile Leu Arg Asn Gln Ile Gln Gln Ala Phe
                470                 475                 480
Val Glu Arg Asp Ile Leu Thr Phe Ala Glu Asn Pro Phe Val Val
                485                 490                 495
Ser Met Phe Cys Ser Phe Asp Thr Lys Arg His Leu Cys Met Val
                500                 505                 510
Met Glu Tyr Val Glu Gly Gly Asp Cys Ala Thr Leu Leu Lys Asn
                515                 520                 525
Ile Gly Ala Leu Pro Val Asp Met Val Arg Leu Tyr Phe Ala Glu
                530                 535                 540
Thr Val Leu Ala Leu Glu Tyr Leu His Asn Tyr Gly Ile Val His
                545                 550                 555
Arg Asp Leu Lys Pro Asp Asn Leu Leu Ile Thr Ser Met Gly His
                560                 565                 570
Ile Lys Leu Thr Asp Phe Gly Leu Ser Lys Ile Gly Leu Met Ser
                575                 580                 585
Leu Thr Thr Asn Leu Tyr Glu Gly His Ile Glu Lys Asp Ala Arg
                590                 595                 600
Glu Phe Leu Asp Lys Gln Val Cys Gly Thr Pro Glu Tyr Ile Ala
                605                 610                 615
Pro Glu Val Ile Leu Arg Gln Gly Tyr Gly Lys Pro Val Asp Trp
                620                 625                 630
Trp Ala Met Gly Ile Ile Leu Tyr Glu Phe Leu Val Gly Cys Val
                635                 640                 645
Pro Phe Phe Gly Asp Thr Pro Glu Glu Leu Phe Gly Gln Val Ile
                650                 655                 660
Ser Asp Glu Ile Val Trp Pro Glu Gly Asp Glu Ala Leu Pro Pro
                665                 670                 675
Asp Ala Gln Asp Leu Thr Ser Lys Leu Leu His Gln Asn Pro Leu
                680                 685                 690
Glu Arg Leu Gly Thr Gly Ser Ala Tyr Glu Val Lys Gln His Pro
                695                 700                 705
Phe Phe Thr Gly Leu Asp Trp Thr Gly Leu Leu Arg Gln Lys Ala
                710                 715                 720
Glu Phe Ile Pro Gln Leu Glu Ser Glu Asp Asp Thr Ser Tyr Phe
                725                 730                 735
Asp Thr Arg Ser Glu Arg Tyr His His Met Asp Ser Glu Asp Glu
                740                 745                 750
Glu Glu Val Ser Glu Asp Gly Cys Leu Glu Ile Arg Gln Phe Ser
                755                 760                 765
Ser Cys Ser Pro Arg Phe Asn Lys Val Tyr Ser Ser Met Glu Arg
                770                 775                 780
Leu Ser Leu Leu Glu Glu Arg Arg Thr Pro Pro Thr Lys Arg
                785                 790                 795
Ser Leu Ser Glu Glu Lys Glu Asp His Ser Asp Gly Leu Ala Gly
                800                 805                 810
Leu Lys Gly Arg Asp Arg Ser Trp Val Ile Gly Ser Pro Glu Ile
                815                 820                 825
```

-continued

```
Leu Arg Lys Arg Leu Ser Val Ser Glu Ser Ser His Thr Glu Ser
            830                 835                 840

Asp Ser Ser Pro Pro Met Thr Val Arg Arg Cys Ser Gly Leu
            845                 850                 855

Leu Asp Ala Pro Arg Phe Pro Glu Gly Pro Glu Ala Ser Ser
            860                 865                 870

Thr Leu Arg Arg Gln Pro Gln Glu Gly Ile Trp Val Leu Thr Pro
            875                 880                 885

Pro Ser Gly Glu Gly Val Ser Gly Pro Val Thr Glu His Ser Gly
            890                 895                 900

Glu Gln Arg Pro Lys Leu Asp Glu Glu Ala Val Gly Arg Ser Ser
            905                 910                 915

Gly Ser Ser Pro Ala Met Glu Thr Arg Gly Arg Gly Thr Ser Gln
            920                 925                 930

Leu Ala Glu Gly Ala Thr Ala Lys Ala Ile Ser Asp Leu Ala Val
            935                 940                 945

Arg Arg Ala Arg His Arg Leu Leu Ser Gly Asp Ser Thr Glu Lys
            950                 955                 960

Arg Thr Ala Arg Pro Val Asn Lys Val Ile Lys Ser Ala Ser Ala
            965                 970                 975

Thr Ala Leu Ser Leu Leu Ile Pro Ser Glu His His Thr Cys Ser
            980                 985                 990

Pro Leu Ala Ser Pro Met Ser Pro His Ser Gln Ser Ser Asn Pro
            995                 1000                1005

Ser Ser Arg Asp Ser Ser Pro Ser Arg Asp Phe Leu Pro Ala Leu
            1010                1015                1020

Gly Ser Met Arg Pro Pro Ile Ile Ile His Arg Ala Gly Lys Lys
            1025                1030                1035

Tyr Gly Phe Thr Leu Arg Ala Ile Arg Val Tyr Met Gly Asp Ser
            1040                1045                1050

Asp Val Tyr Thr Val His His Met Val Trp His Val Glu Asp Gly
            1055                1060                1065

Gly Pro Ala Ser Glu Ala Gly Leu Arg Gln Gly Asp Leu Ile Thr
            1070                1075                1080

His Val Asn Gly Glu Pro Val His Gly Leu Val His Thr Glu Val
            1085                1090                1095

Val Glu Leu Ile Leu Lys Ser Gly Asn Lys Val Ala Ile Ser Thr
            1100                1105                1110

Thr Pro Leu Glu Asn Thr Ser Ile Lys Val Gly Pro Ala Arg Lys
            1115                1120                1125

Gly Ser Tyr Lys Ala Lys Met Ala Arg Arg Ser Lys Arg Ser Arg
            1130                1135                1140

Gly Lys Asp Gly Gln Glu Ser Arg Lys Arg Ser Ser Leu Phe Arg
            1145                1150                1155

Lys Ile Thr Lys Gln Ala Ser Leu Leu His Thr Ser Arg Ser Leu
            1160                1165                1170

Ser Ser Leu Asn Arg Ser Leu Ser Ser Gly Glu Ser Gly Pro Gly
            1175                1180                1185

Ser Pro Thr His Ser His Ser Leu Ser Pro Arg Ser Pro Thr Gln
            1190                1195                1200

Gly Tyr Arg Val Thr Pro Asp Ala Val His Ser Val Gly Gly Asn
            1205                1210                1215
```

-continued

```
Ser Ser Gln Ser Ser Ser Pro Ser Ser Val Pro Ser Ser Pro
                1220                1225                1230

Ala Gly Ser Gly His Thr Arg Pro Ser Ser Leu His Gly Leu Ala
                1235                1240                1245

Pro Lys Leu Gln Arg Gln Tyr Arg Ser Pro Arg Arg Lys Ser Ala
                1250                1255                1260

Gly Ser Ile Pro Leu Ser Pro Leu Ala His Thr Pro Ser Pro Pro
                1265                1270                1275

Pro Pro Thr Ala Ser Pro Gln Arg Ser Pro Ser Pro Leu Ser Gly
                1280                1285                1290

His Val Ala Gln Ala Phe Pro Thr Lys Leu His Leu Ser Pro Pro
                1295                1300                1305

Leu Gly Arg Gln Leu Ser Arg Pro Lys Ser Ala Glu Pro Pro Arg
                1310                1315                1320

Ser Pro Leu Leu Lys Arg Val Gln Ser Ala Glu Lys Leu Ala Ala
                1325                1330                1335

Ala Leu Ala Ala Ser Glu Lys Lys Leu Ala Thr Ser Arg Lys His
                1340                1345                1350

Ser Leu Asp Leu Pro His Ser Glu Leu Lys Lys Glu Leu Pro Pro
                1355                1360                1365

Arg Glu Val Ser Pro Leu Glu Val Val Gly Ala Arg Ser Val Leu
                1370                1375                1380

Ser Gly Lys Gly Ala Leu Pro Gly Lys Gly Val Leu Gln Pro Ala
                1385                1390                1395

Pro Ser Arg Ala Leu Gly Thr Leu Arg Gln Asp Arg Ala Glu Arg
                1400                1405                1410

Arg Glu Ser Leu Gln Lys Gln Glu Ala Ile Arg Glu Val Asp Ser
                1415                1420                1425

Ser Glu Asp Asp Thr Glu Glu Gly Pro Glu Asn Ser Gln Gly Ala
                1430                1435                1440

Gln Glu Leu Ser Leu Ala Pro His Pro Glu Val Ser Gln Ser Val
                1445                1450                1455

Ala Pro Lys Gly Ala Gly Glu Ser Gly Glu Glu Asp Pro Phe Pro
                1460                1465                1470

Ser Arg Asp Pro Arg Ser Leu Gly Pro Met Val Pro Ser Leu Leu
                1475                1480                1485

Thr Gly Ile Thr Leu Gly Pro Pro Arg Met Glu Ser Pro Ser Gly
                1490                1495                1500

Pro His Arg Arg Leu Gly Ser Pro Gln Ala Ile Glu Glu Ala Ala
                1505                1510                1515

Ser Ser Ser Ser Ala Gly Pro Asn Leu Gly Gln Ser Gly Ala Thr
                1520                1525                1530

Asp Pro Ile Pro Pro Glu Gly Cys Trp Lys Ala Gln His Leu His
                1535                1540                1545

Thr Gln Ala Leu Thr Ala Leu Ser Pro Ser Thr Ser Gly Leu Thr
                1550                1555                1560

Pro Thr Ser Ser Cys Ser Pro Ser Ser Thr Ser Gly Lys Leu
                1565                1570                1575

Ser Met Trp Ser Trp Lys Ser Leu Ile Glu Gly Pro Asp Arg Ala
                1580                1585                1590

Ser Pro Ser Arg Lys Ala Thr Met Ala Gly Gly Leu Ala Asn Leu
                1595                1600                1605

Gln Asp Leu Glu Asn Thr Thr Pro Ala Gln Pro Lys Asn Leu Ser
```

-continued

```
                1610                1615                1620

Pro Arg Glu Gln Gly Lys Thr Gln Pro Pro Ser Ala Pro Arg Leu
            1625                1630                1635

Ala His Pro Ser Tyr Glu Asp Pro Ser Gln Gly Trp Leu Trp Glu
            1640                1645                1650

Ser Glu Cys Ala Gln Ala Val Lys Glu Asp Pro Ala Leu Ser Ile
            1655                1660                1665

Thr Gln Val Pro Asp Ala Ser Gly Asp Arg Arg Gln Asp Val Pro
            1670                1675                1680

Cys Arg Gly Cys Pro Leu Thr Gln Lys Ser Glu Pro Ser Leu Arg
            1685                1690                1695

Arg Gly Gln Glu Pro Gly Gly His Gln Lys His Arg Asp Leu Ala
            1700                1705                1710

Leu Val Pro Asp Glu Leu Leu Lys Gln Thr
            1715                1720

<210> SEQ ID NO 10
<211> LENGTH: 449
<212> TYPE: PRT
<213> ORGANISM: Homo sapiens
<220> FEATURE:
<221> NAME/KEY: misc_feature
<223> OTHER INFORMATION: Incyte ID No: 5547067CD1

<400> SEQUENCE: 10

Met Leu Met Gly Phe Cys Arg Leu Glu Glu Ala Gly Leu Val Ser
1               5                  10                  15

Arg Ser Ile Arg Glu Arg Asn Cys Leu Tyr Asn Trp Asp Ser Arg
                20                  25                  30

Phe Ser Arg Glu Arg Arg Gln Arg Leu Gly Met Gly Ala Val Ser
            35                  40                  45

Cys Arg Gln Gly Gln His Thr Gln Gly Glu His Thr Arg Val
            50                  55                  60

Ala Val Pro His Lys Gly Gly Asn Ile Arg Gly Pro Trp Ala Arg
            65                  70                  75

Gly Trp Lys Ser Leu Trp Thr Gly Leu Gly Thr Ile Arg Ser Asp
            80                  85                  90

Leu Glu Glu Leu Trp Glu Leu Arg Gly His His Tyr Leu His Gln
            95                  100                 105

Glu Ser Leu Lys Pro Ala Pro Val Leu Glu Lys Pro Leu Pro
            110                 115                 120

Glu Trp Pro Val Pro Gln Phe Ile Asn Leu Phe Leu Pro Glu Phe
            125                 130                 135

Pro Ile Arg Pro Ile Arg Gly Gln Gln Gln Leu Lys Ile Leu Gly
            140                 145                 150

Leu Val Ala Lys Gly Ser Phe Gly Thr Val Leu Lys Val Leu Asp
            155                 160                 165

Cys Thr Gln Lys Ala Val Phe Ala Val Lys Val Val Pro Lys Val
            170                 175                 180

Lys Val Leu Gln Arg Asp Thr Val Arg Gln Cys Lys Glu Glu Val
            185                 190                 195

Ser Ile Gln Arg Gln Ile Asn His Pro Phe Val His Ser Leu Gly
            200                 205                 210

Asp Ser Trp Gln Gly Lys Arg His Leu Phe Ile Met Cys Ser Tyr
            215                 220                 225
```

Cys Ser Thr Asp Leu Tyr Ser Leu Trp Ser Ala Val Gly Cys Phe
                230                 235                 240

Pro Glu Ala Ser Ile Arg Leu Phe Ala Glu Leu Val Leu Val
                245                 250                 255

Leu Cys Tyr Leu His Asp Leu Gly Ile Met His Arg Asp Val Lys
                260                 265                 270

Met Glu Asn Ile Leu Leu Asp Glu Arg Gly His Leu Lys Leu Thr
                275                 280                 285

Asp Phe Gly Leu Ser Arg His Val Pro Gln Gly Ala Gln Ala Tyr
                290                 295                 300

Thr Ile Cys Gly Thr Leu Gln Tyr Met Ala Pro Glu Val Leu Ser
                305                 310                 315

Gly Gly Pro Tyr Asn His Ala Ala Asp Trp Trp Ser Leu Gly Val
                320                 325                 330

Leu Leu Phe Ser Leu Ala Thr Gly Lys Phe Pro Val Ala Ala Glu
                335                 340                 345

Arg Asp His Val Ala Met Leu Ala Ser Val Thr His Ser Asp Ser
                350                 355                 360

Glu Ile Pro Ala Ser Leu Asn Gln Gly Leu Ser Leu Leu His
                365                 370                 375

Glu Leu Leu Cys Gln Asn Pro Leu His Arg Leu Arg Tyr Leu His
                380                 385                 390

His Phe Gln Val His Pro Phe Phe Arg Gly Val Ala Phe Asp Pro
                395                 400                 405

Glu Leu Leu Gln Lys Gln Pro Val Asn Phe Val Thr Glu Thr Gln
                410                 415                 420

Ala Thr Gln Pro Ser Ser Ala Glu Thr Met Pro Phe Asp Asp Phe
                425                 430                 435

Asp Cys Asp Leu Glu Ser Phe Leu Leu Tyr Pro Ile Pro Ala
                440                 445

<210> SEQ ID NO 11
<211> LENGTH: 358
<212> TYPE: PRT
<213> ORGANISM: Homo sapiens
<220> FEATURE:
<221> NAME/KEY: misc_feature
<223> OTHER INFORMATION: Incyte ID No: 71675660CD1

<400> SEQUENCE: 11

Met Asp Asp Ala Thr Val Leu Arg Lys Lys Gly Tyr Ile Val Gly
1               5                   10                  15

Ile Asn Leu Gly Lys Gly Ser Tyr Ala Lys Val Lys Ser Ala Tyr
                20                  25                  30

Ser Glu Arg Leu Lys Phe Asn Val Ala Val Lys Ile Ile Asp Arg
                35                  40                  45

Lys Lys Thr Pro Thr Asp Phe Val Glu Arg Phe Leu Pro Arg Glu
                50                  55                  60

Met Asp Ile Leu Ala Thr Val Asn His Gly Ser Ile Ile Lys Thr
                65                  70                  75

Tyr Glu Ile Phe Glu Thr Ser Asp Gly Arg Ile Tyr Ile Ile Met
                80                  85                  90

Glu Leu Gly Val Gln Gly Asp Leu Leu Glu Phe Ile Lys Cys Gln
                95                  100                 105

Gly Ala Leu His Glu Asp Val Ala Arg Lys Met Phe Arg Gln Leu
                110                 115                 120

```
Ser Ser Ala Val Lys Tyr Cys His Asp Leu Asp Ile Val His Arg
            125                 130                 135

Asp Leu Lys Cys Glu Asn Leu Leu Asp Lys Asp Phe Asn Ile
            140                 145                 150

Lys Leu Ser Asp Phe Gly Phe Ser Lys Arg Cys Leu Arg Asp Ser
            155                 160                 165

Asn Gly Arg Ile Ile Leu Ser Lys Thr Phe Cys Gly Ser Ala Ala
            170                 175                 180

Tyr Ala Ala Pro Glu Val Leu Gln Ser Ile Pro Tyr Gln Pro Lys
            185                 190                 195

Val Tyr Asp Ile Trp Ser Leu Gly Val Ile Leu Tyr Ile Met Val
            200                 205                 210

Cys Gly Ser Met Pro Tyr Asp Asp Ser Asp Ile Arg Lys Met Leu
            215                 220                 225

Arg Ile Gln Lys Glu His Arg Val Asp Phe Pro Arg Ser Lys Asn
            230                 235                 240

Leu Thr Cys Glu Cys Lys Asp Leu Ile Tyr Arg Met Leu Gln Pro
            245                 250                 255

Asp Val Ser Gln Arg Leu His Ile Asp Glu Ile Leu Ser His Ser
            260                 265                 270

Trp Leu Gln Pro Lys Pro Lys Ala Met Ser Ser Ala Ser Phe
            275                 280                 285

Lys Arg Glu Gly Glu Gly Lys Tyr Arg Ala Glu Cys Lys Leu Asp
            290                 295                 300

Thr Lys Thr Gly Leu Arg Pro Asp His Arg Pro Asp His Lys Leu
            305                 310                 315

Gly Ala Lys Thr Gln His Arg Leu Leu Val Val Pro Glu Asn Glu
            320                 325                 330

Asn Arg Met Glu Asp Arg Leu Ala Glu Thr Ser Arg Ala Lys Asp
            335                 340                 345

His His Ile Ser Gly Ala Glu Val Gly Lys Ala Ser Thr
            350                 355

<210> SEQ ID NO 12
<211> LENGTH: 358
<212> TYPE: PRT
<213> ORGANISM: Homo sapiens
<220> FEATURE:
<221> NAME/KEY: misc_feature
<223> OTHER INFORMATION: Incyte ID No: 71678683CD1

<400> SEQUENCE: 12

Met Asp Asp Ala Thr Val Leu Arg Lys Lys Gly Tyr Ile Val Gly
1               5                   10                  15

Ile Asn Leu Gly Lys Gly Ser Tyr Ala Lys Val Lys Ser Ala Tyr
            20                  25                  30

Ser Glu Arg Leu Lys Phe Asn Val Ala Val Lys Ile Ile Asp Arg
            35                  40                  45

Lys Lys Thr Pro Thr Asp Phe Val Glu Arg Phe Leu Pro Arg Glu
            50                  55                  60

Met Asp Ile Leu Ala Thr Val Asn His Gly Ser Ile Ile Lys Thr
            65                  70                  75

Tyr Glu Ile Phe Glu Thr Ser Asp Gly Arg Ile Tyr Ile Ile Met
            80                  85                  90

Glu Leu Gly Val Gln Gly Asp Leu Leu Glu Phe Ile Lys Cys Gln
```

-continued

```
                 95                 100                 105
Gly Ala Leu His Glu Asp Val Ala Arg Lys Met Phe Arg Gln Leu
            110                 115                 120

Ser Ser Ala Val Lys Tyr Cys His Asp Leu Asp Ile Val His Arg
            125                 130                 135

Asp Leu Lys Cys Glu Asn Leu Leu Asp Lys Asp Phe Asn Ile
            140                 145                 150

Lys Leu Ser Asp Phe Gly Phe Ser Lys Arg Cys Leu Arg Asp Ser
            155                 160                 165

Asn Gly Arg Ile Ile Leu Ser Lys Thr Phe Cys Gly Ser Ala Ala
            170                 175                 180

Tyr Ala Ala Pro Glu Val Leu Gln Ser Ile Pro Tyr Gln Pro Lys
            185                 190                 195

Val Tyr Asp Ile Trp Ser Leu Gly Val Ile Leu Tyr Ile Met Val
            200                 205                 210

Cys Gly Ser Met Pro Tyr Asp Asp Ser Asp Ile Arg Lys Met Leu
            215                 220                 225

Arg Ile Gln Lys Glu His Arg Val Asp Phe Pro Arg Ser Lys Asn
            230                 235                 240

Leu Thr Cys Glu Cys Lys Asp Leu Ile Tyr Arg Met Leu Gln Pro
            245                 250                 255

Asp Val Ser Gln Arg Leu His Ile Asp Glu Ile Leu Ser His Ser
            260                 265                 270

Trp Leu Gln Pro Pro Lys Pro Lys Ala Thr Ser Ser Ala Ser Phe
            275                 280                 285

Lys Arg Glu Gly Glu Gly Lys Tyr Arg Ala Glu Cys Lys Leu Asp
            290                 295                 300

Thr Lys Thr Gly Leu Arg Pro Asp His Arg Pro Asp His Lys Leu
            305                 310                 315

Gly Ala Lys Thr Gln His Arg Leu Leu Val Val Pro Glu Asn Glu
            320                 325                 330

Asn Arg Met Glu Asp Arg Leu Ala Glu Thr Ser Arg Ala Lys Asp
            335                 340                 345

His His Ile Ser Gly Ala Glu Val Gly Lys Ala Ser Thr
            350                 355

<210> SEQ ID NO 13
<211> LENGTH: 929
<212> TYPE: PRT
<213> ORGANISM: Homo sapiens
<220> FEATURE:
<221> NAME/KEY: misc_feature
<223> OTHER INFORMATION: Incyte ID No: 7474567CD1

<400> SEQUENCE: 13

Met Glu Ser Met Leu Asn Lys Leu Lys Ser Thr Val Thr Lys Val
1               5                  10                  15

Thr Ala Asp Val Thr Ser Ala Val Met Gly Asn Pro Val Thr Arg
                20                  25                  30

Glu Phe Asp Val Gly Arg His Ile Ala Ser Gly Gly Asn Gly Leu
                35                  40                  45

Ala Trp Lys Ile Phe Asn Gly Thr Lys Lys Ser Thr Lys Gln Glu
                50                  55                  60

Val Ala Val Phe Val Phe Asp Lys Lys Leu Ile Asp Lys Tyr Gln
                65                  70                  75
```

```
Lys Phe Glu Lys Asp Gln Ile Ile Asp Ser Leu Lys Arg Gly Val
         80                  85                  90

Gln Gln Leu Thr Arg Leu Arg His Pro Arg Leu Leu Thr Val Gln
         95                 100                 105

His Pro Leu Glu Glu Ser Arg Asp Cys Leu Ala Phe Cys Thr Glu
        110                 115                 120

Pro Val Phe Ala Ser Leu Ala Asn Val Leu Gly Asn Trp Glu Asn
        125                 130                 135

Leu Pro Ser Pro Ile Ser Pro Asp Ile Lys Asp Tyr Lys Leu Tyr
        140                 145                 150

Asp Val Glu Thr Lys Tyr Gly Leu Leu Gln Val Ser Glu Gly Leu
        155                 160                 165

Ser Phe Leu His Ser Ser Val Lys Met Val His Gly Asn Ile Thr
        170                 175                 180

Pro Glu Asn Ile Ile Leu Asn Lys Ser Gly Ala Trp Lys Ile Met
        185                 190                 195

Gly Phe Asp Phe Cys Val Ser Ser Thr Asn Pro Ser Glu Gln Glu
        200                 205                 210

Pro Lys Phe Pro Cys Lys Glu Trp Asp Pro Asn Leu Pro Ser Leu
        215                 220                 225

Cys Leu Pro Asn Pro Glu Tyr Leu Ala Pro Glu Tyr Ile Leu Ser
        230                 235                 240

Val Ser Cys Glu Thr Ala Ser Asp Met Tyr Ser Leu Gly Thr Val
        245                 250                 255

Met Tyr Ala Val Phe Asn Lys Gly Lys Pro Ile Phe Glu Val Asn
        260                 265                 270

Lys Gln Asp Ile Tyr Lys Ser Phe Ser Arg Gln Leu Asp Gln Leu
        275                 280                 285

Ser Arg Leu Gly Ser Ser Ser Leu Thr Asn Ile Pro Glu Glu Val
        290                 295                 300

Arg Glu His Val Lys Leu Leu Leu Asn Val Thr Pro Thr Val Arg
        305                 310                 315

Pro Asp Ala Asp Gln Met Thr Lys Ile Pro Phe Phe Asp Asp Val
        320                 325                 330

Gly Ala Val Thr Leu Gln Tyr Phe Asp Thr Leu Phe Gln Arg Asp
        335                 340                 345

Asn Leu Gln Lys Ser Gln Phe Phe Lys Gly Leu Pro Lys Val Leu
        350                 355                 360

Pro Lys Leu Pro Lys Arg Val Ile Val Gln Arg Ile Leu Pro Cys
        365                 370                 375

Leu Thr Ser Glu Phe Val Asn Pro Asp Met Val Pro Phe Val Leu
        380                 385                 390

Pro Asn Val Leu Leu Ile Ala Glu Glu Cys Thr Lys Glu Glu Tyr
        395                 400                 405

Val Lys Leu Ile Leu Pro Glu Leu Gly Pro Val Phe Lys Gln Gln
        410                 415                 420

Glu Pro Ile Gln Ile Leu Leu Ile Phe Leu Gln Lys Met Asp Leu
        425                 430                 435

Leu Leu Thr Lys Thr Pro Pro Asp Glu Ile Lys Asn Ser Val Leu
        440                 445                 450

Pro Met Val Tyr Arg Ala Leu Glu Ala Pro Ser Ile Gln Ile Gln
        455                 460                 465

Glu Leu Cys Leu Asn Ile Ile Pro Thr Phe Ala Asn Leu Ile Asp
```

```
                        470             475             480
Tyr Pro Ser Met Lys Asn Ala Leu Ile Pro Arg Ile Lys Asn Ala
                485             490             495
Cys Leu Gln Thr Ser Ser Leu Ala Val Arg Val Asn Ser Leu Val
                500             505             510
Cys Leu Gly Lys Ile Leu Glu Tyr Leu Asp Lys Trp Phe Val Leu
                515             520             525
Asp Asp Ile Leu Pro Phe Leu Gln Gln Ile Pro Ser Lys Glu Pro
                530             535             540
Ala Val Leu Met Gly Ile Leu Gly Ile Tyr Lys Cys Thr Phe Thr
                545             550             555
His Lys Lys Leu Gly Ile Thr Lys Glu Gln Leu Ala Gly Lys Val
                560             565             570
Leu Pro His Leu Ile Pro Leu Ser Ile Glu Asn Asn Leu Asn Leu
                575             580             585
Asn Gln Phe Asn Ser Phe Ile Ser Val Ile Lys Glu Met Leu Asn
                590             595             600
Arg Leu Glu Ser Glu His Lys Thr Lys Leu Glu Gln Leu His Ile
                605             610             615
Met Gln Glu Gln Gln Lys Ser Leu Asp Ile Gly Asn Gln Met Asn
                620             625             630
Val Ser Glu Glu Met Lys Val Thr Asn Ile Gly Asn Gln Gln Ile
                635             640             645
Asp Lys Val Phe Asn Asn Ile Gly Ala Asp Leu Leu Thr Gly Ser
                650             655             660
Glu Ser Glu Asn Lys Glu Asp Gly Leu Gln Asn Lys His Lys Arg
                665             670             675
Ala Ser Leu Thr Leu Glu Glu Lys Gln Lys Leu Ala Lys Glu Gln
                680             685             690
Glu Gln Ala Gln Lys Leu Lys Ser Gln Gln Pro Leu Lys Pro Gln
                695             700             705
Val His Thr Pro Val Ala Thr Val Lys Gln Thr Lys Asp Leu Thr
                710             715             720
Asp Thr Leu Met Asp Asn Met Ser Ser Leu Thr Ser Leu Ser Val
                725             730             735
Ser Thr Pro Lys Ser Ser Ala Ser Ser Thr Phe Thr Ser Val Pro
                740             745             750
Ser Met Gly Ile Gly Met Met Phe Ser Thr Pro Thr Asp Asn Thr
                755             760             765
Lys Arg Asn Leu Thr Asn Gly Leu Asn Ala Asn Met Gly Phe Gln
                770             775             780
Thr Ser Gly Phe Asn Met Pro Val Asn Thr Asn Gln Asn Phe Tyr
                785             790             795
Ser Ser Pro Ser Thr Val Gly Val Thr Lys Met Thr Leu Gly Thr
                800             805             810
Pro Pro Thr Leu Pro Asn Phe Asn Ala Leu Ser Val Pro Pro Ala
                815             820             825
Gly Ala Lys Gln Thr Gln Gln Arg Pro Thr Asp Met Ser Ala Leu
                830             835             840
Asn Asn Leu Phe Gly Pro Gln Lys Pro Val Ser Met Asn Gln
                845             850             855
Leu Ser Gln Gln Lys Pro Asn Gln Trp Leu Asn Gln Phe Val Pro
                860             865             870
```

-continued

```
Pro Gln Gly Ser Pro Thr Met Gly Ser Val Met Gly Thr Gln
            875                 880                 885

Met Asn Val Ile Gly Gln Ser Ala Phe Gly Met Gln Gly Asn Pro
            890                 895                 900

Phe Phe Asn Pro Gln Asn Phe Ala Gln Pro Pro Thr Thr Met Thr
            905                 910                 915

Asn Ser Ser Ser Ala Ser Asn Asp Leu Lys Asp Leu Phe Gly
            920                 925

<210> SEQ ID NO 14
<211> LENGTH: 523
<212> TYPE: PRT
<213> ORGANISM: Homo sapiens
<220> FEATURE:
<221> NAME/KEY: misc_feature
<223> OTHER INFORMATION: Incyte ID No: 3838946CD1

<400> SEQUENCE: 14

Met Ala Ala Ala Leu Gln Val Leu Pro Arg Leu Ala Arg Ala Pro
1               5                   10                  15

Leu His Pro Leu Leu Trp Arg Gly Ser Val Ala Arg Leu Ala Ser
            20                  25                  30

Ser Met Ala Leu Ala Glu Gln Ala Arg Gln Leu Phe Glu Ser Ala
            35                  40                  45

Val Gly Ala Val Leu Pro Gly Pro Met Leu His Arg Ala Leu Ser
            50                  55                  60

Leu Asp Pro Gly Gly Arg Gln Leu Lys Val Arg Asp Arg Asn Phe
            65                  70                  75

Gln Leu Arg Gln Asn Leu Tyr Leu Val Gly Phe Gly Lys Ala Val
            80                  85                  90

Leu Gly Met Ala Ala Ala Glu Glu Leu Leu Gly Gln His Leu
            95                  100                 105

Val Gln Gly Val Ile Ser Val Pro Lys Gly Ile Arg Ala Ala Met
            110                 115                 120

Glu Arg Ala Gly Lys Gln Glu Met Leu Leu Lys Pro His Ser Arg
            125                 130                 135

Val Gln Val Phe Glu Gly Ala Glu Asp Asn Leu Pro Asp Arg Asp
            140                 145                 150

Ala Leu Arg Ala Ala Leu Ala Ile Gln Gln Leu Ala Glu Gly Leu
            155                 160                 165

Thr Ala Asp Asp Leu Leu Leu Val Leu Ile Ser Gly Gly Gly Ser
            170                 175                 180

Ala Leu Leu Pro Ala Pro Ile Pro Pro Val Thr Leu Glu Glu Lys
            185                 190                 195

Gln Thr Leu Thr Arg Leu Leu Ala Ala Arg Gly Ala Thr Ile Gln
            200                 205                 210

Glu Leu Asn Thr Ile Arg Lys Ala Leu Ser Gln Leu Lys Gly Gly
            215                 220                 225

Gly Leu Ala Gln Ala Ala Tyr Pro Ala Gln Val Val Ser Leu Ile
            230                 235                 240

Leu Ser Asp Val Val Gly Asp Pro Val Glu Val Ile Ala Ser Gly
            245                 250                 255

Pro Thr Val Ala Ser Ser His Asn Val Gln Asp Cys Leu His Ile
            260                 265                 270

Leu Asn Arg Tyr Gly Leu Arg Ala Ala Leu Pro Arg Ser Val Lys
```

```
                     275                 280                 285
Thr Val Leu Ser Arg Ala Asp Ser Asp Pro His Gly Pro His Thr
                 290                 295                 300
Cys Gly His Val Leu Asn Val Ile Ile Gly Ser Asn Val Leu Ala
             305                 310                 315
Leu Ala Glu Ala Gln Arg Gln Ala Glu Ala Leu Gly Tyr Gln Ala
         320                 325                 330
Val Val Leu Ser Ala Ala Met Gln Gly Asp Val Lys Ser Met Ala
     335                 340                 345
Gln Phe Tyr Gly Leu Leu Ala His Val Ala Arg Thr Arg Leu Thr
             350                 355                 360
Pro Ser Met Ala Gly Ala Ser Val Glu Glu Asp Ala Gln Leu His
         365                 370                 375
Glu Leu Ala Ala Glu Leu Gln Ile Pro Asp Leu Gln Leu Glu Glu
     380                 385                 390
Ala Leu Glu Thr Met Ala Trp Gly Arg Gly Pro Val Cys Leu Leu
             395                 400                 405
Ala Gly Gly Glu Pro Thr Val Gln Leu Gln Gly Ser Gly Arg Gly
         410                 415                 420
Gly Arg Asn Gln Glu Leu Ala Leu Arg Val Gly Ala Glu Leu Arg
     425                 430                 435
Arg Trp Pro Leu Gly Pro Ile Asp Val Leu Phe Leu Ser Gly Gly
             440                 445                 450
Thr Asp Gly Gln Asp Gly Pro Thr Glu Ala Ala Gly Ala Trp Val
         455                 460                 465
Thr Pro Glu Leu Ala Ser Gln Ala Ala Ala Glu Gly Leu Asp Ile
     470                 475                 480
Ala Thr Phe Leu Ala His Asn Asp Ser His Thr Phe Cys Cys
             485                 490                 495
Leu Gln Gly Gly Ala His Leu Leu His Thr Gly Met Thr Gly Thr
         500                 505                 510
Asn Val Met Asp Thr His Leu Leu Phe Leu Arg Pro Arg
     515                 520

<210> SEQ ID NO 15
<211> LENGTH: 459
<212> TYPE: PRT
<213> ORGANISM: Homo sapiens
<220> FEATURE:
<221> NAME/KEY: misc_feature
<223> OTHER INFORMATION: Incyte ID No: 72001176CD1

<400> SEQUENCE: 15

Met Asp His Pro Ser Arg Glu Lys Asp Glu Arg Gln Arg Thr Thr
1               5                  10                  15
Lys Pro Met Ala Gln Arg Ser Ala His Cys Ser Arg Pro Ser Gly
             20                  25                  30
Ser Ser Ser Ser Ser Gly Val Leu Met Val Gly Pro Asn Phe Arg
         35                  40                  45
Val Gly Lys Lys Ile Gly Cys Gly Asn Phe Gly Glu Leu Arg Leu
     50                  55                  60
Gly Lys Asn Leu Tyr Thr Asn Glu Tyr Val Ala Ile Lys Leu Glu
             65                  70                  75
Pro Ile Lys Ser Arg Ala Leu Gln Leu His Leu Glu Tyr Arg Phe
         80                  85                  90
```

-continued

```
Tyr Lys Gln Leu Gly Ser Ala Gly Glu Gly Leu Pro Gln Val Tyr
             95                 100                 105

Tyr Phe Gly Pro Cys Gly Lys Tyr Asn Ala Met Val Leu Glu Leu
            110                 115                 120

Leu Gly Pro Ser Leu Glu Asp Leu Phe Asp Leu Cys Asp Arg Thr
            125                 130                 135

Phe Thr Leu Lys Thr Val Leu Met Ile Ala Ile Gln Leu Leu Ser
            140                 145                 150

Arg Met Glu Tyr Val His Ser Lys Asn Leu Ile Tyr Arg Asp Val
            155                 160                 165

Lys Pro Glu Asn Phe Leu Ile Gly Arg Gln Gly Asn Lys Lys Glu
            170                 175                 180

His Val Ile His Ile Ile Asp Phe Gly Leu Ala Lys Glu Tyr Ile
            185                 190                 195

Asp Pro Glu Thr Lys Lys His Ile Pro Tyr Arg Glu His Lys Ser
            200                 205                 210

Leu Thr Gly Thr Ala Arg Tyr Met Ser Ile Asn Thr His Leu Gly
            215                 220                 225

Lys Glu Gln Ser Arg Arg Asp Asp Leu Glu Ala Leu Gly His Met
            230                 235                 240

Phe Met Tyr Phe Leu Arg Gly Ser Leu Pro Trp Gln Gly Leu Lys
            245                 250                 255

Ala Asp Thr Leu Lys Glu Arg Tyr Gln Lys Ile Gly Asp Thr Lys
            260                 265                 270

Arg Asn Thr Pro Ile Glu Ala Leu Cys Glu Asn Phe Pro Glu Glu
            275                 280                 285

Met Ala Thr Tyr Leu Arg Tyr Val Arg Arg Leu Asp Phe Phe Glu
            290                 295                 300

Lys Pro Asp Tyr Glu Tyr Leu Arg Thr Leu Phe Thr Asp Leu Phe
            305                 310                 315

Glu Lys Lys Gly Tyr Thr Phe Asp Tyr Ala Tyr Asp Trp Val Gly
            320                 325                 330

Arg Pro Ile Pro Thr Pro Val Gly Ser Val His Val Asp Ser Gly
            335                 340                 345

Ala Ser Ala Ile Thr Arg Glu Ser His Thr His Arg Asp Arg Pro
            350                 355                 360

Ser Gln Gln Gln Pro Leu Arg Asn Gln Asn Val Ser Ser Glu Arg
            365                 370                 375

Arg Gly Glu Trp Glu Ile Gln Pro Ser Arg Gln Thr Asn Thr Ser
            380                 385                 390

Tyr Leu Thr Ser His Leu Ala Ala Asp Arg His Gly Gly Ser Val
            395                 400                 405

Gln Val Val Ser Ser Thr Asn Gly Glu Leu Asn Val Asp Asp Pro
            410                 415                 420

Thr Gly Ala His Ser Asn Ala Pro Ile Thr Ala His Ala Glu Val
            425                 430                 435

Glu Val Val Glu Glu Ala Lys Cys Cys Cys Phe Phe Lys Arg Lys
            440                 445                 450

Arg Lys Lys Thr Ala Gln Arg His Lys
            455
```

<210> SEQ ID NO 16
<211> LENGTH: 1360
<212> TYPE: PRT

<213> ORGANISM: Homo sapiens
<220> FEATURE:
<221> NAME/KEY: misc_feature
<223> OTHER INFORMATION: Incyte ID No: 55064363CD1

<400> SEQUENCE: 16

```
Met Lys Trp Val Gly Asp Thr Gly Val Gly Asn Ile Pro Pro
1               5                   10                  15

Ser Phe Thr Thr Pro Gly Leu Ser Ser Arg Pro Gly Ala Met Val
                20                  25                  30

Ala Asp Arg Ser Arg Trp Pro Leu Ala Gln Gly Lys Gly Ala Gln
                35                  40                  45

Ala Gly Thr Trp Arg Ala Val Glu Cys Ser Gly Arg Gly Leu
                50                  55                  60

Gly Ala Ala Ser Glu Ser Pro Gln Cys Pro Pro Pro Gly Val
                65                  70                  75

Glu Gly Ala Ala Gly Pro Ala Glu Pro Asp Gly Ala Ala Glu Gly
                80                  85                  90

Ala Ala Gly Gly Ser Gly Glu Gly Glu Ser Gly Gly Pro Arg
                95                  100                 105

Arg Ala Leu Arg Ala Val Tyr Val Arg Ser Glu Ser Ser Gln Gly
                110                 115                 120

Gly Ala Ala Gly Gly Pro Glu Ala Gly Ala Arg Gln Cys Leu Leu
                125                 130                 135

Arg Ala Cys Glu Ala Glu Gly Ala His Leu Thr Ser Val Pro Phe
                140                 145                 150

Gly Glu Leu Asp Phe Gly Glu Thr Ala Val Leu Asp Ala Phe Tyr
                155                 160                 165

Asp Ala Asp Val Ala Val Val Asp Met Ser Asp Val Ser Arg Gln
                170                 175                 180

Pro Ser Leu Phe Tyr His Leu Gly Val Arg Glu Ser Phe Asp Met
                185                 190                 195

Ala Asn Asn Val Ile Leu Tyr His Asp Thr Asp Ala Asp Thr Ala
                200                 205                 210

Leu Ser Leu Lys Asp Met Val Thr Gln Lys Asn Thr Ala Ser Ser
                215                 220                 225

Gly Asn Tyr Tyr Phe Ile Pro Tyr Ile Val Thr Pro Cys Thr Asp
                230                 235                 240

Tyr Phe Cys Cys Glu Ser Asp Ala Gln Arg Arg Ala Ser Glu Tyr
                245                 250                 255

Met Gln Pro Asn Trp Asp Asn Ile Leu Gly Pro Leu Cys Met Pro
                260                 265                 270

Leu Val Asp Arg Phe Ile Ser Leu Leu Lys Asp Ile His Val Thr
                275                 280                 285

Ser Cys Val Tyr Tyr Lys Glu Thr Leu Leu Asn Asp Ile Arg Lys
                290                 295                 300

Ala Arg Glu Lys Tyr Gln Gly Glu Glu Leu Ala Lys Glu Leu Ala
                305                 310                 315

Arg Ile Lys Leu Arg Met Asp Asn Thr Glu Val Leu Thr Ser Asp
                320                 325                 330

Ile Ile Ile Asn Leu Leu Leu Ser Tyr Arg Asp Ile Gln Asp Tyr
                335                 340                 345

Asp Ala Met Val Lys Leu Val Glu Thr Leu Glu Met Leu Pro Thr
                350                 355                 360
```

```
Cys Asp Leu Ala Asp Gln His Asn Ile Lys Phe His Tyr Ala Phe
            365                 370                 375

Ala Leu Asn Arg Arg Asn Ser Thr Gly Asp Arg Glu Lys Ala Leu
            380                 385                 390

Gln Ile Met Leu Gln Val Leu Gln Ser Cys Asp His Pro Gly Pro
            395                 400                 405

Asp Met Phe Cys Leu Cys Gly Arg Ile Tyr Lys Asp Ile Phe Leu
            410                 415                 420

Asp Ser Asp Cys Lys Asp Asp Thr Ser Arg Asp Ser Ala Ile Glu
            425                 430                 435

Trp Tyr Arg Lys Gly Phe Glu Leu Gln Ser Ser Leu Tyr Ser Gly
            440                 445                 450

Ile Asn Leu Ala Val Leu Leu Ile Val Ala Gly Gln Gln Phe Glu
            455                 460                 465

Thr Ser Leu Glu Leu Arg Lys Ile Gly Val Arg Leu Asn Ser Leu
            470                 475                 480

Leu Gly Arg Lys Gly Ser Leu Glu Lys Met Asn Asn Tyr Trp Asp
            485                 490                 495

Val Gly Gln Phe Phe Ser Val Ser Met Leu Ala His Asp Val Gly
            500                 505                 510

Lys Ala Val Gln Ala Ala Glu Arg Leu Phe Lys Leu Lys Pro Pro
            515                 520                 525

Val Trp Tyr Leu Arg Ser Leu Val Gln Asn Leu Leu Leu Ile Arg
            530                 535                 540

Arg Phe Lys Lys Thr Ile Ile Glu His Ser Pro Arg Gln Glu Arg
            545                 550                 555

Leu Asn Phe Trp Leu Asp Ile Ile Phe Glu Ala Thr Asn Glu Val
            560                 565                 570

Thr Asn Gly Leu Arg Phe Pro Val Leu Val Ile Glu Pro Thr Lys
            575                 580                 585

Val Tyr Gln Pro Ser Tyr Val Ser Ile Asn Asn Glu Ala Glu Glu
            590                 595                 600

Arg Thr Val Ser Leu Trp His Val Ser Pro Thr Glu Met Lys Gln
            605                 610                 615

Met His Glu Trp Asn Phe Thr Ala Ser Ser Ile Lys Gly Ile Ser
            620                 625                 630

Leu Ser Lys Phe Asp Glu Arg Cys Cys Phe Leu Tyr Val His Asp
            635                 640                 645

Asn Ser Asp Asp Phe Gln Ile Tyr Phe Ser Thr Glu Glu Gln Cys
            650                 655                 660

Ser Arg Phe Phe Ser Leu Val Lys Glu Met Ile Thr Asn Thr Ala
            665                 670                 675

Gly Ser Thr Val Glu Leu Glu Gly Glu Thr Asp Gly Asp Thr Leu
            680                 685                 690

Glu Tyr Glu Tyr Asp His Asp Ala Asn Gly Glu Arg Val Val Leu
            695                 700                 705

Gly Lys Gly Thr Tyr Gly Ile Val Tyr Ala Gly Arg Asp Leu Ser
            710                 715                 720

Asn Gln Val Arg Ile Ala Ile Lys Glu Ile Pro Glu Arg Asp Ser
            725                 730                 735

Arg Tyr Ser Gln Pro Leu His Glu Glu Ile Ala Leu His Lys Tyr
            740                 745                 750

Leu Lys His Arg Asn Ile Val Gln Tyr Leu Gly Ser Val Ser Glu
```

-continued

```
                755                 760                 765
Asn Gly Tyr Ile Lys Ile Phe Met Glu Gln Val Pro Gly Gly Ser
            770                 775                 780
Leu Ser Ala Leu Leu Arg Ser Lys Trp Gly Pro Met Lys Glu Pro
            785                 790                 795
Thr Ile Lys Phe Tyr Thr Lys Gln Ile Leu Glu Gly Leu Lys Tyr
            800                 805                 810
Leu His Glu Asn Gln Ile Val His Arg Asp Ile Lys Gly Asp Asn
            815                 820                 825
Val Leu Val Asn Thr Tyr Ser Gly Val Val Lys Ile Ser Asp Phe
            830                 835                 840
Gly Thr Ser Lys Arg Leu Ala Gly Val Asn Pro Cys Thr Glu Thr
            845                 850                 855
Phe Thr Gly Thr Leu Gln Tyr Met Ala Pro Glu Ile Ile Asp Gln
            860                 865                 870
Gly Pro Arg Gly Tyr Gly Ala Pro Ala Asp Ile Trp Ser Leu Gly
            875                 880                 885
Cys Thr Ile Ile Glu Met Ala Thr Ser Lys Pro Pro Phe His Glu
            890                 895                 900
Leu Gly Glu Pro Gln Ala Ala Met Phe Lys Val Gly Met Phe Lys
            905                 910                 915
Ile His Pro Glu Ile Pro Glu Ala Leu Ser Ala Glu Ala Arg Ala
            920                 925                 930
Phe Ile Leu Ser Cys Phe Glu Pro Asp Pro His Lys Arg Ala Thr
            935                 940                 945
Thr Ala Glu Leu Leu Arg Glu Gly Phe Leu Arg Gln Val Asn Lys
            950                 955                 960
Gly Lys Lys Asn Arg Ile Ala Phe Lys Pro Ser Glu Gly Pro Arg
            965                 970                 975
Gly Val Val Leu Ala Leu Pro Thr Gln Gly Glu Pro Met Ala Thr
            980                 985                 990
Ser Ser Ser Glu His Gly Ser Val Ser Pro Asp Ser Asp Ala Gln
            995                 1000                1005
Pro Asp Ala Leu Phe Glu Arg Thr Arg Ala Pro Arg His His Leu
            1010                1015                1020
Gly His Leu Leu Ser Val Pro Asp Glu Ser Ser Ala Leu Glu Asp
            1025                1030                1035
Arg Gly Leu Ala Ser Ser Pro Glu Asp Arg Asp Gln Gly Leu Phe
            1040                1045                1050
Leu Leu Arg Lys Asp Ser Glu Arg Arg Ala Ile Leu Tyr Lys Ile
            1055                1060                1065
Leu Trp Glu Glu Gln Asn Gln Val Ala Ser Asn Leu Gln Glu Cys
            1070                1075                1080
Val Ala Gln Ser Ser Glu Glu Leu His Leu Ser Val Gly His Ile
            1085                1090                1095
Lys Gln Ile Ile Gly Ile Leu Arg Asp Phe Ile Arg Ser Pro Glu
            1100                1105                1110
His Arg Val Met Ala Thr Thr Ile Ser Lys Leu Lys Val Asp Leu
            1115                1120                1125
Asp Phe Asp Ser Ser Ser Ile Ser Gln Ile His Leu Val Leu Phe
            1130                1135                1140
Gly Phe Gln Asp Ala Val Asn Lys Ile Leu Arg Asn His Leu Ile
            1145                1150                1155
```

```
Arg Pro His Trp Met Phe Ala Met Asp Asn Ile Ile Arg Arg Ala
            1160                1165                1170
Val Gln Ala Ala Val Thr Ile Leu Ile Pro Glu Leu Arg Ala His
            1175                1180                1185
Phe Glu Pro Thr Cys Glu Thr Glu Gly Val Asp Lys Asp Met Asp
            1190                1195                1200
Glu Ala Glu Glu Gly Tyr Pro Pro Ala Thr Gly Pro Gly Gln Glu
            1205                1210                1215
Ala Gln Pro His Gln Gln His Leu Ser Leu Gln Leu Gly Glu Leu
            1220                1225                1230
Arg Gln Glu Thr Asn Arg Leu Leu Glu His Leu Val Glu Lys Glu
            1235                1240                1245
Arg Glu Tyr Gln Asn Leu Leu Arg Gln Thr Leu Glu Gln Lys Thr
            1250                1255                1260
Gln Glu Leu Tyr His Leu Gln Leu Lys Leu Lys Ser Asn Cys Ile
            1265                1270                1275
Thr Glu Asn Pro Ala Gly Pro Tyr Gly Gln Arg Thr Asp Lys Glu
            1280                1285                1290
Leu Ile Asp Trp Leu Arg Leu Gln Gly Ala Asp Ala Lys Thr Ile
            1295                1300                1305
Glu Lys Ile Val Glu Gly Tyr Thr Leu Ser Asp Ile Leu Asn
            1310                1315                1320
Glu Ile Thr Lys Glu Asp Leu Arg Tyr Leu Arg Leu Arg Gly Gly
            1325                1330                1335
Leu Leu Cys Arg Leu Trp Ser Ala Val Ser Gln Tyr Arg Arg Ala
            1340                1345                1350
Gln Glu Ala Ser Glu Thr Lys Asp Lys Ala
            1355                1360

<210> SEQ ID NO 17
<211> LENGTH: 1345
<212> TYPE: PRT
<213> ORGANISM: Homo sapiens
<220> FEATURE:
<221> NAME/KEY: misc_feature
<223> OTHER INFORMATION: Incyte ID No: 7482044CD1

<400> SEQUENCE: 17

Met Glu Pro Gly Arg Gly Ala Gly Pro Ala Gly Met Ala Glu Pro
1               5                   10                  15
Arg Ala Lys Ala Ala Arg Pro Gly Pro Gln Arg Phe Leu Arg Arg
                20                  25                  30
Ser Val Val Glu Ser Asp Gln Glu Glu Pro Pro Gly Leu Glu Ala
                35                  40                  45
Ala Glu Ala Pro Gly Pro Gln Pro Pro Gln Pro Leu Gln Arg Arg
                50                  55                  60
Val Leu Leu Leu Cys Lys Thr Arg Arg Leu Ile Ala Glu Arg Ala
                65                  70                  75
Arg Gly Arg Pro Ala Ala Pro Ala Pro Ala Ala Leu Val Ala Gln
                80                  85                  90
Pro Gly Ala Pro Gly Ala Pro Ala Asp Ala Gly Pro Glu Pro Val
                95                  100                 105
Gly Thr Gln Glu Pro Gly Pro Asp Pro Ile Ala Ala Ala Val Glu
                110                 115                 120
Thr Ala Pro Ala Pro Asp Gly Gly Pro Arg Glu Glu Ala Ala Ala
```

-continued

```
                125                 130                 135
Thr Val Arg Lys Glu Asp Glu Gly Ala Ala Glu Ala Lys Pro Glu
                140                 145                 150
Pro Gly Arg Thr Arg Arg Asp Glu Pro Glu Glu Glu Glu Asp Asp
                155                 160                 165
Glu Asp Asp Leu Lys Ala Val Ala Thr Ser Leu Asp Gly Arg Phe
                170                 175                 180
Leu Lys Phe Asp Ile Glu Leu Gly Arg Gly Ser Phe Lys Thr Val
                185                 190                 195
Tyr Lys Gly Leu Asp Thr Glu Thr Trp Val Glu Val Ala Trp Cys
                200                 205                 210
Glu Leu Gln Asp Arg Lys Leu Thr Lys Leu Glu Arg Gln Arg Phe
                215                 220                 225
Lys Glu Glu Ala Glu Met Leu Lys Gly Leu Gln His Pro Asn Ile
                230                 235                 240
Val Arg Phe Tyr Asp Phe Trp Glu Ser Ser Ala Lys Gly Lys Arg
                245                 250                 255
Cys Ile Val Leu Val Thr Glu Leu Met Thr Ser Gly Thr Leu Lys
                260                 265                 270
Thr Tyr Leu Lys Arg Phe Lys Val Met Lys Pro Lys Val Leu Arg
                275                 280                 285
Ser Trp Cys Arg Gln Ile Leu Lys Gly Leu Leu Phe Leu His Thr
                290                 295                 300
Arg Thr Pro Pro Ile Ile His Arg Asp Leu Lys Cys Asp Asn Ile
                305                 310                 315
Phe Ile Thr Gly Pro Thr Gly Ser Val Lys Ile Gly Asp Leu Gly
                320                 325                 330
Leu Ala Thr Leu Lys Arg Ala Ser Phe Ala Lys Ser Val Ile Gly
                335                 340                 345
Thr Pro Glu Phe Met Ala Pro Glu Met Tyr Glu Glu His Tyr Asp
                350                 355                 360
Glu Ser Val Asp Val Tyr Ala Phe Gly Met Cys Met Leu Glu Met
                365                 370                 375
Ala Thr Ser Glu Tyr Pro Tyr Ser Glu Cys Gln Asn Ala Ala Gln
                380                 385                 390
Ile Tyr Arg Lys Val Thr Cys Gly Ile Lys Pro Ala Ser Phe Glu
                395                 400                 405
Lys Val His Asp Pro Glu Ile Lys Glu Ile Gly Glu Cys Ile
                410                 415                 420
Cys Lys Asn Lys Glu Glu Arg Tyr Glu Ile Lys Asp Leu Leu Ser
                425                 430                 435
His Ala Phe Phe Ala Glu Asp Thr Gly Val Arg Val Glu Leu Ala
                440                 445                 450
Glu Glu Asp His Gly Arg Lys Ser Thr Ile Ala Leu Arg Leu Trp
                455                 460                 465
Val Glu Asp Pro Lys Lys Leu Lys Gly Lys Pro Lys Asp Asn Gly
                470                 475                 480
Ala Ile Glu Phe Thr Phe Asp Leu Glu Lys Glu Thr Pro Asp Glu
                485                 490                 495
Val Ala Gln Glu Met Ile Glu Ser Gly Phe Phe His Glu Ser Asp
                500                 505                 510
Val Lys Ile Val Ala Lys Ser Ile Arg Asp Arg Val Ala Leu Ile
                515                 520                 525
```

-continued

```
Gln Trp Arg Arg Glu Arg Ile Trp Pro Ala Leu Gln Pro Lys Glu
            530                 535                 540

Gln Gln Asp Val Gly Ser Pro Asp Lys Ala Arg Gly Pro Val
            545                 550                 555

Pro Leu Gln Val Gln Val Thr Tyr His Ala Gln Ala Gly Gln Pro
            560                 565                 570

Gly Pro Pro Glu Pro Glu Pro Glu Ala Asp Gln His Leu Leu
            575                 580                 585

Pro Pro Thr Leu Pro Thr Ser Ala Thr Ser Leu Ala Ser Asp Ser
            590                 595                 600

Thr Phe Asp Ser Gly Gln Gly Ser Thr Val Tyr Ser Asp Ser Gln
            605                 610                 615

Ser Ser Gln Gln Ser Val Met Leu Gly Ser Leu Ala Asp Ala Ala
            620                 625                 630

Pro Ser Pro Ala Gln Cys Val Cys Ser Pro Pro Val Ser Glu Gly
            635                 640                 645

Pro Val Leu Pro Gln Ser Leu Pro Ser Leu Gly Ala Tyr Gln Gln
            650                 655                 660

Pro Thr Ala Ala Pro Gly Leu Pro Val Gly Ser Val Pro Ala Pro
            665                 670                 675

Ala Cys Pro Pro Ser Leu Gln Gln His Phe Pro Asp Pro Ala Met
            680                 685                 690

Ser Phe Ala Pro Val Leu Pro Pro Ser Thr Pro Met Pro Thr
            695                 700                 705

Gly Pro Gly Gln Pro Ala Pro Gly Gln Gln Pro Pro Leu
            710                 715                 720

Ala Gln Pro Thr Pro Leu Pro Gln Val Leu Ala Pro Gln Pro Val
            725                 730                 735

Val Pro Leu Gln Pro Val Pro Pro His Leu Pro Pro Tyr Leu Ala
            740                 745                 750

Pro Ala Ser Gln Val Gly Ala Pro Ala Gln Leu Lys Pro Leu Gln
            755                 760                 765

Met Pro Gln Ala Pro Leu Gln Pro Leu Ala Gln Val Pro Pro Gln
            770                 775                 780

Met Pro Pro Ile Pro Val Val Pro Pro Ile Thr Pro Leu Ala Gly
            785                 790                 795

Ile Asp Gly Leu Pro Pro Ala Leu Pro Asp Leu Pro Thr Ala Thr
            800                 805                 810

Val Pro Pro Met Pro Pro Gln Tyr Phe Ser Pro Ala Val Ile
            815                 820                 825

Leu Pro Ser Leu Ala Ala Pro Leu Pro Pro Ala Ser Pro Ala Leu
            830                 835                 840

Pro Leu Gln Ala Val Lys Leu Pro His Pro Pro Gly Ala Pro Leu
            845                 850                 855

Ala Met Pro Cys Arg Thr Ile Val Pro Asn Ala Pro Ala Thr Ile
            860                 865                 870

Pro Leu Leu Ala Val Ala Pro Pro Gly Val Ala Ala Leu Ser Ile
            875                 880                 885

His Ser Ala Val Ala Gln Leu Pro Gly Gln Pro Val Tyr Pro Ala
            890                 895                 900

Ala Phe Pro Gln Met Ala Pro Thr Asp Val Pro Pro Ser Pro His
            905                 910                 915
```

```
His Thr Val Gln Asn Met Arg Ala Thr Pro Pro Gln Pro Ala Leu
            920                 925                 930

Pro Pro Gln Pro Thr Leu Pro Pro Gln Pro Val Leu Pro Pro Gln
            935                 940                 945

Pro Thr Leu Pro Pro Gln Pro Val Leu Pro Pro Gln Pro Thr Arg
            950                 955                 960

Pro Pro Gln Pro Val Leu Pro Pro Gln Pro Met Leu Pro Pro Gln
            965                 970                 975

Pro Val Leu Pro Pro Gln Pro Ala Leu Pro Val Arg Pro Glu Pro
            980                 985                 990

Leu Gln Pro His Leu Pro Glu Gln Ala Ala Pro Ala Ala Thr Pro
            995                1000                1005

Gly Ser Gln Ile Leu Leu Gly His Pro Ala Pro Tyr Ala Val Asp
           1010                1015                1020

Val Ala Ala Gln Val Pro Thr Val Pro Val Pro Pro Ala Ala Val
           1025                1030                1035

Leu Ser Pro Pro Leu Pro Glu Val Leu Leu Pro Ala Ala Pro Glu
           1040                1045                1050

Leu Leu Pro Gln Phe Pro Ser Ser Leu Ala Thr Val Ser Ala Ser
           1055                1060                1065

Val Gln Ser Val Pro Thr Gln Thr Ala Thr Leu Leu Pro Pro Ala
           1070                1075                1080

Asn Pro Pro Leu Pro Gly Gly Pro Gly Ile Ala Ser Pro Cys Pro
           1085                1090                1095

Thr Val Gln Leu Thr Val Glu Pro Val Gln Glu Gln Ala Ser
           1100                1105                1110

Gln Asp Lys Pro Pro Gly Leu Pro Gln Ser Cys Glu Ser Tyr Gly
           1115                1120                1125

Gly Ser Asp Val Thr Ser Gly Lys Glu Leu Ser Asp Ser Cys Glu
           1130                1135                1140

Gly Ala Phe Gly Gly Gly Arg Leu Glu Gly Arg Ala Ala Arg Lys
           1145                1150                1155

His His Arg Arg Ser Thr Arg Ala Arg Ser Arg Gln Glu Arg Ala
           1160                1165                1170

Ser Arg Pro Arg Leu Thr Ile Leu Asn Val Cys Asn Thr Gly Asp
           1175                1180                1185

Lys Met Val Glu Cys Gln Leu Glu Thr His Asn His Lys Met Val
           1190                1195                1200

Thr Phe Lys Phe Asp Leu Asp Gly Asp Ala Pro Asp Glu Ile Ala
           1205                1210                1215

Thr Tyr Met Val Glu His Asp Phe Ile Leu Gln Ala Glu Arg Glu
           1220                1225                1230

Thr Phe Ile Glu Gln Met Lys Asp Val Met Asp Lys Ala Glu Asp
           1235                1240                1245

Met Leu Ser Glu Asp Thr Asp Ala Asp Arg Gly Ser Asp Pro Gly
           1250                1255                1260

Thr Ser Pro Pro His Leu Ser Thr Cys Gly Leu Gly Thr Gly Glu
           1265                1270                1275

Glu Ser Arg Gln Ser Gln Ala Asn Ala Pro Val Tyr Gln Gln Asn
           1280                1285                1290

Val Leu His Thr Gly Lys Arg Trp Phe Ile Ile Cys Pro Val Ala
           1295                1300                1305

Glu His Pro Ala Pro Glu Ala Pro Glu Ser Ser Pro Pro Leu Pro
```

```
                       1310                1315                1320
Leu Ser Ser Leu Pro Cys Pro Ala Leu Phe Arg Met Ser Cys Ala
               1325                1330                1335
Ser Val Leu Ala Cys Pro Leu Ser Ala Cys
               1340                1345

<210> SEQ ID NO 18
<211> LENGTH: 2038
<212> TYPE: PRT
<213> ORGANISM: Homo sapiens
<220> FEATURE:
<221> NAME/KEY: misc_feature
<223> OTHER INFORMATION: Incyte ID No: 7476595CD1

<400> SEQUENCE: 18

Met Thr Ala Glu Thr Pro Glu Thr Asp Glu Ser Val Ser Ser Ser
1               5                   10                  15

Asn Ala Ser Leu Lys Leu Arg Arg Lys Pro Arg Glu Ser Asp Phe
                20                  25                  30

Glu Thr Ile Lys Leu Ile Ser Asn Gly Ala Tyr Gly Ala Val Tyr
                35                  40                  45

Phe Val Arg His Lys Glu Ser Arg Gln Arg Phe Ala Met Lys Lys
                50                  55                  60

Ile Asn Lys Gln Asn Leu Ile Leu Arg Asn Gln Ile Gln Gln Ala
            65                  70                  75

Phe Val Glu Arg Asp Ile Leu Thr Phe Ala Glu Asn Pro Phe Val
                80                  85                  90

Val Ser Met Tyr Cys Ser Phe Glu Thr Arg Arg His Leu Cys Met
                95                  100                 105

Val Met Glu Tyr Val Glu Gly Gly Asp Cys Ala Thr Leu Met Lys
                110                 115                 120

Asn Met Gly Pro Leu Pro Val Asp Met Ala Arg Met Tyr Phe Ala
                125                 130                 135

Glu Thr Val Leu Ala Leu Glu Tyr Leu His Asn Tyr Gly Ile Val
                140                 145                 150

His Arg Asp Leu Lys Pro Asp Asn Leu Leu Val Thr Ser Met Gly
                155                 160                 165

His Ile Lys Leu Thr Asp Phe Gly Leu Ser Lys Val Gly Leu Met
                170                 175                 180

Ser Met Thr Thr Asn Leu Tyr Glu Gly His Ile Glu Lys Asp Ala
                185                 190                 195

Arg Glu Phe Leu Asp Lys Gln Val Cys Gly Thr Pro Glu Tyr Ile
                200                 205                 210

Ala Pro Glu Val Ile Leu Arg Gln Gly Tyr Gly Lys Pro Val Asp
                215                 220                 225

Trp Trp Ala Met Gly Ile Ile Leu Tyr Glu Phe Leu Val Gly Cys
                230                 235                 240

Val Pro Phe Phe Gly Asp Thr Pro Glu Glu Leu Phe Gly Gln Val
                245                 250                 255

Ile Ser Asp Glu Ile Asn Trp Pro Glu Lys Asp Glu Ala Pro Pro
                260                 265                 270

Pro Asp Ala Gln Asp Leu Ile Thr Leu Leu Leu Arg Gln Asn Pro
                275                 280                 285

Leu Glu Arg Leu Gly Thr Gly Gly Ala Tyr Glu Val Lys Gln His
                290                 295                 300
```

-continued

```
Arg Phe Phe Arg Ser Leu Asp Trp Asn Ser Leu Leu Arg Gln Lys
                305                 310                 315

Ala Glu Phe Ile Pro Gln Leu Glu Ser Glu Asp Thr Ser Tyr
                320                 325                 330

Phe Asp Thr Arg Ser Glu Lys Tyr His His Met Glu Thr Glu Glu
                335                 340                 345

Glu Asp Asp Thr Asn Asp Glu Asp Phe Asn Val Glu Ile Arg Gln
                350                 355                 360

Phe Ser Ser Cys Ser His Arg Phe Ser Lys Leu Phe Leu Asn Asp
                365                 370                 375

Tyr Leu Asp Ala Pro Ala Asn Gly Pro Ala Leu Pro Ser Cys Val
                380                 385                 390

Trp Glu Trp His Arg Gly Lys Asp Phe Pro Gly Glu Gly Gly Ser
                395                 400                 405

Gln Ser Val Leu Glu Pro Gly Gln Lys Leu Ala Lys Cys Gly Leu
                410                 415                 420

Arg Pro Gly Leu Phe Ser Gly Pro Ser Lys Thr Thr Met Pro Thr
                425                 430                 435

Pro Lys His Cys Phe Leu Leu Cys Leu Asp Thr Glu Ser Asn Arg
                440                 445                 450

His Lys Leu Ser Ser Gly Leu Leu Pro Lys Leu Ala Ile Ser Thr
                455                 460                 465

Glu Gly Glu Gln Asp Glu Ala Ala Ser Cys Pro Gly Asp Pro His
                470                 475                 480

Glu Glu Pro Gly Lys Pro Ala Leu Pro Pro Glu Glu Cys Ala Gln
                485                 490                 495

Glu Glu Pro Glu Val Thr Thr Pro Ala Ser Thr Ile Ser Ser Ser
                500                 505                 510

Thr Leu Ser Asp Met Phe Ala Val Ser Pro Leu Gly Ser Pro Met
                515                 520                 525

Ser Pro His Ser Leu Ser Ser Asp Pro Ser Ser Ser Arg Asp Ser
                530                 535                 540

Ser Pro Ser Arg Asp Ser Ser Ala Ala Ser Ala Ser Pro His Gln
                545                 550                 555

Pro Ile Val Ile His Ser Ser Gly Lys Asn Tyr Gly Phe Thr Ile
                560                 565                 570

Arg Ala Ile Arg Val Tyr Val Gly Asp Ser Asp Ile Tyr Thr Val
                575                 580                 585

His His Ile Val Trp Asn Val Glu Glu Gly Ser Pro Ala Cys Gln
                590                 595                 600

Ala Gly Leu Lys Ala Gly Asp Leu Ile Thr His Ile Asn Gly Glu
                605                 610                 615

Pro Val His Gly Leu Val His Thr Glu Val Ile Glu Leu Leu Leu
                620                 625                 630

Lys Ser Gly Asn Lys Val Ser Ile Thr Thr Thr Pro Phe Glu Asn
                635                 640                 645

Thr Ser Ile Lys Thr Gly Pro Ala Arg Arg Asn Ser Tyr Lys Ser
                650                 655                 660

Arg Met Val Arg Arg Ser Lys Lys Ser Lys Lys Glu Ser Leu
                665                 670                 675

Glu Arg Arg Arg Ser Leu Phe Lys Lys Leu Ala Lys Gln Pro Ser
                680                 685                 690

Pro Leu Leu His Thr Ser Arg Ser Phe Ser Cys Leu Asn Arg Ser
```

-continued

```
                695                 700                 705
Leu Ser Ser Gly Glu Ser Leu Pro Gly Ser Pro Thr His Ser Leu
                710                 715                 720
Ser Pro Arg Ser Pro Thr Pro Ser Tyr Arg Ser Thr Pro Asp Phe
                725                 730                 735
Pro Ser Gly Thr Asn Ser Ser Gln Ser Ser Pro Ser Ser Ser
                740                 745                 750
Ala Pro Asn Ser Pro Ala Gly Ser Gly His Ile Arg Pro Ser Thr
                755                 760                 765
Leu His Gly Leu Ala Pro Lys Leu Gly Gln Arg Tyr Arg Ser
                770                 775                 780
Gly Arg Arg Lys Ser Ala Gly Asn Ile Pro Leu Ser Pro Leu Ala
                785                 790                 795
Arg Thr Pro Ser Pro Thr Pro Gln Pro Thr Ser Pro Gln Arg Ser
                800                 805                 810
Pro Ser Pro Leu Leu Gly His Ser Leu Gly Asn Ser Lys Ile Ala
                815                 820                 825
Gln Ala Phe Pro Ser Lys Met His Ser Pro Pro Thr Ile Val Arg
                830                 835                 840
His Ile Val Arg Pro Lys Ser Ala Glu Pro Pro Arg Ser Pro Leu
                845                 850                 855
Leu Lys Arg Val Gln Ser Glu Glu Lys Leu Ser Pro Ser Tyr Gly
                860                 865                 870
Ser Asp Lys Lys His Leu Cys Ser Arg Lys His Ser Leu Glu Val
                875                 880                 885
Thr Gln Glu Glu Val Gln Arg Glu Gln Ser Gln Arg Glu Ala Pro
                890                 895                 900
Leu Gln Ser Leu Asp Glu Asn Val Cys Asp Val Pro Pro Leu Ser
                905                 910                 915
Arg Ala Arg Pro Val Glu Gln Gly Cys Leu Lys Arg Pro Val Ser
                920                 925                 930
Arg Lys Val Gly Arg Gln Glu Ser Val Asp Asp Leu Asp Arg Asp
                935                 940                 945
Lys Leu Lys Ala Lys Val Val Lys Ala Asp Gly Phe Pro
                950                 955                 960
Glu Lys Gln Glu Ser His Gln Lys Ser His Gly Pro Gly Ser Asp
                965                 970                 975
Leu Glu Asn Phe Ala Leu Phe Lys Leu Glu Arg Glu Lys Lys
                980                 985                 990
Val Tyr Pro Lys Ala Val Glu Arg Ser Ser Thr Phe Glu Asn Lys
                995                1000                1005
Ala Ser Met Gln Glu Ala Pro Pro Leu Gly Ser Leu Leu Lys Asp
               1010                1015                1020
Ala Leu His Lys Gln Ala Ser Val Arg Ala Ser Glu Gly Ala Met
               1025                1030                1035
Ser Asp Gly Arg Val Pro Ala Glu His Arg Gln Gly Gly Gly Asp
               1040                1045                1050
Phe Arg Arg Ala Pro Ala Pro Gly Thr Leu Gln Asp Gly Leu Cys
               1055                1060                1065
His Ser Leu Asp Arg Gly Ile Ser Gly Lys Gly Glu Gly Thr Glu
               1070                1075                1080
Lys Ser Ser Gln Ala Lys Glu Leu Leu Arg Cys Glu Lys Leu Asp
               1085                1090                1095
```

```
Ser Lys Leu Ala Asn Ile Asp Tyr Leu Arg Lys Lys Met Ser Leu
            1100                1105                1110

Glu Asp Lys Glu Asp Asn Leu Cys Pro Val Leu Lys Pro Lys Met
            1115                1120                1125

Thr Ala Gly Ser His Glu Cys Leu Pro Gly Asn Pro Val Arg Pro
            1130                1135                1140

Thr Gly Gly Gln Gln Glu Pro Pro Ala Ser Glu Ser Arg Ala
            1145                1150                1155

Phe Val Ser Ser Thr His Ala Ala Gln Met Ser Ala Val Ser Phe
            1160                1165                1170

Val Pro Leu Lys Ala Leu Thr Gly Arg Val Asp Ser Gly Thr Glu
            1175                1180                1185

Lys Pro Gly Leu Val Ala Pro Glu Ser Pro Val Arg Lys Ser Pro
            1190                1195                1200

Ser Glu Tyr Lys Leu Glu Gly Arg Ser Val Ser Cys Leu Lys Pro
            1205                1210                1215

Ile Glu Gly Thr Leu Asp Ile Ala Leu Leu Ser Gly Pro Gln Ala
            1220                1225                1230

Ser Lys Thr Glu Leu Pro Ser Pro Glu Ser Ala Gln Ser Pro Ser
            1235                1240                1245

Pro Ser Gly Asp Val Arg Ala Ser Val Pro Pro Val Leu Pro Ser
            1250                1255                1260

Ser Ser Gly Lys Lys Asn Asp Thr Thr Ser Ala Arg Glu Leu Ser
            1265                1270                1275

Pro Ser Ser Leu Lys Met Asn Lys Ser Tyr Leu Leu Glu Pro Trp
            1280                1285                1290

Phe Leu Pro Pro Ser Arg Gly Leu Gln Asn Ser Pro Ala Val Ser
            1295                1300                1305

Leu Pro Asp Pro Glu Phe Lys Arg Asp Arg Lys Gly Pro His Pro
            1310                1315                1320

Thr Ala Arg Ser Pro Gly Thr Val Met Glu Ser Asn Pro Gln Gln
            1325                1330                1335

Arg Glu Gly Ser Ser Pro Lys His Gln Asp His Thr Thr Asp Pro
            1340                1345                1350

Lys Leu Leu Thr Cys Leu Gly Gln Asn Leu His Ser Pro Asp Leu
            1355                1360                1365

Ala Arg Pro Arg Cys Pro Leu Pro Pro Glu Ala Ser Pro Ser Arg
            1370                1375                1380

Glu Lys Pro Gly Leu Arg Glu Ser Ser Glu Arg Gly Pro Pro Thr
            1385                1390                1395

Ala Arg Ser Glu Arg Ser Ala Ala Arg Ala Asp Thr Cys Arg Glu
            1400                1405                1410

Pro Ser Met Glu Leu Cys Phe Pro Glu Thr Ala Lys Thr Ser Asp
            1415                1420                1425

Asn Ser Lys Asn Leu Leu Ser Val Gly Arg Thr His Pro Asp Phe
            1430                1435                1440

Tyr Thr Gln Thr Gln Ala Met Glu Lys Ala Trp Ala Pro Gly Gly
            1445                1450                1455

Lys Thr Asn His Lys Asp Gly Pro Gly Glu Ala Arg Pro Pro Pro
            1460                1465                1470

Arg Asp Asn Ser Ser Leu His Ser Ala Gly Ile Pro Cys Glu Lys
            1475                1480                1485
```

```
Glu Leu Gly Lys Val Arg Arg Gly Val Glu Pro Lys Pro Glu Ala
            1490                1495                1500

Leu Leu Ala Arg Arg Ser Leu Gln Pro Pro Gly Ile Glu Ser Glu
            1505                1510                1515

Lys Ser Glu Lys Leu Ser Ser Phe Pro Ser Leu Gln Lys Asp Gly
            1520                1525                1530

Ala Lys Glu Pro Glu Arg Lys Glu Gln Pro Leu Gln Arg His Pro
            1535                1540                1545

Ser Ser Ile Pro Pro Pro Leu Thr Ala Lys Asp Leu Ser Ser
            1550                1555                1560

Pro Ala Ala Arg Gln His Cys Ser Ser Pro Ser His Ala Ser Gly
            1565                1570                1575

Arg Glu Pro Gly Ala Lys Pro Ser Thr Ala Glu Pro Ser Ser Ser
            1580                1585                1590

Pro Gln Asp Pro Pro Lys Pro Val Ala Ala His Ser Glu Ser Ser
            1595                1600                1605

Ser His Lys Pro Arg Pro Gly Pro Asp Pro Gly Pro Lys Thr
            1610                1615                1620

Lys His Pro Asp Arg Ser Leu Ser Ser Gln Lys Pro Ser Val Gly
            1625                1630                1635

Ala Thr Lys Gly Lys Glu Pro Ala Thr Gln Ser Leu Gly Gly Ser
            1640                1645                1650

Ser Arg Glu Gly Lys Gly His Ser Lys Ser Gly Pro Asp Val Phe
            1655                1660                1665

Pro Ala Thr Pro Gly Ser Gln Asn Lys Ala Ser Asp Gly Ile Gly
            1670                1675                1680

Gln Gly Glu Gly Gly Pro Ser Val Pro Leu His Thr Asp Arg Ala
            1685                1690                1695

Pro Leu Asp Ala Lys Pro Gln Pro Thr Ser Gly Gly Arg Pro Leu
            1700                1705                1710

Glu Val Leu Glu Lys Pro Val His Leu Pro Arg Pro Gly His Pro
            1715                1720                1725

Gly Pro Ser Glu Pro Ala Asp Gln Lys Leu Ser Ala Val Gly Glu
            1730                1735                1740

Lys Gln Thr Leu Ser Pro Lys His Pro Lys Pro Ser Thr Val Lys
            1745                1750                1755

Asp Cys Pro Thr Leu Cys Lys Gln Thr Asp Asn Arg Gln Thr Asp
            1760                1765                1770

Lys Ser Pro Ser Gln Pro Ala Ala Asn Thr Asp Arg Arg Ala Glu
            1775                1780                1785

Gly Lys Lys Cys Thr Glu Ala Leu Tyr Ala Pro Ala Glu Gly Asp
            1790                1795                1800

Lys Leu Glu Ala Gly Leu Ser Phe Val His Ser Glu Asn Arg Leu
            1805                1810                1815

Lys Gly Ala Glu Arg Pro Ala Ala Gly Val Gly Lys Gly Phe Pro
            1820                1825                1830

Glu Ala Arg Gly Lys Gly Pro Gly Pro Gln Lys Pro Pro Thr Glu
            1835                1840                1845

Ala Asp Lys Pro Asn Gly Met Lys Arg Ser Pro Ser Ala Thr Gly
            1850                1855                1860

Gln Ser Ser Phe Arg Ser Thr Ala Leu Pro Glu Lys Ser Leu Ser
            1865                1870                1875

Cys Ser Ser Ser Phe Pro Glu Thr Arg Ala Gly Val Arg Glu Ala
```

-continued

```
                         1880              1885              1890

Ser Ala Ala Ser Ser Asp Thr Ser Ser Ala Lys Ala Ala Gly Gly
            1895              1900              1905

Met Leu Glu Leu Pro Ala Pro Ser Asn Arg Asp His Arg Lys Ala
            1910              1915              1920

Gln Pro Ala Gly Glu Gly Arg Thr His Met Thr Lys Ser Asp Ser
            1925              1930              1935

Leu Pro Ser Phe Arg Val Ser Thr Leu Pro Leu Glu Ser His His
            1940              1945              1950

Pro Asp Pro Asn Thr Met Gly Gly Ala Ser His Arg Asp Arg Ala
            1955              1960              1965

Leu Ser Val Thr Ala Thr Val Gly Glu Thr Lys Gly Lys Asp Pro
            1970              1975              1980

Ala Pro Ala Gln Pro Pro Ala Arg Lys Gln Asn Val Gly Arg
            1985              1990              1995

Asp Val Thr Lys Pro Ser Pro Ala Pro Asn Thr Asp Arg Pro Ile
            2000              2005              2010

Ser Leu Ser Asn Glu Lys Asp Phe Val Val Arg Gln Arg Arg Gly
            2015              2020              2025

Lys Glu Ser Leu Arg Ser Ser Pro His Lys Lys Ala Leu
            2030              2035

<210> SEQ ID NO 19
<211> LENGTH: 1770
<212> TYPE: PRT
<213> ORGANISM: Homo sapiens
<220> FEATURE:
<221> NAME/KEY: misc_feature
<223> OTHER INFORMATION: Incyte ID No: 71824382CD1

<400> SEQUENCE: 19

Met Ser Gly Glu Val Arg Leu Arg Gln Leu Glu Gln Phe Ile Leu
1               5                  10                  15

Asp Gly Pro Ala Gln Thr Asn Gly Gln Cys Phe Ser Val Glu Thr
                20                  25                  30

Leu Leu Asp Ile Leu Ile Cys Leu Tyr Asp Glu Cys Asn Asn Ser
            35                  40                  45

Pro Leu Arg Arg Glu Lys Asn Ile Leu Glu Tyr Leu Glu Trp Ala
        50                  55                  60

Lys Pro Phe Thr Ser Lys Val Lys Gln Met Arg Leu His Arg Glu
    65                  70                  75

Asp Phe Glu Ile Leu Lys Val Ile Gly Arg Gly Ala Phe Gly Glu
                80                  85                  90

Val Ala Val Val Lys Leu Lys Asn Ala Asp Lys Val Phe Ala Met
                95                  100                 105

Lys Ile Leu Asn Lys Trp Glu Met Leu Lys Arg Ala Glu Thr Ala
            110                 115                 120

Cys Phe Arg Glu Glu Arg Asp Val Leu Val Asn Gly Asp Asn Lys
            125                 130                 135

Trp Ile Thr Thr Leu His Tyr Ala Phe Gln Asp Asp Asn Asn Leu
            140                 145                 150

Tyr Leu Val Met Asp Tyr Tyr Val Gly Gly Asp Leu Leu Thr Leu
            155                 160                 165

Leu Ser Lys Phe Glu Asp Arg Leu Pro Glu Asp Met Ala Arg Phe
            170                 175                 180
```

```
Tyr Leu Ala Glu Met Val Ile Ala Ile Asp Ser Val His Gln Leu
            185                 190                 195

His Tyr Val His Arg Asp Ile Lys Pro Asp Asn Ile Leu Met Asp
            200                 205                 210

Met Asn Gly His Ile Arg Leu Ala Asp Phe Gly Ser Cys Leu Lys
            215                 220                 225

Leu Met Glu Asp Gly Thr Val Gln Ser Val Ala Val Gly Thr
            230                 235                 240

Pro Asp Tyr Ile Ser Pro Glu Ile Leu Gln Ala Met Glu Asp Gly
            245                 250                 255

Lys Gly Arg Tyr Gly Pro Glu Cys Asp Trp Trp Ser Leu Gly Val
            260                 265                 270

Cys Met Tyr Glu Met Leu Tyr Gly Glu Thr Pro Phe Tyr Ala Glu
            275                 280                 285

Ser Leu Val Glu Thr Tyr Gly Lys Ile Met Asn His Lys Glu Arg
            290                 295                 300

Phe Gln Phe Pro Ala Gln Val Thr Asp Val Ser Glu Asn Ala Lys
            305                 310                 315

Asp Leu Ile Arg Arg Leu Ile Cys Ser Arg Glu His Arg Leu Gly
            320                 325                 330

Gln Asn Gly Ile Glu Asp Phe Lys Lys His Pro Phe Phe Ser Gly
            335                 340                 345

Ile Asp Trp Asp Asn Ile Arg Asn Cys Glu Ala Pro Tyr Ile Pro
            350                 355                 360

Glu Val Ser Ser Pro Thr Asp Thr Ser Asn Phe Asp Val Asp Asp
            365                 370                 375

Asp Cys Leu Lys Asn Ser Glu Thr Met Pro Pro Pro Thr His Thr
            380                 385                 390

Ala Phe Ser Gly His His Leu Pro Phe Val Gly Phe Thr Tyr Thr
            395                 400                 405

Ser Ser Cys Val Leu Ser Asp Arg Ser Cys Leu Arg Val Thr Ala
            410                 415                 420

Gly Pro Thr Ser Leu Asp Leu Asp Val Asn Val Gln Arg Thr Leu
            425                 430                 435

Asp Asn Asn Leu Ala Thr Glu Ala Tyr Glu Arg Arg Ile Lys Arg
            440                 445                 450

Leu Glu Gln Glu Lys Leu Glu Leu Ser Arg Lys Leu Gln Glu Ser
            455                 460                 465

Thr Gln Thr Val Gln Ala Leu Gln Tyr Ser Thr Val Asp Gly Pro
            470                 475                 480

Leu Thr Ala Ser Lys Asp Leu Glu Ile Lys Asn Leu Lys Glu Glu
            485                 490                 495

Ile Glu Lys Leu Arg Lys Gln Val Thr Glu Ser Ser His Leu Glu
            500                 505                 510

Gln Gln Leu Glu Glu Ala Asn Ala Val Arg Gln Glu Leu Asp Asp
            515                 520                 525

Ala Phe Arg Gln Ile Lys Ala Tyr Glu Lys Gln Ile Lys Thr Leu
            530                 535                 540

Gln Gln Glu Arg Glu Asp Leu Asn Lys Glu Leu Val Gln Ala Ser
            545                 550                 555

Glu Arg Leu Lys Asn Gln Ser Lys Glu Leu Lys Asp Ala His Cys
            560                 565                 570

Gln Arg Lys Leu Ala Met Gln Glu Phe Met Glu Ile Asn Glu Arg
```

-continued

```
                575                 580                 585
Leu Thr Glu Leu His Thr Gln Lys Gln Lys Leu Ala Arg His Val
            590                 595                 600
Arg Asp Lys Glu Glu Val Asp Leu Val Met Gln Lys Val Glu
            605                 610                 615
Ser Leu Arg Gln Glu Leu Arg Arg Thr Glu Arg Ala Lys Lys Glu
            620                 625                 630
Leu Glu Val His Thr Glu Ala Leu Ala Ala Glu Ala Ser Lys Asp
            635                 640                 645
Arg Lys Leu Arg Glu Gln Ser Glu His Tyr Ser Lys Gln Leu Glu
            650                 655                 660
Asn Glu Leu Glu Gly Leu Lys Gln Lys Gln Ile Ser Tyr Ser Pro
            665                 670                 675
Gly Val Cys Ser Ile Glu His Gln Gln Glu Ile Thr Lys Leu Lys
            680                 685                 690
Thr Asp Leu Glu Lys Lys Ser Ile Phe Tyr Glu Glu Glu Leu Ser
            695                 700                 705
Lys Arg Glu Gly Ile His Ala Asn Glu Ile Lys Asn Leu Lys Lys
            710                 715                 720
Glu Leu His Asp Ser Glu Gly Gln Gln Leu Ala Leu Asn Lys Glu
            725                 730                 735
Ile Met Ile Leu Lys Asp Lys Leu Glu Lys Thr Arg Arg Glu Ser
            740                 745                 750
Gln Ser Glu Arg Glu Glu Phe Glu Ser Glu Phe Lys Gln Gln Tyr
            755                 760                 765
Glu Arg Glu Lys Val Leu Leu Thr Glu Glu Asn Lys Lys Leu Thr
            770                 775                 780
Ser Glu Leu Asp Lys Leu Thr Thr Leu Tyr Glu Asn Leu Ser Ile
            785                 790                 795
His Asn Gln Gln Leu Glu Glu Glu Val Lys Asp Leu Ala Asp Lys
            800                 805                 810
Lys Glu Ser Val Ala His Trp Glu Ala Gln Ile Thr Glu Ile Ile
            815                 820                 825
Gln Trp Val Ser Asp Glu Lys Asp Ala Arg Gly Tyr Leu Gln Ala
            830                 835                 840
Leu Ala Ser Lys Met Thr Glu Glu Leu Glu Ala Leu Arg Asn Ser
            845                 850                 855
Ser Leu Gly Thr Arg Ala Thr Asp Met Pro Trp Lys Met Arg Arg
            860                 865                 870
Phe Ala Lys Leu Asp Met Ser Ala Arg Leu Glu Leu Gln Ser Ala
            875                 880                 885
Leu Asp Ala Glu Ile Arg Ala Lys Gln Ala Ile Gln Glu Glu Leu
            890                 895                 900
Asn Lys Val Lys Ala Ser Asn Ile Ile Thr Glu Cys Lys Leu Lys
            905                 910                 915
Asp Ser Glu Lys Lys Asn Leu Glu Leu Leu Ser Glu Ile Glu Gln
            920                 925                 930
Leu Ile Lys Asp Thr Glu Glu Leu Arg Ser Glu Lys Gly Ile Glu
            935                 940                 945
His Gln Asp Ser Gln His Ser Phe Leu Ala Phe Leu Asn Thr Pro
            950                 955                 960
Thr Asp Ala Leu Asp Gln Phe Glu Asp Ser Phe Ser Ser Ser Ser
            965                 970                 975
```

-continued

Ser Ser Leu Ile Asp Phe Leu Asp Asp Thr Asp Pro Val Glu Asn
            980                 985                 990

Thr Tyr Val Trp Asn Pro Ser Val Lys Phe His Ile Gln Ser Arg
            995                 1000                1005

Ser Thr Ser Pro Ser Thr Ser Ser Glu Ala Glu Pro Val Lys Thr
            1010                1015                1020

Val Asp Ser Thr Pro Leu Ser Val His Thr Pro Thr Leu Arg Lys
            1025                1030                1035

Lys Gly Cys Pro Gly Ser Thr Gly Phe Pro Pro Lys Arg Lys Thr
            1040                1045                1050

His Gln Phe Phe Val Lys Ser Phe Thr Thr Pro Thr Lys Cys His
            1055                1060                1065

Gln Cys Thr Ser Leu Met Val Gly Leu Ile Arg Gln Gly Cys Ser
            1070                1075                1080

Cys Glu Val Cys Gly Phe Ser Cys His Ile Thr Cys Val Asn Lys
            1085                1090                1095

Ala Pro Thr Thr Cys Pro Val Pro Pro Glu Gln Thr Lys Gly Pro
            1100                1105                1110

Leu Gly Ile Asp Pro Gln Lys Gly Ile Gly Thr Ala Tyr Glu Gly
            1115                1120                1125

His Val Arg Ile Pro Lys Pro Ala Gly Val Lys Lys Gly Trp Gln
            1130                1135                1140

Arg Ala Leu Ala Ile Val Cys Asp Phe Lys Leu Phe Leu Tyr Asp
            1145                1150                1155

Ile Ala Glu Gly Lys Ala Ser Gln Pro Ser Val Val Ile Ser Gln
            1160                1165                1170

Val Ile Asp Met Arg Asp Glu Glu Phe Ser Val Ser Ser Val Leu
            1175                1180                1185

Ala Ser Asp Val Ile His Ala Ser Arg Lys Asp Ile Pro Cys Ile
            1190                1195                1200

Phe Arg Val Thr Ala Ser Gln Leu Ser Ala Ser Asn Asn Lys Cys
            1205                1210                1215

Ser Ile Leu Met Leu Ala Asp Thr Glu Asn Glu Lys Asn Lys Trp
            1220                1225                1230

Val Gly Val Leu Ser Glu Leu His Lys Ile Leu Lys Lys Asn Lys
            1235                1240                1245

Phe Arg Asp Arg Ser Val Tyr Val Pro Lys Glu Ala Tyr Asp Ser
            1250                1255                1260

Thr Leu Pro Leu Ile Lys Thr Thr Gln Ala Ala Ala Ile Ile Asp
            1265                1270                1275

His Glu Arg Ile Ala Leu Gly Asn Glu Glu Gly Leu Phe Val Val
            1280                1285                1290

His Val Thr Lys Asp Glu Ile Ile Arg Val Gly Asp Asn Lys Lys
            1295                1300                1305

Ile His Gln Ile Glu Leu Ile Pro Asn Asp Gln Leu Val Ala Val
            1310                1315                1320

Ile Ser Gly Arg Asn Arg His Val Arg Leu Phe Pro Met Ser Ala
            1325                1330                1335

Leu Asp Gly Arg Glu Thr Asp Phe Tyr Lys Leu Ser Glu Thr Lys
            1340                1345                1350

Gly Cys Gln Thr Val Thr Ser Gly Lys Val Arg His Gly Ala Leu
            1355                1360                1365

```
Thr Cys Leu Cys Val Ala Met Lys Arg Gln Val Leu Cys Tyr Glu
            1370                1375                1380

Leu Phe Gln Ser Lys Thr Arg His Arg Lys Phe Lys Glu Ile Gln
            1385                1390                1395

Val Pro Tyr Asn Val Gln Trp Met Ala Ile Phe Ser Glu Gln Leu
            1400                1405                1410

Cys Val Gly Phe Gln Ser Gly Phe Leu Arg Tyr Pro Leu Asn Gly
            1415                1420                1425

Glu Gly Asn Pro Tyr Ser Met Leu His Ser Asn Asp His Thr Leu
            1430                1435                1440

Ser Phe Ile Ala His Gln Pro Met Asp Ala Ile Cys Ala Val Glu
            1445                1450                1455

Ile Ser Ser Lys Glu Tyr Leu Leu Cys Phe Asn Ser Ile Gly Ile
            1460                1465                1470

Tyr Thr Asp Cys Gln Gly Arg Arg Ser Arg Gln Gln Glu Leu Met
            1475                1480                1485

Trp Pro Ala Asn Pro Ser Ser Cys Cys Tyr Asn Ala Pro Tyr Leu
            1490                1495                1500

Ser Val Tyr Ser Glu Asn Ala Val Asp Ile Phe Asp Val Asn Ser
            1505                1510                1515

Met Glu Trp Ile Gln Thr Leu Pro Leu Lys Lys Val Arg Pro Leu
            1520                1525                1530

Asn Asn Glu Gly Ser Leu Asn Leu Leu Gly Leu Glu Thr Ile Arg
            1535                1540                1545

Leu Ile Tyr Phe Lys Asn Lys Met Ala Glu Gly Asp Glu Leu Val
            1550                1555                1560

Val Pro Glu Thr Ser Asp Asn Ser Arg Lys Gln Met Val Arg Asn
            1565                1570                1575

Ile Asn Asn Lys Arg Arg Tyr Ser Phe Arg Val Pro Glu Glu Glu
            1580                1585                1590

Arg Met Gln Gln Arg Arg Glu Met Leu Arg Asp Pro Glu Met Arg
            1595                1600                1605

Asn Lys Leu Ile Ser Asn Pro Thr Asn Phe Asn His Ile Ala His
            1610                1615                1620

Met Gly Pro Gly Asp Gly Ile Gln Ile Leu Lys Asp Leu Pro Met
            1625                1630                1635

Asn Pro Arg Pro Gln Glu Ser Arg Thr Val Phe Ser Gly Ser Val
            1640                1645                1650

Ser Ile Pro Ser Ile Thr Lys Ser Arg Pro Glu Pro Gly Arg Ser
            1655                1660                1665

Met Ser Ala Ser Ser Gly Leu Ser Ala Arg Ser Ser Ala Gln Asn
            1670                1675                1680

Gly Ser Ala Leu Lys Arg Glu Phe Ser Gly Gly Ser Tyr Ser Ala
            1685                1690                1695

Lys Arg Gln Pro Met Pro Ser Pro Ser Glu Gly Ser Leu Ser Ser
            1700                1705                1710

Gly Gly Met Asp Gln Gly Ser Asp Ala Pro Ala Arg Asp Phe Asp
            1715                1720                1725

Gly Glu Asp Ser Asp Ser Pro Arg His Ser Thr Ala Ser Asn Ser
            1730                1735                1740

Ser Asn Leu Ser Ser Pro Pro Ser Pro Val Ser Pro Arg Lys Thr
            1745                1750                1755

Lys Ser Leu Ser Leu Glu Ser Thr Asp Arg Gly Ser Trp Asp Pro
```

-continued

```
                        1760            1765            1770

<210> SEQ ID NO 20
<211> LENGTH: 720
<212> TYPE: PRT
<213> ORGANISM: Homo sapiens
<220> FEATURE:
<221> NAME/KEY: misc_feature
<223> OTHER INFORMATION: Incyte ID No: 3566882CD1

<400> SEQUENCE: 20

Met Ala Ala Asp Pro Thr Glu Leu Arg Leu Gly Ser Leu Pro Val
  1               5                  10                  15

Phe Thr Arg Asp Asp Phe Glu Gly Asp Trp Arg Leu Val Ala Ser
                 20                  25                  30

Gly Gly Phe Ser Gln Val Phe Gln Ala Arg His Arg Arg Trp Arg
                 35                  40                  45

Thr Glu Tyr Ala Ile Lys Cys Ala Pro Cys Leu Pro Pro Asp Ala
                 50                  55                  60

Ala Arg Thr Phe Ala Ala Ser Val Ser Pro Leu Pro Ser Ile Tyr
                 65                  70                  75

Leu Ala Lys Ile Ser Asp Phe Gly Leu Ser Lys Trp Met Glu Gln
                 80                  85                  90

Ser Thr Arg Met Gln Tyr Ile Glu Arg Ser Ala Leu Arg Gly Met
                 95                 100                 105

Leu Ser Tyr Ile Pro Pro Glu Met Phe Leu Glu Ser Asn Lys Ala
                110                 115                 120

Pro Gly Pro Lys Tyr Asp Val Tyr Ser Pro Pro Thr Leu Pro Pro
                125                 130                 135

Arg Ala Gly Val Ile Leu Asp Val Gln Leu Ser His Ser Glu Arg
                140                 145                 150

Val Leu Cys Ile His Ser Phe Ala Ile Val Ile Trp Glu Leu Leu
                155                 160                 165

Thr Gln Lys Lys Pro Tyr Ser Glu Leu Thr Ser Gln Leu Lys Glu
                170                 175                 180

Arg Lys Gly Phe Asn Met Met Ile Ile Ile Arg Val Thr Ala
                185                 190                 195

Gly Met Arg Pro Ser Leu Gln Pro Val Ser Asp Gln Trp Pro Ser
                200                 205                 210

Glu Ala Gln Gln Met Val Asp Leu Met Lys Arg Cys Trp Asp Gln
                215                 220                 225

Asp Pro Lys Lys Arg Pro Cys Phe Leu Asp Ile Thr Ile Glu Thr
                230                 235                 240

Asp Ile Leu Leu Ser Leu Leu Gln Ser Arg Val Ala Val Pro Glu
                245                 250                 255

Ser Lys Ala Leu Ala Arg Lys Val Ser Cys Lys Leu Ser Leu Arg
                260                 265                 270

Gln Pro Gly Glu Val Asn Glu Asp Ile Ser Gln Glu Leu Met Asp
                275                 280                 285

Ser Asp Ser Gly Asn Tyr Leu Lys Arg Ala Leu Gln Leu Ser Asp
                290                 295                 300

Arg Lys Asn Leu Val Pro Arg Asp Glu Glu Leu Cys Ile Tyr Glu
                305                 310                 315

Asn Lys Val Thr Pro Leu His Phe Leu Val Ala Gln Gly Ser Val
                320                 325                 330
```

-continued

```
Glu Gln Val Arg Leu Leu Ala His Glu Val Asp Cys
            335                 340                 345

Gln Thr Ala Ser Gly Tyr Thr Pro Leu Leu Ile Ala Ala Gln Asp
            350                 355                 360

Gln Gln Pro Asp Leu Cys Ala Leu Leu Leu Ala His Gly Ala Asp
            365                 370                 375

Ala Asn Arg Val Asp Glu Asp Gly Trp Ala Pro Leu His Phe Ala
            380                 385                 390

Ala Gln Asn Gly Asp Asp Gly Thr Ala Arg Leu Leu Leu Asp His
            395                 400                 405

Gly Ala Cys Val Asp Ala Gln Glu Arg Glu Gly Trp Thr Pro Leu
            410                 415                 420

His Leu Ala Ala Gln Asn Asn Phe Glu Asn Val Ala Arg Leu Leu
            425                 430                 435

Val Ser Arg Gln Ala Asp Pro Asn Leu His Glu Ala Glu Gly Lys
            440                 445                 450

Thr Pro Leu His Val Ala Ala Tyr Phe Gly His Val Ser Leu Val
            455                 460                 465

Lys Leu Leu Thr Ser Gln Gly Ala Glu Leu Asp Ala Gln Gln Arg
            470                 475                 480

Asn Leu Arg Thr Pro Leu His Leu Ala Val Glu Arg Gly Lys Val
            485                 490                 495

Arg Ala Ile Gln His Leu Leu Lys Ser Gly Ala Val Pro Asp Ala
            500                 505                 510

Leu Asp Gln Ser Gly Tyr Gly Pro Leu His Thr Ala Ala Arg
            515                 520                 525

Gly Lys Tyr Leu Ile Cys Lys Met Leu Leu Arg Tyr Gly Ala Ser
            530                 535                 540

Leu Glu Leu Pro Thr His Gln Gly Trp Thr Pro Leu His Leu Ala
            545                 550                 555

Ala Tyr Lys Gly His Leu Glu Ile Ile His Leu Leu Ala Glu Ser
            560                 565                 570

His Ala Asn Met Gly Ala Leu Gly Ala Val Asn Trp Thr Pro Leu
            575                 580                 585

His Leu Ala Ala Arg His Gly Glu Glu Ala Val Val Ser Ala Leu
            590                 595                 600

Leu Gln Cys Gly Ala Asp Pro Asn Ala Ala Glu Gln Ser Gly Trp
            605                 610                 615

Thr Pro Leu His Leu Ala Val Gln Arg Ser Thr Phe Leu Ser Val
            620                 625                 630

Ile Asn Leu Leu Glu His His Ala Asn Val His Ala Arg Asn Lys
            635                 640                 645

Val Gly Trp Thr Pro Ala His Leu Ala Ala Leu Lys Gly Asn Thr
            650                 655                 660

Ala Ile Leu Lys Val Leu Val Glu Ala Gly Ala Gln Leu Asp Val
            665                 670                 675

Gln Asp Gly Val Ser Cys Thr Pro Leu Gln Leu Ala Leu Arg Ser
            680                 685                 690

Arg Lys Gln Gly Ile Met Ser Phe Leu Glu Gly Lys Glu Pro Ser
            695                 700                 705

Val Ala Thr Leu Gly Gly Ser Lys Pro Gly Ala Glu Met Glu Ile
            710                 715                 720
```

-continued

```
<210> SEQ ID NO 21
<211> LENGTH: 5200
<212> TYPE: DNA
<213> ORGANISM: Homo sapiens
<220> FEATURE:
<221> NAME/KEY: misc_feature
<223> OTHER INFORMATION: Incyte ID No: 4615110CB1

<400> SEQUENCE: 21
cgtggctgag ccagcagctg cagcagctac gggagtggcc gggtggccgg cgggtgccag      60
ccgccatgga ggccgtgccc cgcatgccca tgatctggct ggacctgaag gaggccggtg     120
actttcactt ccagccagct gtgaagaagt ttgtcctgaa gaattatgga gagaacccag     180
aagcctacaa tgaagaactg aagaagctgg agttgctcag acagaatgct gtccgtgtcc     240
cacgagactt tgagggctgt agtgtcctcc gcaagtacct cggccagctt cattacctgc     300
agagtcgggt ccccatgggc tcgggccagg aggccgctgt ccctgtcacc tggacagaga     360
tcttctcagg caagtctgtg gcccatgagg acatcaagta cgagcaggcc tgtattctct     420
acaaccttgg agcgctgcac tccatgctgg ggccatgga caagcgggtg tctgaggagg      480
gcatgaaggt ctcctgtacc catttccagt gcgcagccgg cgccttcgcc tacctacggg     540
agcacttccc tcaagcctac agcgtcgaca tgagccgcca gatccttacg ctcaacgtca     600
acctcatgct gggccaggct caggagtgcc tcctggagaa gtcgatgttg acaacagga      660
agagctttct ggtggcccgc atcagtgcac aggtggtaga ttactacaag gaggcatgcc     720
gggccttgga gaaccccgac actgcctcac tgctgggccg gatccagaag gactggaaga     780
aacttgtgca gatgaagatc tactacttcg cagccgtggc tcatctgcac atgggaaagc     840
aggccgagga gcagcagaag ttcggggagc gggttgcata cttccagagc gccctggaca     900
agctcaatga agccatcaag ttggccaagg ccagcctga cactgtgcaa gacgcgcttc      960
gcttcactat ggatgtcatt gggggaaagt acaattctgc caagaaggac aacgacttca    1020
tttaccatga ggctgtccca gcattggaca cccttcagcc tgtaaaagga gccccttgg     1080
tgaagccctt gccagtgaac cccacagacc cagctgttac aggccctgac atctttgcca    1140
aactggtacc catggctgcc cacgaggcct cgtcactgta cagtgaggag aaggccaagc    1200
tgctccggga tgatggcc aagattgagg acaagaatga ggtcctggac cagttcatgg      1260
attcaatgca gttggatccc gagacggtgg acaaccttga tgcctacagc acatcccac     1320
cccagctcat ggagaagtgc gcggctctca gcgtccggcc cgacactgtc aggaaccttg    1380
tacagtccat gcaagtgctg tcaggtgtgt tcacggatgt ggaggcttcc ctgaaggaca    1440
tcagagatct gttggaggag gatgagctgc tagagcagaa gtttcaggag gcggtgggcc    1500
aggcaggggc catctccatc acctccaagg ctgagctggc agaggtgagg cgagaatggg    1560
ccaagtacat ggaagtccat gagaaggcct ccttcaccaa cagtgagctg caccgtgcca    1620
tgaacctgca cgtcggcaac ctgcgcctgc tcagcgggcc gcttgaccag gtccgggctg    1680
ccctgcccac accggccctc tccccagagg acaaggccgt gctgcaaaac ctaaagcgca    1740
tcctggctaa ggtgcaggag atgcgggacc agcgcgtgtc cctggagcag cagctgcgtg    1800
agcttatcca gaaagatgac atcactgcct cgctggtcac cacagaccac tcagagatga    1860
agaagttgtt cgaggagcag ctgaaaaagt atgaccagct gaaggtgtac ctggagcaga    1920
acctggccgc ccaggaccgt gtcctctgtg cactgacaga ggccaacgtg cagtacgcag    1980
ccgtgcggcg ggtactcagc gacttggacc aaaaagtgga actccacgct gcagaccctgg   2040
tggcctcgta tgaagcctat gaggacctga tgaagaagtc gcaggagggc agggacttct    2100
```

```
acgcagatct ggagagcaag gtggctgctc tgctggagcg cacgcagtcc acctgccagg    2160
cccgcgaggc tgcccgccag cagctcctgg acagggagct gaagaagaag ccgccgccac    2220
ggcccacagc cccaaagccg ctgctgcccc gcagggagga gagtgaggca gtggaagcag    2280
gagacccccc tgaggagctg cgcagcctcc cccctgacat ggtggctggc ccacgactgc    2340
ctgacacctt cctgggaagt gccacccgc tccactttcc tcccagcccc ttccccagct    2400
ccacaggccc aggacccac tatctctcag gcccctgcc ccctggtacc tactcgggcc    2460
ccacccagct gatacagccc agggcccag ggccccatgc aatgcccgta gcacctgggc    2520
ctgccctcta cccagcccct gcctacacac cggagctggg ccttgtgccc cgatcctccc    2580
cacagcatgg cgtggtgagc agtccctatg tgggggtagg gccggcccca ccagttgcag    2640
gtctcccctc ggccccacct cctcaattct caggccccga gttggccatg gcggttcggc    2700
cagccaccac cacagtagat agcatccagg cgcccatccc cagccacaca gcccacggc    2760 caaacccac ccctgctcct ccccgccct gcttccctgt gccccaccg cagccactgc    2820 ccacgcctta cacctaccct gcaggggcta agcaaccat cccagcacag caccacttct    2880
cttctgggat ccccacaggt tttccagccc caaggattgg gccccagccc cagccccatc    2940
ctcagcccca tccttcacaa gcgtttgggc ctcagccccc acagcagccc cttccactcc    3000
agcatccaca tctcttccca ccccaggccc caggactcct accccacaa tcccctacc    3060 cctatgcccc tcagcctggg gtcctggggc agccgccacc ccccctacac acccagctct    3120
acccaggtcc cgctcaagac cctctgccag cccactcagg ggctctgcct ttccccagcc    3180
ctgggccccc tcagcctccc catccccac tggcatatgg tcctgcccct tctaccagac    3240
ccatgggccc ccaggcagcc cctcttacca ttcgagggcc ctcgtctgct ggccagtcca    3300
cccctagtcc ccacctggtg ccttcacctg cccatctcc agggcctggt ccggtaccc    3360 ctcgccccca agcagcagaa ccaccccctt gcctgcgccg aggcgccgca gctgcagacc    3420
tgctctcctc cagcccggag agccagcatg gcggcactca gtctcctggg ggtgggcagc    3480
ccctgctgca gccaccaag gtggatgcag ctgagggtcg tcggccgcag gccctgcggc    3540
tgattgagcg ggaccctat gagcatcctg agaggctgcg gcagttgcag caggagctgg    3600
aggcctttcg gggtcagctg ggggatgtgg gagctctgga cactgtctgg cgagagctgc    3660
aagatgcgca ggaacatgat gcccgaggcc gttccatcgc cattgcccgc tgctactcac    3720
tgaagaaccg gcaccaggat gtcatgccct atgacagtaa ccgtgtggtg ctgcgctcag    3780
gcaaggatga ctacatcaat gccagctgcg tgagggggct ctccccatac tgccccccgc    3840
tagtggcaac ccaggcccca ctgcctggca cagctgctga cttctggctc atggtccatg    3900
agcagaaagt gtcagtcatt gtcatgctgg tttctgaggc tgagatggag aagcaaaaag    3960
tggcacgcta cttccccacc gagagggggcc agcccatggt gcacggtgcc ctgagcctgg    4020
cattgagcag cgtccgcagc accgaaaccc atgtggagcg cgtgctgagc ctgcagttcc    4080
gagaccagag cctcaagcgc tctcttgtgc acctgcactt ccccacttgg cctgagttag    4140
gcctgcccga cagcccagc aacttgctgc gcttcatcca ggaggtgcac gcacattacc    4200
tgcatcagcg gccgctgcac acgcccatca ttgtgcactg cagctctggt gtgggccgca    4260
cgggagcctt tgcactgctc tatgcagctg tgcaggaggt ggaggctggg aacggaatcc    4320
ctgagctgcc tcagctggtg cggcgcatgc ggcagcagag aaagcacatg ctgcaggaga    4380
agctgcacct caggttctgc tatgaggcag tggtgagaca cgtggagcag gtcctgcagc    4440
```

-continued

```
gccatggtgt gcctcctcca tgcaaaccct tggccagtgc aagcatcagc cagaagaacc    4500
accttcctca ggactcccag gacctggtcc tcggtgggga tgtgcccatc agctccatcc    4560
aggccaccat tgccaagctc agcattcggc ctcctggggg gttggagtcc ccggttgcca    4620
gcttgccagg ccctgcagag cccccaggcc tcccgccagc cagcctccca gagtctaccc    4680
caatcccatc ttcctcccca cccccccttt cctccccact acctgaggct ccccagccta    4740
aggaggagcc gccagtgcct gaagccccca gctcggggcc ccctcctcc tccctggaat     4800
tgctggcctc cttgacccca gaggccttct ccctggacag ctccctgcgg ggcaaacagc    4860
ggatgagcaa gcataacttt ctgcaggccc ataacgggca agggctgcgg gccacccggc    4920
cctctgacga cccctcagc cttctggatc cactctggac actcaacaag acctgaacag     4980
gttttgccta cctggtcctt acactacatc atcatcatct catgcccacc tgcccacacc    5040
cagcagagct tctcagtggg cacagtctct tactcccatt tctgctgcct ttggccctgc    5100
ctggcccagc ctgcacccct gtgggtggga aatgtactgc aggctctggg tcaggttctg    5160
ctcctttatg ggacccgaca tttttcagct ctttgctatt                          5200
```

<210> SEQ ID NO 22
<211> LENGTH: 4330
<212> TYPE: DNA
<213> ORGANISM: Homo sapiens
<220> FEATURE:
<221> NAME/KEY: misc_feature
<223> OTHER INFORMATION: Incyte ID No: 4622229CB1

<400> SEQUENCE: 22

```
ctgaggcggg cggcggtat agagcgggcg gcaggaggca agcagcgaaa ccttcccggc       60
cgccgctccc gtcccgacgg cggcttcccc aaggcggcag gactcggcgc gccatggaca    120
ggccggcggc ggcggcggcg gcgggctgcg agggcggcgg gggcccgaac ccggggccgg    180
cgggcggcag gaggcctcct cgggccgcgg ggggcgccac cgccggctcc cggcagccca    240
gcgtggagac cctggacagt cccacaggat cacatgttga atggtgtaaa cagcttatag    300
ctgctacaat ttctagtcag atttcaggtt cagtgacatc agaaaatgtg tccagagatt    360
acaaggtttt caggaggcct gatctaaggg ctctaaggga tggaaataag ctggcacaga    420
tggaagaggc tccactttc ccaggagaat caattaaagc cattgtgaaa gatgtcatgt     480
atatctgccc atttatggga gcagtgagtg gaaccctgac agtgacggac tttaagctgt    540
acttcaaaaa tgtcgagagg gacccgcatt ttatccttga tgttcccctt ggagtgatca    600
gcagagtgga gaagattgga gcacagagcc atggagacaa ttcctgtggt atagagatag    660
tgtgcaagga tatgaggaac ttgcggcttg cttataaaca ggaagaacag agtaaactag    720
ggatatttga aaacctcaac aaacatgcat ttcctctttc taacggacag gcactatttg    780
cattcagcta taagaaaaa tttccaatta atggctggaa agtttatgat ccagtatctg     840
aatataagag acagggcttg ccaaatgaga gttggaaaat atccaaaata aacagtaatt    900
atgagttctg tgacacctac cctgccatca ttgttgtgcc aactagtgta aaagatgatg    960
acctttcaaa agtggcagct tttcgagcaa aaggcagagt ccctgtgttg tcatggattc   1020
atccggaaag tcaagcaacg attacccgtt gcagccagcc acttgtgggt cccaatgata   1080
agcgctgcaa agaggatgaa aaatacttgc aaacaataat ggatgctaac gcacagtcac   1140
acaagcttat catctttgat gctcgacaaa acagtgtcgc tgataccaac aagacaaagg   1200
gtggaggata tgaaagtgaa agtgcttacc caaatgcaga acttgtgttc ttggagatcc   1260
```

```
acaacattca tgtcatgcga gagtcactac gcaaattaaa agagattgtg tacccttcga   1320
tcgatgaggc gcggtggctc tccaatgtgg atgggacgca ttggctggaa tatataagga   1380
tgctgcttgc tggggcagta agaattgcta taaaaataga atctgggaaa acatctgtgg   1440
tggtgcattg cagcgacggt tgggaccgaa cagcccagct cacatctctg gctatgctaa   1500
tgttggacag ttactacagg accattaaag gatttgaaac tctcgtagaa aaggagtgga   1560
taagctttgg acacaggttt gcactgcgag tgggccatgg taatgacaac catgcggatg   1620
ctgaccgatc tcccatattt ctgcagtttg ttgattgtgt ttggcaaatg acaaggcagt   1680
ttccttcagc attcgagttt aatgagctat tcttgattac aattttggat cacctttata   1740
gctgtctttt tgggaccttt ttgtgcaact gtgaacagca gcgattcaaa gaggatgtat   1800
atacaaagac gatatcttta tggtcgtata tcaatagcca gctagacgag ttttctaatc   1860
ccttctttgt gaattatgaa aaccacgtgt tatatcctgt tgctagtctg agtcatttgg   1920
aattgtgggt aaattattat gtacgatgga atccacggat gagacctcag atgcccattc   1980
accagaatct caaggagctg ctggccgtca gggcggagct gcagaagcgt gtggagggtc   2040
tacagcggga ggtggccacg cgcgccgtct catcctcatc tgagcggggc tcctcgccct   2100
cccactccgc cacctccgtc cacacctcgg tctgatgggc gaggtcagcc tgctgctcca   2160
ctgtctcccg gtggctcagg aaagggacct ggcgatcact gttatggctg tagcttgtga   2220
tcttgtcttt taggattagg cccagggacc atttgtgtgg ctaggtgaca gctcccactg   2280
ttggcaaccg ttaccctcct gtcagcggtt tcacagggga gccgtctgtc acgcccaccc   2340
tgtgaagcaa cttctggcat tcaggcagct tgggagaaac taagtgaacg gaatgcagta   2400
ctgaggttca agaaagctgt acgccatttc tttccaactt aaatccttca gtaacaacaa   2460
acaccactca cttcaagatg cattgccagc cccgtggctt ccctcagctc ttggccacaa   2520
cttgaaaact gtcttgaatg aagtacttgg ggagaagaca ggccactgcc ctctgttcca   2580 cagtttttctt catgcacggg gtcctcctgt taacaattac tgttgtgtac atataaggta   2640
tttttagaga agagaaacag gcctttattt tcctatgtcc ttttttacgt ttagaatagt   2700
cacccgaggg gggatcagct caactgtact gtgggagaaa ttcttttcca acaaacctca   2760
tgctcgtttt tctgtggtgc aatttcaagg gcaacgtgtt ctgtcctcac ctcactctgg   2820
tactcgcctc ttggggcggc tcagcccatt catggggatg gcaccaagcg gccatgctca   2880
gtcttccagc cccgctgagg gtaaaccgag gcctctggca gctgtgcaca ggtgctggcc   2940
tctggctcct tcaaggagca ctgcctgtca ctcgctcctg ggctgtctag ccatgtctcc   3000
cacccccact ttaccgcagc cagctgctgg gatcaaagca agtctgttct tatgttattt   3060
gcctgtatga aatcatttct cattttatca caattccttc aactcagctt actcgcgtgg   3120
ctgcctgttc atatttgaaa gcagccaccg tgctgtggct ttggtttgga aaagcatagc   3180
acgcacttcc cttggttttc ccttcccaga gccgaccgca gctggtcagc cctctcttcc   3240
cgctcctgaa cctttactta ctgactttga gctctgtgac tccgtcggtt ctcgcaggaa   3300
ttaactaact taccaattgg ttcaatccac ttgagcgcca tagctctgag ctcctctgtg   3360
tgacatgcca cagatgacta ttgcacacct gggtcctgcc ccagcaggcc atgcccctcc   3420
catgtgccgt gcctgttgct gcagctgccc cccacccccg ccactggctg caggaattca   3480
gcctttagag gcagaggcag ctgcagcggc ccctgaggtc aaaccccagt gtgactgcat   3540
agcagtgtta gctggttggt ttcaaaactac tggattccag gcaaaggcct acagattgac   3600 cttattatttt ttgaaaatat gttaagggtt ttttcataga gagagaaaga atggattttt   3660
```

-continued

| | |
|---|---|
| ttttaactgg gaacctcctg attcttacgg aaaattatcc ttctataaga agataccaga | 3720 |
| gagatttatt caaggtaatt tgataaccta aaatcaattc tccatttttt atcatatgtg | 3780 |
| ggatttgttg ctaagtcgtg ttcaacaata gcttttatgt tcctaacata tctgaaagct | 3840 |
| tatttatgaa tggatatact ggattattga tatactgatt ttttttttaa tggggacatt | 3900 |
| tgccattttc ttcccagaaa tatgtaatcc cctggctgac taggactgtt aaacatagtg | 3960 |
| tggactggac gatgccttcg acaaaccaga gaaaccaagt tggggggagc tggtgcctgg | 4020 |
| agtgggccct gtgcacctca cctggcggag gctggggggg ctctgtcagc aggaccctag | 4080 |
| aggagactct cattcgattt taaagaagca caacgggtca ttttcctttg tatgttccta | 4140 |
| gcgcagaact gtttctaaaa caacttgaag tatagttttg ttatctaagc aattttttgtt | 4200 |
| ttaagtaagt aagtgtacta gaatgcgaag ccgttatggt tcaggttttt aaaaactggt | 4260 |
| acagtattgt atttgtctca tctgttgcac tgtatttcaa tcatctgtaa ttaaaatgat | 4320 |
| catatgttta | 4330 |

<210> SEQ ID NO 23
<211> LENGTH: 2851
<212> TYPE: DNA
<213> ORGANISM: Homo sapiens
<220> FEATURE:
<221> NAME/KEY: misc_feature
<223> OTHER INFORMATION: Incyte ID No: 72358203CB1

<400> SEQUENCE: 23

| | |
|---|---|
| atcttgaatg cagggacagc catttggaag actgtcctcg agggtggcag cagcctctca | 60 |
| ggacggggaa agccaaggtg cccactaagc ccgtctgggg tggagggtgg caggccgggg | 120 |
| tggagaggat tggaggccgc ctgaaggaac ctgtgctcgg tggcatttac tcaatgtggg | 180 |
| ggtctgacac ctcccagctc attttgtccc catcttcccc ttgcgtcagg tccccaccca | 240 |
| gcaggaggag gtccgaggat ctgcgcgacg ctggccccgc ggagtgtggg ggacttttcc | 300 |
| tctcaaccac cagtgccccg caagcgtggg tgaacagtcc tccctggcta ctgtgggacg | 360 |
| ctgggcaggc gacttcgcct ctctaggcct cggttttcct gcttgtcaaa tggggctgat | 420 |
| gccggcgtgg gcttcttcag gcggtcgcga gcgttgaccc ctggagtcag cgaaccagcc | 480 |
| gcgcacgcac tcccgggcgg aggtcgggc tgggggggcga cgcctcccgt ctgcgcgccc | 540 |
| ccggcccccgc ctcccgccgg cgcacccctc cctcggctcc gcccgcggcc cgcttcttcc | 600 |
| tcccgcgggc ggcccagccc tagcgccccg cgctccgcgg gcagccccct gccgccgcgc | 660 |
| catgtccgcc ggctggttcc ggcgccgctt cctgcctggg gagccgctcc ccgcgccgcg | 720 |
| gccgcctggg ccgcatgcca gccccgtgcc ctaccgacgg ccccgcttcc ttcgcggctc | 780 |
| cagctccagc cccggggcgg ccgacgcctc gcgccgccca gactcccggc ccgtgcgcag | 840 |
| ccccgcacga ggacgcacgc taccctggaa tgcaggctac gccagagatta tcaatgcaga | 900 |
| gaaatctgaa ttcaatgagg atcaagccgc ctgtgggaag ctgtgcatcc ggagatgtga | 960 |
| gtttggggct gaagaagagt ggctgaccct gtgcccagag gagttcctga caggccatta | 1020 |
| ctgggcactg ttcgatgggc acggcggtcc tgcagcagcc atcttggctg ccaacaccct | 1080 |
| gcactcctgc ttgcgccggc agctggaggc cgtggtggaa gcttggtgg ccactcagcc | 1140 |
| ccccatgcac ctcaatggcc gctgcatctg ccccagtgac cctcagtttg tggaggaaaa | 1200 |
| gggcatcagg gcagaagact tggtgatcgg ggcattggag agtgcctttc aggaatgtga | 1260 |
| tgaggtgatc gggcgggagc tggaggcctc aggccagatg ggcggctgca cagccctggt | 1320 |

-continued

```
ggctgtgtcc ctgcagggaa agctgtacat ggccaatgct ggggatagca gggccatctt    1380
ggtgcggaga gatgagatac ggccactgag cttcgagttc accccagaga ctgagcggca    1440
gcggatccag cagctggcct ttgtctatcc tgagcttctg gctggtgagt tcacccgact    1500
ggagttccct cggcggctga agggggatga cttgggacag aaggttttgt tcagggatca    1560
ccacatgagt ggctggagct acaaacgtgt ggagaaatcg gatctcaagt acccactgat    1620
ccatggacag ggtaggcagg ctcggttact aggaacactg gctgtctccc ggggcctggg    1680
agaccatcag ctcagagtcc tggacacaaa catccagctc aagcccttct tgctctctgt    1740
gccacaggtg actgtgctgg atgtggacca gctggagcta caggaggatg atgtggttgt    1800
catggcaact gatggactct gggatgtact gtccaacgag caggtggcat ggctggtgcg    1860
gagcttcctc cctgggaacc aagaggaccc acacaggttc tcaaagctgg cccagatgct    1920
gatacacagc acacagggaa aggaagacag tctcacagag aagggcagg tgtcctacga    1980
tgacgtctct gtgttcgtga ttcccttgca cagtcagggc caagagagca gtgaccactg    2040
aggattcaga cactgtatcc cagaactgct ctagtgcccg ggtgtggtct gggcatccct    2100
ccagtgtgac caagagcaaa tcctgcctgc cctatcccta gccaccgccc agtgctctca    2160
ctatccacct caacacacat ccatctcaag aggaacattt ataccaggca gtcagagctg    2220
gaagtgtatg gagagcccag cccaccaggt cctgcctttt gcggtgataa ccttctctgg    2280
cagagtgact ttacaactta actaggaaac ccatgtgagg ctcctcagac aggatcttga    2340
acagcccaaa gtatcattct cagatagggg cacccaagct aagggtatta gccaaagatg    2400
ccaggatggg tagctagccc atgtttagat ccaggtctcc aattcatggt tatcagggca    2460
tgtgttcaac aaccccaaa gtccacgcag gtggcttgta gaaacctttg ggcagcctca    2520
tgtctgctaa aacagccatc ttcaagacag cccctgaaaa gagaccagtt caggtcctgc    2580
cctgctgttc tttgctggag atgaggaaca ggtgctgggg ctaaagtttg gggtagagca    2640
caagggacaa gaggaactct tggagttggc tgggtgagag ggctctccat ttgctacctg    2700
tagtagcctg cctcttaact ggttgcttct ccctagttcc agccctgccc tggtctgatg    2760
ccccaacact gcccttgctt tgttttccct gtcacctccc tattattaaa tgttttctac    2820
agaaaaaaaa aaaaaaaaaa aaaaaaaaaa a                                   2851
```

<210> SEQ ID NO 24
<211> LENGTH: 2361
<212> TYPE: DNA
<213> ORGANISM: Homo sapiens
<220> FEATURE:
<221> NAME/KEY: misc_feature
<223> OTHER INFORMATION: Incyte ID No: 4885040CB1

<400> SEQUENCE: 24

```
ggctcctacc agccattgta ggccaataat ccgttatgga gcatgccttt accccgttgg     60
agcccctgct ttccactggg aatttgaagt actgccttgt aattcttaat cagcctttgg    120
acaactattt tcgtcatctt tggaacaaag ctcttttaag agcctgtgcc gatggaggtg    180
ccaaccgctt atatgatatc accgaaggag agagagaaag cttttgcct gaattcatca    240
atggagactt tgattctatt aggcctgaag tcagagaata ctatgctact aagggatgtg    300
agctcatttc aactcctgat caagaccaca ctgactttac taagtgccctt aaaatgctcc    360
aaaagaaagat agaagaaaaa gacttaaagg ttgatgtgat cgtgacactg ggaggccttg    420
ctgggcgttt tgaccagatt atggcatctg tgaataccctt gttccaagcg actcacatca    480
```

```
ctccttttcc aattataata atccaagagg aatcgctgat ctacctgctc caaccaggaa      540
agcacaggtt gcatgtagac actggaatgg agggtgattg gtgtggcctt attcctgttg      600
gacagccttg tatgcaggtt acaaccacag gcctcaagtg gaacctcaca aatgatgtgc      660
ttgcttttgg aacattggtc agtacttcca atacctacga cgggtctggt gttgtgactg      720
tggaaactga ccacccactc ctctggacca tggccatcaa aagctaacct gttgactggc      780
atccataagt gtgcctctgc cttatctcat ttctcaacag ttcattgctc aacaagaacg      840
attcacctgg gtttgcaaga atctaaacct ctctagggga agcccactgg gtttaaagat      900
gttagtgttt agataataca ggtaacatta taaatgacag atctcaattt tatagtagtg      960
ggaaagatac atgctaagaa agcaaataag ctctattata ttcggttgga acctaatggg     1020
aatcattcca ctatacaatt cagtactgat tattcttctt acattattaa tcattccatt     1080
tatcctagaa aattgttttt aatttgaatc agagaaaact gttgaggttc ctcttggagt     1140
ctagaacatc cttaaatgtc taacaacaag ggctacctct gagtaccttt tagtattagt     1200
tttctgtata tgatatatat tatcttatac tgaaaaaaaa ttccttttcag attggggtgt    1260 tagaagtgca ccaggtcact ctgaccttat tactgtcttt ggtattgtct taaataaatc     1320
aagaatcatt gacctaattg ttaaatttaa aaataggtag ttagcaatag gtggaaagag     1380
aaatgatgtg aaagataaat gatgattcgt ggagccctac tcacacatta accccaaat     1440 tcaaaagtaa gaatgcaaaa gtctagaggg ggtaacagtc tgcatcatca tcacaaccta     1500
aatggagaaa gctgtgcaga ggaaacttaa gcataaaaat tgaattcgtt tctgacatac     1560
cttagactga aaaactgttg gttcatccag aagtgtattc atattaccag aaaatgagtt     1620
tgtctatggg gatacatgaa cttcatatac taaggagcct aactccaaag cctgcgttct     1680
catcccagtc tgatattcac ctaagtttcc ggacccttttt ccttagctgt aaaatggaag    1740
cggttggact gatggtgtct gaggttcttt cccacactga aattctaaat attgacactt     1800
agcagtcata gggctgataa tacacacagt tactgactta gcctaaacaa cctggtgcat     1860
cgaaatgtat tcacctttct tttgtaaaga gaccatcttc tatcttcttt ccacttttct     1920
ctgttttatg aaaccaactg ttgacataca aaccatgatt gaaggagaac ctgtccaaca    1980
tgttttatgt acacaaatcc ctatgttgct ataagaaaag tgaaagtaac tgttttcttc     2040
ttggtgctat gacagtgtga gactcaggtt gtctgtagag aatgaaagga gcagtggccc     2100
gcgtgattgt ggcatttaag gagcagtggc ccatgtgact gtggcatttt cggcactttt     2160
cattactttc tgcttgaccg gaagttgagg cttagctatg tttccatctt cagtttctga     2220
agactagtta tatattcctt actagaaata tattcataat atataaaaga aatatatctg     2280
tgattttaaa attttgctac caaagaatgc atgttctgtg tgccctgaaa atgttaccag     2340
tgttaataaa tggatactta t                                               2361
```

<210> SEQ ID NO 25
<211> LENGTH: 2285
<212> TYPE: DNA
<213> ORGANISM: Homo sapiens
<220> FEATURE:
<221> NAME/KEY: misc_feature
<223> OTHER INFORMATION: Incyte ID No: 7484507CB1

<400> SEQUENCE: 25

```
gcggtccctc ccggcccggc ggaacgcgtc ccttttaagg gggcggggac ctgggggtct       60
ggggccagcg cgcgggaggg acgcctgagt gcctcgaggg cgccgttcgg gcggggagga     120
```

-continued

```
tcccgcgggt cccactgacc cacgcggggt ggggccaggg gtggacgctc gcccgtacgc    180
ggtcgctact gatcatgctt gggccagggt ccaatcgcag gcgcccacg caggggagc      240 gaggcccagg gtcccccgga gagcccatgg agaagtacca ggttttgtac cagctgaatc    300
ctggggcctt gggggtgaac ctggtggtgg aggaaatgga aaccaaagtc aagcatgtga    360
taaagcaggt ggaatgcatg gatgaccatt acgccagtca ggccctggag gagctgatgc    420
cactgctgaa gctgcggcac gcccacatct ctgtgtacca ggagctgttc atcacgtgga    480
atggggagat ctcttctctg tacctctgcc tggtgatgga gttcaatgag ctcagcttcc    540
aggaggtcat tgaggataag aggaaggcaa agaaaatcat tgactctgag tggatgcaga    600
atgtgctggg ccaggtgctg gacgcgctgg aatacctgca ccatttggac atcatccaca    660
ggaatctcaa accctccaac atcatcctca tcagcagtga ccactgcaaa ctgcaggacc    720
tgagttccaa tgtgctaatg acagacaaag ccaaatggaa tattcgtgcg gaggaagacc    780
cctttcgtaa gtcctggatg gcccctgaag ccctcaactt ctccttcagc cagaaatcag    840
acatctggtc cctgggctgc atcattctgg acatgaccag ctgctccttc atggatggca    900
cagaagccat gcatctgcgg aagtcccctcc gccagagccc aggcagcctg aaggccgtcc    960
tgaagacaat ggaggagaag cagatcccgg atgtggaaac cttcaggaat cttctgcctt    1020
tgatgctcca gatcgacccc tcggatcgaa taacgataaa ggacgtggtg cacatcacct    1080
tcttgagagg ctccttcaag tcctcgtgcg tctctctgac cctgcaccgg cagatggtgc    1140
ctgcgtccat caccgacatg ctgttagaag caacgtggc cagcattta ggtgatgctg    1200 gggacacaaa gggggagcgt gccctgaagc tcctgtccat ggccttggca tcctattgtt    1260
tagttccaga gggttcatta tttatgcccc tggccttgct ccacatgcac gaccagtggc    1320
tcagctgtga ccaggacaga gtccctggga agagagactt tgcctccctg gggaaactag    1380
ggaagctgtt gggcccccatc ccaaagggtc tgccgtggcc cccggagctg gtggaggtgg    1440
tggtcacgac catggagcta catgacaggg tcctcgatgt ccagctgtgt gcctgctccc    1500
tgctgctgca cctcctgggc caaggtatca ttgtgaacaa ggccccctgg agaaggtcc    1560 cggacctcat cagccaggtg ttggccacct accctgcgga tggggaaatg cagaagcca    1620 gctgcggagt cttctggctg ctgtccctgc tgggctgcat caaggagcag cagtttgaac    1680
aagtggtggc gctgctcctg caaagcatcc ggctgtgcca ggacagagcc ctgctggtga    1740
acaatgccta ccggggactg gccagcctgg tgaaggtgtc agagctggcg gccttcaagg    1800
tggtggtgca ggaggagggc ggcagtggcc tcagcctcat caaggagacc taccagctcc    1860
acagggacga cccggaggtg gtggagaacg tgggcatgct gctggtccac ctggcttcct    1920
atgaggagat cctgccggag ctggtgtcca gtagtatgaa ggccctgctc caggagatca    1980
aggagcgctt cacctccagc ctggaactgg tttcttgcgc ggaaaaagtg ctcttgaggc    2040
tggaggcagc cacctctccc agcccactgg gtggggaagc agctcagccc tgatgcgggg    2100
gagaagacag atacccccaca ggcccctccc tccacgtgtg ccctctccct gtccttcctt    2160
tccatgggcc actgttccc ttgggtgtgg gggaagggtc atccagcacc agaatgcgca    2220
cctcacactc ctcttaggtg actaataaag aggcccaagg ccagtttctg ccttaaaaaa    2280
aaaaa                                                                2285
```

<210> SEQ ID NO 26
<211> LENGTH: 4858
<212> TYPE: DNA

<213> ORGANISM: Homo sapiens
<220> FEATURE:
<221> NAME/KEY: misc_feature
<223> OTHER INFORMATION: Incyte ID No: 7198931CB1

<400> SEQUENCE: 26

| | |
|---|---|
| atggcggcgg cggcggggaa tcgcgcctcg tcgtcgggat tcccgggcgc cagggctacg | 60 |
| agccctgagg caggcggcgg cggaggagcc ctcaaggcga gcagcgcgcg cgcggctgcc | 120 |
| gcgggactgc tgcgggaggc gggcagcggg ggccgcgagc gggcggactg cggcggcgg | 180 |
| cagctgcgca aagtgcggag tgtggagctg accagctgc ctgagcagcc gctcttcctt | 240 |
| gccgcctcac cgccggcctc ctcgacttcc ccgtcgccgg agcccgcgga cgcagcgggg | 300 |
| agtgggaccg gcttccagcc tgtggcggtg ccgccgcccc acggagccgc cagccggcgc | 360 |
| ggcgcccacc ttaccgagtc ggtggcggcg ccggacagcg gcgcctcgag tcccgcagcg | 420 |
| gccgagcccg gggagaagcg ggcgcccgcc gccgagccgt ctcctgcagc ggcccccgcc | 480 |
| ggtcgtgaga tggagaataa agaaactctc aaagggttgc acaagatgga tgatcgtcca | 540 |
| gaggaacgaa tgatcaggga gaaactgaag gcaacctgta tgccagcctg aagcacgaa | 600 |
| tggttggaaa ggagaaatag gcgagggcct gtggtggtaa accaatccc agttaaagga | 660 |
| gatggatctg aaatgaatca cttagcagct gagtctccag agaggtcca ggcaagtgcg | 720 |
| gcttcaccag cttccaaagg ccgacgcagt ccttctcctg caactcccc atcaggtcgc | 780 |
| acagtgaaat cagaatctcc aggagtaagg agaaaagag tttccccagt gccttttcag | 840 |
| agtggcagaa tcacaccacc ccgaagagcc ccttcaccag atggcttctc accatatagc | 900 |
| cctgaggaaa caaccgccg tgttaacaaa gtgatgcggg ccagactgta cttactgcag | 960 |
| cagatagggc ctaactcttt cctgattgga ggagacagcc cagacaataa ataccgggtg | 1020 |
| tttattgggc tcagaactg cagctgtgca cgtggaacat tctgtattca tctgctattt | 1080 |
| gtgatgctcc gggtgtttca actagaacct tcagacccca tgttatggag aaaaacttta | 1140 |
| aagaattttg aggttgagag tttgttccag aaatatcaca gtaggcgtag ctcaaggatc | 1200 |
| aaagctccat ctcgtaacac catccagaag tttgtttcac gcatgtcaaa ttctcataca | 1260 |
| ttgtcatcat ctagtacttc tacatctagt tcagaaaaca gcataaagga tgaagaggaa | 1320 |
| cagatgtgtc ctatttgctt gttgggcatg cttgatgaag aaagtcttac agtgtgtgaa | 1380 |
| gacggctgca ggaacaagct gcaccaccac tgcatgtcaa tttgggcaga agagtgtaga | 1440 |
| agaaatagag aacctttaat atgtcccctt tgtagatcta agtggagatc tcatgatttc | 1500 |
| tacagccacg agttgtcaag tcctgtggat tccccttctt ccctcagagc tgcacagcag | 1560 |
| caaaccgtac agcagcagcc tttggctgga tcacgaagga tcaagagag caattttaac | 1620 |
| cttactcatt atggaactca gcaaatccct cctgcttaca agatttagc tgagccatgg | 1680 |
| attcaggtgt ttggaatgga actcgttggc tgcttatttt ctagaaactg gaatgtgaga | 1740 |
| gagatggccc tcaggcgtct ttcccatgat gtcagtgggg ccctgctgtt ggcaaatggg | 1800 |
| gagagcactg gaaattctgg gggcagcagt ggaagcagcc cgagtggggg agccaccagt | 1860 |
| gggtcttccc agaccagtat ctcaggagat gtggtggagg catgctgcag cgttctgtca | 1920 |
| atggtctgtg ctgaccctgt ctacaaagtg tacgttgctg ctttaaaaac attgagagcc | 1980 |
| atgctggtat atactccttg ccacagttta gcggaaagaa tcaaacttca gagacttctc | 2040 |
| cagccagttg tagacaccat cctagtcaaa tgtgcagatg ccaatagccg cacaagtcag | 2100 |
| ctgtccatat caacactgtt ggaactgtgc aaaggccaag caggagagtt ggcagttggc | 2160 |

```
agagaaatac taaaagctgg atccattggt attggtggtg ttgattatgt cttaaattgt    2220
attcttggaa accaaactga atcaaacaat tggcaagaac ttcttggccg cctttgtctt    2280
atagatagac tgttgttgga atttcctgct gaattttatc ctcatattgt cagtactgat    2340
gtttcacaag ctgagcctgt tgaaatcagg tataagaagc tgctgtccct cttaaccttt    2400
gctttgcagt ccattaataa ttcccactca atggttggca aactttccag aaggatctac    2460
ttgagttctg caagaatggt tactacagta ccccatgtgt tttcaaaact gttagaaatg    2520
ctgagtgttt ccagttccac tcacttcacc aggatgcgtc gccgtttgat ggctattaca    2580
gatgaggtgg aaattgccga agccatccag ttgggcgtag aagacacttt ggatggtcaa    2640
caggacagct tcttgcaggc atctgttccc aacaactatc tggaaaccac agagaacagt    2700
tcccctgagt gcacaatcca tttagagaaa actggaaaag gattatgtgc tacaaaattg    2760
agtgccagtt cagaggacat ttctgagaga ctggccagca tttcagtagg accttctagt    2820
tcaacaacaa caacaacaac aacagagcaa ccaaagccaa tggttcaaac aaaaggcaga    2880
ccccacagtc agtgtttgaa ctcctctcct ttatctcatc attcccaatt aatgtttcca    2940
gccttgtcaa ccccttcttc ttctacccca tctgtaccag ctggcactgc aacagatgtc    3000
tctaagcata gacttcaggg attcattccc tgcagaatac cttctgcatc tcctcaaaca    3060
cagcgcaagt tttctctaca attccacaga aactgtcctg aaaacaaaga ctcagataaa    3120
ctttccccag tctttactca gtcaagaccc ttgccctcca gtaacataca caggccaaag    3180
ccatctcgac ctaccccagg taatacaagt aaacagggag atccctcaaa aaatagcatg    3240
acacttgatc tgaacagtag ttccaaatgt gatgacagct ttggctgtag cagcaatagt    3300
agtaatgctg ttatacccag tgacgagaca gtgttcaccc cagtagagga gaaatgcaga    3360
ttagatgtca atacagagct caactccagt attgaggacc ttcttgaagc atctatgcct    3420
tcaagtgata caacagtaac ttttaagtca gaagttgctg tcctgtctcc tgaaaaggct    3480
gaaaatgatg atacctacaa agatgatgtg aatcataatc aaaagtgcaa agagaagatg    3540
gaagctgaag aagaagaagc tttagcaatt gccatggcaa tgtcagcgtc tcaggatgcc    3600
ctccccatag ttcctcagct gcaggttgaa aatggagaag atatcatcat tattcaacag    3660
gatacaccag agactctacc aggacatacc aaagcaaaac aaccgtatag agaagacact    3720
gaatggctga aggtcaaca gataggcctt ggagcatttt cttcttgtta tcaggctcaa    3780
gatgtgggaa ctggaacttt aatggctgtt aaacaggtga cttatgtcag aaacacatct    3840
tctgagcaag aagaagtagt agaagcacta agagaagaga taagaatgat gagccatctg    3900
aatcatccaa acatcattag gatgttggga gccacgtgtg agaagagcaa ttacaatctc    3960
ttcattgaat ggatggcagg gggatcggtg gctcatttgc tgagtaaata tggagccttc    4020
aaagaatcag tagttattaa ctacactgaa cagttactcc gtggcctttc gtatctccat    4080
gaaaaccaaa tcattcacag agatgtcaaa ggtgccaatt tgctaattga cagcactggt    4140
cagagactaa gaattgcaga ttttggagct gcagccaggt ggcatcaaa aggaactggt    4200
gcaggagagt ttcagggaca attactgggg acaattgcat ttatggcacc tgaggtacta    4260
agaggtcaac agtatggaag gagctgtgat gtatggagtg ttggctgtgc tattatagaa    4320
atggcttgtg caaaccacc atggaatgca gaaaaacact ccaatcatct tgctttgata    4380
tttaagattg ctagtgcaac tactgctcca tcgatccctt cacatttgtc tcctggttta    4440
cgagatgtgc tcttcgttg tttagaactt caacctcagg acagacctcc atcaagagag    4500
ctactgaagc atccagtctt tcgtactaca tggtagccaa ttatgcagat caactacagt    4560
```

-continued

| | |
|---|---|
| agaaacagga tgctcaacaa gagaaaaaaa acttgtgggg aaccacattg atattctact | 4620 |
| ggccatgatg ccactgaaca gctatgaacg aggccagtgg ggaaccctta cctaagtatg | 4680 |
| tggattgaca aatcatgatc tgtacctaag ctcagtatgc aaaagcccaa actagtgcag | 4740 |
| aaactgtaaa ctgtgccttt caagaactgg cctaagtgaa ccaggaaaac aatgaagttt | 4800 |
| gctgacttaa tttgaaagct attttttctc ctggaccctt tttcgaaaaa ttacgcta | 4858 |

<210> SEQ ID NO 27
<211> LENGTH: 2903
<212> TYPE: DNA
<213> ORGANISM: Homo sapiens
<220> FEATURE:
<221> NAME/KEY: misc_feature
<223> OTHER INFORMATION: Incyte ID No: 7482905CB1

<400> SEQUENCE: 27

| | |
|---|---|
| tatgacgtcg cctgtacagc ggtaccgtga gcttcgagta gttcgtgcat ctgggaccgt | 60 |
| tattccatac taacgtcctg tgtcactgag tttttaaat gtctagcata tctgtaaaga | 120 |
| tgccttagaa aaagaatcat ggagaagtat gttagactac agaagattgg agaaggttca | 180 |
| tttggaaaag ccattcttgt taaatctaca gaagatggca gacagtatgt tatcaaggaa | 240 |
| attaacatct caagaatgtc cagtaaagaa agagaaggct ggaatttatt gaaaaagaaa | 300 |
| agaaacaaaa ggatcagatt attagtttaa tgaaggctga acaaatgaaa aggcaagaaa | 360 |
| aggaaaggtt ggaaagaata aatagggcca gggaacaagg atggagaaat gtgctaagtg | 420 |
| ctggtggaag tggtgaagta aaggctcctt ttctgggcag tggagggact atagctccat | 480 |
| catctttttc ttctcgagga cagtatgaac attaccatgc cattttгтgac caaatgcagc | 540 |
| aacaaagagc agaagataat gaagctaaat ggaaaagaga aatatatggt cgaggtcttc | 600 |
| cagaaaggca aaaagggcag ctagctgtag aaagagctaa acaagtagaa gagttcctgc | 660 |
| agcgaaaacg ggaagctatg cagaataaag ctcgagccga aggacatatg gtttatctgg | 720 |
| caagactgag gcaaataaga ctacagaatt tcaatgagcg ccaacagatt aaagccaaac | 780 |
| ttcgtggtga aagaaagaa gctaatcatt ctgaaggaca gaaggaagt gaagaggctg | 840 |
| acatgaggcg caaaaaaatc gaatcactga aggcccatgc aaatgcacgt gctgctgtac | 900 |
| taaaagaaca actagaacga aagagaaagg aggcttatga gagagaaaaa aaagtgtggg | 960 |
| aagagcattt ggtggctaaa ggagttaaga gttctgatgt ttctccacct ttgggacagc | 1020 |
| atgaaacagg tggctctcca tcaaagcaac agatgagatc tgttatttct gtaacttcag | 1080 |
| ctttgaaaga agttggcgtg gacagtagtt taactgatac ccgggaaact tcagaagaga | 1140 |
| tgcaaaagac caacaatgct atttcaagta agcgagaaat acttcgtaga ttaaatgaaa | 1200 |
| atcttaaagc tcaagaagat gaaaaggaa agcagaatct ctctgatact tttgagataa | 1260 |
| atgttcatga agatgccaaa gagcatgaaa agaaaaaatc agtttcatct gatcgcaaga | 1320 |
| agtgggaggc aggaggtcaa cttgtgattc ctctggatga gttaacacta gatacatcct | 1380 |
| tctctacaac tgaaagacat acagtgggag aagttattaa attaggtcct aatggatctc | 1440 |
| caagaagagc ctgggggaaa agtccgacag attctgttct aaagatactt ggagaagctg | 1500 |
| aactacaact tcagacagaa ctattagaaa atacaactat tagaagtgag atttctcccg | 1560 |
| aagggtaaa gtacaaaccc ttaattactg gagaaaaaaa agtacaatgt atttcacatg | 1620 |
| aaataaaccc atcagctatt gttgattctc ctgttgagac aaaaagtccc gagttcagtg | 1680 |
| aggcatctcc acagatgtca ttgaaactgg aaggaaattt agaagaacct gatgatttgg | 1740 |

-continued

```
aaacagaaat tctacaagag ccaagtggaa caaacaaaga tgagagcttg ccatgcacta     1800
ttactgatgt gtggattagt gaggaaaaag aaacaaagga aactcagtcg gcagatagga     1860
tcaccattca ggaaaatgaa gtttctgaag atggagtctc gagtactgtg gaccaactta    1920
gtgacattca tatagagcct ggaaccaatg attctcagca ctctaaatgt gatgtagata    1980
agtctgtgca accggaacca ttttcccata aggtggttca ttctgaacac ttgaacttag    2040
tccctcaagt tcaatcagtt cagtgttcac cagaagaatc ctttgcattt cgatctcact    2100
cgcatttacc accaaaaaat aaaaacaaga attccttgct gattggactt tcaactggtc    2160
tgtttgatgc aaacaaccca agatgttaa ggacatgttc acttccagat ctctcaaagc     2220
tgttcagaac ccttatggat gttcccaccg taggagatgt tcgtcaagac aatcttgaaa    2280
tagatgaaat tgaagatgaa acattaaag aaggaccttc tgattctgaa gacattgtgt     2340
ttgaagaaac tgcacagat ttacaagagc tgcaggcctc gatggaacag ttacttaggg     2400
aacaacctgg tgaagaatac agtgaagaag aagagtcagt cttgaagaac agtgatgtgg    2460
agccaactgc aaatgggaca gatgtggcag atgaagatga caatcccagc agtgaaagtg    2520
ccctgaacga agaatggcac tcagataaca gtgatggtga aattgctagt gaatgtgaat    2580
gcgatagtgt cttaaccat ttagaggaac tgagacttca tctggagcag gaaatgggct     2640
ttgaaaaatt ctttgaggtt tatgagaaaa taaaggctat tcatgaagat gaagatgaaa    2700
atattgaaat ttgttcaaaa atagttcaaa atattttggg aaatgaacat cagcatcttt    2760
atgccaagat tcttcattta gtcatggcag atggagccta ccaagaagat aatgatgaat    2820
aatcctcaaa atgttttta atcctcaact atatgaaagc atttgaattt ggcttatcag     2880
aataacagct tcagtgggag gcg                                             2903
```

<210> SEQ ID NO 28
<211> LENGTH: 1812
<212> TYPE: DNA
<213> ORGANISM: Homo sapiens
<220> FEATURE:
<221> NAME/KEY: misc_feature
<223> OTHER INFORMATION: Incyte ID No: 7483019CB1

<400> SEQUENCE: 28

```
cttttccttc cctgtgccca ggccttgctc agtgcccatg acacgatagc tcagaaagat      60
tttgaacccc ttctccctcc actgccagac aatatccctg agagtgagga agcaatgagg     120
attgtttgtt tagtgaaaaa ccaacagccc ctggagccca ccatcaagcg ccacgagatg     180 acagggaca tcttggtggc caggatcatc cacggtgggc tggcggagag aagtgggttg     240
ctatatgctg gagacaaact ggtagaagtg aatggagttt cagttgaggg actggaccct    300
gaacaagtga tccatattct ggccatgtct cgaggcacaa tcatgttcaa ggtggttcca    360
gtctctgacc ctcctgtgaa tagccagcag atggtgtacg tccgtgccat gactgagtac    420
tggccccagg aggatcccga catcccctgc atggacgctg gattgccttt ccagaagggg    480
gacatcctcc agattgtgga ccagaatgat gccctctggt ggcaggcccg aaaaatctca    540
gaccctgcta cctgcgctgg gcttgtccct tctaaccacc ttctgaagag gaagcaacgg    600
gaattctggt ggtctcagcc gtaccagcct cacacctgcc tcaagtcaac ctatacaag    660 gaggagtttg ttggctacgg tcagaagttc tttatagctg gcttccgccg cagcatgcgc   720
ctttgtcgca ggaagtctca cctcagcccg ctgcatgcca gtgtgtgctg caccggcagc    780
tgctacagtg cagtgggtgc cccttacgag gaggtggtga ggtaccagcg acgcccttca    840
```

```
gacaagtacc gcctcatagt gctcatggga ccctctggtg ttggagtaaa tgagctcaga      900
agacaactta ttgaatttaa tcccagccat tttcaaagtg ctgtgccaca cactactcgt      960
actaaaaaga gttacgaaac gaatgggcgt gagtatcact atgtgtccaa ggaaacattt     1020
gaaaacctca tatatagtca caggatgctg gagtatggtg agtacaaagg ccacctgtat     1080
ggcactagtg tgggtgctgt tcaaacagtc cttgtcgaag aaagatctg tgtcatggac      1140
ctagagcctc aggatattca aggggttcga acccatgaac tgaagcccta tgtcatattt     1200
ataaagccat cgaatatgag gtgtatgaaa caatctcgga aaaatgccaa ggttattact     1260
gactactatg tggacatgaa gttcaaggat gaagacctac aagagatgga aaatttagcc     1320
caaagaatgg aaactcagtt tggccaattt tttgatcatg tgattgtgaa tgacagcttg     1380
cacgatgcat gtgcccagtt gttgtctgcc atacagaagg ctcaggagga gcctcagtgg     1440
gtaccagcaa catggatttc ctcagatact gagtctcaat gagacttctt gtttaatgct     1500
ggagttttaa cactgtaccc ttgatacagc gatccatagt tgcaatctaa acaacagta     1560
tttgacccat tttaatgtgt acaactttaa aagtgcagca atttattaat taatcttatt     1620
tgaaaaaat ttttattgta tggttatgtg gttaccatt ttaacttaat tttttttcct      1680
ttacctcata tgcagctgtg gtagaaatat gaataatgtt aggtcactga gtatgagaac     1740
ctttcgcaga tttcacatga tcttttaag atttaaataa agagctttcc taaataaaaa     1800
aaaaaaaaaa gg                                                         1812

<210> SEQ ID NO 29
<211> LENGTH: 5480
<212> TYPE: DNA
<213> ORGANISM: Homo sapiens
<220> FEATURE:
<221> NAME/KEY: misc_feature
<223> OTHER INFORMATION: Incyte ID No: 5455490CB1

<400> SEQUENCE: 29
ggtgtttcgg aagatcatgt ttttttgaaga aaagtactta atttttttgcc gtaagtttgg     60
gaagcttttta taaatttcct ttggctgaca gaactgcata ccccttgtgt gagagaactt    120
cctaccaaga ctccagtgtg agggcaaaaa cttgagtagc caggagaatg atgaaacgga    180
ggcgagagag actgggagca ccatgtctgc ggattcaaat ctctactctt tgccgaggag    240
ctgaagtaaa ccagcacatg tttttcaccca catctgctcc agccctcttc ctcactaaag    300
tcccatttag tgctgattgt gctttggcta cttctcctct tgccattttc ctgaacccac    360
gagcccacag cagtcctggc actccttgtt ccagccgccc actgccgtgg agttgtcgga    420
caagtaaccg caagagcttg attgtgacct ctagcacatc acctacacta ccacggccac    480
actcaccact ccatggccac acaggtaaca gtcctttgga cagccccgg aatttctctc      540
caaatgcacc tgctcacttt tcttttgttc ctgcccgtag ccatagccac agagctgaca    600
ggactgatgg gcggcgctgg tctttggcct ctttgccctc ttcaggatat ggaactaaca    660
ctcctagctc cactgtctca tcatcatgct cctcacagga aaagctgcat cagttgcctt    720
tccagcctac agctgatgag ctgcacttt tgacgaagca tttcagcaca gagagcgtac    780
cagatgagga aggacggcag tcccagcca tgcggcctcg ctcccggagc tcagtcccg      840
gacgatcccc agtatccttt gacagtgaaa taataatgat gaatcatgtt tacaaagaaa    900
gattcccaaa ggccaccgca caaatggaag agcgactagc agagtttatt tcctccaaca    960
ctccagacag cgtgctgccc ttggcagatg gagccctgag ctttattcat catcaggtga   1020
```

-continued

```
ttgagatggc ccgagactgc ctggataaat ctcggagtgg cctcattaca tcacaatact    1080
tctacgaact tcaagagaat ttggagaaac ttttacaaga tgctcatgag cgctcagaga    1140
gctcagaagt ggcttttgtg atgcagctgg tgaaaaagct gatgattatc attgcccgcc    1200
cagcacgtct cctggaatgc ctggagtttg accctgaaga gttctaccac cttttagaag    1260
cagctgaggg ccacgccaaa gagggacaag ggattaaatg tgacattccc cgctacatcg    1320
ttagccagct gggcctcacc cgggatcccc tagaagaaat ggcccagttg agcagctgtg    1380
acagtcctga cactccagag acagatgatt ctattgaggg ccatgggcca tctctgccat    1440
ctaaaaagac ccctctgaa gaggacttcg agaccattaa gctcatcagc aatggcgcct     1500
atggggctgt atttctggtg cggcacaagt ccacccggca gcgctttgcc atgaagaaga    1560
tcaacaagca gaacctgatc ctacggaacc agatccagca ggccttcgtg gagcgtgaca    1620
tactgacttt cgctgagaac ccctttgtgg tcagcatgtt ctgctccttt gataccaagc    1680
gccacttgtg catggtgatg gagtacgttg aaggggaga ctgtgccact ctgctgaaga     1740
atattggggc cctgcctgtg acatggtgc gtctatactt tgcggaaact gtgctggccc     1800
tggagtactt acacaactat ggcatcgtgc accgtgacct caagcctgac aacctcctaa    1860
ttacatccat ggggcacatc aagctcacg actttggact gtccaaaatt ggcctcatga     1920
gtctgacaac gaacttgtat gagggtcata ttgaaaagga tgcccgggaa ttcctggaca    1980
agcaggtatg cgggacccca gaatacattg cgcctgaggt gatcctgcgc cagggctatg    2040
ggaagccagt ggactggtgg gccatgggca ttatcctgta tgagttcctg gtgggctgcg    2100
tccctttttt tggagatact ccggaggagc tctttgggca ggtgatcagt gatgagattg    2160
tgtggcctga gggtgatgag gcactgcccc cagacgccca ggacctcacc tccaaactgc    2220
tccaccagaa ccctctggag agacttggca caggcagtgc ctatgaggtg aagcagcacc    2280
cattctttac tggtctggac tggacaggac ttctccgcca gaaggctgaa tttattcctc    2340
agttggagtc agaggatgat actagctatt ttgacacccg ctcagagcga taccaccaca    2400
tggactcgga ggatgaggaa gaagtgagtg aggatgctg ccttgagatc cgccagttct     2460
cttcctgctc tccaaggttc aacaaggtgt acagcagcat ggagcggctc tcactgctcg    2520
aggagcgccg gacaccaccc ccgaccaagc gcagcctgag tgaggagaag gaggaccatt    2580
cagatggcct ggcagggctc aaaggccgag accggagctg ggtgattggc tcccctgaga    2640
tattacggaa gcggctgtcg gtgtctgagt catcccacac agagagtgac tcaagccctc    2700
caatgacagt gcgacgccgc tgctcaggcc tcctggatgc gcctcggttc ccggagggcc    2760
ctgaggaggc cagcagcacc ctcaggaggc aaccacagga gggtatatgg gtcctgacac    2820
ccccatctgg agaggggta tctgggcctg tcactgaaca ctcaggggag cagcggccaa     2880
agctggatga ggaagctgtt ggccggagca gtggttccag tccagctatg agacccgag    2940
gccgtgggac ctcacagctg gctgagggag ccacagccaa ggccatcagt gacctggctg    3000
tgcgtagggc ccgccaccgg ctgctctctg gggactcaac agagaagcgc actgctcgcc    3060
ctgtcaacaa agtgatcaag tccgcctcag ccacagccct ctcactcctc attccttcgg    3120
aacaccacac ctgctccccg ttggccagcc ccatgtcccc acattctcag tcgtccaacc    3180
catcatcccg ggactcttct ccaagcaggg acttcttgcc agcccttggc agcatgaggc    3240
ctcccatcat catccaccga gctggcaaga agtatggctt caccctgcgg gccattcgcg    3300
tctacatggg tgactccgat gtctacaccg tgcaccatat ggtgtggcac gtggaggatg    3360
```

-continued

```
gaggtccggc cagtgaggca gggcttcgtc aaggtgacct catcacccat gtcaatgggg    3420
aacctgtgca tggcctggtg cacacggagg tggtagagct gatcctgaag agtggaaaca    3480
aggtggccat ttcaacaact cccctggaga acacatccat taaagtgggg ccagctcgga    3540
agggcagcta caaggccaag atggcccgaa ggagcaagag gagccgcggc aaggatgggc    3600
aagaaagcag aaaaaggagc tccctgttcc gcaagatcac caagcaagca tccctgctcc    3660
acaccagccg cagcctttcc tcccttaacc gctccttgtc atcaggggag agtgggccag    3720
gctctcccac acacagccac agcctttccc ccgatctcc cactcaaggc taccgggtga     3780
cccccgatgc tgtgcattca gtgggaggga attcatcaca gagcagctcc cccagctcca    3840
gcgtgcccag ttccccagcc ggctctgggc acacggcc cagctccctc acggtctgg       3900 cacccaagct ccaacgccag taccgctctc acggcgcaa gtcagcaggc agcatcccac     3960
tgtcaccact ggcccacacc ccttctcccc cacccccaac agcttcacct cagcggtccc    4020
catcgcccct gtctggccat gtagcccagg cctttcccac aaagcttcac ttgtcacctc    4080
ccctgggcag gcaactctca cggcccaaga gtgcggagcc accccgttca ccactactca    4140
agagggtgca gtcggctgag aaactggcag cagcacttgc cgcctctgag aagaagctag    4200
ccacttctcg caagcacagc cttgacctgc cccactctga actaaagaag gaactgccgc    4260
ccagggaagt gagccctctg gaggtagttg gagccaggag tgtgctgtct ggcaaggggg    4320
ccctgccagg gaaggggtg ctgcagcctg ctccctcacg ggcctaggc accctccggc      4380 aggaccgagc cgaacgacgg gagtcgctgc agaagcaaga agccattcgt gaggtggact    4440
cctcagagga cgacaccgag gaagggcctg agaacagcca gggtgcacag gagctgagct    4500
tggcacctca cccagaagtg agccagagtg tggcccctaa aggagcagga gagagtgggg    4560
aagaggatcc tttcccgtcc agagaccta ggagcctggg cccaatggtc ccaagcctat     4620
tgacagggat cacactgggg cctcccagaa tggaaagtcc cagtggtccc cacaggaggc    4680
tcgggagccc acaagccatt gaggaggctg ccagctcctc ctcagcaggc cccaacctag    4740
gtcagtctgg agccacagac cccatccctc ctgaaggttg ctggaaggcc cagcacctcc    4800
acacccaggc actaacagca ctttctccca gcacttcggg actcaccccc accagcagtt    4860
gctctcctcc cagctccacc tctgggaagc tgagcatgtg gtcctggaaa tcccttattg    4920
agggcccaga cagggcatcc ccaagcagaa aggcaaccat ggcaggtggg ctagccaacc    4980
tccaggattt ggaaaacaca actccagccc agcctaagaa cctgtctccc agggagcagg    5040
ggaagacaca gccacctagt gcccccagac tggcccatcc atcttatgag gatcccagcc    5100
agggctggct atgggagtct gagtgtgcac aagcagtgaa agaggatcca gccctgagca    5160
tcacccaagt gcctgatgcc tcaggtgaca gaaggcagga cgttccatgc cgaggctgcc    5220
ccctcaccca gaagtctgag cccagcctca ggaggggcca agaaccaggg ggccatcaaa    5280
agcatcggga tttggcattg gttccagatg agctttttaaa gcaaacatag cagttgtttg   5340
ccatttcttg cactcagacc tgtgtaatat atgctcctgg aaaccatctt tatgtctttt    5400
gcttgcttgt tttccttcgg tcaacccaca tgtaactagg tcctgtgttg ctgctgggaa    5460
tatagtggtg aataaagcat                                                5480
```

```
<210> SEQ ID NO 30
<211> LENGTH: 1568
<212> TYPE: DNA
<213> ORGANISM: Homo sapiens
<220> FEATURE:
<221> NAME/KEY: misc_feature
```

```
<223> OTHER INFORMATION: Incyte ID No: 5547067CB1

<400> SEQUENCE: 30
caggaaaaaa agatatttta aatttgatgc tcattttgt gtgtgtgtgt tgagtgcatg     60
cattcaatct gtgtattcct ccctcatcaa cccagaacat cctgcagctg ccactctgag    120
ggtggcccct tccttcctct gccctgaagc tgtatcacag agatttctag tcctagtgtg    180
actctggccc catgctgatg ggtttctgca gactggaaga ggcggggctc gtgtcacgca    240
gcatcaggga gaggaattgc ttatataact gggacagcag atttagcaga gagaggaggc    300
agaggctggg aatgggagca gtaagctgtc ggcaggggca gcacacccag caggggaac     360
acacccgggt ggctgtccct cacaaggtg gcaacatccg gggtccctgg gcccgaggct     420
ggaagagcct ctggacaggt ttgggaacca tcaggtcaga tctggaagaa ctctgggaac    480
tacgggggca ccactatctg caccaggaat ccctaaagcc agcccagta ctggtagaga     540
agcctctgcc agagtggcca gtgcctcagt tcatcaacct ctttctacca gagtttccca    600
ttaggcccat tagggggcag cagcagctga agattttagg cctcgtggct aaaggctcct   660
ttggaactgt cctcaaggtg ctagattgca cccagaaagc tgtatttgca gtgaaggtgg    720
tgcccaaggt aaaggtccta cagagggata ccgtgaggca gtgcaaagag gaggttagca    780
tccagcgaca gatcaaccat ccctttgtac acagcttggg ggacagctgg cagggaaaac    840
ggcaccttt cattatgtgt agctactgca gcacagatct gtactccctt tggtcggctg    900
ttggctgctt tcctgaggct tccatccgtc tctttgctgc cgagttggtg ctggtactgt    960
gttatctcca tgacttgggc atcatgcatc gagatgtgaa gatggagaat attcttctag   1020
atgaacgagg ccatctgaaa ctgacagact tggtctgtc cgccacgtg ccccagggag    1080
ctcaagccta cactatctgt ggcactcttc agtacatggc cccagaggtc ctaagtggag   1140
gaccttacaa ccatgctgct gattggtggt ccctgggtgt cttgcttttc tctctggcga   1200
ctggaaagtt tccagtggct gcagagagag atcatgtggc catgttggca agtgtgaccc   1260
acagtgactc tgagatccca gcttctctta accaggcct ctcactcctg ctccatgagc    1320
tcttatgcca gaacccctc catcgtctac gttatctgca tcacttccag gtccaccctt    1380
tctttcgggg tgtggccttc gacccagagc tcctacagaa gcagccagtg aactttgtca   1440
cggagacaca agctacccag cccagttcag cggagaccat gcccttgac gactttgact    1500
gtgatctgga gtccttcttg ctctacccta tccctgcttg agcctctcta ctgtaaattg   1560
gggcccgg                                                            1568

<210> SEQ ID NO 31
<211> LENGTH: 2365
<212> TYPE: DNA
<213> ORGANISM: Homo sapiens
<220> FEATURE:
<221> NAME/KEY: misc_feature
<223> OTHER INFORMATION: Incyte ID No: 71675660CB1

<400> SEQUENCE: 31
cccctttttt tttttttcta ggaaagaagg gagtttatca ctgtaactgg atacagggag    60
aaggctggag ataattccag cagaccaact caaagtgcta caattttctt actgtttata   120
taggttgggg ttatgtgcct acatgcagta cagcaatcac ctaagtctac tggtaactaa   180
ttttgttcca aggagaaggt cagaggcaaa aaaaatgctt gctaagtccg attaaaaggg   240
gcccagtgcc ttcaaggcct gtctactgtg gtaccggagt gattatttcg attgtatctc   300
```

```
ctttacagct tggtccagag agctgcctta gactatccaa ttgatctatt caaacagctg    360
cctgttccct taacttgtct tcagattttg tcgacccgag atgggtcctg gcactaggaa    420
tgtaaaaccg ttcctattat tttggcttgc tccagcaaaa gagaagccca tgcaaggctc    480
ctgctgacca tgtttcattt ctagctttga tgtctgggca ctgatttccc tagatttaac    540
tatgtgctca atggtaaggc agtgctgtgg aaatctgtct gtgtaactgg ggtgctatgc    600
aggcctgtct gggtgactgt cagggacaac tgtcctacca caccaaggac acagccctgg    660
gggtgctttt cttcatagcc aaagaagctg caggaaaccc accctagtgg gacaaagacc    720
aatgcagggt cagtccccac agccaggtga tgcaaacagg ctggacgtgg gccgcctccc    780
ctccagcttg acttgtgaca gggaaaccaa tgcagcagca gcaggccac cagagtcctg     840 tcctggggac aggcttcctt ccagcgggcg ggagtgggt gctcctgcca gaccagcctg     900
gcttccacgg ttccagagac cctgttcccc ctcagcccag tccccgcccc cactccttgg    960
ctttatgagt tcattggctg aagtcacccg gagacaatgc tgagtgttcc accctgagt   1020 cgaagcccag cccagggcag cccagccaga cgcctccggt agtgtaaatg aggacaatgc   1080
ctgctggccc acatgacggg gggatgtaga cggcagcggc gccagtcgct cctggcacca   1140
tggacgatgc cacagtccta aggaagaagg gttacatcgt aggcatcaat cttggcaagg   1200
gttcctacgc aaaagtcaaa tctgcctact ctgagcgcct caagttcaat gtggctgtca   1260
agatcatcga ccgcaagaaa cacctactg actttgtgga gagattcctt cctcgggaga   1320
tggacatcct ggcaactgtc aaccacggct ccatcatcaa gacttacgag atctttgaga   1380
cctctgacgg acggatctac atcatcatgg agcttggcgt ccagggcgac ctcctcgagt   1440
tcatcaagtg ccagggagcc ctgcatgagg acgtggcacg caagatgttc cgacagctct   1500
cctccgccgt caagtactgc cacgacctgg acatcgtcca ccgggacctc aagtgcgaga   1560
accttctcct cgacaaggac ttcaacatca agctgtctga cttttggcttc tccaagcgct   1620 gcctgcggga cagcaatggg cgcatcatcc tcagcaagac cttctgcggg tcggcagcat   1680
atgcagcccc cgaggtgctg cagagcatcc cctaccagcc caaggtgtat gacatctgga   1740
gcctgggcgt gatcctgtac atcatggtct gtggctccat gccctatgac gactccgaca   1800
tcaggaagat gctgcgtatc cagaaggagc accgtgtgga cttcccgcgc tccaagaacc   1860
tgacctgcga gtgcaaggac ctcatctacc gcatgctgca gcccgacgtc agtcagcggc   1920
tccacatcga tgagatcctc agccactcgt ggctgcagcc ccccaagccc aaagccatgt   1980
cttctgcctc cttcaagagg gagggggagg gcaagtaccg cgctgagtgc aaactggaca   2040
ccaagacagg cttgaggccc gaccaccggc ccgaccacaa gcttggagcc aaaacccagc   2100
accggctgct ggtggtgccc gagaacgaga acaggatgga ggacaggctg gccgagacct   2160
ccagagccaa agaccatcac atctccggag ctgaggtggg gaaagcaagc acctagcatg   2220
acaatggccc cgttgtgtgt ggtggggtc ggggttgggg ggcatggtgc agtcggcctt    2280
cacgtaaact aagtaggcag gtaggatctg aagaaggcac aggtgcaagt aaaattcgtc   2340
aattaaacca ctattttgat taaaa                                        2365
```

<210> SEQ ID NO 32
<211> LENGTH: 2626
<212> TYPE: DNA
<213> ORGANISM: Homo sapiens
<220> FEATURE:
<221> NAME/KEY: misc_feature
<223> OTHER INFORMATION: Incyte ID No: 71678683CB1

<400> SEQUENCE: 32

```
cccctttttt ttttttttcta ggaaagaagg gagtttatca ctgtaactgg atacagggag      60
aaggctggag ataattccag cagaccaact caaagtgcta cattttcttt actgtttata     120
taggttgggg ttatgtgcct acatgcagta cagcaatcac ctaagtctac tggtaactaa     180
ttttgttcca aggagaaggt cagaggcaaa aaaaatgctt gctaagtccg attaaaaggg     240
gcccagtgcc ttcaaggcct gtctactgtg gtaccggagt gattatttcg attgtatctc     300
ctttacagct tggtccagag agctgcctta gactatccaa ttgatctatt caaacagctg     360
cctgttccct taacttgtct tcagattttg tcgacccgag atgggtcctg cactaggaa      420
tgtaaaaccg ttcctattat tttggcttgc tccagcaaaa gagaagccca tgcaaggctc     480
ctgctgacca tgtttcattt ctagctttga tgtctgggca ctgatttccc tagatttaac     540
tatgtgctca atggtaaggc agtgctgtgg aaatctgtct gtgtaactgg ggtgctatgc     600
aggcctgtct gggtgactgt cagggacaac tgtcctacca caccaaggac acagccctgg     660
gggtgctttt cttcatagcc aaagaagctg caggaaaccc accctagtgg gacaaagacc     720
aatgcagggt cagtccccac agccaggtga tgcaaacagg ctggacgtgg gccgcctccc     780
ctccagcttg acttgtgaca gggaaaccaa tgcagcagca gcagggccac cagagtcctg     840
tcctggggac aggcttcctt ccagcgggcg gggagtgggt gctcctgcca gaccagcctg     900
gcttccacgg ttccagagac cctgttcccc ctcagcccag tccccgcccc cactccttgg     960
ctttatgagt tcattggctg aagtcacccg gagacaatgc tgagtgttcc accctgagt    1020
cgaagcccag cccagggcag cccagccaga cgcctccggt agtgtaaatg aggacaatgc    1080
ctgctggccc acatgacggg gggatgtaga cggcagcggc gccagtcgct cctggcacca    1140
tggacgatgc cacagtccta aggaagaagg gttacatcgt aggcatcaat cttggcaagg    1200
gttcctacgc aaaagtcaaa tctgcctact ctgagcgcct caagttcaat gtggctgtca    1260
agatcatcga ccgcaagaaa acacctactg actttgtgga gagattcctt cctcgggaga    1320
tggacatcct ggcaactgtc aaccacggct ccatcatcaa gacttacgag atctttgaga    1380
cctctgacgg acggatctac atcatcatgg agcttggcgt ccagggcgac ctcctcgagt    1440
tcatcaagtg ccagggagcc ctgcatgagg acgtggcacg caagatgttc cgacagctct    1500
cctccgccgt caagtactgc cacgacctgg acatcgtcca ccgggacctc aagtgcgaga    1560
accttctcct cgacaaggac ttcaacatca agctgtctga ctttggcttc tccaagcgct    1620
gcctgcggga cagcaatggg cgcatcatcc tcagcaagac cttctgcggg tcggcagcat    1680
atgcagcccc cgaggtgctg cagagcatcc cctaccagcc caaggtgtat gacatctgga    1740
gcctgggcgt gatcctgtac atcatggtct gcggctccat gcctatgac gactccgaca    1800
tcaggaagat gctgcgtatc cagaaggagc accgtgtgga cttcccgcgc tccaagaacc    1860
tgacctgcga gtgcaaggac ctcatctacc gcatgctgca gcccgacgtc agccagcggc    1920
tccacatcga tgagatcctc agccactcgt ggctgcagcc ccccaagccc aaagccacgt    1980
cttctgcctc cttcaagagg gaggggggagg gcaagtaccg cgctgagtgc aaactggaca    2040
ccaagacagg cttgaggccc gaccaccggc ccgaccacaa gcttggagcc aaaacccagc    2100
accggctgct ggtggtgccc gagaacgaga acaggatgga ggacaggctg gccgagacct    2160
ccagggccaa agaccatcac atctccggag ctgaggtggg gaaagcaagc acctagcatg    2220
acaatggccc cgttgtgtgt ggtggggggtc ggggttgggg ggcatggtgc agtcggcctt    2280
cacgtaaaact aagtaggcag gtaggatctg aagaaggcac aggtgcaagt aaaattcgtc    2340
```

```
aattaaacca ctattttgat tacgttccat tagctttctt ccacttagca gcaaagacgt   2400
tccttactga ccaccaaata aaccacaggg tgtgtgcaag catcaagagt gcccagtgag   2460
gagtgttttt ctctgggact cagccaaccg ccccacctga cacacagtgg tctccggcct   2520
aggagcacag gacagatgct caggtacagg cagaatcaca gtgtggcctg gccttgtggg   2580
ggacaagagg gcctctgcca gggtccaccc accaggccca cactgt              2626
```

<210> SEQ ID NO 33
<211> LENGTH: 3961
<212> TYPE: DNA
<213> ORGANISM: Homo sapiens
<220> FEATURE:
<221> NAME/KEY: misc_feature
<223> OTHER INFORMATION: Incyte ID No: 7474567CB1

<400> SEQUENCE: 33

```
ccctgtaata cgaactcact atagggcgac cagtgtgctg gaaagcggcc gcggggggcgg     60 cggaggatat ggagtaaagc cagagtcagt ggccaggcac gaaggcagag caggaacagc    120
caggaggcgt ttattagggg ggcgggggga aagagcccca gcaccgcccc tcctggaaga    180
aggaagaggt aactataact acccaatatt gcagccatgg agtccatgct taataaattg    240
aagagtactt ttacaaaagt aacagctgat gtcactagtg ctgtaatggg aaatcctgtc    300
actagagaat ttgatgttgg tcgacacatt gccagtggtg gcaatgggct agcttggaag    360 attttttaatg gcacaaaaaa gtcaacaaag caggaagtgg cagtttttgt ctttgataaa    420
aaactgattg acaagtatca aaaatttgaa aaggatcaaa tcattgattc tctaaaacga    480
ggagtccaac agttaactcg gcttcgacac cctcgacttc ttactgtcca gcatccttta    540
gaagaatcca gggattgctt ggcattttgt acagaaccag ttttttgccag tttagccaat    600 gttcttggta actgggaaaa tctaccttcc cctatatctc cagacattaa ggattataaa    660
ctttatgatg tagaaaccaa atatggtttg cttcaggttt ctgaaggatt gtcattcttg    720
catagcagtg tgaaaatggt gcatggaaat atcactcctg aaaatataat tttgaataaa    780
agtggagcct ggaaaataat gggttttgat ttttgtgtat catcaaccaa tccttctgaa    840
caagagccta aatttccttg taaagaatgg gacccaaatt taccttcatt gtgtcttcca    900
aatcctgaat atttggctcc tgaatacata cttttctgtga gctgtgaaac agccagtgat    960
atgtattctt taggaactgt tatgtatgct gtatttaata aagggaaacc tatatttgaa   1020
gtcaacaagc aagatattta caagagtttc agtaggcagt tggatcagtt gagtcgttta   1080
ggatctagtt cacttacaaa tatacctgag gaagttcgtg aacatgtaaa gctactgtta   1140
aatgtaactc cgactgtaag accagatgca gatcaaatga caaagattcc cttcttttgat   1200 gatgttggtg cagtaacact gcaatatttt gataccttat tccaaagaga taatcttcag   1260
aaatcacagt ttttcaaagg actgccaaag gttctaccaa aactgcccaa gcgtgtcatt   1320
gtgcagagaa ttttgccttg tttgacttca gaatttgtaa accctgacat ggtaccttt   1380 gttttgccca atgttctact tattgctgag gaatgcacca agaagaata tgtcaaatta   1440 attcttcctg aacttggccc tgtgtttaag cagcaggagc caatccagat tttgttaatt   1500
ttcctacaaa aaatggattt gctactaacc aaaacccctc ctgatgagat aaagaacagt   1560
gttctaccca tggtttacag agcactagaa gctccttcca ttcagatcca ggagctctgt   1620
ctaaacatca ttccaacctt tgcaaatctt atagactacc catccatgaa aaacgctttg   1680
ataccaagaa ttaaaaatgc ttgtctacaa acatcttccc ttgcggttcg tgtaaattca   1740
```

```
ttagtgtgct taggaaagat tttggaatac ttggataagt ggtttgtact tgatgatatc    1800
ctacccttct tacaacaaat tccatccaag gaacctgcgg tcctcatggg aattttaggt    1860
atttacaaat gtacttttac tcataagaag ttgggaatca ccaaagagca gctggccgga    1920
aaagtgttgc ctcatcttat tcccctgagt attgaaaaca atcttaatct taatcagttc    1980
aattctttca tttccgtcat aaaagaaatg cttaatagat tggagtctga acataagact    2040
aaactggagc aacttcatat aatgcaagaa cagcagaaat ctttggatat aggaaatcaa    2100
atgaatgttt ctgaggagat gaaagttaca aatattggga atcagcaaat tgacaaagtt    2160
tttaacaaca ttggagcaga ccttctgact ggcagtgagt ccgaaaataa agaggacggg    2220
ttacagaata aacataaaag agcatcactt acacttgaag aaaacaaaa attagcaaaa     2280
gaacaagagc aggcacagaa gctgaaaagc cagcagcctc ttaaaccca agtgcacaca     2340
cctgttgcta ctgttaaaca gactaaggac ttgacagaca cactgatgga taatatgtca    2400
tccttgacca gcctttctgt tagtacccct aaatcttctg cttcaagtac tttcacttct    2460
gttccttcca tgggcattgg tatgatgttt tctacaccaa ctgataatac aaagagaaat    2520
ttgacaaatg gcctaaatgc caatatgggc tttcagactt caggattcaa catgcccgtt    2580
aatacaaacc agaacttcta cagtagtcca agcacagttg gagtgaccaa gatgactctg    2640
ggaacacctc ccactttgcc aaacttcaat gctttgagtg ttcctcctgc tggtgcaaag    2700
cagacccaac aaagacccac agatatgtct gcccttaata atctctttgg ccctcagaaa    2760
cccaaagtta gcatgaacca gttatcacaa cagaaaccaa atcagtggct taatcagttt    2820
gtacctcctc aaggttctcc aactatgggc agttcagtaa tggggacaca gatgaacgtg    2880
ataggacaat ctgcttttgg tatgcagggt aatcctttct taacccaca gaactttgca    2940
cagccaccaa ctactatgac caatagcagt tcagctagca atgatttaaa agatcttttt    3000
gggtgaggtg tcttacttct attttgaagg attatttcag tttcaatcat gggtgagctg    3060
atttacatct ttatatagtt ggcttggagg aagtacttct atgggaaagt gaacagttct    3120
gtgacaggaa acatctctgt ccatgccagc atagtagttg tatggacttc taaccagttg    3180
agttttttaa agcattgagg attttttcct cttaccaact cctcttcagg tttttaaaga    3240
cccagcccct cccaatctca aagagaaaaa ggaaactgag ttatcttgaa taacataact    3300
ttttaatcaa atgtttattt tggcttgtgg atcttggtgt tatttaaaaa attgaggtga    3360
tggtcattgc aagctcatct attaagtact atatggtaca cagtctatga gtcattagtc    3420
ttcatttaa tatgtaaaaa atcttgatgc tgtattgatt tgtttgcatt taagatgaca    3480
gtgagaaaat gataagcata aagagaagta tcaggttatt tgcttttcc aaacttttca     3540
gatgaactat tgtttagtac agagactgag caaatactac aaaattcaac ttaaccttca    3600
tttcattggt ttaaatgcgt tattaaccat cttaagtgca aactaatcat tgtaaattat    3660
attttagcat ggtctgcctc aaatagtaat gtatttttct gcattcactt ggatatattt    3720
agaatcactt ttttcctcct gtatcaagga agaggtatgt gctgatttgt ttggatattt    3780
gacaaggcac tctgatgtga cttccctgac tactaccttc atatttcatt tcaaattcaa    3840
acttctgagg ttgcagcata tatgaattgc attttcaaaa gaagatttgt aagaattaaa    3900
ctatatttat gagtaaactt ttgaggtttc tgctgtattg tttcaaatgt aataaacttt    3960
a                                                                    3961
```

<210> SEQ ID NO 34

-continued

```
<211> LENGTH: 2210
<212> TYPE: DNA
<213> ORGANISM: Homo sapiens
<220> FEATURE:
<221> NAME/KEY: misc_feature
<223> OTHER INFORMATION: Incyte ID No: 3838946CB1

<400> SEQUENCE: 34
ccagagggcc ggcatgtggt ctgcagaaga ggaggacgtg gctgggtggc agggctggtc      60
tccaaggacg agtaagatcc tgcagctgca ggcttcagga agtctcctgg ggctatcaga     120
tggctccttc ttgtagcagc agctgtgggg tccactggcc ctgagccctc agaggggcgg     180
ccgtggggga cctcctgtct tttgccttgc aagggcctca gttgtgcttt ttccctctag     240
gcagccatgg gtgccaggca gtgctgagag cagtggggca tggctgcagc cctgcaggtc     300
ctgccccgct tggcccgagc ccccttgcat ccactcctct ggcggggctc agtggcccgt     360
ctggccagca gcatggcctt ggcagagcag gccaggcagc tgtttgagag tgctgtaggt     420
gcagtgctgc cgggccccat gctgcaccgg gcactatcct tggaccctgg tggcagacag     480
ctgaaggtgc gggaccggaa ctttcagctg aggcaaaacc tctacctggt gggctttggc     540
aaggctgtgc tgggtatggc agctgcagct gaggaactac tgggccagca tcttgtgcag     600
ggcgtgatca gcgttcccaa ggggatccgt gctgccatgg agcgtgccgg caagcaggag     660
atgctgctga agccacatag ccgtgtccag gtattcgagg gtgcggagga caacctcccg     720
gaccgcgatg cgctgcgggc tgcactggcc atccagcaac tggctgaggg actcacagct     780
gatgacctgc tgctcgtgct gatctcaggt gggggttcag ctctgctgcc tgcccccatc     840
ccacctgtca cactggagga gaagcagaca ctcactagac tgctggcagc ccgtggagcc     900
accatccagg agttgaacac cattcggaag gccctgtccc agctcaaggg tgggggctg      960
gctcaggccg cctaccctgc ccaggtggtg agcctcatcc tgtcagatgt ggtgggggac    1020
cctgtggagg tgattgccag tggccccacc gtggccagtt cccacaatgt gcaagattgc    1080
ctgcatatcc tcaatcgcta cggcctccgt gcagccctgc cacgttctgt gaagactgtg    1140
ctgtctcggg ccgactctga cccccatggg ccacacacct gtggccatgt cctgaatgtg    1200
atcattggct ctaatgtgct ggcgctagct gaggcccagc ggcaggccga ggcactgggc    1260
taccaggctg tggtgctgag tgcagccatg caaggtgatg taaaaagtat ggcccagttc    1320
tacgggctgc tggcccatgt ggctagaacc cgcctcaccc catccatggc tggggcttct    1380
gtggaggaag atgcacagct ccatgagctg gcagctgagc ttcagatccc agacctgcag    1440
ctggaggagg ctctggagac catggcatgg ggaaggggcc cagtctgcct gctggctggt    1500
ggcgagccca cagtacagct gcagggctcg gcaggggtg gccggaacca ggaactggcc    1560
ctgcgtgttg gagcagagtt gagaaggtgg ccgctggggc cgatagatgt gctgttttg    1620
agcggtggca ccgatgggca ggatgggccc acagaggctg ctggggcctg ggtcacacct    1680
gagcttgcca gccaggctgc agctgagggc ctggacatag ccaccttcct agcccacaat    1740
gactcacata ccttcttctg ctgcctccag ggtgggggcac acctgctgca cacagggatg    1800
acaggtacca atgtcatgga cacccacctc ttgttcctgc ggcctcggtg atggcatagg    1860
tcacattttg ggagttcaga ggaggcctac aagggcaagg tcagatggca gagcaaggtt    1920
ggtcctcagg gcctctctaa gccttagggc ccctcctctc cttggccttg gctgtttggt    1980
taactgtcac cttccactca gggcctctgc tctatatcta ttcccttcca gccagactgg    2040
cagatggggg cttccccta cccctgagga tgaggacaag cccctcggcc agttcagcgt    2100
```

| | |
|---|---|
| tcccgtgctt ctcccttggg cagcctctct cttgagcccc tcaccctgtt tctttctgtg | 2160 |
| aagcgagaat gtctgaaaat aaataggacc atgccaaaaa aaaaaaaaa | 2210 |

<210> SEQ ID NO 35
<211> LENGTH: 4869
<212> TYPE: DNA
<213> ORGANISM: Homo sapiens
<220> FEATURE:
<221> NAME/KEY: misc_feature
<223> OTHER INFORMATION: Incyte ID No: 72001176CB1

<400> SEQUENCE: 35

| | |
|---|---|
| ctgcgcttct cgcgaaacgg caggcatcgc ggggctggcc acttccgtac ttccgctttc | 60 |
| cggcccagcc agcgcccgcg atgactgcca ctctccgccc ctacctgagt gccgtgcggg | 120 |
| ccacattgca ggctgccctc tgcctggaga acttctcctc ccaggttgtg aacgacaca | 180 |
| acaagccgga agtggaagtc aggagtagca aagagctcct gttacaacct gtgaccatca | 240 |
| gcaggaatga gaaggaaaag gttctgattg agggctccat caactctgtc cgggtcagca | 300 |
| ttgctgtgaa acaggctgat gagatcgaga agattttgtg ccacaagttc atgcgcttca | 360 |
| tgatgatgcg agcagagaac ttctttatcc ttcgaaggaa gcctgtggag gggtatgata | 420 |
| tcagcttcct gatcaccaac ttccacacag agcagatgta caaacacaag ttggtggact | 480 |
| tgtgatcca cttcatggag gagattgaca aggagatcag tgagatgaag ctgtcagtca | 540 |
| atgcccgtgc ccgcattgtg gctgaagagt tccttaagaa ttttttaaacc atctggctgg | 600 |
| atctcgtggc cttcccccctc agactaccca tgtctccacg aaggcgtcct ggagtcactc | 660 |
| cccgcgctgc tctacccacc cgcccctcgg ctcctcgcct tcccctcccc gtccgccttc | 720 |
| tccctccct cccgctcctg ggaaagagag aaaccaccgc tgcgggtggg tagagaagca | 780 |
| cttggcgcct cggggagggg accgcgcccg cctcatttgc gccttgcagc actgctggac | 840 |
| caggttacaa gatgttcacc taagattgag acctagtgac tacatttcct acgggaacaa | 900 |
| ataaatggtt tttcatctcc cggagataca ttacaaacaa atatggtgct aaaagaactc | 960 |
| cttacctttc tctgactaca atttatttgg acatactttt gtattgaaga gaggtataca | 1020 |
| tactgaagct acttgctgta ctataggaga ctctgtcctg taggatcatg gaccatccta | 1080 |
| gtagggaaaa ggatgaaaga caacggacaa ctaaacccat ggcacaaagg agtgcacact | 1140 |
| gctctcgacc atctggctcc tcatcgtcct ctggggttct tatggtggga cccaacttca | 1200 |
| gggttggcaa gaagatagga tgtgggaact tcggagagct cagattaggt aaaaatctct | 1260 |
| acaccaatga atatgtagca atcaaactgg aaccaataaa atcacgtgct ctacagcttc | 1320 |
| atttagagta cagattttat aaacagcttg gcagtgcagg tgaaggtctc ccacaggtgt | 1380 |
| attactttgg accatgtggg aaatataatg ccatggtgct ggagctcctt ggccctagct | 1440 |
| tggaggactt gtttgacctc tgtgaccgaa catttacttt gaagacggtg ttaatgatag | 1500 |
| ccatccagtt gctttctcga atggaatacg tgcactcaaa gaacctcatt taccgagatg | 1560 |
| tcaagccaga gaacttcctg attggtcgac aaggcaataa gaaagagcat gttatacaca | 1620 |
| ttatagactt tggactggcc aaggaataca ttgaccccga accaaaaaa cacataccctt | 1680 |
| atagggaaca caaagtttta actgaactg caagatatat gtctatcaac acgcatcttg | 1740 |
| gcaaagagca aagccggaga gatgatttgg aagccctagg ccatatgttc atgtatttcc | 1800 |
| ttcgaggcag cctcccctgg caaggactca aggctgacac attaaaagag agatatcaaa | 1860 |
| aaattggtga caccaaaagg aatactccca ttgaagctct ctgtgagaac tttccagagg | 1920 |

```
agatggcaac ctaccttcga tatgtcaggc gactggactt ctttgaaaaa cctgattatg    1980
agtatttacg gaccctcttc acagacctct ttgaaaagaa aggctacacc tttgactatg    2040
cctatgattg ggttgggaga cctattccta ctccagtagg gtcagttcac gtagattctg    2100
gtgcatctgc aataactcga gaaagccaca cataggga tcggccatca caacagcagc      2160
ctcttcgaaa tcagaatgta tcatcagagc gccgaggaga gtgggaaatt cagcccagcc    2220
ggcagaccaa tacctcatac ctaacgtctc acttggctgc agaccgccat ggggatcag     2280 tgcaggtggt tagctcaacc aatggagagc tgaatgttga tgatcccacg ggagcccact    2340
ccaatgcacc aatcacagct catgccgagg tggaggtagt ggaggaagct aagtgctgct    2400
gtttctttaa gaggaaaagg aagaagactg ctcagcgcca caagtgacca gtgcctccca    2460
ggagtcctca ggccctgggg actctgactc aattgtacct gcagctcctg ccatttctca    2520
ttggaaggga ctcctctttg ggggaggtg gatatccaaa ccaaaaagaa gaaacagat      2580 gccccagaa ggggccagtg cggcagcca ggcctagtg ggtcattggc catctccgcc        2640
tgcctaaggc tctgagcagg tcccagagct gctgttcctc cactgcttgc ccatagggct    2700
gcctggttga ctctccttcc cattgtttac agtgaaggtg tcattcacaa aaactcaagg    2760
actgctattc tccttcttcc ccttagttta ctcctggttt ttaccccacc ctcaaccctc    2820
tccagcataa aacctagtga gctaaaggct ttgtctgcag aaggagatca agaggctggg    2880
ggtaaggcca agaaggtagg aggaaaatgg cagacctggg ctggagaaga accttctccg    2940
tatcccaggt gtgcctggca gtatggtttc ctcttcctct gtgcctgtgc agcattcatc    3000
ccagctggcc ttggggttca ggttccttct tccctccctc ctgtgaagtt acactgtagg    3060
acacaagctg tgagcaatct gcagtctact gtccctgtgt gttggcgttc ttagcttttt    3120
tgacaaactc ttttctccag gtagtaggac aatgaaaatt gttctaagca aggaaagaa     3180 aactgacttt gttgcacttt tagttttttt aaaaaaaacc aaaacaaaac atggcagatg    3240
catattgtgt ctggttatat tgggggtttt acttttacct gttttgaggg ggatggggcc    3300
ggccaagcca ttcagagaga acatgggtcc agaggacatt ctcagtggaa agagtttgat    3360
ctgcagcacc cagaagagaa gccaactcgg tgtcattctg agtgaacact caggttggca    3420
agaaaacata cttgaatttt cattcatctt ctcagcagct gaagaatgtc cctaccagag    3480
catcttgacc taatcagctt acagtttgaa aacctagctc tccagaacat gagatgagcc    3540
agccgagcca gactgtgacc aggaaacagc tcatcccaga gaaggagatg cttaacaaaa    3600
aaaaattgaa attgtttccc atgctgccag ggacttccaa ctagatagcc atgtgacgtc    3660
ctggtgactt gggggaaaaa ttagtgatga aacagccacc accatattgc cattagtgga    3720 aaaaagagg acagtgaacc tgccttccac ctgccagagg gacctcaggg tgtggcatta    3780
tagggccagg aaaagaaaat cggtgtatcc tatctgcccc aatagctgag ctgtagcatt    3840
tgggctggcc tgccttatca gaaaccaagc ttatgaagat cttctcccag caggtccata    3900
gcagtaggct taggatgcag tatatggggc cgcatttaaa aggagggaaa gattgtttgg    3960
tgctggaaca ttccagggaa aaggagactg gaatgaaagg tctgaaatta tcttctcaat    4020
tggactcctt ccagaaaggt ggccgtgcct ctaagcatgt ttttcccagt atgccctagg    4080 cctccccca tggtgttttc atatgaggta ctactgtgaa ggatctggtt cctcattcac     4140
tgtttgacaa gtctttcatg tgtggagtta ctcttctcat gcccaatttt catttgagtt    4200
tagtggctta accaaacaat gactcctcat tccagcggtg acagaagaga aagggtcatt    4260
tacatcagga aagaggtctt gtatctggga gtagagagct aaccatggag cacagtggct    4320
```

-continued

```
ggtgggtgac ttagtctgat ggtttgtgga ccatagaagt cttcacctct ggtttgaggt    4380
gcagggctgt cttttgtact ggagggtgtg gggatatttt ctgatagttg ccatttcttg    4440
aaaaattccc ttgatgtacc ttacacagag cagaaataac attaacatgg atcagaggta    4500
ctgggcttca tctgttccat tggaccttgg ctagggaata tcatttcact ggcatcaaac    4560
ctgcttagct tatgaaaaga tggtaatatg tcatttctat aaatgtttct atatatgaaa    4620
cataaaagtg gcagggagat acaatatcac accccttttcc cccaaaggac tgtgaaaaat    4680
tgggggttta tggcccttgc caattcccta gtgggttaaa agcccctatt ccttaaaatt    4740
ttaacatcgg tttcctccaa tttgggggtt ttgggggatt tgtccaactt aacctggtta    4800
gggaaaagtt taacatggtc ccctcacccc ccctgtttg gagaaaagcc cctgtgcctc    4860
ccccaaaga                                                           4869
```

<210> SEQ ID NO 36
<211> LENGTH: 4480
<212> TYPE: DNA
<213> ORGANISM: Homo sapiens
<220> FEATURE:
<221> NAME/KEY: misc_feature
<223> OTHER INFORMATION: Incyte ID No: 55064363CB1

<400> SEQUENCE: 36

```
atgaagtggg tagggacac tggagtgggg ggaaacatcc ctccatcctt cactacccca      60
gggctctcct ccagaccggg tgctatggtg gcggatcgca gccgctggcc actcgcccag    120
gggaagggcg cgcaggcggg cacatggaga gcggcggtgg aatgctccgg ccggggcctc    180
ggggcggcga gcgagtcccc tcagtgcccg ccgccgccgg gggtggaggg cgcggccggg    240
ccggcggagc ccgacggggc ggcggagggc gcggcaggcg gcagcggcga gggcgagagt    300
gggggcgggc cgcggcgggc tctgcgggca gtatacgtgc gcagtgagag ctcccagggc    360
ggcgcggccg gcggcccgga ggctggggcg cggcagtgcc tgctgcgggc ctgcgaggcc    420
gagggcgctc acctcacctc cgtgcccttc ggggagctgg acttcgggga gacgccgtg    480 ctcgacgcct tctacgacgc agatgttgct gtggtagaca tgagcgatgt ctccagacag    540
ccttccctct tctaccatct tggagtccga gaaagctttg acatggccaa taatgtgatc    600
ttgtaccatg acaccgatgc cgacactgct ctctctttga aggacatggt aactcaaaaa    660
aacacagcat ccagtggaaa ttattatttc atcccataca tcgtgacacc gtgcactgat    720 tattttttgct gcgagagtga tgcccagaga cgagcctccg agtacatgca gcccaactgg    780
gacaacatcc tgggcccgct gtgcatgcct ttggtggaca ggttcattag cctccttaag    840
gacatccacg tgacctcatg tgtttattac aaagaaacct tgttaaatga catccggaaa    900
gccagagaga aataccaagg tgaggaactg gcgaaggagc tagctcggat caagctccgc    960
atggataata ctgaggttct gacctcagac atcatcatta acttactcct gtcctaccgt   1020
gatatccagg actatgatgc gatggtgaag ctggtggaaa cactggagat gctgcctacg   1080
tgtgatttgg ccgatcagca taacattaaa ttccactatg cgtttgcact gaataggaga   1140
aacagcacag gtgaccgtga gaaggctctg cagatcatgc tccaggttct gcagagctgt   1200
gatcacccgg gccccgacat gttctgcctg tgtggggaga tctacaagga catcttcttg   1260
gattcagact gcaaagatga caccagccgc gacagcgcca ttgagtggta tcgcaagggg   1320
tttgaactcc agtcatccct ctattcggga attaatcttg cagttttgct gattgttgct   1380
ggacaacaat ttgaaacttc cttggaacta aggaaaatag gtgtccggct gaacagtttg   1440
```

-continued

```
ttgggaagaa aagggagctt ggagaaaatg aacaattact gggatgtggg tcagttcttc    1500
agcgtcagca tgctggccca tgatgtcggg aaagccgtcc aggcagcaga gaggttgttc    1560
aaactgaaac ctccagtctg gtacctgcga tcattagttc agaacttgtt actaattcgg    1620
cgcttcaaga aaaccattat tgaacactcg cccaggcaag agcggctgaa cttctggtta    1680
gatataattt tgaggcaac aaatgaagtc actaatggac tcagatttcc agttctggtc     1740
atagagccaa ccaaagtgta ccagccttct tatgtttcca taaacaatga agccgaggag    1800
agaacagttt ctttatggca tgtctcaccc acagaaatga aacagatgca cgaatggaat    1860
tttacagcct cttccataaa gggaataagc ctatcaaagt ttgatgaaag gtgttgtttt    1920
ctttatgtcc atgataattc tgatgacttt caaatctact tttccaccga agagcagtgc    1980
agtagatttt tctctttggt caaagagatg ataaccaata cagcaggcag tacggtggag    2040
ctggagggag agaccgatgg agacaccttg gagtatgagt atgaccatga tgcaaatggt    2100
gagagagttg tcttggggaa aggcacgtat gggattgtgt atgctggccg agatctgagc    2160
aatcaagtgc gaatagccat caaagaaatc ccggagagag atagcaggta ttctcagcct    2220
ctgcacgagg agatagccct gcacaagtac cttaagcacc gcaatatcgt tcagtacctg    2280
ggctctgttt cagagaacgg ctacattaag atatttatgg agcaggtgcc tggaggaagc    2340
cttttctgctc ttctgcgatc caaatggggg ccgatgaagg aaccgacaat caagttttac    2400
accaaacaga tcctgagggg ccttaagtat cttcatgaaa accagatcgt gcacagagac    2460
ataaagggcg ataatgttct ggtgaacacc tacagcggag tggtgaaaat ctccgatttt    2520
ggaacctcga aacgtcttgc gggtgtgaac ccctgcacag agacttttac tggcaccctg    2580
cagtacatgg cacctgagat aattgaccaa gggcctcgcg gatatggtgc cccagccgat    2640
atctggtccc tgggctgcac catcattgag atggccacca gcaagcctcc gttccatgag    2700
cttggtgagc cgcaggcagc catgttcaaa gtgggcatgt ttaagatcca ccctgagatt    2760
ccagaagccc tttcagctga gcccgagcc ttcattttat cctgtttcga gcctgacccc    2820
cacaaacgtg ccaccactgc tgagctactg agagagggtt tcttaaggca ggtgaacaag    2880
ggcaagaaga accgaattgc cttcaagccc tcagaaggtc cccgcggtgt cgtcctggcc    2940
ctgcccacac agggagagcc catggccacc agcagcagcg agcacggctc tgtctcccca    3000
gactccgacg cccagcctga cgcactcttt gagaggaccc gggcgcccag gcaccacctt    3060
ggccacctcc tcagtgttcc agacgagagc tcagccttgg aagaccgggg cttggcctcg    3120
tccccggagg acagggacca gggcctcttc ctgctacgca aggacagtga gcgccgtgcc    3180
atcctgtaca aaatcctctg ggaggagcag aaccaggtgg cttccaacct gcaggagtgt    3240
gtggcccaga gttccgaaga gttgcatctc tcagttggac acatcaagca aatcattggg    3300
atcctgaggct acttcatccg ctccccagag caccgggtga tggcgaccac aatatcaaag    3360
ctcaaggtgg acctggactt tgacagctcg tccatcagtc agattcacct ggtgctgttc    3420
ggatttcagg atgccgtaaa taaaattttg aggaaccact taattaggcc ccactggatg    3480
ttcgcgatgg acaacatcat ccgccgagcg gtgcaggccg cggtcaccat tctcatccca    3540
gagctccgag cccactttga gcctaccgt gagactgaag gggtagataa ggacatggat    3600
gaagcggaag agggctatcc cccagccacc ggacctggcc aggaggccca gccccaccag    3660
cagcacctga gcctccagct gggtgagctc agacaggaga ccaacagact tttggaacac    3720
ctagttgaaa aagagagaga gtaccagaat cttctgcggc aaactctaga acagaaaact    3780
```

-continued

| | |
|---|---|
| caagaattgt atcaccttca gttaaaatta aaatcgaatt gtattacaga gaacccagca | 3840 |
| ggcccctacg ggcagagaac agataaagag cttatagact ggttgcggct gcaaggagct | 3900 |
| gatgcaaaga caattgaaaa gattgttgaa gagggttata cactttcgga tattcttaat | 3960 |
| gagatcacta aggaagatct aagatacctt cgactacggg tggtctcct ctgcagactc | 4020 |
| tggagtgcgg tctcccagta cagaagggct caggaggcct cagaaaccaa agacaaggct | 4080 |
| tgataccaat cagctaagct gtggcagagt gtcccaccac gctacatgtt ttgttaaagc | 4140 |
| ttctgttagt gtatacacga attccgctgt gtttacatat ttaaaaatgc cattgttcaa | 4200 |
| ttaatagttt aagaacttgt tttaaatact gtcctgagtt tcttttgaaa cctgttattt | 4260 |
| ataaacatag aactgtgtgt attgtgaaaa cagtgagcct tggttttgac ctcccggaat | 4320 |
| attaggaaat tcacttgtag tcccagctat gcaggaggct gaggtgggag gattgcttga | 4380 |
| gcccaggagg tgtggaggct gcagtgagcc atgatcacac cactgcactc cagcctgggc | 4440 |
| aacagagccc gacctgtctc aaaaaaaagt acacccttca | 4480 |

<210> SEQ ID NO 37
<211> LENGTH: 4415
<212> TYPE: DNA
<213> ORGANISM: Homo sapiens
<220> FEATURE:
<221> NAME/KEY: misc_feature
<223> OTHER INFORMATION: Incyte ID No: 7482044CB1

<400> SEQUENCE: 37

| | |
|---|---|
| cgagacgtcc ccggcacgct gatggagccc gggcgcggcg cggggcccgc gggcatggcg | 60 |
| gagcctcggg cgaaggcggc gcggccgggg ccccagcgct ttctgcggcg cagcgtggta | 120 |
| gagtcggacc aggaggagcc gccgggcttg gaggcagccg aggcgccggg cccgcagccc | 180 |
| ccgcagcccc tgcagcgccg ggtgcttctg ctctgcaaga cgcgccgcct catcgcggag | 240 |
| cgcgcccgcg gacgccccgc cgccccgcg ccgcagcgc tggtagcgca gccgggagcc | 300 |
| cccggagccc ccgcggacgc cggccccgag cccgtgggca cgcaggagcc cggcccggac | 360 |
| cccatcgcag ccgctgtcga aaccgcgcct gcccccgacg gcggcccag ggaggaggcg | 420 |
| gcggcgaccg tgaggaagga ggatgagggg gcggccgagg cgaagcctga gcccgggcgc | 480 |
| actcgccggg acgagcccga agaggaggag gacgacgagg acgacctcaa ggccgtggcc | 540 |
| acctctctgg acggccgctt cctcaagttc gacatcgagc tgggccgcgg ttccttcaag | 600 |
| acggtctaca aggggctgga cacggagacc tgggtggagg tggcctggtg tgagctgcag | 660 |
| gaccggaagc tcaccaagct ggagcggcag cggttcaagg aagaggctga gatgctgaaa | 720 |
| ggcctgcagc accccaacat cgtgcgcttc tacgacttct gggagtccag cgccaagggc | 780 |
| aagcggtgca ttgtgctggt gacggagctg atgacctcag ggacgctgaa gacataccctg | 840 |
| aagcggttca aggtgatgaa gcccaaggtt ctccgcagct ggtgccggca gatcctgaag | 900 |
| ggcctgctgt tcctgcacac aaggacgcca cccatcatcc accgagacct gaaatgtgac | 960 |
| aatattttca tcaccggacc aactgggtct gtgaagattg gcgacttggg cctggccact | 1020 |
| ctgaaaagag cgtcatttgc caaaagtgtg ataggtactc ccgagttcat ggcgcccgag | 1080 |
| atgtacgagg agcactacga tgagtccgtg gacgtctatg cctttgggat gtgcatgctg | 1140 |
| gagatggcca cctcggagta cccctactcg gagtgccaga atgcggccca gatctaccgc | 1200 |
| aaggtcaccc tggtgtatca agccgccagc tttgagaaag tgcacgatcc tgaaatcaag | 1260 |
| gagattattg gggagtgtat ctgcaaaaac aaggaggaaa ggtacgagat caagacctg | 1320 |

-continued

```
ctgagccacg ccttcttcgc agaggacaca ggcgtgaggg tggagctcgc ggaggaggac      1380
cacggcagga agtccaccat cgccctgagg ctctggtgg aagaccccaa gaaactgaag        1440
ggaaagccca aggacaatgg agccatagag ttcaccttcg acctggagaa ggagacgccg      1500
gatgaggtgg cccaagagat gattgagtct ggattcttcc acgagagtga cgtcaagatc      1560
gtggccaagt ccatccgtga ccgcgtggcc ttgatccagt ggcggcggga gaggatctgg      1620
cccgcgctgc agcccaagga gcagcaggat gtgggcagcc cggacaaggc cagggggtccg    1680 ccggtgcccc tgcaggtcca ggtgacctac catgcacagg ctgggcagcc cgggccacca     1740
gagcccgagg agccggaggc cgaccagcac ctcctgccac ctacgttgcc gaccagcgcc      1800
acctccctgg cctcggacag caccttcgac agcggccagg gctctaccgt gtactcagac     1860
tcgcagagca gccagcagag cgtgatgctt ggctcccttg ccgacgcagc gccgtccccg     1920
gcccagtgtg tgtgcagccc ccctgtgagc gaggggcccg tcctgccgca gagcctgccc     1980
tcgctggggg cctaccagca gcccacggct gcacctggct tgccggtggg ctctgtcccg    2040
gcccccgcct gccctccgtc cctccagcag cacttcccgg atccggccat gagcttcgcc    2100
cccgtgctgc cgccgcccag cacccccatg cccacgggcc caggccagcc agcacccccc    2160
ggccagcagc ctcctccgct ggcccagccg acaccctgc cgcaggtcct ggccccacag     2220
cccgtggtcc cctccagcc ggttccccc cacctgccac cgtacctggc tccagcctcc     2280
caggtggggg ccccgctca gctgaagccc ctccagatgc acaggcgcc cctgcagccg    2340 cttgctcaag tccctccgca gatgcccccg attcctgttg tgcccccat cacgccctg    2400 gcgggaatcg acggcctccc tccggccctc ccagacctgc cgaccgcgac tgtgcctccc    2460
atgccaccac ctcagtattt ctctccagcc gtgatcttgc cgagcctcgc tgccccactc    2520
ccccctgcgt cccagcctt gcctctgcag gctgtgaagc tgccccaccc ccctggggcg    2580
cccctggcca tgcctgccg gaccattgtg ccaaatgcac cggccactat cccctgctg    2640 gccgtagccc caccgggcgt ggctgccctg tccattcatt ctgccgtggc ccagctccca    2700
ggccaacctg tgtacccagc ggccttccca cagatggcgc ctactgacgt ccctccttcc    2760
ccccatcaca cggtgcagaa tatgagggcc acccctccac agccggcact gcctccacaa    2820
cccacactgc cccacaaacc cgtgctgccc ccgcaaccca cgctgccccc tcaacctgtg    2880 ttgccccgc aacccacacg gccccctcaa cctgtgctgc ccccgcaacc catgctgccc    2940
ccacaacctg tgctgccccc gcagccggca ctgcctgtgc gcctgagcc cctccagccc    3000 caccttcctg aacaagctgc tccagctgct acaccaggga gccagattct gcttggccac    3060
ccagctccct atgctgtgga cgtcgccgct caggtcccca ccgtgcctgt gccaccggct    3120
gcggtcctct cgccgcctct gccggaagtg ctgctgcctg ccgcccctga gctcctgcct    3180
cagttcccca gctccctggc cacggtgtct gcctctgtgc agagtgtgcc cacccagact    3240
gccacacttc tgccaccagc aaacccaccg ctgcctggcg ggcccgggat cgccagccct    3300
tgcccaactg tccagctgac ggtggaacca gtccaagagg agcaggcctc acaggacaag    3360
ccgcccggcc tccgcagag ctgtgagagc tatgaggtt ctgatgtcac ttctggaaaa       3420
gagctgagtg acagctgtga aggcgccttt ggaggggca ggctggaggg cagggcagcc     3480
cgaaaacacc accgcaggtc cacgcgtgcg cgctcccgc aggagagggc cagccggccc    3540
cggcttacca tcttgaacgt gtgcaacact ggggacaaga tggtggagtg ccagctggag    3600
acgcacaacc acaagatggt gaccttcaag ttcgacttgg acgggacgc acccgatgaa     3660 attgccacgt atatggtgga gcatgacttt atcctgcagg ccgagcggga aacgttcatc     3720
```

| | |
|---|---|
| gagcagatga aggatgtcat ggacaaggca gaggacatgc tcagcgagga cacagacgcc | 3780 |
| gaccgtggct ccgacccagg gaccagcccg ccacacctca gcacctgcgg cctgggcacc | 3840 |
| ggggaggaga gccgacaatc ccaagccaac gcccccgtgt atcagcagaa cgtcctgcac | 3900 |
| accgggaaga ggtggttcat catctgtccg gtggctgagc accccgcccc cgaggcccct | 3960 |
| gaatcttcgc ccccacttcc tctaagctcc ctgcccctgcc ctgccctgtt ccgcatgagc | 4020 |
| tgcgcctctg tgctcgcctg ccccctctct gcttgttagt tgctctttct ggctctgcct | 4080 |
| ctcctttgct ttcctcggga tgccactctg tgcccaggag ggtgcctgat ttcggggagt | 4140 |
| cctgacccga gcctgttgtc agagttggga ggggctctga gcagtgttgg gcaggccggg | 4200 |
| tctcccatcc cgaggccagc gttcctgtgc agagccccat ccactggttc ttgccctgag | 4260 |
| ccacatatgt ctgtgccatg ggctgagtgc cacgacaggc ccgtgtgaca gctgctgccc | 4320 |
| acgcatgtgg aagctaggtg ggactcattc ctaattctgc cgttgtaatg agacttgatt | 4380 |
| aaaacaccgc cacttttttg caaaaaaaaa aaaa | 4415 |

<210> SEQ ID NO 38
<211> LENGTH: 6306
<212> TYPE: DNA
<213> ORGANISM: Homo sapiens
<220> FEATURE:
<221> NAME/KEY: misc_feature
<223> OTHER INFORMATION: Incyte ID No: 7476595CB1

<400> SEQUENCE: 38

| | |
|---|---|
| agacacagaa acagatgaca gcagaaacac cagaaacaga tgacagcaga aacaccagaa | 60 |
| acagatgaca gcagaaacac cagaaacaga tgacagcaga aacaccagaa acagatgaca | 120 |
| gcagaaacac cagaaacaga tgacagcaga aacaccagaa acagatgaca gcagaaacac | 180 |
| cagaaacaga tgacagcaga aacaccagaa acagatgaat cagtgagtag ctctaatgcc | 240 |
| tccctgaaac ttcgaaggaa acctcgggaa agtgattttg aaacgattaa attgattagc | 300 |
| aatggagcct atggggcagt ctactttgtt cggcataaag aatcccggca gaggtttgcc | 360 |
| atgaagaaga ttaataaaca gaacctcatc cttcgaaacc agatccagca ggcctttgtg | 420 |
| gagcgggata tcctgacttt tgcagaaaac ccctttgttg tcagcatgta ttgctccttt | 480 |
| gaaacaaggc gccacttgtg catggtcatg gaatatgtgg aagggggaga ctgtgctact | 540 |
| ttaatgaaaa acatgggtcc tctccctgtt gatatggcca gaatgtactt tgctgagacg | 600 |
| gtcttggcct tggaatattt acataattat ggaattgtac acaggatttt gaaaccagac | 660 |
| aacttgttgg ttacctccat ggggcacata aagctgacag attttggatt atctaaggtg | 720 |
| ggactaatga gcatgactac caacctttac gagggtcata ttgagaagga tgctagagag | 780 |
| ttcctggata acaggtctg tggcacacct gaatacattg caccagaagt gattctgagg | 840 |
| cagggttatg gaaagccggt ggactggtgg gccatgggga ttatcctcta tgaatttctg | 900 |
| gttggatgcg tgccattctt tggggatact ccagaggagc tatttggaca agtcatcagt | 960 |
| gatgagatca actggcctga gaaggatgag gcaccccac ctgatgccca ggatctgatt | 1020 |
| accttactcc tcaggcagaa tccctggag aggctgggaa caggtggtgc atatgaagtc | 1080 |
| aaacagcatc gattcttccg ttcttttgac tggaacagtt tgctgagaca gaaggcagaa | 1140 |
| tttattcccc aactggaatc tgaggatgac acaagttatt tgatactcg gtctgagaag | 1200 |
| tatcatcata tggaaacgga ggaagaagat gacacaaatg atgaagactt taatgtggaa | 1260 |
| ataaggcagt tttcttcatg ttcacacagg ttttcaaaac tttttctaaa tgattaccta | 1320 |

```
gatgcacctg caaatgggcc agcactaccc tcctgtgtat gggaatggca tcgaggtaag    1380
gatttccctg gagaaggtgg tagccagtct gtcctagagc caggacagaa gcttgctaag    1440
tgtggactca gaccaggact gttctctggg ccatcaaaga caacaatgcc aacccctaaa    1500
cactgcttcc ttctttgcct tgatactgaa agcaacagac ataaactcag ttctggccta    1560
cttcccaaac tggctatttc aacagaggga gagcaagatg aagctgcctc ctgccctgga    1620
gacccccatg aggagccagg aaagccagcc cttcctcctg aagagtgtgc ccaggaggag    1680
cctgaggtca ccaccccagc cagcaccatc agcagctcca ccctgtcaga tatgtttgct    1740 gtttccctc tgggaagtcc aatgtctccc cattccctgt cctcggaccc ttcttcttca    1800
cgagattcct ctcccagccg agattcctca gcagcttctg ccagtccaca tcagccgatt    1860
gtgatccaca gttcggggaa gaactacggc tttaccatcc gagccatccg ggtgtatgtg    1920
ggagacagtg acatctatac agtgcaccat atcgtctgga atgtagaaga aggaagtccg    1980
gcatgccagg caggactgaa ggctggagat cttatcactc acatcaatgg agaaccagtg    2040
catggacttg tccacacaga agttatagaa ctcctactga agagtgggaa taaggtgtca    2100
atcactacta ccccatttga aaacacatca atcaaaactg accagccag gagaaacagc    2160 tataagagcc ggatggtgag gcggagcaag aaatccaaga agaaagaaag tctcgaaagg    2220
aggagatctc ttttcaaaaa gctagccaag cagccttctc ctttactcca caccagccga    2280
agtttctcct gcttgaacag atccctgtca tcgggtgaga gcctcccagg ttcccccact    2340
catagcttgt ctccccggtc tccaacacca agctaccgct ccacccctga cttcccatct    2400
ggtactaatt cctcccagag cagctcccct agttctagtg cccccaattc cccagcaggg    2460
tccgggcaca tccggcccag cactctccac ggtcttgcac ccaaactcgg cgggcagcgg    2520
taccggtccg gaaggcgaaa gtccgccggc aacatcccac tgtccccgct ggcccggacg    2580
ccctctccaa ccccgcaacc cacctccccg cagcggtcac catcccctct tctgggacac    2640
tcactgggca attccaagat cgcgcaagcc tttcccagca agatgcactc cccgcccacc    2700
atcgtcagac acatcgtgag gcccaagagt gcggagcccc caggtccccc gctgctcaag    2760
cgcgtgcagt ccgaggagaa gctgtcgccc tcttacggca gtgacaagaa gcacctgtgc    2820
tcccgcaagc acagcctgga ggtgacccaa gaggaggtgc agcgggagca gtcccagcgg    2880
gaggcgccgc tgcagagcct ggatgagaac gtgtgcgacg tgccgccgct cagccgcgcc    2940
cggccagtgg agcaaggctg cctgaaacgc ccagtctccc ggaaggtggg ccgccaggag    3000
tctgtggacg acctggaccg cgacaagctg aaggccaagg tggtggtgaa gaaagcagac    3060
ggcttcccag agaaacagga atcccaccag aaatcccatg gacccgggag tgatttggaa    3120
aactttgctc tgtttaagct ggaagagaga gagaagaaag tctatccgaa ggctgtggaa    3180
aggtcaagta cttttgaaaa caaagcgtct atgcaggagg cgccaccgct gggcagcctg    3240
ctgaaggatg ctcttcacaa gcaggccagc gtgcgcgcca gcgagggtgc gatgtcggat    3300
ggccgggtgc ctgcggagca ccgccagggt ggcggggact tcagacgggc ccccgctcct    3360
ggcaccctcc aggatggtct ctgccactcc ctcgacaggg gcatctctgg aagggggaa    3420 ggcacggaga agtcctccca ggccaaggag cttctccgat gtgaaaagtt agacagcaag    3480
ctggccaaca tcgattacct ccgaaagaaa atgtcacttg aggacaaaga ggacaacctc    3540
tgccctgtgc tgaagcccaa gatgacagct ggctcccacg aatgcctgcc agggaaccca    3600
gtccgaccca cgggtgggca gcaggagccc ccgccggctt ctgagagccg agcttttgtc    3660
```

```
agcagcaccc atgcagctca gatgagtgcc gtctcttttg ttcccctcaa ggccttaaca    3720
ggccgggtgg acagtggaac ggagaagcct ggcttggttg ctcctgagtc ccctgttagg    3780
aagagcccct ccgagtataa gctggaaggt aggtctgtct catgcctgaa gccgatcgag    3840
ggcactctgg acattgctct cctgtccgga cctcaggcct ccaagacaga actgccttcc    3900
ccagagtctg cacagagccc cagcccaagt ggtgacgtga gggcctctgt gccaccagtt    3960
ctccccagca gcagtgggaa aaagaacgat accaccagtg caagagagct ttctccttcc    4020
agcttaaaga tgaataaatc ctacctgctg gagccttggt tcctgccccc cagccgaggt    4080
ctccagaatt caccagcagt ttccctgcct gacccagagt tcaagaggga caggaaaggt    4140
ccccatccta ctgccaggag ccctggaaca gtcatggaaa gcaatcccca acagagagag    4200
ggcagctccc ctaaacacca agaccacacc actgacccca agcttctgac ctgcctgggg    4260
cagaacctcc acagccctga cctggccagg ccacgctgcc cgctcccacc tgaagcttcc    4320
ccctcaaggg agaagccagg cctgagggaa tcgtctgaaa gaggccctcc cacagccaga    4380
agcgagcgct ctgctgcgag ggctgacaca tgcagagagc cctccatgga actgtgcttt    4440
ccagaaactg cgaaaaccag tgacaactcc aaaaatctcc tctctgtggg aaggacccac    4500
ccagatttct atacacagac ccaggccatg gagaaagcat gggcgccggg tgggaaaacg    4560
aaccacaaag atgcccagg tgaggcgagg cccccgccca gagacaactc ctctctgcac    4620
tcagctggaa ttccctgtga aaggagctg ggcaaggtga ggcgtggcgt ggaacccaag    4680
cccgaagcgc ttcttgccag gcggtctctg cagccacctg gaattgagag tgagaagagt    4740
gaaaagctct ccagtttccc atctttgcag aaagatggtg ccaaggaacc tgaaaggaag    4800
gagcagcctc tacaaaggca tcccagcagc atccctccgc cccctctgac ggccaaagac    4860
ctgtccagcc cggctgccag gcagcattgc agttccccaa gccacgcttc tggcagagag    4920
ccggggccca gcccagcac tgcagagccc agctcgagcc cccaggaccc tcccaagcct    4980
gttgctgcgc acagtgaaag cagcagccac aagccccggc ctggccctga cccgggccct    5040
ccaaagacta agcaccccga ccggtccctc tcctctcaga aaccaagtgt cggggccaca    5100
aagggcaaag agcctgccac tcagtccctc ggtggctcta gcagagaggg gaagggccac    5160
agtaagagtg ggccggatgt gtttcctgct accccaggct cccagaacaa agccagcgat    5220
gggattggcc agggagaagg tgggccctct gtcccactgc acactgacag ggctcctcta    5280
gacgccaagc cacaacccac cagtggtggg cggcccctgg aggtgctgga aagcctgtg    5340 catttgccaa ggccgggaca cccagggcct agtgagccag cggaccagaa actgtccgct    5400
gttggtgaaa agcaaaccct gtctccaaag caccccaaac catccactgt gaaagattgc    5460
cccaccctgt gcaaacagac agacaacaga cagacagaca aaagcccgag tcagccggcc    5520
gccaacaccg acagaagggc ggaagggaag aaatgcactg aagcacttta tgctccagca    5580
gagggcgaca agctcgaggc cggcctttcc tttgtgcata gcgagaaccg gttgaaaggc    5640
gcggagcggc cagccgcggg ggtggggaag ggcttccctg aggccagagg gaaagggccc    5700
ggtccccaga agccaccgac ggaggcagac aagcccaatg gcatgaaacg gtcccccctca    5760 gccactgggc agagttcttt ccgatccacg gccctcccgg aaaagtctct gagctgctcc    5820
tccagcttcc ctgaaaccag gccggagtt agagaggcct ctgcagccag cagcgacacc    5880
tcttctgcca aggccgccgg gggcatgctg agcttccag ccccagcaa cagggaccat    5940 aggaaggctc agcctgccgg ggagggccga acccacatga caaagagtga ctccctgccc    6000
tccttccggg tctccaccct gcctctggag tcacaccacc ccgacccaaa caccatgggc    6060
```

-continued

| | |
|---|---|
| ggggccagcc accgggacag ggctctctcg gtgactgcca ccgtaggga aaccaaaggg | 6120 |
| aaggaccctg ccccagccca gcctccccca gctaggaaac agaacgtggg cagagacgtg | 6180 |
| accaagccat ccccagcccc aaacactgac cgccccatct ctctttctaa tgagaaggac | 6240 |
| tttgtggtac ggcagaggcg ggggaaagag agtttgcgta gcagccctca caaaaaggcc | 6300 |
| ttgtaa | 6306 |

<210> SEQ ID NO 39
<211> LENGTH: 7151
<212> TYPE: DNA
<213> ORGANISM: Homo sapiens
<220> FEATURE:
<221> NAME/KEY: misc_feature
<223> OTHER INFORMATION: Incyte ID No: 71824382CB1

<400> SEQUENCE: 39

| | |
|---|---|
| aatatacgac ttaattgtat tcttttaaaa atgcattaag tatatatttt atggtaattt | 60 |
| accctcaaaa tagatgtata tgggtgaaat tgaagacgct tcagttaagt gaggttactg | 120 |
| gtgtgttgga tgtttaattc agcaccagca ttgcatgaca gttgtttgaa taacaagtgg | 180 |
| tttattttta aaaccatacc ttttaaaatt taggttcaga taatagtaaa agtcatcata | 240 |
| ataatttaaa ggaaaaccag cagaaatcga agcaaacatg tctggagaag tgcgtttgag | 300 |
| gcagttggag cagtttattt tggacgggcc cgctcagacc aatgggcagt gcttcagtgt | 360 |
| ggagacatta ctggatatac tcatctgcct ttatgatgaa tgcaataatt ctccattgag | 420 |
| aagagagaag aacattctcg aatacctaga atgggctaaa ccatttactt ctaaagtgaa | 480 |
| acaaatgcga ttacatagag aagactttga aatattaaag gtgattggtc gaggagcttt | 540 |
| tggggaggtt gctgtagtaa aactaaaaaa tgcagataaa gtgtttgcca tgaaaatatt | 600 |
| gaataaatgg gaaatgctga aaagagctga gacagcatgt tttcgtgaag aaagggatgt | 660 |
| attagtgaat ggagacaata atggattac aaccttgcac tatgctttcc aggatgacaa | 720 |
| taacttatac ctggttatgg attattatgt tggtggggat ttgcttactc tactcagcaa | 780 |
| atttgaagat agattgcctg aagatatggc tagattttac ttggctgaga tggtgatagc | 840 |
| aattgactca gttcatcagc tacattatgt acacagagac attaaacctg acaatatact | 900 |
| gatggatatg aatggacata ttcggttagc agattttggt tcttgtctga agctgatgga | 960 |
| agatggaacg gttcagtcct cagtggctgt aggaactcca gattatatct ctcctgaaat | 1020 |
| ccttcaagcc atggaagatg gaaagggag atatggacct gaatgtgact ggtggtcttt | 1080 |
| gggggtctgt atgtatgaaa tgcttacgg agaaacacca ttttatgcag aatcgctggt | 1140 |
| ggagacatac ggaaaaatca tgaaccacaa agagaggttt cagtttccag cccaagtgac | 1200 |
| tgatgtgtct gaaatgcta aggatcttat tcgaaggctc atttgtagca gagaacatcg | 1260 |
| acttggtcaa aatggaatag aagactttaa gaaacacca tttttcagtg gaattgattg | 1320 |
| ggataatatt cggaactgtg aagcaccta tattccagaa gttagtagcc aacagatac | 1380 |
| atcgaatttt gatgtagatg atgattgtt aaaaaattct gaaacgatgc ccccaccaac | 1440 |
| acatactgca ttttctggcc accatctgcc atttgttggt tttacatata ctagtagctg | 1500 |
| tgtactttct gatcggagct gtttaagagt tacggctggt cccacctcac tggatcttga | 1560 |
| tgttaatgtt cagaggactc tagacaacaa cttagcaact gaagcttatg aaagaagaat | 1620 |
| taagcgcctt gagcaagaaa aacttgaact cagtagaaaa cttcaagagt caacacagac | 1680 |
| tgtccaagct ctgcagtatt caactgttga tggtccacta acagcaagca aagatttaga | 1740 |

```
aataaaaaac ttaaaagaag aaattgaaaa actaagaaaa caagtaacag aatcaagtca    1800
tttggaacag caacttgaag aagctaatgc tgtgaggcaa gaactagatg atgcttttag    1860
acaaatcaag gcttatgaaa aacaaatcaa aacgttacaa caagaaagag aagatctaaa    1920
taaggaacta gtccaggcta gtgagcgatt aaaaaaccaa tccaaagagc tgaaagacgc    1980
acactgtcag aggaaactgg ccatgcagga attcatggag atcaatgagc ggctaacaga    2040
attgcacacc caaaaacaga aacttgctcg ccatgtccga gataaggaag aagaggtgga    2100
cctggtgatg caaaaagttg aaagcttaag gcaagaactg cgcagaacag aaagagccaa    2160
aaaagagctg gaagttcata cagaagctct agctgctgaa gcatctaaag acaggaagct    2220
acgtgaacag agtgagcact attctaagca actggaaaat gaattggagg gactgaagca    2280
aaaacaaatt agttactcac caggagtatg cagcatagaa catcagcaag agataaccaa    2340
actaaagact gatttggaaa agaaaagtat cttttatgaa gaagaattat ctaaaagaga    2400
aggaatacat gcaaatgaaa taaaaaatct taagaaagaa ctgcatgatt cagaaggtca    2460
gcaacttgct ctcaacaaag aaattatgat tttaaaagac aaattggaaa aaaccagaag    2520
agaaagtcaa agtgaaaggg aggaatttga aagtgagttc aaacaacaat atgaacgaga    2580
aaaagtgttg ttaactgaag aaaataaaaa gctgacgagt gaacttgata agcttactac    2640
tttgtatgag aacttaagta tacacaacca gcagttagaa gaagaggtta aagatctagc    2700
agacaagaaa gaatcagttg cacattggga agcccaaatc acagaaataa ttcagtgggt    2760
cagcgatgaa aaggatgcac gagggtatct tcaggcctta gcttctaaaa tgactgaaga    2820
attggaggca ttaagaaatt ccagcttggg tacacgagca acagatatgc cctggaaaat    2880
gcgtcgtttt gcgaaactgg atatgtcagc tagactggag ttgcagtcgg ctctggatgc    2940
agaaataaga gccaaacagg ccatccaaga agagttgaat aaagttaaag catctaatat    3000
cataacagaa tgtaaactaa aagattcaga gaagaagaac ttggaactac tctcagaaat    3060
cgaacagctg ataaaggaca ctgaagagct tagatctgaa aagggtatag agcaccaaga    3120
ctcacagcat tctttcttgg cattttgaa tacgcctacc gatgctctgg atcaatttga    3180
agattccttt tcttcttcct catcttcact gattgatttt ttggatgaca ctgatcccgt    3240
tgagaacaca tatgtatgga acccgagcgt caagtttcac atccagtcac ggtccacatc    3300
tccttccaca tctagtgaag ctgagccagt taagactgta gactccactc cactttcagt    3360
tcacacacca accttaagga aaaaggatg tcctggttca actggctttc cacctaagcg    3420
caagactcac cagttttttg taaaatcttt tactactcct accaagtgtc atcagtgtac    3480
ctccttgatg gtgggtttaa taagacaggg ctgttcatgt gaagtgtgtg gattctcatg    3540
ccatataact tgtgtaaaca aagctccaac cacttgtcca gttcctcctg aacagacaaa    3600
aggtcccctg ggtatagatc ctcagaaagg aataggaaca gcatatgaag gtcatgtcag    3660
gattcctaag ccagctggag tgaagaaagg gtggcagaga gcactggcta gtgtgtgtga    3720
cttcaaactc tttctgtacg atattgctga aggaaaagca tctcagccca gtgttgtcat    3780
tagtcaagtg attgacatga gggatgaaga attttctgtg agttcagtct ggcttctga    3840 tgttatccat gcaagtcgga agatatacc ctgtatattt agggtcacag cttcccagct    3900
ctcagcatct aataacaaat gttcaatcct gatgctagca gacactgaga atgagaagaa    3960
taagtgggtg ggagtgctga gtgaattgca caagattttg aagaaaaaca aattcagaga    4020
ccgctcagtc tatgttccca agaggctta tgacagcact ctaccctca ttaaaacaac    4080
```

```
ccaggcagcc gcaatcatag atcatgaaag aattgctttg ggaaacgaag aagggttatt    4140
tgttgtacat gtcaccaaag atgaaattat tagagttggt gacaataaga agattcatca    4200
gattgaactc attccaaatg atcagcttgt tgctgtgatc tcaggacgaa atcgtcatgt    4260 acgactttt cctatgtcag cattggatgg gcgagagacc gatttttaca agctgtcaga    4320
aactaaaggg tgtcaaaccg taacttctgg aaaggtgcgc catggagctc tcacatgcct    4380
gtgtgtggct atgaaaaggc aggtcctctg ttatgaacta tttcagagca agacccgtca    4440
cagaaaattt aaagaaattc aagtcccata taatgtccag tggatggcaa tcttcagtga    4500
acaactctgt gtgggattcc agtcaggatt tctaagatac cccttgaatg gagaaggaaa    4560
tccatacagt atgctccatt caaatgacca tacactatca tttattgcac atcaaccaat    4620
ggatgctatc tgcgcagttg agatctccag taaagaatat ctgctgtgtt ttaacagcat    4680
tgggatatac actgactgcc agggccgaag atctagacaa caggaattga tgtggccagc    4740
aaatccttcc tcttgttgtt acaatgcacc atatctctcg gtgtacagtg aaaatgcagt    4800
tgatatcttt gatgtgaact ccatggaatg gattcagact cttcctctca aaaaggttcg    4860
acccttaaac aatgaaggat cattaaatct tttagggttg gagaccatta gattaatata    4920
tttcaaaaat aagatggcag aaggggacga actggtagta cctgaaacat cagataatag    4980
tcggaaacaa atggttagaa acattaacaa taagcggcgt tattccttca gagtcccaga    5040
agaggaaagg atgcagcaga ggagggaaat gctacgagat ccagaaatga gaaataaatt    5100
aatttctaat ccaactaatt ttaatcacat agcacacatg ggtcctggag atggaataca    5160
gatcctgaaa gatctgccca tgaaccctcg gcctcaggaa agtcggacag tattcagtgg    5220
ctcagtcagt attccatcta tcaccaaatc ccgccctgag ccaggccgct ccatgagtgc    5280
tagcagtggc ttgtcagcaa ggtcatccgc acagaatggc agcgcattaa agagggaatt    5340
ctctggagga agctacagtg ccaagcggca gcccatgccc tccccgtcag agggctcttt    5400
gtcctccgga ggcatggacc aaggaagtga tgccccagcg agggactttg acggagagga    5460
ctctgactct ccgaggcatt ccacagcttc aacagttcc aacctaagca gcccccaag    5520 cccagtttca ccccgaaaaa ccaagagcct ctccctggag agcactgacc gcgggagctg    5580
ggacccgtga gctgcctcag cactgggacc tctcgctctc cgctccctgc cactcgcctc    5640
ctctcacttt catctcttcc ctccacctcg cctgctcggc ctgaaagcca ccaggggctg    5700
gcagcagtag caggacaggg cttcaggagt tctgacgaca cgactctcag atccacgccc    5760
ccagcctaac agcaacaaca aagacagact ttccgtagca gcttagatta cgttgatt    5820 cattccatgc acttagagtt gctttcagta acattttacc cctactccca aaggtagctt    5880
aaatagacag attacacaaa tgtaagtgat aagaataaga ttagacagat tttgctttca    5940
cagtagagtc tcattatagt cctaaaatag ctcatgggct tctccgcatc cagaagggag    6000
aattggtccc tggagtggct cactaagctc ttaatcagca aacgcagtga gtatcaacct    6060
gattgttgcc aggaaatcct tatgaattaa acaatgcat attttactac agtacagagt    6120
ttaaatgaat acataaatgt agaagtactg aatgtatata tttaaaagga gcctcttgta    6180
ttcaacaaaa gatggatgca tatataagag agatgattta attttaaagaa atatgttgtt    6240 tcttgtctgt aatgtaatgt aaaggtgga aaggcctcaa gctcacattt gtagagagag    6300
agcgagagaa atcagagttc cctttattgc cctgtcctca aactggtcat aggctctagt    6360
cacctgggga gctgtagaaa acacttgcag agccaggttt tgctggtttg ggcatgccc    6420 tgggcaccag agctttaaca tttgaagcca cttcagcagc agcagcaaaa ggcgaactca    6480
```

-continued

| | |
|---|---|
| tctctaccca agatgtttct tttcctagtg gtggaatttg aacacttctc acttttat | 6540 |
| gtattttatc ttccgcagat aaatgtagaa atacacggtt ctgtcacctc tgatcccttc | 6600 |
| catctgaaag ggtacaagga gtgttgtagc ttctgaaggt gcagaaaaca atttctaaaa | 6660 |
| atgcttttat tcctgggcta atcctgtccc tccctaagtc gcagcgaggt gtctgtccca | 6720 |
| gggctggaga tgcttcccaa ggaggagtct gttttgttga gagtgggcgt gggcttcttc | 6780 |
| acataagcct ggggaaggaa gaaaaaacgg ctttcattac caaataatgt aaaacctcaa | 6840 |
| aagcaagggc ttcaacagcc ttaaccaaat attattcccc atagccagtg gaaaatggat | 6900 |
| gtgacaaccc cagtgcgcag gccagagtga gtgagcccag cacggcgctc cgactggctt | 6960 |
| cctctctcag gtgctggatt gtggggttag tggcatttcc agctggattc ctcctgttgt | 7020 |
| agttgccata aggaaatgag atgcagaatc agaaggatct atttctacag aatcatttca | 7080 |
| ccagttaagc acatgagtag agaaagagat aaaaataaaa gtatctcatg aaggaaagaa | 7140 |
| aaaaaaaaaa a | 7151 |

<210> SEQ ID NO 40
<211> LENGTH: 2378
<212> TYPE: DNA
<213> ORGANISM: Homo sapiens
<220> FEATURE:
<221> NAME/KEY: misc_feature
<223> OTHER INFORMATION: Incyte ID No: 3566882CB1

<400> SEQUENCE: 40

| | |
|---|---|
| aggcagcagc cacagcgggg agtgcgcggc gcggggacag gaagagaggg gcaatggctg | 60 |
| ccgaccccac cgagctgcgg ctgggcagcc tccccgtctt cacccgcgac gacttcgagg | 120 |
| gcgactggcg cctagtggcc agcggcggct tcagccaggt gttccaggcg cggcacaggc | 180 |
| gctggcggac ggagtacgcc atcaagtgcg ccccctgcct tccacccgac gccgccagga | 240 |
| cctttgcagc ttctgtttcc ccactcccct ctatttacct agcgaagatt tcagacttcg | 300 |
| gcctgtccaa gtggatggaa cagtccaccc ggatgcagta catcgagagg tcggctctgc | 360 |
| ggggcatgct cagctacatc ccccctgaga tgttcctgga gagtaacaag gccccaggac | 420 |
| ctaaatatga tgtgtacagc cccccgaccc tgccacccccg ggctgggtg atcttggatg | 480 |
| ttcaactaag tcattcagaa agggttctct gcatccacag ctttgcaatt gtcatctggg | 540 |
| agctactcac tcagaagaaa ccatactcag agctcacgtc acagctaaag gaaaggaaag | 600 |
| ggttcaacat gatgatgatt attatccgag tgacggcagg catgcggccc tccctacagc | 660 |
| ctgtctctga ccaatggcca agcgaggccc agcagatggt ggacctgatg aaacgctgct | 720 |
| gggaccagga ccccaagaag aggccatgct ttctagacat taccatcgag acagacatac | 780 |
| tgctgtcact gctgcagagt cgtgtggcag tcccagagag caaggccctg gccaggaagg | 840 |
| tgtcctgcaa gctgtcgctg cgccagcccg ggaggttaa tgaggacatc agccaggaac | 900 |
| tgatggacag tgactcagga aactacctga agcgggccct tcagctctcc gaccgtaaga | 960 |
| atttggtccc gagagatgag gaactgtgta tctatgagaa caaggtcacc ccctccact | 1020 |
| tcctggtggc ccagggcagt gtggagcagg tgaggttgct gctggcccac gaggtagacg | 1080 |
| tggactgcca gacggcctct ggatacacgc ccctcctgat cgccgcccag gaccagcaac | 1140 |
| ccgacctctg tgccctgctt ttggcacatg gtgctgatgc caaccgagtg gatgaggatg | 1200 |
| gctgggcccc actgcacttt gcagcccaga atggggatga cggcactgcg cgcctgctcc | 1260 |
| tggaccacgg ggcctgtgtg gatgcccagg aacgtgaagg gtggaccccct cttcacctgg | 1320 |

-continued

```
ctgcacagaa taactttgag aatgtggcac ggcttctggt ctcccgtcag gctgacccca    1380
acctgcatga ggctgagggc aagacccccc tccatgtggc cgcctactt  ggccatgtta    1440 gcctggtcaa gctgctgacc agccaggggg ctgagttgga tgctcagcag agaaacctga    1500
gaacaccact gcacctggca gtagagcggg gcaaagtgag ggccatccaa cacctgctga    1560
agagtggagc ggtccctgat gcccttgacc agagcggcta tggcccactg cacactgcag    1620
ctgccagggg caaatacctg atctgcaaga tgctgctcag gtacggagcc agccttgagc    1680
tgcccaccca ccagggctgg acaccctgc atctagcagc ctacaagggc cacctggaga    1740
tcatccatct gctggcagag agccacgcaa acatgggtgc tcttggagct gtgaactgga    1800
ctcccctgca cctagctgca cgccacgggg aggaggcggt ggtgtcagca ctgctgcagt    1860
gtggggctga ccccaatgct gcagagcagt caggctggac acccctccac ctggcggtcc    1920
agaggagcac cttcctgagt gtcatcaacc tcctagaaca tcacgcaaat gtccacgccc    1980
gcaacaaggt gggctggaca cccgcccacc tggccgccct caagggcaac acagccatcc    2040
tcaaagtgct ggtcgaggca ggcgcccagc tggacgtcca ggatggagtg agctgcacac    2100
ccctgcaact ggccctccgc agccgaaagc agggcatcat gtccttccta gagggcaagg    2160
agccgtcagt ggccactctg ggtggttcta agccaggagc cgagatggaa atttagacaa    2220
cttggccagc cgtggtggct cacgtctgta atcccagcac tttgggaggc tgaggcaggc    2280
agatcacctg agatcaagag tttgaggcca gcctggccaa catggcaaaa ccctgtctct    2340
gctaaaaata caaaatttag ctgggaaaaa aaaaaaaa                            2378
```